US008900595B2

(12) United States Patent
Kawaoka et al.

(10) Patent No.: US 8,900,595 B2
(45) Date of Patent: *Dec. 2, 2014

(54) FILOVIRUS VECTORS AND NONINFECTIOUS FILOVIRUS-BASED PARTICLES

(75) Inventors: Yoshihiro Kawaoka, Middleton, WI (US); Luke D. Jasenosky, Madison, WI (US); Gabriele Neumann, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 556 days.

This patent is subject to a terminal disclaimer.

(21) Appl. No.: 12/245,296

(22) Filed: Oct. 3, 2008

(65) Prior Publication Data

US 2010/0080825 A1    Apr. 1, 2010

Related U.S. Application Data

(60) Continuation of application No. 11/654,863, filed on Jan. 18, 2007, which is a division of application No. 10/353,856, filed on Jan. 29, 2003, now Pat. No. 7,211,378.

(60) Provisional application No. 60/353,972, filed on Jan. 31, 2002.

(51) Int. Cl.
*A61K 39/12*    (2006.01)
*C12N 15/86*    (2006.01)
*C07K 14/005*   (2006.01)
*A61K 39/00*    (2006.01)

(52) U.S. Cl.
CPC .............. *C07K 14/005* (2013.01); *C12N 15/86* (2013.01); *C12N 2760/14123* (2013.01); *C12N 2760/14143* (2013.01); *A61K 2039/525* (2013.01); *C12N 2810/6072* (2013.01); *C12N 2760/14145* (2013.01); *C12N 2760/14122* (2013.01)
USPC ................... 424/204.1; 435/235.1; 435/320.1

(58) Field of Classification Search
None
See application file for complete search history.

(56) References Cited

U.S. PATENT DOCUMENTS

| | | | |
|---|---|---|---|
| 7,211,378 B2 | 5/2007 | Kawaoka et al. | |
| 7,682,618 B2* | 3/2010 | Bavari et al. | 424/204.1 |
| 2004/0057967 A1 | 3/2004 | Bavari et al. | |
| 2005/0266023 A1 | 12/2005 | Bavari et al. | |
| 2006/0088909 A1 | 4/2006 | Compans | |
| 2006/0099609 A1 | 5/2006 | Bavari et al. | |
| 2006/0216702 A1 | 9/2006 | Compans et al. | |
| 2010/0267116 A1 | 10/2010 | Kawaoka et al. | |

FOREIGN PATENT DOCUMENTS

WO    WO-0060050 A2    10/2000

OTHER PUBLICATIONS

Warfield et al., PNAS, 2003, 100(26):15889-15894.*
http://www.abcam.com/index.html?datasheet=6556, GFP antibody (ab6556) datasheet from abcam, (2004).
Giddings, A M., et al., "The matrix protein of HIV-1 is not sufficient for assembly and release of virus-like particles", *Virology*, 248(1), (1998),108-16.
Harty, R. N., et al., "A PPxY Motif within the VP40 Protein of Ebola Virus Interacts Physically and Functionally with a Ubiquitin Ligase: Implications for Filovirus Budding", *Proc. Natl. Acad.* Sci, 97 (25), (Dec. 5, 2000),13871-13876.
Harty, Ronald N., "A Proline-Rich Motif within the Matrix Protein of Vesicular Stomatitis Virus and Rabies Virus Interacts with WW Domains of Cellular Proteins: Implications for Viral Budding", *Journal of Virology*, 73 (4), (1999),2921-2929.
Hevey, Michael, et al., "Marburg virus vaccines based upon alphavirus replicons protect guinea pigs and nonhuman primates", *Virology*, 251(1), (Nov. 10, 1998),28-37.
Jasenosky, Luke D., et al., "Ebola Virus VP40-Induced Particle Formation and Association with the Lipid Bilayer", *Journal of Virology*, 75 (110, (Jun. 2001),5205-5214.
Li, Y, et al., "Viral liposomes released from insect cells infected with recombinant baculovirus expressing the matrix protein of vesicular stomatitis virus", *Journal of Virology*, 67 (7), (1993), 4415-4420.
Mebatsion, Teshome, et al., "Budding of Rabies Virus Particles in the Absence of the Spike Glycoprotein", *Cell*, 84(6), (1996),941-951.
Mebatsion, Teshome, et al., "Matrix Protein of Rabies Virus Is Responsible for the Assembly and Budding of Bullet-Shaped Particles and Interacts with the Transmembrane Spike Glycoprotein G", *Journal of Virology*, 73 (1), (Jan. 1999),242/250.
Neumann, Gabriele, et al., "Reverse Genetics Demonstrates that Proteolytic Processing of the Ebola Virus Glycoprotein Is Not Essential for Replication in Cell Culture", *Journal of Virology*, 76 (1), (Jan. 2002),406-410.
Robison, C. S., et al., "The Membrane-Proximal Stem Region of Vesicular Stomatitis Virus G Protein Confers Efficient Virus Assembly", Journal of Virology, 74 (5), (Mar. 2000),2239-2246.
Ruigrok, R W., et al., "Structural Characterization and Membrane Binding Properties of the Matrix Protein VP40 of Ebola Virus", *Journal of Molecular Biology*, 300(1), (2000),103-112.
Ruiz-Arguello, M. B., et al., "Phosphatidylinositol-Dependent Membrane Fusion Induced by a Putative Fusogenic Sequence of Ebola Virus", *Journal of Virology*, 72(3), (Mar. 1998),1775-1781.
Schnell, Matthias J., et al., "Requirement for a non-specific glycoprotein cytoplasmic domain sequence to drive efficient budding of vesicular stomatitis virus", *EMBO Journal*, 17 (5), (1998),1289-1296.
Volchkov, Viktor E., et al., "Recovery of Infectious Ebola Virus from Complementary DNA: RNA Editing of the GP Gene and Viral Cytotoxicity", *Science Magazine*, 291, (Mar. 2001),1965-1969.
Wilson, Julie A., et al., "Epitopes Involved in Antibody-Mediated Protection from Ebola Virus", *Science*, 287, (Mar. 2000),1664-1666.
Wilson, et al., "Vaccine Potential of Ebola Virus VP24, VP30, VP35 and VP40 Proteins", *Virology* 286, (2001),384-90.

(Continued)

*Primary Examiner* — Stacy B Chen
(74) *Attorney, Agent, or Firm* — Schwegman Lundberg & Woessner, P.A.

(57) ABSTRACT

Cloned filovirus genomic cDNA and methods of using the cDNA are provided. Further provided are noninfectious lipid encapsulated filovirus-based particles.

7 Claims, 87 Drawing Sheets

(56) References Cited

OTHER PUBLICATIONS

"U.S. Appl. No. 10/353,856, Final Office Action mailed Jun. 1, 2006", 10 pgs.

"U.S. Appl. No. 10/353,856, Non-Final Office Action mailed Sep. 30, 2005", 9 pgs.

"U.S. Appl. No. 10/353,856, Non-Final Office Action mailed Dec. 16, 2004", 11 pgs.

"U.S. Appl. No. 10/353,856, Notice of Allowance mailed Oct. 18, 2006", 9 pgs.

"U.S. Appl. No. 10/353,856, Preliminary Amendment filed May 20, 2003", 2 pgs.

"U.S. Appl. No. 10/353,856, Response filed Feb. 28, 2006 to Non-Final Office Action mailed Sep. 30, 2005", 10 pgs.

"U.S. Appl. No. 10/353,856, Response filed Apr. 7, 2005 to Non-Final Office Action mailed Dec. 16, 2004", 10 pgs.

"U.S. Appl. No. 10/353,856, Response filed Aug. 17, 2006 to Final Office Action mailed Jun. 1, 2006", 11 pgs.

"U.S. Appl. No. 10/353,856, Response filed Oct. 8, 2004 to Restriction Requirement mailed Sep. 10, 2004", 2 pgs.

"U.S. Appl. No. 10/353,856, Response to Rule 312 Communication mailed Mar. 8, 2007", 2 pgs.

"U.S. Appl. No. 10/353,856, Restriction Requirement mailed Sep. 10, 2004", 5 pgs.

"U.S. Appl. No. 10/353,856, Supplemental Amendment filed Jan. 9, 2007", 4 pgs.

"U.S. Appl. No. 10/353,856, Supplemental Preliminary Amendment filed Jun. 23, 2003", 4 pgs.

"U.S. Appl. No. 11/654,863, Preliminary Amendment filed May 7, 2007", 15 pgs.

"U.S. Appl. No. 11/654,863 Restriction Requirement mailed Sep. 3, 2010", 5 pgs.

"U.S. Appl. No. 11/654,863, Response filed Sep. 28, 2010 to Restriction Requirement mailed Sep. 3, 2010", 6 pgs.

Bukreyev, A., et al., "Chimeric human parainfluenza virus bearing the Ebola virus glycoprotein as the sole surface protein is immunogenic and highly protective against Ebola virus challenge", Virology, 383(2), (Abstract Only), (2009), 1 pg.

Craven, R. C., et al., "Late Domain Function Identified in the Vesicular Stomatitis Virus M Protein by Use of Rhabdovirus-Retrovirus Chimeras", Journal of Virology, 73(4), (1999), 3359-3365.

Justice, P. A., et al., "Membrane Vesiculation Function and Exocytosis of Wild-Type and Mutant Matrix Proteins of Vesicular Stomatitis Virus", Journal of Virology, 69(5), (1995), 3156-3160.

Pattnaik, A. K., et al., "Cells That Express All Five Proteins of Vesicular Stomatitis Virus From Cloned cDNAs Support Replication, Assembly, and Budding of Defective Interfering Particles", Proc. Natl. Acad. Sci. USA, 88(4), (1991), 1379-1383.

Pushko, P., et al., "Replicon-Helper Systems from Attenuated Venezuelan Equine Encephalitis Virus: Expression of Heterologous Genes in Vitro and Immunization against Heterologous Pathogens in Vivo", Virology, 239(2), (Abstract Only), (1997), 1 pg.

Wills, J. W., et al., "An Assembly Domain of the Rous Sarcoma Virus Gag Protein Required Late in Budding", Journal of Virology, 68(10), (1994), 6605-6618.

Yonezawa, A., et al., "Studies of Eboa Virus Glycoprotein-Mediated Entry and Fusion by Using Pseudotyped Human Immunodeficiency Virus Type 1 Virions: Involvement of Cytoskeletal Proteins and Enhancement by Tumor Necrosis Factor Alpha", Journal of Virology, 79(2), (2005), 918-926.

"U.S. Appl. No. 11/654,863, Non Final Office Action mailed Dec. 2, 2010", 8 pgs.

"U.S. Appl. No. 11/654,863, Final Office Action mailed Oct. 25, 2011", 9 pgs.

"U.S. Appl. No. 11/654,863, Non Final Office Action mailed Feb. 11, 2013", 10 pgs.

"U.S. Appl. No. 11/654,863, Non Final Office Action mailed Jun. 27, 2011", 9 pgs.

"U.S. Appl. No. 11/654,863, Response filed Apr. 18, 2012 to Final Office Action mailed Oct. 25, 2011", 8 pgs.

"U.S. Appl. No. 11/654,863, Response filed Jun. 2, 2011 to Non Final Office Action mailed Dec. 2, 2010", 6 pgs.

"U.S. Appl. No. 11/654,863, Response filed Oct. 6, 2011 to Non Final Office Action mailed Jun. 27, 2011", 9 pgs.

Abram, M. E, et al., "Nature, position, and frequency of mutations made in a single cycle of HIV-1 replication", J Virol., 84(19), (Oct. 2010), 9864-78.

Bedford, M. T, et al., "FBP WW domains and the Abl SH3 domain bind to a specific class of proline-rich ligands", EMBO J., 16(9), (May 1, 1997), 2376-83.

Daddario-Dicaprio, K. M, et al., "Cross-protection against Marburg virus strains by using a live, attenuated recombinant vaccine", J Virol., 80(19), (Oct. 2006), 9659-66.

Harvey, K. F, et al., "All three WW domains of murine Nedd4 are involved in the regulation of epithelial sodium channels by intracellular Na+.", J Biol Chem., 274(18), (Apr. 30, 1999), 12525-30.

Johnson, R. F., et al., "Ebola Virus VP35-VP40 Interaction Is Sufficient for Packaging 3E-5E Minigenome RNA into Virus-Like Particles", Journal of Virology, 80(11), (Jun. 2006), 5135-5144.

Konduru, K., et al., "Ebola virus glycoprotein Fc fusion protein confers protection against lethal challenge in vaccinated mice", Vaccine, 29(16), (Apr. 5, 2011), 2968-77.

Kopecky, S. A, et al., "Matrix protein and another viral component contribute to induction of apoptosis in cells infected with vesicular stomatitis virus", J Virol., 75(24), (Dec. 2001), Abstract Only.

Le, T., "CaSpeR5, a family of *Drosophila* transgenesis and shuttle vectors with improved multiple cloning sites", Biotechniques, 42(2), (Feb. 2007), 164-166.

Longnecker, R., et al., "WW- and SH3-domain interactions with Epstein-Barr virus LMP2A", Exp Cell Res., 257(2), (Jun. 15, 2000), Abstract Only.

Mansky, L. M, "Retrovirus mutation rates and their role in genetic variation", J Gen Virol., 79 (Pt 6), (Jun. 1998), 1337-45.

Mittler, E., et al., "Role of the transmembrane domain of marburg virus surface protein GP in assembly of the viral envelope.", J Virol., 81(8), (Apr. 2007), 3942-8.

Mühlberger, E., et al., "Comparision orf the Transcription and Replication Strategies of Marburg Virus and Ebola Virus by Using Artificial Replication Systems", Journal of Virology, 73(3), (1999), 2333-2342.

Shimojima, M., et al., "Tyro3 family-mediated cell entry of Ebola and Marburg viruses", J Virol., 80(20), (Oct. 2006), 10109-16.

Takada, A., et al., "Downregulation of beta1 integrins by Ebola virus glycoprotein: implication for virus entry", Virology, 278(1), (Dec. 2000), Abstract Only.

Via, L. E, et al., "Isolation of restriction fragments from large plasmids recovered from bacteria with multiple plasmids", Biotechniques, 11(4), (Oct. 1991), Abstract Only.

Volchkov, Viktor E, et al., "Recovery of Infectious Ebola Virus from Complementary DNA: RNA Editing of the GP Gene and Viral Cytotoxicity", Science Magazine, 291, (Mar. 2001), 1965-1969.

Watanabe, S., et al., "Production of Novel Ebola Virus-Like Particles from cDNAs: an Alternative to Ebola Virus Generation by Reverse Genetics", Journal of Virology, 78(2), (Jan. 2004), 999-1005.

Wiedmer, T., et al., "Identification of three new members of the phospholipid scramblase gene family", Biochim Biophys Acta, 1467(1), (Jul. 31, 2000), Abstract Only.

Yang, Z. Y, et al., "Identification of the Ebola virus glycoprotein as the main viral determinant of vascular cell cytotoxicity and injury", Nat Med., 6(8), (Aug. 2000), Abstract Only.

Zhang, V. Q, et al., "Easy two-step method for randomizing and cloning gene fragments", Methods Mol Biol., 634, (2010), Abstract Only.

"U.S. Appl. No. 11/654,863, Final Office Action mailed Jul. 11, 2013", 9 pgs.

"U.S. Appl. No. 11/654,863, Pre-Appeal Brief Request for Review filed Nov. 11, 2013", 5 pgs.

"U.S. Appl. No. 11/654,863, Response filed Jun. 7, 2013 to Non Final Office Action mailed Feb. 11, 2013", 10 pgs.

\* cited by examiner

| PLASMID | SCHEMATIC DIAGRAM | EBOLA VIRAL RNA SYMTHESIZED | VIRUS TITERS IN THE SUPERNATANT OF CELLS TRANSFECTED WITH PLASMIDS (TCID$_{50}$/ml) |
|---|---|---|---|
| pTM-Rib-Ebo-GT7 | [T7｜G｜EBOLA(reversed)｜RIB] | vRNA | $10^2$ |
| pTM-T7G-Ebo-Rib | [T7｜G｜EBOLA｜RIB] | cRNA | $10^2$ |

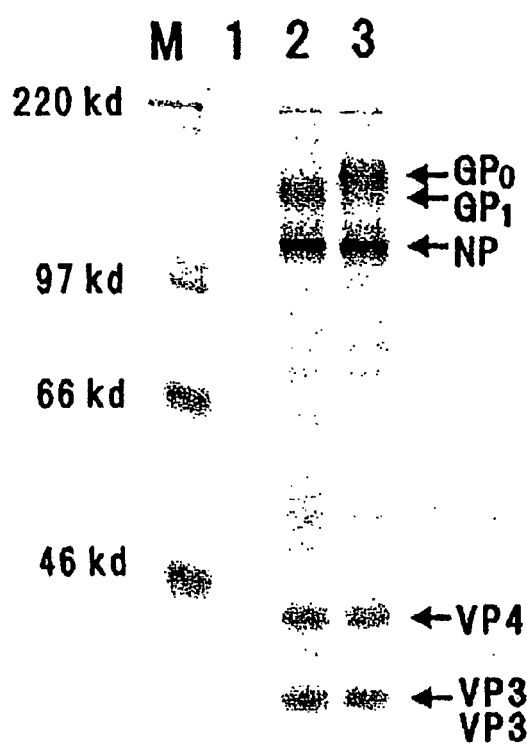
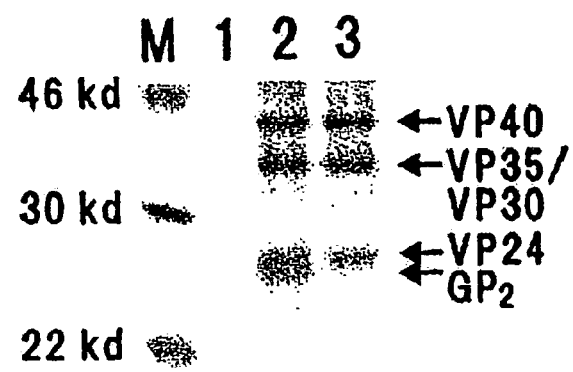
FIG. 4A
FIG. 4B

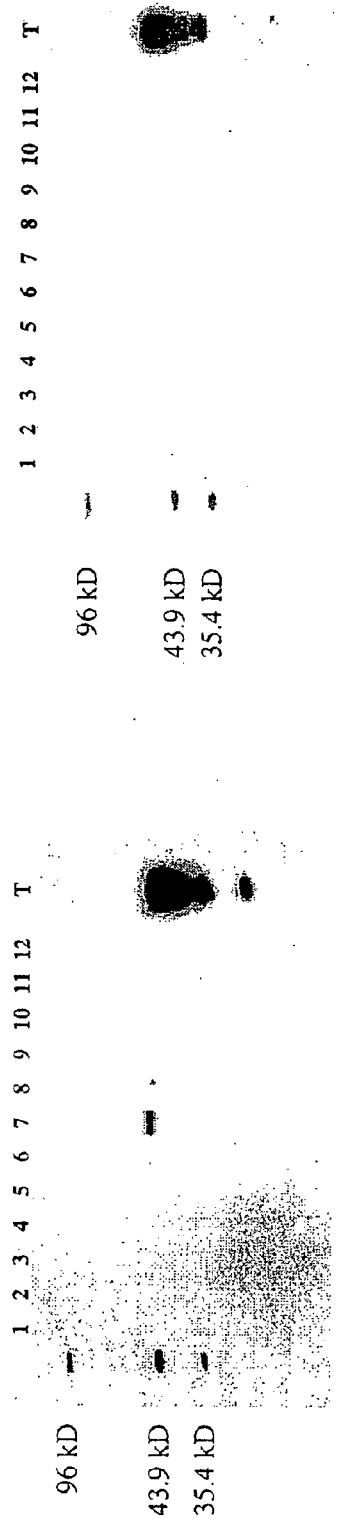
FIG. 7A  FIG. 7B  FIG. 7C  FIG. 7D

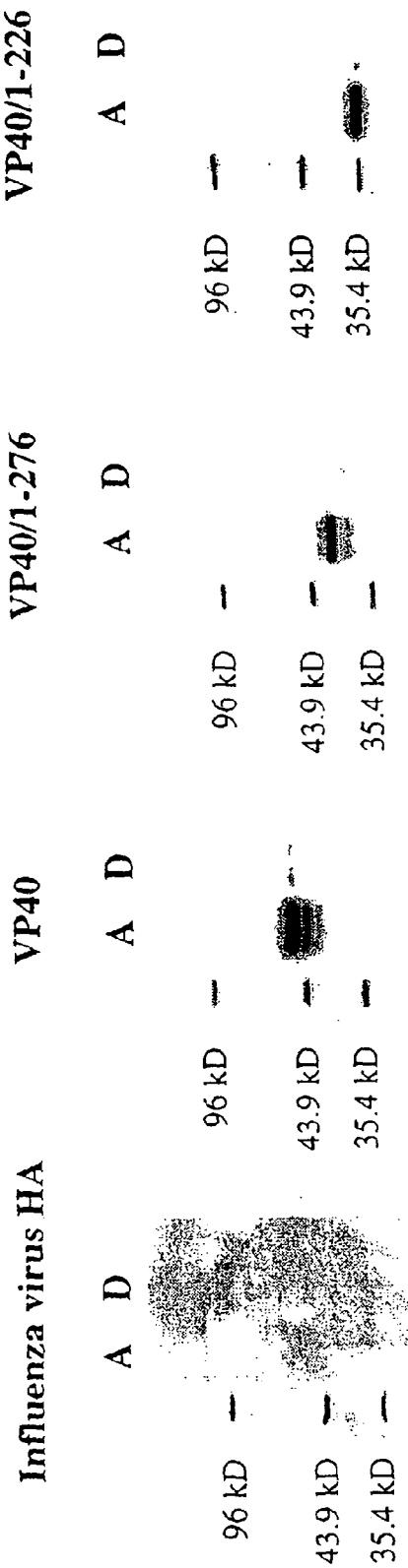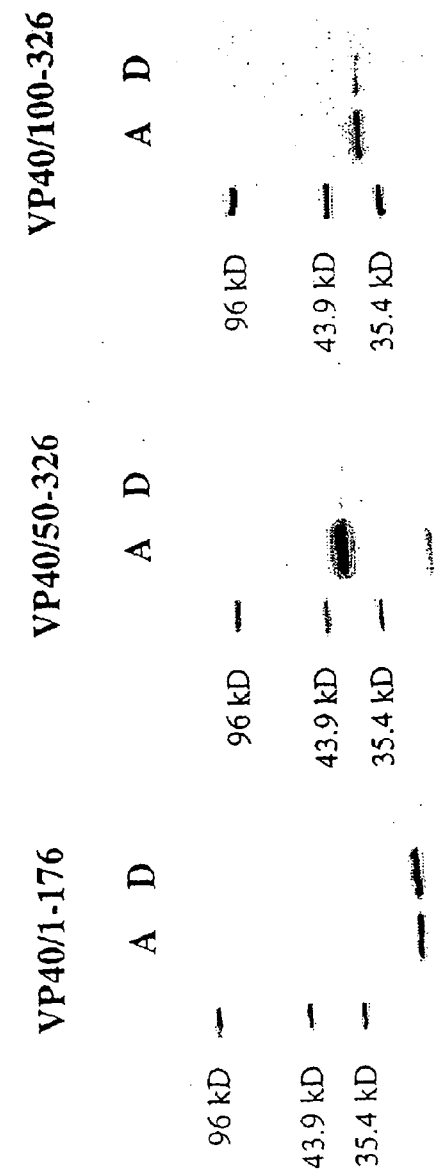

A

B

AB050936 Reston Ebola virus genomic RNA, complete genome, 18890 bp, RNA, linear.

| | |
|---|---|
| 5'UTR | 1 – 53, putative leader region |
| gene | 54 - 3011, NP |
| mRNA | 54 – 3011, NP |
| misc signal | 54 – 65, transcription start signal for NP |
| CDS | 462 – 2681, NP, encapsidation of genomic RNA |

MDRGTRRIWVSQNQGDTDLDYHKILTAGLTVQQGIVRQKIISVYLVDNLEAMCQLVIQAFEAGIDF
QENADSFLLMLCLHHAYQGDYKLFLESNAVQYLEGHGFKFELRKKDGVNRLEELLPAATSGKNI
RRTLAALPEEETTEANAGQFLSFASLFLPKLVVGEKACLEKVQRQIQVHAEQGLIQYPTAWQSVG
HMMVIFRLMRTNFLIKYLLIHQGMHMVAGHDANDAVIANSVAQARFSGLLIVKTVLDHILQKTDQG
VRLHPLARTAKVRNEVNAFKAALSSLAKHGEYAPFARLLNLSGVNNLEHGLYPQLSAIALGVATA
HGSTLAGVNVGEQYQQLREAATEAEKQLQQYAESRELDSLGLDDQERRILMNFHQKKNEISFQ
QTNAMVTLRKERLAKLTEAITLASRPNLGSRQDDDNEIPFPGPISNNPDQDHLEDDPRDSRDTIIP
NSAIDPEDGDFENYNGYHDDEVGTAGDLVLFDLDDHEDDNKAFELQDSSPQSQREIERERLIHP
PPGNNKDDNRASDNNQQSADSEEQEGQYNRHRGPERTTANRRLSPVHEEDTPIDQGDDDPSS
PPPLESDDDDASSSQQDPDYTAVAPPAPVYRSAEAHEPPHKSSNEPAETSQLNEDPDIGQSKS
MQKLGETYHHLLRTQGPFEAINYYHMMKDEPVIFSTDDGKEYTYPDSLEEAYPPWLTEKERLDN
ENRYIYINNQQFFWPVMSPRDKFLAILQHHQ (SEQ ID NO:1)

| | |
|---|---|
| polyA signal | 3001 – 3011, NP |
| misc feature | 3012 – 3016, intergenic region |
| gene | 3017 – 4411, VP35 |
| mRNA | 3017 – 4411, VP35 |
| misc signal | 3017 – 3028, transcription start signal for VP35 |
| CDS | 3153 – 4142, VP35, polymerase complex protein |

MYNDKLKICSGPETTGWISEQLMTGKIPVTDIFIDIDNKPDQMEVRLKPSSRSSTRTCTSSSQTEV
NYVPLLKKVEDTLTMLVSATSRQNAAIEALENRLSTLESSLKPIQDMGKVISSLNRSCAEMVAKYD
LLVMTTGRATSTAAAVDAYWKEHKQPPPGPALYEENALKGKIDDPNSYVPDAVQEAYKNLDSTS
TLTEENFGKPYISAKDLKEIMYDHLPGFGTAFHQLVQVICKIGKDNNLLDTIHAEFQASLADGDSP
QCALIQITKRVPIFQDVPPPTIHIRSRGDIPRACQKSLRPAPPSPKIDRGWVCLFKMQDGKTLGLKI
(SEQ ID NO:2)

| | |
|---|---|
| gene | 4394 – 5891, VP40 |
| mRNA | 4394 – 5891, VP40 |

FIG. 18A misc signal    4394 – 4405, transcription start signal for VP40
polyA_signal   4401 – 4411, VP35
CDS            4483 – 5478, VP40, matrix protein MRRGVLPTAPPAYNDIAYSMSILPTRPSVIVNETKSDVLAVPGADVPSNSMRPVADDNIDHSSHT
PSGVASAFILEAKVNVISGTKVLMKQIPIWLPLGVADQKIYSFDSTTAAIMLASYTVTHFGKISNPLV
RVNRLGPGIPDHPLRLLRLGNQAFLQEFVLPPVQLPQYFTFDLTALKLITQPLPAATWTDETPAGA
VNALRPGLSLHPKLRPILLPGKIGKKGHASDLTSPDKIQTIMNAIPDLKIVPIDPIKNIVGIEVPELLVQ
RLTGKKPQPKNGQPIIPVLLPKYVGLDPISPGDLTMVITQDCDSCHSPASHPYHMDKQDSYQ
(SEQ ID NO:3)

polyA signal   5881 – 5891, VP40
misc feature   5892 – 5898, intergenic region
gene           5899 – 8254, GP
mRNA           5899 – 8254, sGP
misc signal    5899 – 5910, transcription start signal for GP
CDS            6040 – 8072, GP, receptor binding and fusion, additional A residue is inserted
during transcription, encodes two disulfide linked subunits GP1 and GP2

MGSGYQLLQLPRERFRKTSFLVWVIILFQRAISMPLGIVTNSTLKATEIDQLVCRDKLSSTSQLKSV
GLNLEGNGIATDVPSATKRWGFRSGVPPKVVSYEAGEWAENCYNLEIKKSDGSECLPLPPDGV
RGFPRCRYVHKVQGTGPCPGDLAFHKNGAFFLYDRLASTVIYRGTTFAEGVIAFLILSEPKKHFW
KATPAHEPVNTTDDSTSYYMTLTLSYEMSNFGGEESNTLFKVDNHTYVQLDRPHTPQFLVQLNE
TLRRNNRLSNSTGRLTWTVDPKIEPDVGEWAFWETKKNFSQQLHGENLHFQILSTHTNNSSDQ
SPAGTVQGKISYHPPTNNSELVPTDSPPVVSVLTAGRTEEMSTQGLTNGETITGFTANPMTTTIA
PSPTMTSEVDNNVPSEQPNNTASIEDSPPSASNETIDHSEMNSIQGSNNSAQSPQTKATPAPTA
SPMTLDPQETANISKPGTSPGSAAGPSQPGLTINTISKVADSLSPTRKQKRSVRQNTANKCNPDL
HYWTAVDEGAAAGLAWIPYFGPAAEGIYIEGVMHNQNGLICGLRQLANETTQALQLFLRATTELR
TYSLLNRKAIDFLLQRWGGTCRILGPSCCIEPHDWTKNITDEINQIKHDFIDNPLPDHGDDLNLWT
GWRQWIPAGIGIIGVIIAIIALLCICKILC (SEQ ID NO:4)

CDS            6040 – 7143, GP, small non-structural, secreted glycoprotein; sGP; secreted as a
anti-parallel oriented homodimer MGSGYQLLQLPRERFRKTSFLVWVIILFQRAISMPLGIVTNSTLKATEIDQLVCRDKLSSTSQLKSV
GLNLEGNGIATDVPSATKRWGFRSGVPPKVVSYEAGEWAENCYNLEIKKSDGSECLPLPPDGV
RGFPRCRYVHKVQGTGPCPGDLAFHKNGAFFLYDRLASTVIYRGTTFAEGVIAFLILSEPKKHFW

FIG. 18B

KATPAHEPVNTTQDSTSYYMTLTLSYEMSNFGGEESNTLFKVDNHTYVQLDRPHTPQFLVQLNE
TLRRNNRLSNSTGRLTWTVDPKIEPDVGEWAFWETKKTFPNNFMEKTCISKFYQPTPTTPQIRA
RRELSKEKLATTHPPTTPSWFQRIPLQWFQCSLQDGQRKCRPKV (SEQ ID NO:5)

| | | |
|---|---|---|
| misc feature | 6922 – 6928, | GP, additional A residues are inserted or deleted during transcription of the GP gene by the viral polymerase |
| misc feature | 7794 – 7871, | GP, immunosuppressive motif |
| misc feature | 7992 – 8056, | GP, transmembrane anchor; transmembrane-region site |
| polyA signal | 8244 – 8254, | GP |
| misc feature | 8255 – 8259, | intergenic region |
| gene | 8260 – 9699, | VP30 |
| mRNA | 8260 – 9699, | VP30 |
| misc signal | 8260 – 8271, | transcription start signal for VP30 |
| CDS | 8488 – 9351, | VP30, minor nucleoprotein |

MEHSRERGRSSNMRHNSREPYENPSRSRSLSRDPNQVDRRQPRSASQIRVPNLFHRKKTDALI
VPPAPKDICPTLKKGFLCDSKFCKKDHQLDSLNDHELLLLIARRTCGIIESNSQITSPKDMRLANPT
AEDFSQGNSPKLTLAVLLQIAEHWATRDLRQIEDSKLRALLTLCAVLTRKFSKSQLGLLCETHLRH
EGLGQDQADSVLEVYQRLHSDKGGNFEAALWQQWDRQSLIMFISAFLNIALQTPCESSSVVVSG
LATLYPAQDNSTPSEATNDTTWSSTVE (SEQ ID NO:6)

| | | |
|---|---|---|
| polyA signal | 9688 – 9699, | VP30 |
| misc feature | 9700 – 9829, | intergenic region |
| gene | 9830 – 11479, | VP24 |
| mRNA | 9830 – 11479, | VP24 |
| misc signal | 9830 – 9841, | transcription start signal for VP24 |
| CDS | 10301 – 11056, | VP24, membrane-associated protein |

MAKATGRYNLVPPKKDMEKGVIFSDLCNFLITQTLQGWKVYWAGIEFDVSQKGMALLTRLKTND
FAPAWAMTRNLFPHLFQNPNSVIQSPIWALRVILAAGLQDQLLDHSLVEPLTGALGLISDWLLTTT
STHFNLRTRSVKDQLSLRMLSLIRSNILQFINKLDALHVVNYNGLLSSIEIGTSTHTIIITRTNMGFLV
EVQEPDKSAMNSKRPGPVKFSLLHESAFKPFTRVPQSGMQSLIMEFNSLLAI (SEQ ID NO:7)

| | | |
|---|---|---|
| gene | 11462 – 18864, | L |
| mRNA | 11462 – 18864, | L |
| misc signal | 11462 – 11473, | transcription start signal for L |
| polyA signal | 11469 – 11479, | VP24 |

FIG. 18C

CDS     11548 - 18186, L, synthesis of viral RNAs; transcriptional RNA edition

MATQHTQYPDARLSSPIVLDQCDLVTRACGLYSSYSLNPQLRQCKLPKHIYRLKFDTIVSKFLSDT
PVATLPIDYLVPILLRSLTGHGDRPLTPTCNQFLDGIINYTLHDAAFLDYYLKATGAQDHLTNITTRE
KLKNEILNNDYVHQLFFWHDLSILARRGRLNRGNNRSTWFVHDEFIDILGYGDYIFWKIPLSLLPV
TIDGVPHAATDWYQPTLFKESILGHSQILSVSTAEILIMCKDIITCRFNTSLIASIAKLEDVDVSDYPD
PSDILKIYNAGDYVISILGSEGYKIIKYLEPLCLAKIQLCSKFTERKGRFLTQMHLSVINDLRELISNR
RLKDYQQEKIRDFHKILLQLQLSPQQFCELFSVQKHWGHPILHSEKAIQKVKRHATILKALRPNVIF
ETYCVFKYNIAKHYFDSQGTWYSVISDRNLTPGLNSFIKRNHFPSLPMIKDLLWEFYHLNHPPLFS
TKVISDLSIFIKDRATAVEQTCWDAVFEPNVLGYNPPNKFSTKRVPEQFLEQEDFSIESVLNYAQE
LHYLLPQNRNFSFSLKEKELNIGRTFGKLPYLTRNVQTLCEALLADGLAKAFPSNMMVVTEREQK
ESLLHQASWHHTSDDFGENATVRGSSFVTDLEKYNLAFRYEFTAPFIEYCNHCYGVRNVFNWM
HYLIPQCYMHVSDYYNPPHNVNLSNREYPPEGPSSYRGHLGGIEGLQQKLWTSISCAQISLVEIK
TGFKLRSAVMGDNQCITVLSVFPLETDPEEQEQSAEDNAARVAASLAKVTSACGIFLKPEETFVH
SGFIYFGKKQYLNGVQLPQSLKTAARMAPLSDAIFDDLQGTLASIGTAFERAISETRHILPCRIVAA
FHTYFAVRILQYHHLGFNKGIDLGQLSLSKPLDYGTITLTLAVPQVLGGLSFLNPEKCFYRNFGDP
VTSGLFQLRVYLEMVNMKDLFYPLISKNPGNCSAIDFVLNPSGLNVPGSQDLTSFLRQIVRRSITL
TARNKLINTLFHASADLEDEMVCKWLLSSNPVMSRFAADIFSRTPSGKRLQILGYLEGTRTLLASK
IINNNSETPVLDKLRKITLQRWNLWFSYLDHCDQLLADALQKISCTVDLAQILREYTWSHILEGRPL
IGATLPCMVEQFKVKWLRQYEPCPECLNKKGSNAYVSVAVKDQVVSAWPNTSRISWTIGSGVP
YIGSRTEDKIGQPAIKPRCPSSALKEAIELASRLTWVTQGSSNSEQLIRPFLEARVNLSVSEVLQM
TPSHYSGNIVHRYNDQYSPHSFMANRMSNTATRLIVSTNTLGEFSGGGQAARDSNIIFQNVINLA
VALYDIRFRNTNTSDIRHNRAHLHLTECCTKEVPAQYLTYTSALNLDLSRYRDNELIYDSNPLRGG
LNCNLTMDSPLVKGPRLNMIEDDLLRFPHLSGWELAKTVVQSIISDNSNSSTDPISSGETRSFTTH
FLTYPQIGLLYSFGAVLCFYLGNTILWTKKLDYEQFLYYLHNQLHNLPHRALRVFKPTFKHASVMS
RLMEIDSNFSIYIGGTSGDRGLSDAARLFLRTAIASFLQFLKSWIIDRQKAIPLWIVYPLEGQQPESI
NEFLHKIFGLLKQGPKNIPKEVSIQNDGHLDLAENNYVYNSKSTASNFFHASLAYWRSRKSRKTQ
DHNDFSRGDGTLTEPVCKFSSNHQSDEKYYNVTCGKSPKPQERKDFSQYRLSNNGQTMSNHR
KKGKFHKWNPCKVLMESQRGTVLKEGDYFQNNTPPTDDVSSPHRLILPFFKLGNHNHAHDQDA
QELINQNIKQYLHQLRSMLDTTIYCRFTGIVSSMHYKLDEVLLEYNSFDSAITLAEGEGSGALLLLQ
KYSTRLLFLNTLATEHSIESEVVSGFSTPRMLLPIMQKVHEGQVTVILNNSASQITDITSSMWLSN
QKYNLPCQVEIITMDAETTENLNRSQLYRAVYNLILDHIDPQYLKVVVLKVFLSDIEGILWINDYLAP
LFGAGYLIKPITSSARSSEWYLCLSNLISTNRRSAHQTHKACLGVIRDALQAQVQRGVYWLSHIA
QYATKNLHCEYICLGFPPLEKVLYHRYNLVDTGLGPLSSVIRHLTNLQAEIRDLVLDYTLMRESRT
QTYHFIKTAKGRITKLVNDFLKFSLIVQALKNNSSWYTELKKLPEVINVCNRFYHTHSCECQEKFF
VQTLYLQRLRDAEIKLIERLTGLMRFYPEGLIYSNHT (SEQ ID NO:8)

FIG. 18D polyA signal   18854 – 18864 for L

3'UTR          18865 – 18890, trailer region 1 gggacacaca aaagaaaaag gtttttaag attttttgtg tgcgagtaac tatgaggaag
   61 attaacagtt ttcctcagtt taaggtatac actgaaattg agattgagat tctcctcttt
  121 gctattctgt aactttccct ggttgtgaca attgaatcag ttttatctat taccaattac
  181 catcaacatg gtatgtctag tgatcttggg actcttcttc atctggtttt tcctagagct
  241 ctgaatctat tttgtgagaa gttcatccaa acgacccagt gtctgaaaat acaagaggtt
  301 cccctttccg tcaagtttaa ggggttgttt tgattgtgtg tagattttat aatcctagag
  361 tgccaaggag ttgcgtgtca tcattaattg ggaagatcaa ggaaacaatt tgttccaata
  421 atatcgtaca tcttgactaa gtcgaacaag gggaagtcga tatggatcgt gggaccagaa
  481 gaatctgggt gtcgcaaaat caaggtgata ctgatttaga ttatcataaa attttgacag
  541 ctggccttac tgttcaacag ggaattgtca ggcagaaaat aatttctgta tatcttgttg
  601 ataacttgga ggctatgtgt caattggtaa tacaagcctt tgaggccgga attgatttcc
  661 aagaaaatgc cgacagcttc cttctgatgc tttgcctaca tcatgcttac caaggtgact
  721 ataaattgtt cttggagagc aatgctgtac agtatttgga aggtcatgga ttcaaatttg
  781 agctccggaa gaaggacggt gtcaatcggc tcgaggaatt gcttcctgct gcaacgagtg
  841 gaaaaaacat caggcgtacg ttggccgcac tgcctgaaga ggagactaca gaagcaaatg
  901 cagggcaatt tctctcattt gcgagtttgt ttcttcccaa actggttgtg ggagagaagg
  961 cttgcttgga aaaagtccag cgacaaattc aggttcatgc agaacagggt ttaattcaat
 1021 atcccactgc atggcaatca gttggacaca tgatggtaat cttcagattg atgaggacta
 1081 atttcttgat taaatattta ctgatccacc agggtatgca tatggtagct ggccacgatg
 1141 ccaatgatgc tgtcattgct aattcagttg ctcaggctcg ctttttcagga ctcctaattg
 1201 tcaaaaccgt tcttgatcat attctgcaga aaaccgacca aggagtaaga cttcacccct
 1261 tggcccgaac agccaaagtg cgtaatgagg ttaatgcatt taaggccgcc ctaagctcac
 1321 ttgctaagca tgggagtat gccccttttg ctcgccttct caatctctcg ggagttaaca
 1381 acctagaaca tggtctctac ccacagttat cagcaattgc tcttggagtt gccacagcac
 1441 atggtagcac ccttgcagga gttaatgttg gtgagcagta tcagcagctt agagaggctg
 1501 ccactgaagc tgagaagcaa ctccaacaat atgctgagtc cagagaactc gacagcctag
 1561 gcctagacga tcaggaaaga agaatactaa tgaacttcca tcagaagaaa aatgaaatta
 1621 gtttccagca gaccaatgca atggtaaccc ttaggaaaga gcgactggct aaattaacag
 1681 aagctataac gctggcctca agacctaacc tcgggtctag acaagacgac gacaatgaaa
 1741 taccgttccc tgggcctata agcaacaacc cagaccaaga tcatctggag gatgatccta
 1801 gagactccag agacactatc attcctaata gtgcaattga ccccgaggat ggtgatttg
 1861 aaaattacaa tggctatcat gatgatgaag ttgggacggc aggtgacttg gtcttgttcg
 1921 atcttgacga tcatgaggat gacaataaag ctttgagct acaggacagc tcaccacaat
 1981 cccaagggga aatagagaga gaaagattaa ttcatccacc cccaggcaac aacaaggacg
 2041 acaatcgggc ctcagacaac aatcaacaat cagcagattc tgaggaacaa gaaggtcaat

FIG. 18E 2101 acaacaggca ccgaggccca gaacgtacga ccgccaatcg aagactctca ccagtgcacg
2161 aagaggacac ccctatagat caaggcgatg atgatccctc aagcccacct ccgctggaat
2221 ctgatgatga cgatgcatca agtagccaac aagatcccga ttatacagct gttgcccctc
2281 ctgctcctgt ataccgcagt gcagaagccc acgagcctcc ccacaaatcc tcgaacgagc
2341 cagctgaaac atcacaattg aatgaagacc ctgatatcgg tcaatcaaag tctatgcaaa
2401 aattaggaga gacatatcac catctgctga gaactcaagg tccatttgaa gctatcaatt
2461 attatcacat gatgaaggat gagccggtaa tatttagcac tgatgatggg aaggaataca
2521 cctacccgga ttcacttgag gaagcctatc ctccatggct caccgagaaa gaacgactgg
2581 acaatgaaaa tcgatacatt tacataaata atcaacagtt cttctggcct gtcatgagtc
2641 ccagagacaa atttcttgca atcttgcagc accatcagta accacagcac aaagcgcggt
2701 ccacttcgta aagctaaata cacttaaagc ttgaccgatt catctacaaa aactaatcca
2761 ttataactta ttagtgctac ttttctataa gtgattctca atctaaggcc attaagagtt
2821 taagcaatat acatatacac ttacaccggt ctatccaaga tgtggctcaa tgttcttaat
2881 ttgaacatag tcataagggg ataaataata ctttatattt ctgattgtgg actgacccat
2941 tctgcttaaa atgcttcgcc cattaaaaat gtgatctaat agatagccct gactagacca
3001 attaagaaaa acatttgatg aagattaaaa ccttcatcgc cagtaaatga ttatattgtc
3061 tgtaggcagg tgtttactcc accttaaagt cggaaatatc ctaccttagg accattgtta
3121 agaggtgcat aggcattacc atccttgaga acatgtataa tgataaattg aagatatgtt
3181 caggcccaga aacaactgga tggatttctg agcaactaat gacaggtaag attccagtaa
3241 ctgatatatt cattgatatt gataacaagc cagatcaaat ggaagtccgg ctcaaaccat
3301 catcaaggag ctcaaccaga acttgtacaa gtagcagtca gacggaggtc aactatgtac
3361 ctctccttaa aaaggttgag gatacattaa ctatgctagt gagtgcaacc agtcgtcaga
3421 atgctgcaat cgaggccctt gaaaaccgcc tcagcacact tgagagtagc ttaaagccaa
3481 tccaagacat gggtaaagtg atttcatcat tgaatcgcag ttgtgccgaa atggtggcaa
3541 aatatgatct tctagttatg acaactggac gggctacttc aaccgcagct gcagtagatg
3601 cgtactggaa agagcacaaa cagccaccac cagggccagc gttgtatgaa gagaatgcgc
3661 ttaaaggaaa aatcgatgat ccaaacagct atgtaccaga tgctgtgcag gaggcttaca
3721 agaaccttga cagtacatcg accctgaccg aggaaaattt tgggaaacct tatatatctg
3781 ctaaagatct gaaggagatc atgtatgatc atctacctgg ttttgggact gcctttcacc
3841 aacttgttca agtgatttgt aaaataggaa aggataacaa cctcttggac acaatccatg
3901 ctgagttcca ggcaagtcta gcagatggtg actctcccca atgtgcactc atacagataa
3961 ccaaaagagt cccaatcttt caggatgtgc cgcccccgac aatccacatt agatcccgtg
4021 gtgatatccc acgagcatgc caaaagagtc tccgaccagc accaccatca cccaaaattg
4081 atcgtggttg ggtttgtttg tttaagatgc aagatggtaa aacgcttgga cttaagatct
4141 aaggatcaag atttatttaa caaggcaagc cacaacctta gatagaacct cagccagact
4201 attgaactat tgacgctgtt gatgataata tataattaat ggtcatattt gaatatgaca
4261 acatcttgct tcttgttttg ccttgtatct ctttgagttg gaagatcatt ccaaacttac

FIG. 18F 4321 aaacatgcac aagatgttat ggtttagcaa agaattgata ggagtactgg tatataatgt
4381 aaatataaca agtgatgaag attaagaaaa accagtcggt attttccaga cttggcattt
4441 cttatcttca tcttctaaag tgagatattt tatcatcaaa aaatgagacg cggagtgtta
4501 ccaacggctc ctccagcata taatgatatt gcatactcta tgagcatact cccaacccga
4561 ccaagtgtca tagtcaatga gaccaaatca gatgtactgg cagtgccagg agcagatgtt
4621 ccatcaaact ccatgagacc agtggctgat gataacattg atcactcaag ccatactcca
4681 agcggagtag cttctgcctt tatattggaa gctaaagtga atgtaatttc gggaacaaaa
4741 gtcctgatga agcaaatacc tatttggctt ccactgggtg tagctgatca gaagatatac
4801 agctttgatt caacaacagc cgcaattatg ttggcttcct acacagtgac acacttcggg
4861 aagatatcta acccgctggt acgtgtcaac aggctaggcc caggaatacc cgatcatccg
4921 ctacgactcc taaggttggg caatcaggca ttccttcaag agtttgttct tccaccagtc
4981 cagcttcccc agtatttcac atttgatcta acagctctaa agctcatcac tcaaccattg
5041 ccagctgcaa cctggacaga cgaaactcca gcaggagcag tcaatgctct tcgtcctggg
5101 ctctcactcc atcccaagct tcgtccaatt cttctaccgg ggaagatagg aaagaaaggt
5161 catgcttcag acttaacatc acctgacaaa attcaaacaa tcatgaatgc aataccggac
5221 ctcaaaattg tcccgattga tccaatcaag aacatagttg gaattgaggt tccagaatta
5281 ctagttcaaa ggctgaccgg caaaaaacca caacccaaaa atggccaacc aattattcca
5341 gttcttcttc cgaaatatgt tggacttgat cctatatcgc caggggactt aactatggtt
5401 atcacccagg attgtgattc atgccactct ccagccagcc atccgtatca catggacaag
5461 caggatagtt accaataatt taaattccat tcgagctatt attctgctag taattccgac
5521 gggatcaata gactaaaaat ctgattgtat agaattataa aagaatcaag cagaggcaac
5581 agactcacag cttacgccta gatgactaat attaaggagt ttttaatct aattttccag
5641 tcttaagtaa taatcatttc ttttgtaatt aattatgcat ttgttaactt atcggtgcga
5701 gatttccttg agaacccggc ggggcttcta ctatctgtag taaccagaag agaagttcaa
5761 cccagtcaaa actaaaccaa gcaatattct gaatgctcta tagtctattc taatcagagg
5821 tataacaatg gctaagattt caatgactcg ttaacaatcg ctagtaattt taatctccag
5881 attaagaaaa agatatacga tgaagattaa ggcgacaacg agccgaaact tcatctcttt
5941 taaagatcta acattatctg ttccaaagtc atacaaggac acattcaaat cagggattgt
6001 aagctgctat ttcttacctc cccaaatcac ctatacaaca tggggtcagg atatcaactt
6061 ctccaattgc ctcgggaacg ttttcgtaaa acttcgttct tagtatgggt aatcatcctc
6121 ttccagcgag caatctccat gccgcttggt atagtgacaa atagcactct caaagcaaca
6181 gaaattgatc aattggtttg tcgggacaaa ctgtcatcaa ccagtcagct caagtctgtg
6241 gggctgaatc tggaaggaaa tggaattgca accgatgtcc catcagcaac aaaacgctgg
6301 ggattccgtt caggtgtgcc tcccaaggtg gtcagctatg aagccggaga atgggcagaa
6361 aattgctaca atctggagat caaaaagtca gacggaagtg agtgcctccc tctccctccc
6421 gacggtgtac ggggattccc tagatgtcgc tatgtccaca aagttcaagg aacaggtcct
6481 tgtcccggtg acttagcttt ccataaaaat ggggcttttt tcttgtatga tagattggcc

FIG. 18G 6541 tcaactgtca tctaccgtgg gacaactttt gctgaaggtg tcatagcttt tttaattctg 6601 tcagagccca agaagcattt ttggaaggct acaccagctc atgaaccggt gaacacaaca 6661 gatgattcca caagctacta catgaccctg acactcagct acgagatgtc aaattttgga 6721 ggcgaggaaa gtaacaccct ttttaaggta gacaaccaca catatgtgca actagatcgt 6781 ccacacactc cgcagttcct tgttcagctc aatgaaacac ttcgaagaaa taatcgcctt 6841 agcaacagta cagggagatt gacttggaca gtggatccca aaattgaacc agatgttggt 6901 gagtgggcct tctgggaaac taaaaaaact tttcccaaca acttcatgga gaaaacttgc 6961 atttccaaat tctatcaacc cacaccaaca actcctcaga tcagagcccg gcgggaactg 7021 tccaaggaaa aattagctac cacccaccca ccaacaactc cgagctggtt ccaacggatt 7081 cccctccagt ggtttcagtg ctcactgcag gacggacaga ggaaatgtcg acccaaggtc 7141 taactaacgg agagacaatc acaggtttca ccgcgaaccc aatgacaacc accattgccc 7201 caagtccaac catgacaagc gaggttgata acaatgtacc aagtgaacaa ccgaacaaca 7261 cagcatccat tgaagactcc cccccatcgg caagcaacga gacaattgac cactccgaaa 7321 tgaattcgat ccaaggctcg aacaactccg cccagagccc acagaccaag gccacgccag 7381 cgcccacagc atccccgatg accctggacc cgcaagagac ggccaacatc agcaaaccag 7441 gaaccagccc aggaagcgca gccggaccaa gtcagcccgg actcactata aatacaataa 7501 gtaaggtagc tgattcactg agtcccacca ggaaacaaaa gcgatcggtt cgacaaaaca 7561 ccgctaataa atgtaaccca gatcttcact attggacagc tgttgatgag ggggcagcag 7621 caggattggc atggattcca tattttggac ctgcagcaga aggcatctac attgagggtg 7681 taatgcataa tcagaatggg cttatttgcg ggctacgtca gctagccaat gaaactaccc 7741 aggctcttca attattctg cgggccacaa cagaactgag gacttactca cttcttaaca 7801 gaaaagctat tgattttctt cttcaacgat ggggaggtac ctgtcgaatc ctaggaccat 7861 cttgttgcat tgagccacat gattggacaa aaaatattac tgatgaaatt aaccaaatta 7921 aacatgactt tattgacaat cccctaccag accacggaga tgatcttaat ctatggacag 7981 gttggagaca atggatcccg gctggaattg ggattattgg agttataatt gctataatag 8041 ccctactttg tatatgtaag attttgtgtt gatttattct gagatctgag agaaaaaat 8101 ctcagggtta ctctaaggag aaatattatt ttaaaatttt acttaaatgc tgaccactta 8161 tcttaaatga gcaattaata atatgttttt ctgcttcttt gcttgattta caatatgata 8221 tttctcttaa taatgattaa tatattaaga aaaacttatg acgaagatta aaggggagga 8281 tcgttaacgg gaaaatctcc catctcgttc gtcgaagcca cgttggtggt gcttgcagct 8341 gagaacaact ccagagattg taggtagaaa ggaccagcat ttataggtag gggtcagaaa 8401 gcaacaatag ccataaaagg agagcctgac attgctattt aatatcctag aacctgattt 8461 ctaggttcta gttgtacaat ccggatgatg gagcattcaa gagaacgggg tagatctagc 8521 aacatgcgac ataatagccg ggaaccatac gaaaatccat caaggtctcg ctcattatct 8581 cgggaccctta atcaggttga tcgtaggcag cctcgaagtg catcccaaat tcgtgttccg 8641 aatctgttcc atcggaaaaa gactgatgca ctcatagttc ctccggctcc caaagatata 8701 tgcccaacac tcaaaaaagg attcctctgc gatagtaaat tttgcaaaaa agatcaccaa

FIG. 18H 8761 ttggatagct taaatgatca tgaattacta ctgctaattg caagaagaac atgtggaatt
8821 atcgagagca attcgcagat tacatcccca aaagatatgc ggttagcgaa tccaacagct
8881 gaagacttct cacaaggtaa tagtcctaaa ttaacacttg cagtccttct tcaaattgct
8941 gaacattggg caaccagaga cctaaggcaa attgaggact ctaaacttag agctctttta
9001 acccttgtg ccgtattaac aaggaaattt tctaaatccc aactgggtct tctatgtgag
9061 acccaccctac ggcatgaggg cctcggacag gaccaagctg attctgtatt agaggtctac
9121 caaagactcc acagtgataa aggagggaat tttgaggctg ccctgtggca acaatgggac
9181 cgacagtcgt taataatgtt catctctgct tttctcaaca ttgctctcca gacaccttgt
9241 gaaagttcta gtgtcgtagt ctcaggtctt gccacattgt acccagcaca agacaattct
9301 acaccgtccg aggcaactaa tgataccacc tggtcaagta cagttgaata gaaaaccact
9361 ggagctattt tccacgatt gctctcagtc aataaattaa tatagatata atacgacttc
9421 ggtgtgcaat tgtcaagggt tccatttggt aataatgatt cttaaaacaa tctactatcg
9481 taattatcga tggatctacc ctatttgacg gtacatgact tgaatgtaat aaggtaagtt
9541 ggtatctgag gtattttgtc tagagtatac tcaaaatcgt atgtctagca aattatcaat
9601 agcaaagtta aattctccta acctcatatt ttgatcaagt aatcatgatt ttatggtaat
9661 tctttgcaga ttatcggttt aatctttatt aagaaaaaat catgattgta gacaatttac
9721 tggtagtccc tgggtatcca agtttatgaa cagagctaga gagaatttgc tacttccgag
9781 gtataactt attatttgct acttcgaatg cctaaaacca gtaatgcagg atgaagatta
9841 attgcggagg aatcaggaat tcaactttag ttccttaagg cctcgtctga atcttcatca
9901 gttagtaagt tctttatag aagtcattag cttctaaggt gattatattt tagtattaaa
9961 ttttgttaat tgcttgctat aaagttgaaa tgtctaatgc ttaaatgaac atttctttga
10021 agctgacata cgaatacatc atatcatatg aaaacatcgc aattagagcg tccttgaagt
10081 ctgccattga cagtcaccag gctgttctca gtagtctgtc cttggaagct cttggggaga
10141 caagaagagg tcccagagag tcccaacagg ttggcataag gtcattaaca ccagcatagt
10201 cagctcgatc aagactgtaa gcgagtcgat tgcaactaaa aagattattt cttgttgttt
10261 aaacaaattc cttttgtgtg agacaccctc aaggcacaag atggctaaag ccacaggccg
10321 atacaatctc gtgccccaa agaaagatat ggaaaaggga gtgattttta gtgatctttg
10381 taatttcttg attactcaaa ccctgcaagg ttggaaggtt tattgggcag gaattgagtt
10441 tgatgtaagt caaaaaggca tggctcttct gacaagactc aaaacaaatg actttgctcc
10501 tgcctgggcg atgacaagaa atctcttccc acatctgttc caaaacccaa attcggttat
10561 tcaatctccc atctgggctt tgagggtgat tttggcagcc ggattgcagg atcagttgtt
10621 agaccattca ttggttgagc cattgacagg ggctctcggt ctaatttctg attggctcct
10681 aactacaacg tcaacacatt tcaatcttcg tactagaagc gtaaaggacc agcttagtct
10741 tcgtatgtta tctttgatca ggtcaaacat cttgcagttc atcaacaagc ttgacgccct
10801 gcatgttgtc aattacaatg gtttactcag tagtattgag atcgggactt ctacacacac
10861 aatcattata actcgtacaa atatgggttt tctcgtggaa gttcaggagc ctgacaaatc
10921 agctatgaat tctaagcgcc caggaccagt caagttctca ttacttcatg agtctgcctt

FIG. 18I 10981 caaaccttc actcgtgttc cacaatctgg gatgcaatca ttaataatgg agttcaacag 11041 tttgttggca atttaacaag gtgatcttaa aataagtaca tgaatgagaa ttagttgtgg 11101 gtcttaccta gcattgttga gttagctatc taatctattt tcactaattg cattgagcac 11161 tgctagtagg tttgcaccac gttaaagatt cagagtgtat gaattgtgca gatttaaact 11221 tgggttttgc cttatgcttc acaggtggtc tttttaaaat ggagattatc agcatttctt 11281 caatgggagg agttagcaat cagaaattgg agataaatgg acatcgggat agaacaatgc 11341 ctaactattg ggcggctttc attttttaaat gtgtatataa ccaatctttt cctatctttg 11401 cttatattgg tgtaaacttta ctttaataac atgtcaatgc tatactgtta agagaaggtc 11461 tgaggaagat taagaaaaag gtctcgtgtt cacttggttg ccgtcaagta tcctgtggtt 11521 tttttctacc taacttcctc atgccatatg gctacccagc atacccagta cccggatgca 11581 cgtttatctt cacctatagt cctggatcaa tgtgatttgg taactcgagc atgtgggtta 11641 tattcatctt attctctaaa tcctcagcta aggcaatgta aattaccaaa acatatatat 11701 cgacttaagt tcgacacaat agtatccaaa ttcctaagtg atacacctgt agcaacactg 11761 ccgatagact atttagtacc aattctcctg cgttccctaa cggggcacgg tgataggccg 11821 ttgaccccga cttgtaatca attccttgat ggaattatta attacactct tcatgatgca 11881 gcctttcttg attactatct caaggcaaca ggtgcacagg accatttgac aaacattaca 11941 actagagaga agcttaaaaa cgaaattcta aacaatgatt atgtccatca attgttcttc 12001 tggcatgacc tgtctatttt ggctcgacgt gggcgtctga atcgcgggaa caaccgttca 12061 acctggtttg ttcatgatga attcattgat attttaggat atggcgatta tattttttgg 12121 aaaataacctt tatcattatt accagttact atagacgggg tcccacacgc ggcaactgac 12181 tggtatcaac cgactctttt taaagaatcc atcctagggc acagccaaat cctatctgtg 12241 tcgacagctg aaatactaat tatgtgtaaa gatattatca cctgtaggtt taatacatca 12301 ctgattgcat ccattgcaaa attagaggat gtagatgtgt ctgattatcc tgacccgagt 12361 gatattctta agatatacaa tgctggagac tatgtaatat ctattccttgg ctcagaaggt 12421 tataagataa taaagtacct tgaaccactt tgtttggcca aaatccaact ttgctctaaa 12481 ttcacagaaa gaaaaggtcg tttcctcaca cagatgcatt tatcagtaat aaatgatctt 12541 cgggagttga tttctaaccg caggttaaag gactatcagc aagagaagat tagggatttt 12601 cacaaaatat tattacaatt gcaattatct cctcaacagt tttgtgaatt attctctgtt 12661 caaaaacatt gggggcatcc aattttacat agtgagaaag ctatacaaaa agtaaaacgg 12721 catgcaacca tccttaaggc tctcagacct aatgtcattt ttgagacata ttgtgtattc 12781 aagtacaata ttgccaagca ctattcgac agccaaggaa cttggtacag tgtaatctca 12841 gacaggaatt taactccagg actcaactcc ttcataaaac gtaatcactt tccttcacta 12901 cccatgatta aggatcttct atgggaattc tatcatctta atcaccctcc gttattctct 12961 acaaaggtga ttagtgactt aagtattttc atcaaggata gggccacagc tgttgaacag 13021 acatgttggg atgcagtctt tgaacccaat gtgctaggtt acaatcctcc aaacaaattc 13081 tccactaaaa gggtgccgga acaattcta gaacaggagg attttcaat cgaaagtgtc 13141 ctgaattatg cacaggaatt acattattta ttaccacaga ataggaattt ttccttttct

FIG. 18J 13201 cttaaagaaa aagaattaaa tattggacga acatttggta agctaccata tctcacacgg 13261 aatgtccaaa ctttatgtga ggctctgtta gcagatggac tggctaaggc cttccccagt 13321 aacatgatgg tagtaactga acgtgaacaa aaagagagcc ttcttcatca ggcatcatgg 13381 caccacacca gtgatgattt tggagagaat gctaccgttc gagggagtag ttttgtaact 13441 gatttagaga agtacaatct tgcatttcgc tatgagttca ctgcaccatt tattgagtac 13501 tgcaaccatt gctatggtgt gcgtaatgtc tttaattgga tgcattattt aatcccgcag 13561 tgttacatgc atgtaagtga ttattataat ccgcctcaca atgttaatct tagcaatcga 13621 gaatatcctc ctgaaggccc gagttcgtac cgagggcact taggaggcat agagggatta 13681 caacaaaaac tgtggacgag tatatcctgt gcacaaatct ccttagtgga aattaaaact 13741 ggttttaagt tacgatcagc ggtcatggga gacaatcagt gtataaccgt attgtctgtt 13801 tttccacttg aaacagaccc tgaagagcag gagcaaagcg ccgaagacaa tgctgcaaga 13861 gtagcagcaa gtcttgcaaa agtaaccagt gcatgtggga tctttcttaa accagaagag 13921 acattcgtac actcaggttt catttatttc ggaaaaaaac aatatctcaa tggtgtacaa 13981 ttaccgcaat cactcaaaac agcagcaaga atggcgccac tctctgatgc tatattcgat 14041 gatctacaag gaacacttgc cagtattgga actgccttcg aacgtgctat atcggaaacg 14101 cgacatatcc tcccatgtcg tattgtagca gctttccata cgtatttcgc cgttcggatt 14161 ttacaatatc accatcttgg atttaataaa ggcatcgatt tagggcagtt gtcacttagt 14221 aaaccattag actatgggac tattactcta acattggcgg ttccacaagt ccttggggga 14281 ttgtcttttc taaatccaga aaagtgtttt tatcgaaact tcggagatcc tgtgacttct 14341 ggacttttcc agctacgggt gtacctagaa atggttaaca tgaaagacct attttatcca 14401 ttaatatcga aaaatccagg aaattgtagt gccattgatt ttgtcttaaa tccatccgga 14461 ttaaatgttc caggatcaca agacttgaca tcctttttgc gacagatcgt taggcgtagt 14521 attacactaa ctgcaagaaa taagttaatt aacactctct tccatgcctc tgctgatttg 14581 gaagatgaga tggtttgtaa atggctcctt tcatcaaacc ctgtcatgag tcgctttgca 14641 gcggatattt tttccaggac acctagtggt aaacgtctcc aaatattagg ttatcttgaa 14701 gggaccagga ctctattggc ctccaaaatc ataaacaaca acagtgagac acctgtactt 14761 gataagctga ggaagatcac cctacaaaga tggaatctgt ggttcagtta tttggaccat 14821 tgtgaccaat tactagcaga tgctctacag aaaattagtt gcacggtgga tttggcccag 14881 attttgcgtg agtatacatg gtcacacatc ttagagggta gaccattgat cggagcgaca 14941 ttaccatgta tggtggagca attcaaagtt aagtggctaa gacaatatga accttgtcca 15001 gaatgcctca acaaaaaagg ctcaaatgct tatgtctcag ttgcagtcaa agatcaagtg 15061 gtcagtgctt ggcctaatac ttctcgaata agttggacaa tagggagtgg tgtcccctat 15121 atagggtcaa gaaccgagga taaaatcgga cagcctgcaa tcaagccgcg atgcccttca 15181 tctgccctca aggaggctat agaattagca tcaaggctca cttgggttac acaaggaagt 15241 tctaatagtg aacaattaat ccggcctttc ttagaagcga gagtcaacct tagtgtcagt 15301 gaagtcctgc aaatgacacc atcacattat tcaggaaata ttgtccatcg atataacgac 15361 caatatagcc cgcactcatt tatggcgaat cgcatgagca atactgcgac ccgtctcata

FIG. 18K 15421 gtgtcaacta atacacttgg agaattttca ggtggagggc aggccgccag ggatagcaat
15481 ataattttcc agaatgttat aaatttagca gttgcccttt atgatattag attccggaat
15541 acgaacacct ctgatataag gcataatagg gctcatcttc acctgacaga gtgctgtact
15601 aaagaggtcc cggcccagta tttgacatat acaagtgcac tcaatctgga tttaagccgt
15661 tatcgtgata atgaactaat atatgactca aatccactga ggggaggatt gaactgcaat
15721 ttaacaatgg atagtccttt agtgaagggt cctaggctta acatgattga agatgatctt
15781 ctccgctttc cacaccttc tggatgggag ttagcgaaaa cggtggtaca atccatcatc
15841 tcagacaata gcaactcatc aacagatcca atcagtagcg gagaaacacg ctctttcaca
15901 actcattttc tcacttaccc tcagattggc cttctttaca gtttcggggc agtattatgc
15961 ttttatctag gcaatactat cctatggact aaaaaacttg attatgaaca gtttctatat
16021 tatttgcata accagctgca caacttacct catcgagcac tccgtgtttt taaaccaaca
16081 tttaagcatg ccagtgtgat gtcccgatta atggaaattg attccaactt ctcaatttat
16141 attggcggga catctggaga tcgagggctg tctgatgctc ctcgactgtt tcttcggaca
16201 gcaatcgcga gttttttaca atttcttaaa agctggatca tcgatcgcca aaaggcaatt
16261 cctttatgga tagtatatcc gcttgaaggt caacagccgg aatccatcaa tgaatttcta
16321 cataaaattt tggtctgct caaacaaggc cccaaaaata ttccaaagga ggtcagcatt
16381 caaaatgatg gacatttgga tttggcagaa aataattatg tttacaatag taagagcact
16441 gctagtaatt tcttccatgc atccttagct tactggagaa gtaggaaatc tcggaaaact
16501 caagaccata atgatttctc aagaggggat ggaacactta cagaacccgt gtgtaagttc
16561 tcaagcaatc atcagtcaga tgaaaagtac tacaatgtga catgtggaaa gtcaccgaag
16621 ccgcaagaac gcaaagactt ctcgcaatac agactcagca ataacgggca aacaatgagt
16681 aatcatcgta agaaagggaa gttccacaag tggaatccct gcaaagtgtt aatggagagt
16741 caaagggaa ctgttctaaa agagggtgac tactttcaaa acaatactcc accaacagat
16801 gatgtatcaa gtcctcaccg actcattcta ccattttta aattgggaaa tcacaaccat
16861 gcacatgatc aagatgccca agaattgata aatcaaaata ttaaacagta cctacatcag
16921 ctaaggtcta tgttggacac cactatatat tgtagattca cagggattgt ctcatccatg
16981 cattacaaat tggacgaagt tcttctagaa tacaatagtt tcgattcagc tatcacatta
17041 gctgaaggtg aggggtcagg ggctctatta cttttgcaga aatataglac aaggttatta
17101 ttttgaaca cattggcaac agaacacagt atagagtcag aagttgtatc aggtttttct
17161 actccgagaa tgttgttacc aataatgcaa aaggttcatg aaggacaagt cactgttatc
17221 ttaaataatt cagcaagtca gataactgac ataactagct caatgtggtt aagtaatcaa
17281 aaatataatc taccttgtca agttgaaatc attacgatgg atgctgaaac aacagagaac
17341 ttaaacaggt cccaactcta ccgagcagta taaacttaa tacttgatca cattgatccg
17401 cagtatctca aggtggtggt actcaaagta tttctgagtg atatagaagg aatatatatgg
17461 attaatgatt acttggctcc attattcggg gctggttact tgattaaacc gattacatca
17521 agtgcccggt caagtgaatg gtacctttgc ttatcaaatt tgatatctac taacaggaga
17581 tcggcccatc agactcacaa ggcatgtctt ggtgttatca gagatgcttt gcaagcacaa 17641 gtccagcgag gcgtgtactg gttgagtcac atcgcacagt atgctacaaa gaatctccat
17701 tgtgaataca tatgccttgg tttcccacct ctagaaaagg tcctatatca caggtataat
17761 ctagttgata ctggactcgg tccattgtcg tcagttatta gacatttaac taacctccag
17821 gcagagatac gagacttagt attagattat accctgatga gagagagtcg cactcaaacg
17881 taccatttta ttaagactgc aaaaggcaga atcacaaagt tagtcaatga ctttctgaag
17941 ttttctttaa ttgtccaggc actcaaaaat aattcttctt ggtatactga gcttaaaaaa
18001 ttacctgagg tgattaatgt gtgtaatcga ttttatcata ctcacagttg cgaatgtcag
18061 gaaaaattct ttgtccagac gctttattta caacgcctac gcgatgcaga aatcaagcta
18121 attgaacgcc ttaccgggtt aatgcgattt tatccagaag ggttaatata ttccaatcac
18181 acataggtac taaatcatca tagtatgagg aataaaataa tgataattcc tgacgacagt
18241 tttagttccg attctaagta tatcggaaga gagtatgcca atcttaatta ttaaaggtaa
18301 caagctatta gttattactt attgataaga ataaactta tcatagcgta acacatcata
18361 actttatagc gattttgcat ttctaatcct agtatttatt agaatgtact atcagagaaa
18421 tgaccccagt tcctatcttt aaataatgat tgtgtgtatt aaattattag tttattaggt
18481 ttatgagttg gttacacagt gagtattagt aattgaggat tatgtagata ggtaatctaa
18541 cactgaatca cccatctgat gtcaccatat ccaaatattg tgctagtcgc atttaaacat
18601 gctatcttca gttaagtaac atagactgaa aatgctaaga agagattgga gtaaaagtat
18661 aaaataaatt taattaaact tcaaagtgat taaatgataa tgatcttggg aactcgatat
18721 gacctcaagt caaaaataat gtcaatataa ttgtttagta atatgagtta taatgtgaat
18781 tttgataact aactagcttt agtagttaag atcaaatgca aacattctaa gaatgttaag
18841 cgcacacaaa aacattataa aaaaccaatt ttttcctttt tgtgtgtccc NC_002549 Zaire Ebola virus, complete genome, 18959 bp, ssRNA, linear

| 5'UTR | 1 – 55, leader region |
|---|---|
| gene | 56 – 3026, NP |
| mRNA | 56 – 3026, NP |
| misc signal | 56 – 67, transcription start signal for NP |
| CDS | 470 – 2689, NP, encapsidation of genomic RNA |

MDSRPQKIWMAPSLTESDMDYHKILTAGLSVQQGIVRQRVIPVYQVNNLEEICQLIIQAFEAGVDF
QESADSFLLMLCLHHAYQGDYKLFLESGAVKYLEGHGFRFEVKKRDGVKRLEELLPAVSSGKNI
KRTLAAMPEEETTEANAGQFLSFASLFLPKLVVGEKACLEKVQRQIQVHAEQGLIQYPTAWQSV
GHMMVIFRLMRTNFLIKFLLIHQGMHMVAGHDANDAVISNSVAQARFSGLLIVKTVLDHILQKTER
GVRLHPLARTAKVKNEVNSFKAALSSLAKHGEYAPFARLLNLSGVNNLEHGLFPQLSAIALGVAT
AHGSTLAGVNVGEQYQQLREAATEAEKQLQQYAESRELDHLGLDDQEKKILMNFHQKKNEISFQ
QTNAMVTLRKERLAKLTEAITAASLPKTSGHYDDDDDIPFPGPINDDDNPGHQDDDPTDSQDTTI

FIG. 18M

PDVVVDPDDGSYGEYQSYSENGMNAPDDLVLFDLDEDDEDTKPVPNRSTKGGQQKNSQKGQH
IEGRQTQSRPIQNVPGPHRTIHHASAPLTDNDRRNEPSGSTSPRMLTPINEEADPLDDADDETSS
LPPLESDDEEQDRDGTSNRTPTVAPPAPVYRDHSEKKELPQDEQQDQDHTQEARNQDSDNTQ
SEHSFEEMYRHILRSQGPFDAVLYYHMMKDEPVVFSTSDGKEYTYPDSLEEEYPPWLTEKEAM
NEENRFVTLDGQQFYWPVMNHKNKFMAILQHHQ (SEQ ID NO:10)

| | |
|---|---|
| polyA signal | 3015 – 3026, NP |
| misc feature | 3027 – 3031, intergenic region |
| gene | 3032 – 4407, VP35 |
| mRNA | 3032 – 4407, VP35 |
| misc signal | 3032 – 3043, transcription start signal for VP35 |
| CDS | 3129 – 4151, VP35, polymerase complex protein |

MTTRTKGRGHTAATTQNDRMPGPELSGWISEQLMTGRIPVSDIFCDIENNPGLCYASQMQQTKP
NPKTRNSQTQTDPICNHSFEEVVQTLASLATVVQQQTIASESLEQRITSLENGLKPVYDMAKTISS
LNRVCAEMVAKYDLLVMTTGRATATAAATEAYWAEHGQPPPGPSLYEESAIRGKIESRDETVPQ
SVREAFNNLNSTTSLTEENFGKPDISAKDLRNIMYDHLPGFGTAFHQLVQVICKLGKDSNSLDIIH
AEFQASLAEGDSPQCALIQITKRVPIFQDAAPPVIHIRSRGDIPRACQKSLRPVPPSPKIDRGWVC
VFQLQDGKTLGLKI (SEQ ID NO:11)

| | |
|---|---|
| gene | 4390 – 5894, VP40 |
| mRNA | 4390 – 5894, VP40 |
| misc signal | 4390 – 4401, transcription start signal for VP40 |
| polyA signal | 4397 – 4407, VP35 |
| CDS | 4479 – 5459, VP40 |

MRRVILPTAPPEYMEAIYPVRSNSTIARGGNSNTGFLTPESVNGDTPSNPLRPIADDTIDHASHTP
GSVSSAFILEAMVNVISGPKVLMKQIPIWLPLGVADQKTYSFDSTTAAIMLASYTITHFGKATNPLV
RVNRLGPGIPDHPLRLLRIGNQAFLQEFVLPPVQLPQYFTFDLTALKLITQPLPAATWTDDTPTGS
NGALRPGISFHPKLRPILLPNKSGKKGNSADLTSPEKIQAIMTSLQDFKIVPIDPTKNIMGIEVPETL
VHKLTGKKVTSKNGQPIIPVLLPKYIGLDPVAPGDLTMVITQDCDTCHSPASLPAVIEK (SEQ ID
NO:12)

| | |
|---|---|
| polyA signal | 5883 – 5894, VP40 |
| misc feature | 5895 – 5899, intergenic region |
| gene | 5900 – 8305, GP |
| mRNA | 5900 – 8305, sGP |

FIG. 18N misc signal   5900 – 5911, transcription start signal for GP
CDS           join(6039..6923,6923..8068), receptor binding and fusion; an additional A residue is inserted during transcription; encodes two disulfide linked subunits GP1 and GP2

MGVTGILQLPRDRFKRTSFFLWVIILFQRTFSIPLGVIHNSTLQVSDVDKLVCRDKLSSTNQLRSV
GLNLEGNGVATDVPSATKRWGFRSGVPPKVVNYEAGEWAENCYNLEIKKPDGSECLPAAPDGI
RGFPRCRYVHKVSGTGPCAGDFAFHKEGAFFLYDRLASTVIYRGTTFAEGVVAFLILPQAKKDFF
SSHPLREPVNATEDPSSGYYSTTIRYQATGFGTNETEYLFEVDNLTYVQLESRFTPQFLLQLNETI
YTSGKRSNTTGKLIWKVNPEIDTTIGEWAFWETKKNLTRKIRSEELSFTVVSNGAKNISGQSPART
SSDPGTNTTTEDHKIMASENSSAMVQVHSQGREAAVSHLTTLATISTSPQSLTTKPGPDNSTHN
TPVYKLDISEATQVEQHHRRTDNDSTASDTPSATTAAGPPKAENTNTSKSTDFLDPATTTSPQN
HSETAGNNNTHHQDTGEESASSGKLGLITNTIAGVAGLITGGRRTRREAIVNAQPKCNPNLHYW
TTQDEGAAIGLAWIPYFGPAAEGIYIEGLMHNQDGLICGLRQLANETTQALQLFLRATTELRTFSIL
NRKAIDFLLQRWGGTCHILGPDCCIEPHDWTKNITDKIDQIIHDFVDKTLPDQGDNDNWWTGWR
QWIPAGIGVTGVIIAVIALFCICKFVF (SEQ ID NO:13)

misc feature   7529 – 7540, encodes the GP cleavage site, precursor GP is cleaved by subtilisin-like cellular protease furin into subunits GP1 and GP2 that are linked by a disulfide bond
misc feature   7793 – 7870, GP, immunosuppressive motif
misc feature   7988 – 8053, transmembrane anchor (transmembrane-region site) for GP
CDS            6039 – 7133, GP, small non-structural, secreted glycoprotein; sGP secreted as a anti-parallel oriented homodimer MGVTGILQLPRDRFKRTSFFLWVIILFQRTFSIPLGVIHNSTLQVSDVDKLVCRDKLSSTNQLRSV
GLNLEGNGVATDVPSATKRWGFRSGVPPKVVNYEAGEWAENCYNLEIKKPDGSECLPAAPDGI
RGFPRCRYVHKVSGTGPCAGDFAFHKEGAFFLYDRLASTVIYRGTTFAEGVVAFLILPQAKKDFF
SSHPLREPVNATEDPSSGYYSTTIRYQATGFGTNETEYLFEVDNLTYVQLESRFTPQFLLQLNETI
YTSGKRSNTTGKLIWKVNPEIDTTIGEWAFWETKKTSLEKFAVKSCLSQLYQTEPKTSVVRVRRE
LLPTQGPTQQLKTTKSWLQKIPLQWFKCTVKEGKLQCRI (SEQ ID NO:14)

CDS           join(6039..6922,6924..6933), GP, second non-structural secreted glycoprotein; secreted in a monomeric form; one A residue is deleted or two additional A residues are inserted at the editing site during transcription of the GP gene MGVTGILQLPRDRFKRTSFFLWVIILFQRTFSIPLGVIHNSTLQVSDVDKLVCRDKLSSTNQLRSV
GLNLEGNGVATDVPSATKRWGFRSGVPPKVVNYEAGEWAENCYNLEIKKPDGSECLPAAPDGI
RGFPRCRYVHKVSGTGPCAGDFAFHKEGAFFLYDRLASTVIYRGTTFAEGVVAFLILPQAKKDFF

FIG. 180

SSHPLREPVNATEDPSSGYYSTTIRYQATGFGTNETEYLFEVDNLTYVQLESRFTPQFLLQLNETI
YTSGKRSNTTGKLIWKVNPEIDTTIGEWAFWETKKPH (SEQ ID NO:15)

misc signal    6918 – 6924, GP, additional A residues are inserted or deleted during transcription of the GP gene by the viral polymerase for RNA editing

| | |
|---|---|
| gene | 8288 – 9740, VP30 |
| mRNA | 8288 – 9740, VP30 |
| misc signal | 8288 – 8299, transcription start signal for VP30 |
| polyA signal | 8295 – 8305, GP |
| CDS | 8509 – 9375, VP30 |

MEASYERGRPRAARQHSRDGHDHHVRARSSSRENYRGEYRQSRSASQVRVPTVFHKKRVEPL
TVPPAPKDICPTLKKGFLCDSSFCKKDHQLESLTDRELLLLIARKTCGSVEQQLNITAPKDSRLAN
PTADDFQQEEGPKITLLTLIKTAEHWARQDIRTIEDSKLRALLTLCAVMTRKFSKSQLSLLCETHLR
REGLGQDQAEPVLEVYQRLHSDKGGSFEAALWQQWDRQSLIMFITAFLNIALQLPCESSAVVVS
GLRTLVPQSDNEEASTNPGTCSWSDEGTP (SEQ ID NO:16)

| | |
|---|---|
| polyA signal | 9730 – 9740, VP30 |
| misc feature | 9741 – 9884, intergenic region |
| gene | 9885 – 11518, VP24 |
| mRNA | 9885 – 11496, VP24 |
| misc signal | 9885 – 9896, transcription start signal for VP24 |
| CDS | 10345 – 11100, VP24 |

MAKATGRYNLISPKKDLEKGVVLSDLCNFLVSQTIQGWKVYWAGIEFDVTHKGMALLHRLKTND
FAPAWSMTRNLFPHLFQNPNSTIESPLWALRVILAAGIQDQLIDQSLIEPLAGALGLISDWLLTTNT
NHFNMRTQRVKEQLSLKMLSLIRSNILKFINKLDALHVVNYNGLLSSIEIGTQNHTIIITRTNMGFLV
ELQEPDKSAMNRMKPGPAKFSLLHESTLKAFTQGSSTRMQSLILEFNSSLAI (SEQ ID NO:17)

| | |
|---|---|
| polyA signal | 11485 – 11496, VP24 |
| misc feature | 11497 – 11500, intergenic region |
| gene | 11501 – 18282, L |
| mRNA | 11501 – 18282, L |
| misc signal | 11501 – 11512, transcription start signal for L |
| polyA signal | 11508 – 11518, VP24 |
| CDS | 11581 – 18219, L |

FIG. 18P

MATQHTQYPDARLSSPIVLDQCDLVTRACGLYSSYSLNPQLRNCKLPKHIYRLKYDVTVTKFLSD
VPVATLPIDFIVPVLLKALSGNGFCPVEPRCQQFLDEIIKYTMQDALFLKYYLKNVGAQEDCVDEH
FQEKILSSIQGNEFLHQMFFWYDLAILTRRGRLNRGNSRSTWFVHDDLIDILGYGDYVFWKIPISM
LPLNTQGIPHAAMDWYQASVFKEAVQGHTHIVSVSTADVLIMCKDLITCRFNTTLISKIAEIEDPVC
SDYPNFKIVSMLYQSGDYLLSILGSDGYKIIKFLEPLCLAKIQLCSKYTERKGRFLTQMHLAVNHTL
EEITEMRALKPSQAQKIREFHRTLIRLEMTPQQLCELFSIQKHWGHPVLHSETAIQKVKKHATVLK
ALRPIVIFETYCVFKYSIAKHYFDSQGSWYSVTSDRNLTPGLNSYIKRNQFPPLPMIKELLWEFYH
LDHPPLFSTKIISDLSIFIKDRATAVERTCWDAVFEPNVLGYNPPHKFSTKRVPEQFLEQENFSIEN
VLSYAQKLEYLLPQYRNFSFSLKEKELNVGRTFGKLPYPTRNVQTLCEALLADGLAKAFPSNMM
VVTEREQKESLLHQASWHHTSDDFGEHATVRGSSFVTDLEKYNLAFRYEFTAPFIEYCNRCYGV
KNVFNWMHYTIPQCYMHVSDYYNPPHNLTLENRDNPPEGPSSYRGHMGGIEGLQQKLWTSISC
AQISLVEIKTGFKLRSAVMGDNQCITVLSVFPLETDADEQEQSAEDNAARVAASLAKVTSACGIFL
KPDETFVHSGFIYFGKKQYLNGVQLPQSLKTATRMAPLSDAIFDDLQGTLASIGTAFERSISETRHI
FPCRITAAFHTFFSVRILQYHHLGFNKGFDLGQLTLGKPLDFGTISLALAVPQVLGGLSFLNPEKC
FYRNLGDPVTSGLFQLKTYLRMIEMDDLFLPLIAKNPGNCTAIDFVLNPSGLNVPGSQDLTSFLRQ
IVRRTITLSAKNKLINTLFHASADFEDEMVCKWLLSSTPVMSRFAADIFSRTPSGKRLQILGYLEGT
RTLLASKIINNNTETPVLDRLRKITLQRWSLWFSYLDHCDNILAEALTQITCTVDLAQILREYSWAHI
LEGRPLIGATLPCMIEQFKVFWLKPYEQCPQCSNAKQPGGKPFVSVAVKKHIVSAWPNASRISW
TIGDGIPYIGSRTEDKIGQPAIKPKCPSAALREAIELASRLTWVTQGSSNSDLLIKPFLEARVNLSV
QEILQMTPSHYSGNIVHRYNDQYSPHSFMANRMSNSATRLIVSTNTLGEFSGGGQSARDSNIIFQ
NVINYAVALFDIKFRNTEATDIQYNRAHLHLTKCCTREVPAQYLTYTSTLDLDLTRYRENELIYDSN
PLKGGLNCNISFDNPFFQGKRLNIIEDDLIRLPHLSGWELAKTIMQSIISDSNNSSTDPISSGETRSF
TTHFLTYPKIGLLYSFGAFVSYYLGNTILRTKKLTLDNFLYYLTTQIHNLPHRSLRILKPTFKHASVM
SRLMSIDPHFSIYIGGAAGDRGLSDAARLFLRTSISSFLTFVKEWIINRGTIVPLWIVYPLEGQNPTP
VNNFLYQIVELLVHDSSRQQAFKTTISDHVHPHDNLVYTCKSTASNFFHASLAYWRSRHRNSNR
KYLARDSSTGSSTNNSDGHIERSQEQTTRDPHDGTERNLVLQMSHEIKRTTIPQENTHQGPSFQ
SFLSDSACGTANPKLNFDRSRHNVKFQDHNSASKREGHQIISHRLVLPFFTLSQGTRQLTSSNES
QTQDEISKYLRQLRSVIDTTVYCRFTGIVSSMHYKLDEVLWEIESFKSAVTLAEGEGAGALLLIQK
YQVKTLFFNTLATESSIESEIVSGMTTPRMLLPVMSKFHNDQIEIILNNSASQITDITNPTWFKDQR
ARLPKQVEVITMDAETTENINRSKLYEAVYKLILHHIDPSVLKAVVLKVFLSDTEGMLWLNDNLAPF
FATGYLIKPITSSARSSEWYLCLTNFLSTTRKMPHQNHLSCKQVILTALQLQIQRSPYWLSHLTQY
ADCELHLSYIRLGFPSLEKVLYHRYNLVDSKRGPLVSITQHLAHLRAEIRELTNDYNQQRQSRTQ
TYHFIRTAKGRITKLVNDYLKFFLIVQALKHNGTWQAEFKKLPELISVCNRFYHIRDCNCEERFLVQ
TLYLHRMQDSEVKLIERLTGLLSLFPDGLYRFD (SEQ ID NO:18)

polyA signal    18272 – 18282, L
3'UTR           18283 – 18959, trailer region

FIG. 18Q 1   cggacacaca aaaagaaaga agaattttta ggatcttttg tgtgcgaata actatgagga
61  agattaataa ttttcctctc attgaaattt atatcggaat ttaaattgaa attgttactg
121 taatcacacc tggtttgttt cagagccaca tcacaaagat agagaacaac ctaggtctcc
181 gaagggagca agggcatcag tgtgctcagt tgaaaatccc ttgtcaacac ctaggtctta
241 tcacatcaca agttccacct cagactctgc agggtgatcc aacaaccta atagaaacat
301 tattgttaaa ggacagcatt agttcacagt caaacaagca agattgagaa ttaaccttgg
361 ttttgaactt gaacacttag gggattgaag attcaacaac cctaaagctt ggggtaaaac
421 attggaaata gttaaaagac aaaattgctcg gaatcacaaa attccgagta tggattctcg
481 tcctcagaaa atctggatgg cgccgagtct cactgaatct gacatggatt accacaagat
541 cttgacagca ggtctgtccg ttcaacaggg gattgttcgg caaagagtca tccagtgta
601 tcaagtaaac aatcttgaag aaatttgcca acttatcata caggcctttg aagcaggtgt
661 tgattttcaa gagagtgcgg acagtttcct tctcatgctt tgtcttcatc atgcgtacca
721 gggagattac aaacttttct tggaaagtgg cgcagtcaag tatttggaag ggcacgggtt
781 ccgttttgaa gtcaagaagc gtgatggagt gaagcgcctt gaggaattgc tgccagcagt
841 atctagtgga aaaaacatta agagaacact tgctgccatg ccggaagagg agacaactga
901 agctaatgcc ggtcagtttc tctcctttgc aagtctattc cttccgaaat tggtagtagg
961 agaaaaggct tgccttgaga aggttcaaag gcaaattcaa gtacatgcag agcaaggact
1021 gatacaatat ccaacagctt ggcaatcagt aggacacatg atggtgattt tccgtttgat
1081 gcgaacaaat tttctgatca aatttctcct aatacaccaa gggatgcaca tggttgccgg
1141 gcatgatgcc aacgatgctg tgatttcaaa ttcagtggct caagctcgtt tttcaggctt
1201 attgattgtc aaaacagtac ttgatcatat cctacaaaag acagaacgag gagttcgtct
1261 ccatcctctt gcaaggaccg ccaaggtaaa aaatgaggtg aactccttta aggctgcact
1321 cagctccctg gccaagcatg gagagtatgc tcctttcgcc cgacttttga accttctgg
1381 agtaaataat cttgagcatg gtcttttccc tcaactatcg gcaattgcac tcggagtcgc
1441 cacagcacac gggagtaccc tcgcaggagt aaatgttgga gaacagtatc aacaactcag
1501 agaggctgcc actgaggctg agaagcaact ccaacaatat gcagagtctc gcgaacttga
1561 ccatcttgga cttgatgatc aggaaaagaa aattcttatg aacttccatc agaaaaagaa
1621 cgaaatcagc ttccagcaaa caaacgctat ggtaactcta agaaaagagc gcctggccaa
1681 gctgacagaa gctatcactg ctgcgtcact gcccaaaaca agtggacatt acgatgatga
1741 tgacgacatt cccttttccag gacccatcaa tgatgacgac aatcctggcc atcaagatga
1801 tgatccgact gactcacagg atacgaccat tcccgatgtg gtggttgatc ccgatgatgg
1861 aagctacggc gaataccaga gttactcgga aaacggcatg aatgcaccag atgacttggt
1921 cctattcgat ctagacgagg acgacgagga cactaagcca gtgcctaata gatcgaccaa
1981 gggtggacaa cagaagaaca gtcaaaaggg ccagcatata gagggcagac agacacaatc
2041 caggccaatt caaatgtcc caggccctca cagaacaatc caccacgcca gtgcgccact
2101 cacggacaat gacagaagaa atgaaccctc cggctcaacc agccctcgca tgctgacacc
2161 aattaacgaa gaggcagacc cactggacga tgccgacgac gagacgtcta gccttccgcc

FIG. 18R

```
2221 cttggagtca gatgatgaag agcaggacag ggacggaact tccaaccgca cacccactgt
2281 cgccccaccg gctcccgtat acagagatca ctctgaaaag aaagaactcc cgcaagacga
2341 gcaacaagat caggaccaca ctcaagaggc caggaaccag gacagtgaca acacccagtc
2401 agaacactct tttgaggaga tgtatcgcca cattctaaga tcacaggggc catttgatgc
2461 tgttttgtat tatcatatga tgaaggatga gcctgtagtt ttcagtacca gtgatggcaa
2521 agagtacacg tatccagact cccttgaaga ggaatatcca ccatggctca ctgaaaaaga
2581 ggctatgaat gaagagaata gatttgttac attggatggt caacaatttt attggccggt
2641 gatgaatcac aagaataaat tcatggcaat cctgcaacat catcagtgaa tgagcatgga
2701 acaatgggat gattcaaccg acaaatagct aacattaagt agtcaaggaa cgaaaacagg
2761 aagaattttt gatgtctaag gtgtgaatta ttatcacaat aaaagtgatt cttattttg
2821 aatttaaagc tagcttatta ttactagccg tttttcaaag ttcaatttga gtcttaatgc
2881 aaataggcgt taagccacag ttatagccat aattgtaact caatattcta actagcgatt
2941 tatctaaatt aaattacatt atgcttttat aacttaccta ctagcctgcc caacatttac
3001 acgatcgttt tataattaag aaaaaactaa tgatgaagat taaaaccttc atcatcctta
3061 cgtcaattga attctctagc actcgaagct tattgtcttc aatgtaaaag aaaagctggt
3121 ctaacaagat gacaactaga acaaagggca ggggccatac tgcggccacg actcaaaacg
3181 acagaatgcc aggccctgag ctttcgggct ggatctctga gcagctaatg accggaagaa
3241 ttcctgtaag cgacatcttc tgtgatattg agaacaatcc aggattatgc tacgcatccc
3301 aaatgcaaca aacgaagcca aacccgaaga cgcgcaacag tcaaacccaa acggacccaa
3361 tttgcaatca tagttttgag gaggtagtac aaacattggc ttcattggct actgttgtgc
3421 aacaacaaac catcgcatca gaatcattag acaacgcat tacgagtctt gagaatggtc
3481 taaagccagt ttatgatatg gcaaaaacaa tctcctcatt gaacagggtt tgtgctgaga
3541 tggttgcaaa atatgatctt ctggtgatga caaccggtcg ggcaacagca accgctgcgg
3601 caactgaggc ttattgggcc gaacatggtc aaccaccacc tggaccatca ctttatgaag
3661 aaagtgcgat tcggggtaag attgaatcta gagatgagac cgtccctcaa agtgttaggg
3721 aggcattcaa caatctaaac agtaccactt cactaactga ggaaaatttt gggaaacctg
3781 acatttcggc aaaggatttg agaaacatta tgtatgatca cttgcctggt tttggaactg
3841 cttccacca attagtacaa gtgatttgta aattgggaaa agatagcaac tcattggaca
3901 tcattcatgc tgagttccag gccagcctgg ctgaaggaga ctctcctcaa tgtgccctaa
3961 ttcaaattac aaaaagagtt ccaatcttcc aagatgctgc tccacctgtc atccacatcc
4021 gctctcgagg tgacattccc cgagcttgcc agaaaagctt gcgtccagtc ccaccatcgc
4081 ccaagattga tcgaggttgg gtatgtgttt ttcagcttca agatggtaaa acacttggac
4141 tcaaaatttg agccaatctc ccttccctcc gaaagaggcg aataatagca gaggcttcaa
4201 ctgctgaact atagggtacg ttacattaat gatacacttg tgagtatcag ccctggataa
4261 tataagtcaa ttaaacgacc aagataaaat tgttcatatc tcgctagcag cttaaaatat
4321 aaatgtaata ggagctatat ctctgacagt attataatca attgttatta agtaacccaa
4381 accaaaagtg atgaagatta agaaaaacct acctcggctg agagagtgtt ttttcattaa
```

FIG. 18S

```
4441 ccttcatctt gtaaacgttg agcaaaattg ttaaaaatat gaggcgggtt atattgccta
4501 ctgctcctcc tgaatatatg gaggccatat accctgtcag gtcaaattca acaattgcta
4561 gaggtggcaa cagcaataca ggcttcctga caccggagtc agtcaatggg gacactccat
4621 cgaatccact caggccaatt gccgatgaca ccatcgacca tgccagccac acaccaggca
4681 gtgtgtcatc agcattcatc cttgaagcta tggtgaatgt catatcgggc cccaaagtgc
4741 taatgaagca aattccaatt tggcttcctc taggtgtcgc tgatcaaaag acctacagct
4801 ttgactcaac tacggccgcc atcatgcttg cttcatacac tatcacccat ttcggcaagg
4861 caaccaatcc acttgtcaga gtcaatcggc tgggtcctgg aatcccggat catcccctca
4921 ggctcctgcg aattggaaac caggctttcc tccaggagtt cgttcttccg ccagtccaac
4981 taccccagta tttcacccttt gatttgacag cactcaaact gatcacccaa ccactgcctg
5041 ctgcaacatg gaccgatgac actccaacag gatcaaatgg agcgttgcgt ccaggaattt
5101 catttcatcc aaaacttcgc cccattcttt tacccaacaa aagtgggaag aaggggaaca
5161 gtgccgatct aacatctccg gagaaaatcc aagcaataat gacttcactc caggactttta
5221 agatcgttcc aattgatcca accaaaaata tcatgggaat cgaagtgcca gaaactctgg
5281 tccacaagct gaccggtaag aaggtgactt ctaaaaatgg acaaccaatc atccctgttc
5341 ttttgccaaa gtacattggg ttggacccgg tggctccagg agacctcacc atggtaatca
5401 cacaggattg tgacacgtgt cattctcctg caagtcttcc agctgtgatt gagaagtaat
5461 tgcaataatt gactcagatc cagttttata gaatcttctc agggatagtg ataacatcta
5521 tttagtaatc cgtccattag aggagacact tttaattgat caatatacta aaggtgcttt
5581 acaccattgt ctttttctc tcctaaatgt agaacttaac aaaagactca taatatactt
5641 gttttttaaag gattgattga tgaaagatca taactaataa cattacaaat aatcctacta
5701 taatcaatac ggtgattcaa atgttaatct ttctcattgc acatactttt tgcccttatc
5761 ctcaaattgc ctgcatgctt acatctgagg atagccagtg tgacttggat tggaaatgtg
5821 gagaaaaaat cgggacccat ttctaggttg ttcacaatcc aagtacagac attgcccttc
5881 taattaagaa aaaatcggcg atgaagatta agccgacagt gagcgtaatc ttcatctctc
5941 ttagattatt tgttttccag agtaggggtc gtcaggtcct tttcaatcgt gtaaccaaaa
6001 taaactccac tagaaggata ttgtggggca acaacacaat gggcgttaca ggaatattgc
6061 agttacctcg tgatcgattc aagaggacat cattctttct ttgggtaatt atccttttcc
6121 aaagaacatt ttccatccca cttggagtca tccacaaatag cacattacag gttagtgatg
6181 tcgacaaact agtttgtcgt gacaaactgt catccacaaa tcaattgaga tcagttggac
6241 tgaatctcga agggaatgga gtggcaactg acgtgccatc tgcaactaaa agatgggggct
6301 tcaggtccgg tgtcccacca aaggtggtca attatgaagc tggtgaatgg gctgaaaact
6361 gctacaatct tgaaatcaaa aaacctgacg ggagtgagtg tctaccagca gcgccagacg
6421 ggattcgggg cttccccccgg tgccggtatg tgcacaaagt atcaggaacg ggaccgtgtg
6481 ccggagactt tgccttccat aaagagggtg ctttcttcct gtatgatcga cttgcttcca
6541 cagttatcta ccgaggaacg actttcgctg aaggtgtcgt tgcatttctg atactgcccc
6601 aagctaagaa ggacttcttc agctcacacc ccttgagaga gccggtcaat gcaacggagg
```

FIG. 18T 6661 acccgtctag tggctactat tctaccacaa ttagatatca ggctaccggt tttggaacca
6721 atgagacaga gtacttgttc gaggttgaca atttgaccta cgtccaactt gaatcaagat
6781 tcacaccaca gtttctgctc cagctgaatg agacaatata tacaagtggg aaaaggagca
6841 ataccacggg aaaactaatt tggaaggtca accccgaaat tgatacaaca atcggggagt
6901 gggccttctg ggaaactaaa aaaacctcac tagaaaaatt cgcagtgaag agttgtcttt
6961 cacagttgta tcaaacggag ccaaaaacat cagtggtcag agtccggcgc gaacttcttc
7021 cgacccaggg accaacacaa caactgaaga ccacaaaatc atggcttcag aaaattcctc
7081 tgcaatggtt caagtgcaca gtcaaggaag ggaagctgca gtgtcgcatc taacaaccct
7141 tgccacaatc tccacgagtc cccaatccct cacaaccaaa ccaggtccgg acaacagcac
7201 ccataataca cccgtgtata aacttgacat ctctgaggca actcaagttg aacaacatca
7261 ccgcagaaca gacaacgaca gcacagcctc cgacactccc tctgccacga ccgcagccgg
7321 acccccaaaa gcagagaaca ccaacacgag caagagcact gacttcctgg accccgccac
7381 cacaacaagt ccccaaaacc acagcgagac cgctggcaac aacaacactc atcaccaaga
7441 taccggagaa gagagtgcca gcagcgggaa gctaggctta attaccaata ctattgctgg
7501 agtcgcagga ctgatcacag gcgggagaag aactcgaaga gaagcaattg tcaatgctca
7561 acccaaatgc aaccctaatt tacattactg gactactcag gatgaaggtg ctgcaatcgg
7621 actgcctgg ataccatatt tcgggccagc agccgaggga atttacatag aggggctaat
7681 gcacaatcaa gatggtttaa tctgtgggtt gagacagctg gccaacgaga cgactcaagc
7741 tcttcaactg ttcctgagag ccacaactga gctacgcacc ttttcaatcc tcaaccgtaa
7801 ggcaattgat ttcttgctgc agcgatgggg cggcacatgc cacattctgg gaccggactg
7861 ctgtatcgaa ccacatgatt ggaccaagaa cataacagac aaaattgatc agattattca
7921 tgattttgtt gataaaaccc ttccggacca gggggacaat gacaattggt ggacaggatg
7981 gagacaatgg ataccggcag gtattggagt tacaggcgtt ataattgcag ttatcgcttt
8041 attctgtata tgcaaatttg tcttttagtt tttcttcaga ttgcttcatg gaaaagctca
8101 gcctcaaatc aatgaaacca ggatttaatt atatggatta cttgaatcta agattacttg
8161 acaaatgata atataataca ctggagcttt aaacatagcc aatgtgattc taactccttt
8221 aaactcacag ttaatcataa acaaggtttg acatcaatct agttatctct ttgagaatga
8281 taaacttgat gaagattaag aaaaaggtaa tctttcgatt atctttaatc ttcatccttg
8341 attctacaat catgacagtt gtctttagtg acaagggaaa gaagcctttt tattaagttg
8401 taataatcag atctgcgaac cggtagagtt tagttgcaac ctaacacaca taaagcattg
8461 gtcaaaaagt caatagaaat ttaaacagtg agtggagaca acttttaaat ggaagcttca
8521 tatgagagag gacgcccacg agctgccaga cagcattcaa gggatggaca cgaccaccat
8581 gttcgagcac gatcatcatc cagagagaat tatcgaggtg agtaccgtca atcaaggagc
8641 gcctcacaag tgcgcgttcc tactgtattt cataagaaga gagttgaacc attaacagtt
8701 cctccagcac ctaaagacat atgtccgacc ttgaaaaaag gattttgtg tgacagtagt
8761 ttttgcaaaa aagatcacca gttggagagt ttaactgata gggaattact cctactaatc
8821 gcccgtaaga cttgtggatc agtagaacaa caattaaata taactgcacc caaggactcg

FIG. 18U

```
8881 cgcttagcaa atccaacggc tgatgatttc cagcaagagg aaggtccaaa aattaccttg
8941 ttgacactga tcaagacggc agaacactgg gcgagacaag acatcagaac catagaggat
9001 tcaaaattaa gagcattgtt gactctatgt gctgtgatga cgaggaaatt ctcaaaatcc
9061 cagctgagtc ttttatgtga gacacaccta aggcgcgagg ggcttgggca agatcaggca
9121 gaacccgttc tcgaagtata tcaacgatta cacagtgata aaggaggcag ttttgaagct
9181 gcactatggc aacaatggga ccgacaatcc ctaattatgt ttatcactgc attcttgaat
9241 attgctctcc agttaccgtg tgaaagttct gctgtcgttg tttcagggtt aagaacattg
9301 gttcctcaat cagataatga ggaagcttca accaacccgg ggacatgctc atggtctgat
9361 gagggtaccc cttaataagg ctgactaaaa cactatataa ccttctactt gatcacaata
9421 ctccgtatac ctatcatcat atatttaatc aagacgatat cctttaaaac ttattcagta
9481 ctataatcac tctcgtttca aattaataag atgtgcatga ttgccctaat atatgaagag
9541 gtatgataca accctaacag tgatcaaaga aaatcataat ctcgtatcgc tcgtaatata
9601 acctgccaag cataccctctt gcacaaagtg attcttgtac acaaataatg ttttactcta
9661 caggaggtag caacgatcca tcccatcaaa aataagtat ttcatgactt actaatgatc
9721 tcttaaaata ttaagaaaaa ctgacggaac ataaattctt tatgcttcaa gctgtggagg
9781 aggtgtttgg tattggctat tgttatatta caatcaataa caagcttgta aaaatattgt
9841 tcttgtttca agaggtagat tgtgaccgga aatgctaaac taatgatgaa gattaatgcg
9901 gaggtctgat aagaataaac cttattattc agattaggcc ccaagaggca ttcttcatct
9961 ccttttagca aagtactatt tcagggtagt ccaattagtg gcacgtcttt tagctgtata
10021 tcagtcgccc ctgagatacg ccacaaaagt gtctctaagc taaattggtc tgtacacatc
10081 ccatacattg tattaggggc aataatatct aattgaactt agccgtttaa aatttagtgc
10141 ataaatctgg gctaacacca ccaggtcaac tccattggct gaaaagaagc ttacctacaa
10201 cgaacatcac tttgagcgcc ctcacaatta aaaatagga acgtcgttcc aacaatcgag
10261 cgcaaggttt caaggttgaa ctgagagtgt ctagacaaca aaatattgat actccagaca
10321 ccaagcaaga cctgagaaaa aaccatggct aaagctacgg gacgatacaa tctaatatcg
10381 cccaaaaagg acctggagaa aggggttgtc ttaagcgacc tctgtaactt cttagttagc
10441 caaactattc aggggtggaa ggtttattgg gctggtattg agtttgatgt gactcacaaa
10501 ggaatggccc tattgcatag actgaaaact aatgactttg cccctgcatg gtcaatgaca
10561 aggaatctct ttcctcattt atttcaaaat ccgaattcca caattgaatc accgctgtgg
10621 gcattgagag tcatccttgc agcagggata caggaccagc tgattgacca gtctttgatt
10681 gaacccttag caggagccct tggtctgatc tctgattggc tgctaacaac caacactaac
10741 catttcaaca tgcgaacaca acgtgtcaag gaacaattga gcctaaaaat gctgtcgttg
10801 attcgatcca atattctcaa gtttattaac aaaattggatg ctctacatgt cgtgaactac
10861 aacggattgt tgagcagtat tgaaattgga actcaaaatc atacaatcat cataactcga
10921 actaacatgg gttttctggt ggagctccaa gaacccgaca aatcggcaat gaaccgcatg
10981 aagcctgggc cggcgaaatt ttccctcctt catgagtcca cactgaaagc atttacacaa
11041 ggatcctcga cacgaatgca agtttgatt cttgaattta atagctctct tgctatctaa
```

FIG. 18V 11101 claaggtaga atacttcata ttgagctaac tcatatatgc tgactcaata gttatcttga 11161 catctctgct ttcataatca gatatataag cataataaat aaatactcat atttcttgat 11221 aatttgttta accacagata aatcctcact gtaagccagc ttccaagttg acacccttac 11281 aaaaaccagg actcagaatc cctcaaacaa gagattccaa gacaacatca tagaattgct 11341 ttattatatg aataagcatt ttatcaccag aaatcctata tactaaatgg ttaattgtaa 11401 ctgaacccgc aggtcacatg tgttaggttt cacagattct atatattact aactctatac 11461 tcgtaattaa cattagataa gtagattaag aaaaaagcct gaggaagatt aagaaaaact 11521 gcttattggg tctttccgtg ttttagatga agcagttgaa attcttcctc ttgatattaa 11581 atggctacac aacatacccca atacccagac gctaggttat catcaccaat tgtattggac 11641 caatgtgacc tagtcactag agcttgcggg ttatattcat catactccct taatccgcaa 11701 ctacgcaact gtaaactccc gaaacatatc taccgtttga aatacgatgt aactgttacc 11761 aagttcttga gtgatgtacc agtggcgaca ttgcccatag atttcatagt cccagttctt 11821 ctcaaggcac tgtcaggcaa tggattctgt cctgttgagc cgcggtgcca acagttctta 11881 gatgaaatca ttaagtacac aatgcaagat gctctcttct tgaaatatta tctcaaaaat 11941 gtgggtgctc aagaagactg tgttgatgaa cactttcaag agaaaatctt atcttcaatt 12001 cagggcaatg aatttttaca tcaaatgttt ttctggtatg atctggctat tttaactcga 12061 aggggtagat taaatcgagg aaactctaga tcaacatggt ttgttcatga tgatttaata 12121 gacatcttag gctatgggga ctatgttttt tggaagatcc caatttcaat gttaccactg 12181 aacacacaag gaatccccca tgctgctatg gactggtatc aggcatcagt attcaaagaa 12241 gcggttcaag ggcatacaca cattgtttct gtttctactg ccgacgtctt gataatgtgc 12301 aaagatttaa ttacatgtcg attcaacaca actctaatct caaaaatagc agagattgag 12361 gatccagttt gttctgatta tcccaatttt aagattgtgt ctatgcttta ccagagcgga 12421 gattacttac tctccatatt agggtctgat gggtataaaa ttattaagtt cctcgaacca 12481 ttgtgcttgg ccaaaattca attatgctca aagtacactg agaggaaggg ccgattctta 12541 acacaaatgc atttagctgt aaatcacacc ctagaagaaa ttacagaaat gcgtgcacta 12601 aagccttcac aggctcaaaa gatccgtgaa ttccatagaa cattgataag gctggagatg 12661 acgccacaac aactttgtga gctatttttcc attcaaaaac actgggggca tcctgtgcta 12721 catagtgaaa cagcaatcca aaaagttaaa aaacatgcta cggtgctaaa agcattacgc 12781 cctatagtga ttttcgagac atactgtgtt tttaaatata gtattgccaa acattatttt 12841 gatagtcaag gatcttggta cagtgttact tcagatagga atctaacacc gggtcttaat 12901 tcttatatca aaagaaatca attccctccg ttgccaatga ttaaagaact actatgggaa 12961 ttttaccacc ttgaccaccc tccacttttc tcaaccaaaa ttattagtga cttaagtatt 13021 tttataaaag acagagctac cgcagtagaa aggacatgct gggatgcagt attcgagcct 13081 aatgttctag gatataatcc acctcacaaa tttagtacta aacgtgtacc ggaacaattt 13141 ttagagcaag aaaacttttc tattgagaat gttctttcct acgcacaaaa actcgagtat 13201 ctactaccac aatatcggaa ctttctttc tcattgaaag agaaagagtt gaatgtaggt 13261 agaaccttcg gaaaattgcc ttatccgact cgcaatgttc aaacactttg tgaagctctg

FIG. 18W

```
13321 ttagctgatg gtcttgctaa agcatttcct agcaatatga tggtagttac ggaacgtgag
13381 caaaaagaaa gcttattgca tcaagcatca tggcaccaca caagtgatga ttttggtgaa
13441 catgccacag ttagagggag tagctttgta actgatttag agaaatacaa tcttgcattt
13501 agatatgagt ttacagcacc ttttatagaa tattgcaacc gttgctatgg tgttaagaat
13561 gtttttaatt ggatgcatta tacaatccca cagtgttata tgcatgtcag tgattattat
13621 aatccaccac ataacctcac actggagaat cgagacaacc cccccgaagg gcctagttca
13681 tacaggggtc atatgggagg gattgaagga ctgcaacaaa aactctggac aagtatttca
13741 tgtgctcaaa tttcttagt tgaaattaag actggtttta agttacgctc agctgtgatg
13801 ggtgacaatc agtgcattac tgttttatca gtcttcccct tagagactga cgcagacgag
13861 caggaacaga gcgccgaaga caatgcagcg agggtggccg ccagcctagc aaaagttaca
13921 agtgcctgtg gaatcttttt aaaacctgat gaaacatttg tacattcagg ttttatctat
13981 tttggaaaaa aacaatattt gaatggggtc caattgcctc agtcccttaa aacggctaca
14041 agaatggcac cattgtctga tgcaattttt gatgatcttc aagggaccct ggctagtata
14101 ggcactgctt ttgagcgatc catctctgag acacgacata tctttccttg caggataacc
14161 gcagctttcc atacgttttt ttcggtgaga atcttgcaat atcatcatct cgggttcaat
14221 aaaggttttg accttggaca gttaacactc ggcaaacctc tggatttcgg aacaatatca
14281 ttggcactag cggtaccgca ggtgcttgga gggttatcct tcttgaatcc tgagaaatgt
14341 ttctaccgga atctaggaga tccagttacc tcaggcttat tccagttaaa aacttatctc
14401 cgaatgattg agatggatga tttattctta cctttaattg cgaagaaccc tgggaactgc
14461 actgccattg actttgtgct aaatcctagc ggattaaatg tccctgggtc gcaagactta
14521 acttcatttc tgcgccagat tgtacgcagg accatcaccc taagtgcgaa aaacaaactt
14581 attaatacct tatttcatgc gtcagctgac ttcgaagacg aaatggtttg taaatggcta
14641 ttatcatcaa ctcctgttat gagtcgtttt gcggccgata tcttttcacg cacgccgagc
14701 gggaagcgat tgcaaattct aggatacctg gaaggaacac gcacattatt agcctctaag
14761 atcatcaaca ataatacaga gacaccggtt ttggacagac tgaggaaaat aacattgcaa
14821 aggtggagcc tatggtttag ttatcttgat cattgtgata atatcctggc ggaggcttta
14881 acccaaataa cttgcacagt tgatttagca cagattctga gggaatattc atgggctcat
14941 attttagagg gaagacctct tattggagcc acactcccat gtatgattga gcaattcaaa
15001 gtgttttggc tgaaacccta cgaacaatgt ccgcagtgtt caaatgcaaa gcaaccaggt
15061 gggaaaccat tcgtgtcagt ggcagtcaag aaacatattg ttagtgcatg gcgaacgca
15121 tcccgaataa gctggactat cggggatgga atcccataca ttggatcaag gacagaagat
15181 aagataggac aacctgctat taaaccaaaa tgtccttccg cagccttaag agaggccatt
15241 gaattggcgt cccgtttaac atgggtaact caaggcagtt cgaacagtga cttgctaata
15301 aaaccatttt tggaagcacg agtaaattta agtgttcaag aaatacttca aatgacccct
15361 tcacattact caggaaatat tgttcacagg tacaacgatc aatacagtcc tcattcttc
15421 atggccaatc gtatgagtaa ttcagcaacg cgattgattg ttctacaaa cactttaggt
15481 gagttttcag gaggtggcca gtctgcacgc gacagcaata ttatttttcca gaatgttata
```

FIG. 18X

```
15541 aattatgcag ttgcactgtt cgatattaaa tttagaaaca ctgaggctac agatatccaa
15601 tataatcgtg ctcaccttca tctaactaag tgttgcaccc gggaagtacc agctcagtat
15661 ttaacataca catctacatt ggatttagat ttaacaagat accgagaaaa cgaattgatt
15721 tatgacagta atcctctaaa aggaggactc aattgcaata tctcattcga taatccattt
15781 ttccaaggta aacggctgaa cattatagaa gatgatctta ttcgactgcc tcacttatct
15841 ggatgggagc tagccaagac catcatgcaa tcaattattt cagatagcaa caattcatct
15901 acagacccaa ttagcagtgg agaaacaaga tcattcacta cccatttctt aacttatccc
15961 aagataggac ttctgtacag ttttggggcc tttgtaagtt attatcttgg caatacaatt
16021 cttcggacta agaaattaac acttgacaat tttttatatt acttaactac tcaaattcat
16081 aatctaccac atcgctcatt gcgaatactt aagccaacat tcaaacatgc aagcgttatg
16141 tcacggttaa tgagtattga tcctcatttt tctatttaca taggcggtgc tgcaggtgac
16201 agaggactct cagatgcggc caggttattt ttgagaacgt ccatttcatc ttttcttaca
16261 tttgtaaaag aatggataat taatcgcgga acaattgtcc ctttatggat agtatatccg
16321 ctagagggtc aaaacccaac acctgtgaat aattttctct atcagatcgt agaactgctg
16381 gtgcatgatt catcaagaca acaggctttt aaaactacca taagtgatca tgtacatcct
16441 cacgacaatc ttgtttacac atgtaagagt acagccagca atttcttcca tgcatcattg
16501 gcgtactgga ggagcagaca cagaaacagc aaccgaaaat acttggcaag agactcttca
16561 actggatcaa gcacaaacaa cagtgatggt catattgaga gaagtcaaga acaaaccacc
16621 agagatccac atgatggcac tgaacggaat ctagtcctac aaatgagcca tgaaataaaa
16681 agaacgacaa ttccacaaga aaacacgcac cagggtccgt cgttccagtc ctttctaagt
16741 gactctgctt gtggtacagc aaatccaaaa ctaaatttcg atcgatcgag acacaatgtg
16801 aaatttcagg atcataactc ggcatccaag agggaaggtc atcaaataat ctcacaccgt
16861 ctagtcctac cttctttac attatctcaa gggacacgcc aattaacgtc atccaatgag
16921 tcacaaaccc aagacgagat atcaaagtac ttacggcaat tgagatccgt cattgatacc
16981 acagtttatt gtagatttac cggtatagtc tcgtccatgc attacaaact tgatgaggtc
17041 ctttgggaaa tagagagttt caagtcggct gtgacgctag cagagggaga aggtgctggt
17101 gccttactat tgattcagaa ataccaagtt aagaccttat ttttcaacac gctagctact
17161 gagtccagta tagagtcaga aatagtatca ggaatgacta ctcctaggat gcttctacct
17221 gttatgtcaa aattccataa tgaccaaaatt gagattattc ttaacaactc agcaagccaa
17281 ataacagaca taacaaatcc tacttggttt aaagaccaaa gagcaaggct acctaagcaa
17341 gtcgaggtta taaccatgga tgcagagaca acagagaata taaacagatc gaaattgtac
17401 gaagctgtat ataaattgat cttacaccat attgatccta gcgtattgaa agcagtggtc
17461 cttaaagtct ttctaagtga tactgagggt atgttatggc taaatgataa tttagccccg
17521 ttttttgcca ctggttattt aattaagcca ataacgtcaa gtgctagatc tagtgagtgg
17581 tatctttgtc tgacgaactt cttatcaact acacgtaaga tgccacacca aaaccatctc
17641 agttgtaaac aggtaatact tacggcattg caactgcaaa ttcaacgaag cccatactgg
17701 ctaagtcatt taactcagta tgctgactgt gagttacatt taagttatat ccgccttggt
```

FIG. 18Y 17761 tttccatcat tagagaaagt actataccac aggtataacc tcgtcgattc aaaaagaggt
17821 ccactagtct ctatcactca gcacttagca catcttagag cagagattcg agaattaact
17881 aatgattata atcaacagcg acaaagtcgg actcaaacat atcactttat tcgtactgca
17941 aaaggacgaa tcacaaaact agtcaatgat tatttaaaat tctttcttat tgtgcaagca
18001 ttaaaacata atgggacatg gcaagctgag tttaagaaat taccagagtt gattagtgtg
18061 tgcaataggt tctaccatat tagagattgc aattgtgaag aacgtttctt agttcaaacc
18121 ttatatttac atagaatgca ggattctgaa gttaagctta tcgaaaggct gacagggctt
18181 ctgagtttat ttccggatgg tctctacagg tttgattgaa ttaccgtgca tagtatcctg
18241 atacttgcaa aggttggtta ttaacataca gattataaaa aactcataaa ttgctctcat
18301 acatcatatt gatctaatct caataaacaa ctatttaaat aacgaaagga gtccctatat
18361 tatatactat atttagcctc tctccctgcg tgataatcaa aaaattcaca atgcagcatg
18421 tgtgacatat tactgccgca atgaatttaa cgcaacataa taaactctgc actctttata
18481 attaagcttt aacgaaaggt ctgggctcat attgttattg atataataat gttgtatcaa
18541 tatcctgtca gatggaatag tgttttggtt gataacacaa cttcttaaaa caaaattgat
18601 ctttaagatt aagtttttta taattatcat tactttaatt tgtcgtttta aaaacggtga
18661 tagccttaat ctttgtgtaa aataagagat taggtgtaat aaccttaaca ttttgtcta
18721 gtaagctact atttcataca gaatgataaa attaaaagaa aaggcaggac tgtaaaatca
18781 gaaatacctt ctttacaata tagcagacta gataataatc ttcgtgttaa tgataattaa
18841 gacattgacc acgctcatca gaaggctcgc cagaataaac gttgcaaaaa ggattcctgg
18901 aaaaatggtc gcacacaaaa atttaaaaat aaatctattt cttctttttt gtgtgtcca (SEQ ID NO:19)

NC_001608 Marburg virus, complete genome, 19112 bp, ss-RNA, linear
    gene      103 – 2190, NP
    CDS       103 – 2190, NP MDLHSLLELGTKPTAPHVRNKKVILFDTNHQVSICNQIIDAINSGIDLGDLLEGGLLTLCVEHYYNS
DKDKFNTSPIAKYLRDAGYEFDVVKNADATRFLDVIPNEPHYSPLILALKTLESTESQRGRIGLFLS
FCSLFLPKLVVGDRASIEKALRQVTVHQEQGIVTYPNHWLTTGHMKVIFGILRSSFILKFVLIHQGV
NLVTGHDAYDSIISNSVGQTRFSGLLIVKTVLEFILQKTDSGVTLHPLVRTSKVKNEVASFKQALSN
LARHGEYAPFARVLNLSGINNLEHGLYPQLSAIALGVATAHGSTLAGVNVGEQYQQLREAAHDA
EIKLQRRHEHQEIQAIAEDDEERKILEQFHLQKTEITHSQTLAVLSQKREKLARLAAEIENNIVEDQ
GFKQSQNQVSQSFLNDPTPVEVTVQARPINRPTALPPPVDNKIEHESTEDSSSSSSFVDLNDPFA
LLNEDEDTLDDSVMIPSTTSREFQGIPAPPRQSQDLNNSQGKQEDESTNPIKKQFLRYQELPPVQ
EDDESEYTTDSQESIDQPGSDNEQGVDLPPPPLYAQEKRQDPIQHPAVSSQDPFGSIGDVNGDI
LEPIRSPSSPSAPQEDTRAREAYELSPDFTNYEDNQQNWPQRVVTKKGRTFLYPNDLLQTNPPE
SLITALVEEYQNPVSAKELQADWPDMSFDERRHVAMNL (SEQ ID NO:20)

FIG. 18Z

| | | |
|---|---|---|
| gene | 2944 – 3933, VP35 | |
| CDS | 2944 – 3933, VP35 | |

MWDSSYMQQVSEGLMTGKVPIDQVFGANPSEKLHKRRKPKGTVGLQCSPCLMSKATSTDDIV
WDQLIVKKTLADLLIPINRQISDIQSTLNEVTTRVHEIERQLHEITPVLKMGRTLEAISKGMSEMLAK
YDHLVISTGRTTAPAAAFDAYLNEHGVPPPQPAIFKDLGVAQQACSKGTMVKNETTDAADKMSK
VLELSEETFSKPNLSAKDLALLLFTHLPGNNTPFHILAQVLSKIAYKSGKSGAFLDAFHQILSEGEN
AQAALTRLSRTFDAFLGVVPPVIRVKNFQTVPRPCQKSLRAVPPNPTIDKGWVCVYSSEQGETR
ALKI (SEQ ID NO:21)

| | | |
|---|---|---|
| gene | 4567 – 5478, VP40 | |
| CDS | 4567 – 5478, VP40 | |

MASSSNYNTYMQYLNPPPYADHGANQLIPADQLSNQQGITPNYVGDLNLDDQFKGNVCHAFTL
EAIIDISAYNEPTVKGVPAWLPLGIMSNFEYPLAHTVAALLTGSYTITQFTHNGQKFVRVNRLGTGI
PAHPLRMLREGNQAFIQNMVIPRNFSTNQFTYNLTNLVLSVQKLPDDAWRPSKDKLIGNTMHPA
VSIHPNLPPIVLPTVKKQAYRQHKNPNNGPLLAISGILHQLRVEKVPEKTSLFRISLPADMFSVKEG
MMKKRGENSPVVYFQAPENFPLNGFNNRQVVLAYANPTLSAV (SEQ ID NO:22)

| | | |
|---|---|---|
| gene | 5940 – 7985, GP | |
| CDS | 5940 – 7985, GP | |

MKTTCLFISLILIQGIKTLPILEIASNNQPQNVDSVCSGTLQKTEDVHLMGFTLSGQKVADSPLEAS
KRWAFRTGVPPKNVEYTEGEEAKTCYNISVTDPSGKSLLLDPPTNIRDYPKCKTIHHIQGQNPHA
QGIALHLWGAFFLYDRIASTTMYRGRVFTEGNIAAMIVNKTVHKMIFSRQGQGYRHMNLTSTNKY
WTSNNGTQTNDTGCFGALQEYNSTKNQTCAPSKIPSPLPTARPEIKPTSTPTDATTLNTTDPNND
DEDLITSGSGSGEQEPYTTSDAVTKQGLSSTMPPTPSPQPSTPQQEGNNTDHSQGTVTEPNKT
NTTAQPSMPPHNTTAISTNNTSKNNFSTLSVSLQNTTNYDTQSTATENEQTSAPSKTTLPPTGNL
TTAKSTNNTKGPTTTAPNMTNGHLTSPSPTPNPTTQHLVYFRKKRSILWREGDMFPFLDGLINAP
IDFDPVPNTKTIFDESSSSGASAEEDQHASPNISLTLSYFPNINENTAYSGENENDCDAELRIWSV
QEDDLAAGLSWIPFFGPGIEGLYTAGLIKNQNNLVCRLRRLANQTAKSLELLLRVTTEERTFSLIN
RHAIDFLLTRWGGTCKVLGPDCCIGIEDLSRNISEQIDQIKKDEQKEGTGWGLGGKWWTSDWGV
LTNLGILLLLSIAVLIALSCICRIFTKYIG (SEQ ID NO:23)

| | | |
|---|---|---|
| gene | 8867 – 9712, VP30 | |
| CDS | 8867 – 9712, VP30 | |

FIG. 18AA

MQQPRGRSRTRNHQTASSIYHETQLPSKPHYTNHHPRARSMSSTRSSAESSPTNHIPRARPPP
TFNLSKPPPPPKDMCRNMKIGLPCTDPTCNRDHDLDNLTNRELLLLMARKMLPNTDKTFRSLQD
CGSPSLSKGLSKDKQEQTKDVLTLENLGHILNYLHRSDIGKLDETSLRAALSLTCAGIRKTNRSLIN
TMTELHINHENLPQDQNGVIKQTYTGIHLDKGGQFEAALWQGWDKRSISLFVQAALYVMNNIPC
ESSTSVQASYDHFILPQSQSKGQ (SEQ ID NO:24)

gene  10205 – 10966, VP24
  CDS  10205 – 10966, VP24

MAELSTRYNLPANVTEKSINLDLNSTARWIKEPSVGGWTVKWGNFVFHIPNTGMALLHHLKSNF
VVPEWQQTRNLFSHLFKNPKSTIIEPFLALRILLGVALKDQELQQSLIPGFRSIVHMLSEWLLLEVT
SAIHISPNLLGIYLTSDMFKILMAGVKNFFNKMFTLHVVNDHGKPSSIEIKLTGQQIIITRVNMGFLV
EVRRIDIEPCCGETVLSESVVFGLVAEAVLREHSQMEKGQPLDLTQYMNSKIAI (SEQ ID NO:25)

gene  11479 – 18474, L
  CDS  11479 – 18474, L

MQHPTQYPDARLSSPIILDQCDLLARSLGLYSHYSHNPKLRNCRIPHHIYRLRNSTALKTFLQNCS
ILTVPFHSIWDHILTSIQYDAINHVDDFKYLLPSELVKYANWDNEFLKAYLNKILGLDHVFPASARS
QWEDFSPKENPYYWGMLLLVHLSQLARRIKGQRGSLRSNWKFIGTDLELFGIADFIIFKVPVKTIIR
NAVSLQASKPGLRVWYRDQNLTPYLCDDEFIVSVASYECFIMIKDVFIERYNTWEICARAWLEDS
DGADYLPLDVLGELYNQGDQIIAMYLEDGFKLIKHLEPLCVSCIQTHGIFTPGKYWFQSQRIESYY
EELCSLNWKFKISGNKAECAQNFIKTIIQGKLTPQQYCELFSLQKHWGHPVLYIDVALDKVKKHAQ
SVKILKPKVMFETFCVFKFIVAKNHYHSQGSWYKTTMDLHLTPYLRQHIVSNSFPSQAEIYQHLW
EWYFVEHEPLFSTKIISDLSIFIKDRATAVNQECWDSVFDRSVLGYNPPVRFQSKRVPEQFLGQA
DFSLNQILDFAEKLEYLAPSYRNFSFSLKEKELNIGRTFGKLPYRVRNVQTLAEALLADGLAKAFP
SNMMVVTEREQKEALLHQASWHHNSASIGENAIVRGASFVTDLEKYNLAFRYEFTRHFIDYCNR
CYGVKNLFDWMHFLIPLCYMHVSDFYSPPHCVTEDNRNNPPDCANAYHYHLGGIEGLQQKLWT
CISCAQITLVELKTKLKLKSSVMGDNQCITTLSLFPIDAPDDYQENEAELNAARVAVELAITTGYDG
IFLKPEETFVHSGFIYFGKKQYLNGVQLPQSLKTMARCGPLSDSIFDDLQGSLASIGTSFERGTSE
TRHIFPSRWIASFHSMLAINLLNQNHLGFPLGFSIDISCFKKPLTFSEKLIALITPQVLGGLSFLNPE
KLFYRNISDPLTSGLFQLKNALEFLEKEELFYILIAKKPGLADASDFVMNPLGLNVPGSREIITFLRQ
TVRENITITSQNRIINSLFHIGSDLEDQRVCEWLLSSNPVMSRFAADIFSRTPSGKRLQVLGYLEGT
RTLLASRTISLTTEGTMLMKLRELTRNRWKSWFSYIDALDDDLSESLEKFTCTVDIANFLRAYSWL
DVLKGKRLIGATLPCLLEQFKVKWINLSEDLREQFNMSSESESTINLLPYDCKELRLGRSNDTELN
YVSCALDRKVVQKHPSVNRLAWTIGNRAPYIGSRTEDKIGYPPLRVNCPSAALKEAIEMVSRLLW
VTQGTADREKLLIPLLNSRVNLDYQTVLNFLPTHYSGNIVHRYNDQYGQHSFMANRMSNTSTRAI

FIG. 18BB

ISTNTLGKYAGGGQAAVDSNIIFQNTINLGVAVLDIALSLAKLSSASNVTFRLMLNKCCTRHVPSEY
LFFDKPLDVDLNKYMDNELVYDNDPLCSGIKGRLGRVSRSTLSLSLNVSDIGSYDFPTIAAWTLG
ETIVGSIFSDESSQSTDPISSGCTKTFVTHFLVYPVESIFYAFGANLIVESLSLSRIKSIKNLSDLTFLI
SSTIRNLSHRSLRILQSTFRHELVLTRLAHHIPLISLMLGGSAGEKSSSDAVRLFLTASYQNFINNF
SCLMKKGQSSLPVWLYFPSEGQQLKPILKILQRLSDLLSPDKVQKHQILADTCCPIDSFWVYPSK
STRTNHYYASLNYWRDKANKVKNTPFSHLINCSFLELSSHTSSVSSNQQVTNSKYIVHPENIPEIN
ARTKLIDYGSTALQGMDIKMPLSEQNLVGNCRPSKGIRFKDNPKTTKHDQGFVGKDSSPRPMSP
EDNMQTPAYIHSSPPYQTLTKSPDVHEDFDASKVILNSEINNLNLTDCTLNTKSLTTPTGTEILGIS
PFRSSRYSSTSRERSRLSREQASYLYVDCSNIPSISLDPGFQNMSDQNQVQMLINTYKRDLHAC
FDSNQFCRFTGVVSSMHYKLYDLLPPGELRKAICLAEGEGSGARLLLKWKKTDYLFFNTLATDS
QQEAEILSGRVIPRMLYNIDRLNALLESRRLILNNLTIQITDITSPLWLDSVIQYLPEDSDILTMDAET
TKDETREQLYKTIVNIWTRTSPNIPKISIIKVFLLDYEGTLFLMRNAIQYYGQVQLKKPYSSNAKNSE
WYLCCGKRRIQRLKIDFSDQVGIFLICKAMSRQRQAIPYWLKHIEKNYPASLHKFFLTLGFPSLES
SFCHRYTIPFSEGKALFHKVQSYVRQGKQHLHSLMLDYENNSPLLDLRNHFICSLRGKITKYYNDI
LKLNLVIKAVEKGKNWSQLVETLPNMHSVCIVHVDHECFGCEKRLLLKLDFIRNTKIAEQKLLNRVI
GYILFFPFGLFKSESLTA (SEQ ID NO:26)

```
   1 gacacacaaa aacaagagat gatgattttg tgtatcatat aaataaagaa gaatattaac
  61 attgacattg agacttgtca gtctgttaat attcttgaaa agatggattt acatagcttg
 121 ttagagttgg gtacaaaacc cactgcccct catgttcgta ataagaaggt gatattattt
 181 gacacaaatc atcaggttag tatctgtaat cagataatag atgcaataaa ctcagggatt
 241 gatcttggag atcttctaga agggggtttg ctgacgttgt gtgttgaaca ttactataat
 301 tccgataaag ataaattcaa cacaagtcct atcgcaaaat acttgcgtga tgcgggctat
 361 gagtttgatg tcgtcaagaa tgcagatgca acccgctttc tggatgtgat tcctaacgaa
 421 cctcattaca gtcctttaat tttggcccct aagacattgg aaagtactga atctcagagg
 481 gggagaattg ggctcttttt gtcattttgc agtcttttc tcccgaaact tgttgtcgga
 541 gatcgggcta gtatcgaaaa ggctttaaga caagtaacag tacatcaaga acagggggatc
 601 gtcacatacc ctaatcactg gcttactaca ggccatatga agtaattttt tgggattttg
 661 aggtctagct ttatcttaaa atttgtgtta attcatcaag gagtaaattt ggtgacaggt
 721 catgatgcct atgacagtat cattagtaat tcagtaggtc aaactagatt ctcaggactt
 781 cttattgtga aaacagttct tgagttcatc ttgcaaaaaa ctgattcagg ggtgacacta
 841 catcctttgg tgcggacctc aaagtaaaa atgaagttg ctagtttcaa gcaggcgttg
 901 agcaacctag cccgacatgg agaatacgca ccgttcgcac gggttctgaa tttatcaggg
 961 attaacaacc tcgaacatgg actctatcct cagctttcgg cgattgcgct gggtgttgca
1021 acagcacacg gcagtacatt ggctggtgtc aatgttggcg aacagtatca acagctacga
1081 gaggcggcac atgatgcgga aataaaacta caaaggcgac atgaacatca ggaaattcaa
```

FIG. 18CC 1141 gctattgcag aggatgatga ggagaggaag atattagaac aattccacct tcagaaaact
1201 gaaatcacac acagtcagac actagccgtc ctcagccaga aacgagaaaa attagctcgt
1261 cttgctgcag aaattgaaaa caatattgtg gaagatcagg gatttaaaca atcacagaat
1321 caggtgtcac agtcgttttt gaatgaccct acacctgtgg aagtaacggt tcaagccagg
1381 cccataaatc gaccaactgc tctgcctccc ccagttgaca acaaaattga gcacgaatct
1441 acagaagata gctcttcttc aagcagcttt gttgatctta atgatccatt tgcgctgctg
1501 aatgaggacg aagacactct tgacgacagt gtcatgatcc cgagcacaac atcgagagaa
1561 tttcaaggga ttccagcacc accaagacaa tctcaggacc tcaacaacag ccaaggaaag
1621 caggaagatg aatcaacaaa tccgattaag aaacagtttc tgagatatca agaactgcct
1681 ccggttcaag aggatgatga atcggaatac acaaccgact ctcaggagag tatcgaccaa
1741 ccaggatctg acaatgaaca aggagttgat cttccacctc ctccattgta cgctcaggaa
1801 aaaaggcaag atccaataca gcacccagca gtaagctctc aggatccctt tggcagtatt
1861 ggtgatgtaa atggtgatat cttagaaccc ataagatcac cttcttcacc atctgctcct
1921 caggaagaca caagggcaag agaagcctat gaattgtcgc ctgatttcac aaattatgag
1981 gacaatcagc agaattggcc acaaagagtg gtgacaaaga agggtaggac tttcctttat
2041 cctaatgatc ttctgcagac aaatcctcca gaatcactta taacagccct cgtagaggaa
2101 taccaaaatc ctgtctcagc taaggagctc caagcagatt ggcccgacat gtcatttgat
2161 gaaaggagac atgttgctat gaacttgtag tccagataac acagcacggt tacctactta
2221 tctactttga tccgattcgt cctcagatca cagtaatcaa atttattga atattcaaac
2281 tacttttag gatcctatta cttgttacta ttgtgtgaga caacataagc tatcaaataa
2341 caatcacggg caagaaccgg gcatactatg gtgatgcgag ggcattattc agtgctacaa
2401 attctttttt caattgctat aatgatacaa ctacgaacct ccatacattt gccgcaatac
2461 tgtaatcaac actgctgtat ctctccttca agccatctga tttaacttaa taaacatgac
2521 ttgattcaga gagtgtgctg aaaatgttat tgattgagct tctcaaatgg tgcactatcc
2581 tactgttttg ctcagcctag tatactgtaa catataagtg gactctccac ttctcttctc
2641 gagtattccc tataagtgat ttacttgata gaatgtcaag tccactggtt tggagtttcc
2701 ttactctaat gattgtaata attaactgtt ggcttagatg ataacagata cgaggttata
2761 taattactca tagtataaag tataattctt gcctctgttt cttctgtttt ctctttcctt
2821 tgtaatatgc caattaagaa aaactaaaaa tcgaagaata ttaaaggttt tctttaatat
2881 tcagaaaagg ttttttattc tcttctttct ttttgcaaac atattgaaat aataattttc
2941 acaatgtggg actcatcata tatgcaacaa gtcagtgagg ggttgatgac tggaaaagtt
3001 cccatagatc aagtgtttgg tgccaatccc tcagagaagt tacacaagag aaggaaacca
3061 aaaggcacag ttggactaca atgcagccct tgtctaatgt caaaggcgac aagcactgat
3121 gatattgttt gggaccaact gatcgtgaag aaaacactag ctgatctact tataccgata
3181 aataggcaga tatcggacat tcaaagcact ctaaacgaag taacaacaag agtccatgaa
3241 attgagcggc aattacatga gataacccca gtgttaaaaa tgggaaggac actggaagca
3301 atttccaagg ggatgtcaga aatgttagcc aaatacgacc acctcgtaat ttcaactgga

FIG. 18DD

```
3361 agaaccactg caccagctgc tgcctttgat gcttacttaa atgagcatgg tgtccctccc
3421 ccccaacctg cgattttcaa agatcttggg gttgctcaac aagcttgtag taaggggacc
3481 atggttaaaa atgaaacaac agatgcagcc gacaagatgt cgaaagttct tgaactcagt
3541 gaggagacgt tctccaagcc aaatctttca gctaaggatt tagcccttt gttgtttacc
3601 catctacccg gcaacaacac tccattccat atcctagctc aagtcctttc aaaaattgct
3661 tacaagtcag gaaagtccgg agcattttg gatgcatttc accagattct aagtgaagga
3721 gagaatgctc aggcagcatt gactcgacta agcagaacat ttgatgcttt cctcggagta
3781 gttcctccag tgataagagt caaaaacttc caaacagtcc ctcgcccatg tcaaaaaagt
3841 cttcgggctg ttcctcccaa cccaacaatt gacaaaggat gggtctgtgt ttattcatct
3901 gagcaaggtg agacacgggc cctgaaaatc taattctcat tgttaacagt tgcagggga
3961 gtgatctttc cgagttgata caaagacact aaacatttca aaagcatata tgtgggcaaa
4021 acgtgactag accatcttaa tagaagtagt aatttatttc tgtcttaagt gtgattttca
4081 ccttgaaaga gttaaatggt gatagattaa tccttgaagt aacttttta tatattatag
4141 aggaactaat attactaaca aaagggtct acctaacagg tatgactgag tgatcagtat
4201 attttataaa ccaagcaatt gacttctcac ttttaagaa tcaactaaca acatagaaaa
4261 catatttatc cttgtgtaat tctcggctta gttggaatta acttttgttg caattcaaga
4321 cgcttattca tagtagatta tatgattttt tataagttta agatatctta aattataccc
4381 acaagagata ctgttttaat taagaaaaac tatgaagaac attaagaaga tctttctctc
4441 gtagtgttct tttactggaa ggagtatccc aatctcagct tgttgaatta attgttactt
4501 aagtcattct ttttaaaatt aattcacaca aggtagtttg ggtttatatc tagaacaaat
4561 tttaatatgg ccagttccag caattacaac acatacatgc aatacttgaa ccccctcct
4621 tatgctgatc acggtgcaaa ccagttgatc ccggcggatc agctatcaaa tcagcagggt
4681 ataactccaa attatgtggg tgacttaaac ctagatgatc agttcaaagg gaatgtctgc
4741 catgctttca ctttagaggc aataattgac atatctgcgt ataatgaacc aacagtcaaa
4801 ggtgttccag catggctgcc tctcgggatt atgagcaatt ttgaatatcc tttagctcat
4861 actgtggctg cgttgctcac aggcagctat acaatcaccc aatttactca taatgggcaa
4921 aaattcgtcc gtgtaaatcg actcggtaca ggaatcccag cacacccact cagaatgttg
4981 cgtgaaggaa atcaagcttt tattcagaat atggtgatcc ccagaaattt ttccactaat
5041 caattcacct acaatctcac taacttagta ttgagtgtgc aaaagcttcc tgatgatgcc
5101 tggcgcccat ccaaggacaa attaattggg aacaccatgc atcccgcagt ctccatacac
5161 ccgaatttgc cacccattgt tctaccaaca gtcaagaagc aggcttatcg tcagcataaa
5221 aatcccaaca atggaccact gctggccata tctggcatcc ttcaccaact gagggtcgag
5281 aaagtcccag agaagacaag cctgtttagg atttcacttc ctgccgatat gttctcagta
5341 aaagaaggta tgatgaagaa aaggggagaa aattccccgg tggtttattt tcaagcacct
5401 gagaacttcc ctttgaatgg cttcaacaac agacaagttg tactagcgta tgcgaatcca
5461 acgctcagtg ccgtttgaaa taatgctcaa atgagacagg agtccatctg catatagaagc
5521 atggcctaaa tgggtgtctg ttaagttctc acaagattag tttgtattga tttcaataat
```

FIG. 18EE

```
5581 gctttaacct tacattgctg ctttaaatgg ttaattaagc tgatcagctt gcaagatgta
5641 atctcttttg ggtcatcaga tctataatgg gtttactaga ttatataaaa gaaatagtaa
5701 tgttttataa acaattcttg cttagtttta ctttgattta ctaacatata tcattgtgcc
5761 cttcattgct aagtaaactc aactgatgat gatattcctt ctgaaatagt aagaaaaact
5821 aatgaagaac attaattgcc gggtaagagt gattaagttc tttaaatttg accaaagtaa
5881 tgttttgtta gtgaatacat tcttatattg cttgattaaa aacaagaaat tatcctaaca
5941 tgaagaccac atgtctcttt atcagtctta tcttaatcca agggataaaa actctcccta
6001 ttttagagat agctagtaac aatcaacccc aaaatgtgga ttcggtatgc tccggaactc
6061 tccagaagac agaagatgtc catctgatgg gattcacact gagtgggcaa aaagttgctg
6121 attccccttt ggaggcatcc aagcgatggg ctttcaggac aggtgtacct cccaagaatg
6181 ttgagtatac agaaggggag gaagccaaaa catgctacaa tataagtgta acggatccct
6241 ctggaaaatc cttgctgttg gatcctccta ccaacatccg tgactatcct aaatgcaaaa
6301 ctatccatca tattcaaggt caaaaccctc atgcgcaagg gatcgccctc catttgtggg
6361 gagcattttt cctgtatgat cgcattgcct ccacaacaat gtaccgaggc agagtcttca
6421 ctgaagggaa catagcagct atgattgtca ataagacagt gcacaaaatg attttctcga
6481 ggcaaggaca ggggtaccgt cacatgaatc tgacttctac taataaatat tggacaagta
6541 acaatggaac acaaacgaat gacactggat gcttcggtgc tcttcaagaa tacaactcca
6601 cgaagaatca aacatgtgct ccgtccaaaa taccctcacc actgcccaca gcccgtccag
6661 agatcaaacc cacaagcacc ccaactgatg ccaccacact caacaccaca gacccaaaca
6721 atgatgatga ggacctcata acatccggtt cagggtccgg agaacaggaa ccctatacaa
6781 cttcagatgc ggtcactaag caagggcttt catcaacaat gccacccact ccctcaccac
6841 aaccaagcac gccacagcaa gaaggaaaca acacagacca ttcccaaggt actgtgactg
6901 aacccaacaa aaccaacaca acggcacaac cgtccatgcc cccccacaac accactgcaa
6961 tctctactaa caacacctcc aagaacaact tcagcaccct ctctgtatca ctacaaaaca
7021 ccaccaatta cgacacacag agcacagcca ctgaaaatga acaaaccagt gcccccctcga
7081 aaacaaccct gcctccaaca ggaaatctta ccacagcaaa gagcactaac aacacgaaag
7141 gccccaccac aacggcacca aatatgacaa atgggcattt aaccagtccc tcccccaccc
7201 ccaacccgac cacacaacat cttgtatatt tcagaaagaa acgaagtatc ctctggaggg
7261 aaggcgacat gtttccttt ctggacgggt taataaatgc tccaattgat tttgatccag
7321 ttccaaatac aaagacgatc tttgatgaat cttctagttc tggtgcttcg gctgaggaag
7381 atcaacatgc ctcccccaat atcagtttaa ctttatccta ttttcctaat ataaatgaaa
7441 acactgccta ctctggagaa aatgagaacg attgtgatgc agagttaaga atttggagcg
7501 ttcaggagga tgacctggca gcagggctca gttggatacc gttttttggc cctggaatcg
7561 aaggacttta tactgctggt ttaattaaaa accaaaacaa tttggtctgc aggttgaggc
7621 gtctagccaa tcaaactgcc aaatccttgg aactcttatt aagagtcaca accgaggaaa
7681 ggacattttc cttaattaat agacatgcca ttgactttct actcacaagg tggggaggaa
7741 catgcaaagt gcttggacct gattgttgca ttggaataga agacttgtcc aggaatattt
```

FIG. 18FF 7801 cggaacaaat tgaccaaatc aaaaaagatg aacaaaaaga ggggactggt tggggtctag
7861 gtggtaaatg gtggacatcc gactggggtg ttcttactaa cttgggcatt ttgctactat
7921 tatccatagc tgtcttgatt gctctatcct gtatttgtcg tatctttacc aaatatatcg
7981 ggtaatatta agtgtgtatt gattaaagct ttaggacaat tgctactgag cccttcttct
8041 aatctactga aatcaacttg ggagattttt aagaagctga taatttaatg tgaatcagta
8101 gtttacgtat tgttgattgt tatggtttga tattcaattg ttatcatagt caagagtaac
8161 cttttctatt tgatgcatta atgttttaaa ctacctctta agcttttgtg gatggtttca
8221 atatgtgcgt agaggttaat ttaaagagat ttcttgttgc acagtttttt gtattactta
8281 cttgggcttg aagacatagt taagactggc cgaaaatgct ctccagtcaa ctccattccc
8341 cctcagaaga gacgtgccgt tcaaagagtc ttgatttata actaaccatt gtaagaatta
8401 atttactctt tccgttatac ttatctacat taattccttg aatgtccagc atcattaacg
8461 acttgtctta attcaatctt ttggatgcaa accataagga aaaatgagcc actttccctc
8521 tactctgaac taaggaaatt tctcttatca gcctaaaatc tgatccgtta ggtcatgggc
8581 ccttcataat ctgtttgagc atgaatgttg atcaaatgac caaataatag tgcatttgta
8641 tagattcaat tatcctttat taagaaaaag atagacagaa cacaagaat tgataaaata
8701 ttactttgat caattttgcg aggaattata aaaatcttga gggacaaatt attgtaacgt
8761 agagtcgaag aacattaagt gttctttgtt agaattattc atccaagttg ttttgagtat
8821 actcgcttca atacaacttc ccttcatatt tgattcaaga tttaaaatgc aacaacccg
8881 tggaaggagt cgaactcgca accaccaaac cgcatcatct atatatcatg aaactcagtt
8941 gccctccaaa cctcactaca ccaatcatca tccacgtgca agatcgatga gctcaacccg
9001 cagtagtgca gaaagcagtc ccaccaatca tattcccgt gctcgaccac ccccaacatt
9061 caacttatcg aaacccctc ctcctccaaa agacatgtgt aggaacatga aaattggatt
9121 gccgtgcact gatcccactt gtaatagaga tcatgacctt gataatctaa caaatcgtga
9181 acttttgcta ttgatggccc gaaaaatgct ccccaataca gacaagactt ttagaagtct
9241 gcaggattgt gggtcaccgt ctctttctaa agggctctca aaagataaac aggagcaaac
9301 gaaagatgtg ttgaccttgg aaaatctagg acacattctg aactacctcc acagatcaga
9361 tattgggaaa ttggatgaga catcactccg tgcagcatta agtttgacgt gcgctggaat
9421 tcgaaagacg aatagatcct tgatcaacac catgaccgaa ttacacatta accatgaaaa
9481 tctcccgcaa gaccaaaacg gtgttatcaa acagacatat acaggtattc accttgacaa
9541 aggaggtcaa ttcgaagccg ccttatggca aggttgggat aagagatcga tatctttatt
9601 cgtacaagca gctttatatg taatgaacaa tatcccttgt gaatcatcaa ccagtgtgca
9661 agcctcatac gatcatttta ttcttcctca aagtcaaagt aaaggacaat gattattgtt
9721 tgaaagttga caatcaaatc actttcagtt tttagtttca actcttattg cgagacttga
9781 acacaattct actaacttca ataagtgacc ccaaattcaa gtttactgaa gactacgacg
9841 ataataatca ccaattcatt gtaaattact cgattaaaat attcttaagc tatcttaaac
9901 ttgatgatgc agctctgttt caccttctg ttgatttcaa tgttacagct atatctaagt
9961 gtctaattaa caacttgtac ctctaaggaa aatcatgaag aacattaaga aaaaggatgt

FIG. 18GG 10021 tcttattttt caactaaact tgcatatcct ttgttgatac ccttgagaga caactttga
10081 cactagatca cggatcaagc atatttcatt caaacacccc aaattttcaa tcatacacat
10141 aataaccatt ttagtagcgt tacctttcaa tacaatctag gtgattgtga aaagacttcc
10201 aaacatggca gaattatcaa cgcgttacaa cttgcctgca aatgttacgg aaaaaagcat
10261 aaatcttgac cttaattcca cagcacgatg gataaaagaa cccagtgttg ggggctggac
10321 agtgaagtgg ggaaactttg ttttccacat accaaatact gggatggcat tgttgcatca
10381 tttaaagtct aacttcgttg ttccagagtg gcaacaaaca aggaatctat tctcccacct
10441 ctttaaaaac ccaaagtcaa caattataga accgttcttg gctttgagga tcttgcttgg
10501 agttgctttg aaggatcaag aattacagca atcattaatt cctggattta gatctattgt
10561 tcatatgctt tcagaatggt tgctcctaga ggtaacgtcg gcaatccata ttagccccaa
10621 tctgttggga atctatttga cctcagacat gtttaagatt ctgatggcag gtgtgaaaaa
10681 tttctttaat aagatgttca ctcttcatgt tgtaaatgac cacggaaaac ccagcagtat
10741 tgaaataaag ttaactggac aacagatcat tatcactcgt gttaatatgg ggtttctagt
10801 ggaagtcagg aggattgata ttgaaccttg ttgtggtgag acagtcctct cagaatcagt
10861 tgtttttggg ctagtggctg aggcagttct aagagaacac agtcaaatgg agaagggcca
10921 accctcgat ctgacacaat acatgaacag caaaattgct atataagtgg cttaaattag
10981 catggatatt catagtttaa ccacataata atgttggagg cacagtacat tatagttaat
11041 tatcctgtat aacaaagaat atacctaccc tgatttatat ttactggtat aaaatagtgg
11101 tatcatctta ttaaatagtt gtcatataac aggctgttcc tataatctga ttgtgagatt
11161 ataaacttgt agaattaccg tggatcacaa ctgttgcata tcttccaaaa tatatctttt
11221 gcaagcgatg tgtgcttgaa tacgtcgata taatacatac taataacgat tgattaagaa
11281 aaaccaatga tggatattaa atatccatca agcaggtgtc gcagaatacc agggtttca
11341 tatgctgcca tatttactaa atcttacata ggattatatc attctcttcg atacacgtta
11401 tatctttagc aaagtaatga aaatagcctt gtcatgttag acgccagtta tccatcttaa
11461 gtgaatcctt tcttcaatat gcagcatcca actcaatatc ctgatgcaag gttgtcctcc
11521 cctataatcc tagaccagtg tgacttatta gccagaagtt taggggttgta tagtcattat
11581 tcacataatc cgaaattgcg taattgtagg attccacatc atatttaccg tttaaggaat
11641 tcgacagcat taaaaacatt tcttcagaac tgttcaatac tcaccgtccc ttttcattca
11701 atctgggatc atattttaac ttccattcaa tatgatgcaa ttaatcatgt tgatgatttt
11761 aaatacctat tgccctctga gctagtcaag tatgcaaatt gggacaacga gttcttgaag
11821 gcatatctta ataagatctt aggacttgac catgttttc cagcttctgc aaggtcacaa
11881 tgggaggatt tttctcctaa ggaaaatcct tattattggg ggatgctgtt actcgtgcat
11941 ttatctcaac ttgccaggag gataaaagga caaagagggt cattaagaag taactggaag
12001 tttataggaa cagatttaga gctgtttgga atagcagatt ttattatttt taaagttcca
12061 gtaaaaacaa taatccgaaa tgctgtaagc ttacaagctt caaaaccagg gttaagagta
12121 tggtaccgtg accaaaactt gaccccttat ctatgcgatg atgagtttat tgtaagcgtc
12181 gctagttatg aatgttttat catgattaaa gacgtcttca ttgagaggta taacacgtgg

FIG. 18HH

```
12241 gaaatatgtg cccgcgcctg gctcgaagac agtgatggag ctgattatct ccctcttgat
12301 gtgttaggtg agttatacaa ccaggggagat caaattattg ccatgtactt ggaagacggt
12361 ttcaaattga tcaaacactt ggaacccttg tgtgtcagct gtatacaaac acatggcatc
12421 tttacaccag gaaaatactg gttccaatca cagaggattg agtcatatta tgaggagctc
12481 tgtagtctca attggaaatt taaaatttca ggcaataaag ctgagtgtgc tcaaaacttt
12541 attaaaacta taattcaggg gaaattgact cctcaacaat actgtgaatt attctctcta
12601 caaaagcatt ggggtcaccc cgttttatac attgatgttg cactagataa ggttaaaaaa
12661 catgcgcaat ctgtaaaaat cttaaaacct aaagtcatgt ttgaaacttt ttgtgttttc
12721 aaatttatag tagcaaagaa tcattatcat tctcaaggat catggtataa aaccacaatg
12781 gatttgcatt taactccata tcttagacaa catattgtgt caaattcatt tccgtcacaa
12841 gccgaaattt atcagcatct ttgggagtgg tatttcgtgg agcatgaacc tcttttctca
12901 actaaaataa taagtgattt aagtattttt ataaaagaca gggctactgc tgtgaaccag
12961 gagtgttggg acagtgtttt cgatagaagt gtattagggt ataacccctcc tgttagattt
13021 cagtcaaaga gagtgccaga gcaattttg ggccaagcag acttttcctt gaatcaaata
13081 ttggattttg ctgaaaagtt agaatatttg gctccttctt ataggaattt ttccttctca
13141 ttaaaagaaa aagagttgaa tataggaaga acttttggga aattaccata tcgtgtcaga
13201 aatgtccaaa cactcgcaga agccttgcta gcagatggac tagcaaaagc attccctagc
13261 aacatgatgg ttgttactga gagggaacag aaagaagcat tattgcatca ggcttcttgg
13321 caccacaatt cagcaagcat aggggaaaac gctataglaa ggggtgcaag tttgttact
13381 gatcttgaga atacaaacct tgccttccga tatgaattta cacgacattt catagactac
13441 tgtaatcgat gttatggtgt gaagaattta ttcgattgga tgcacttttt aataccacta
13501 tgttatatgc atgtcagtga tttttatagc ccaccacatt gcgtaacaga agataaccga
13561 aataacccac cggattgtgc taatgcttat cattatcact taggggggtat agagggactt
13621 caacagaaat tgtggacatg tatatcatgt gcccagatca cccttgtaga gttaaaaact
13681 aaattaaaat taaaatccag tgttatgggt gataatcaat gtaacaaac tctaagtctt
13741 tttccaattg atgctcccga cgattatcaa gagaacgaag ctgaattaaa tgcggcacga
13801 gttgctgtcg aattagctat tactacgggt tatgatggta tattttgaa gcctgaagaa
13861 acatttgtcc attcagggtt cattttatttt ggtaaaaagc aatacctcaa cggtgttcaa
13921 ctgccacaat cattgaaaac aatggcaaga tgtggaccct tatctgactc tattttgat
13981 gatcttcaag gttccctggc cagtattggt acatccttg agagaggaac aagtgagaca
14041 cggcacattt ttccgagtcg ttggatagct tcatttcatt caatgttagc aataaattta
14101 ttaaatcaga atcacccttg gtttcccta gggttcagta ttgatatttc ttgtttcaaa
14161 aagcctctta cctttttcgga aaaattaatt gctcttataa cgccccaagt tctaggaggg
14221 ttatcatttt tgaatccgga gaaattgttc taccggaaca taagtgatcc gctcacttcg
14281 ggtctatttc aacttaagaa tgcattagaa tttcttgaaa aggaagaatt attctatatc
14341 ttgattgcta aaaaacctgg tttagcagat gcctcagatt tcgtcatgaa tccattaggc
14401 ttaaatgtac caggatcaag ggaaataata acgttcctta gacaaacagt tcgtgaaaat
```

FIG. 18II

```
14461 atcacgatca cgtcacaaaa tagaataata aattcccttt ttcacatagg ttctgattta
14521 gaggaccaaa gggtgtgtga gtggcttta tcatcaaacc ccgtaatgag tcgatttgct
14581 gctgacatct tttcaagaac gcctagtgga aaacggcttc aggtcttagg ctatctggaa
14641 ggaacaagaa cattactagc ttctcggaca ataagtttaa ctacagaagg gacaatgttg
14701 atgaaattaa gggaattaac aagaaaccga tggaaaagct ggttttctta tattgatgca
14761 ttggacgatg atttatctga gtccttagaa aaattcacat gtactgttga tatagctaat
14821 ttcttgaggg catattcatg gctcgacgtc ttaaaaggga aaaggctaat tggtgccaca
14881 ttgccatgtt tactagagca atttaaggta aagtggatta atttgtctga ggatttaagg
14941 gaacaattta atatgtcttc agaatcagaa tcaactataa atttattgcc gtatgactgc
15001 aaggaactgc gacttggaag aagcaatgac acagagttaa actatgtcag ttgtgctctc
15061 gaccggaaag ttgtccagaa acatccctct gttaatcgtc tggcttggac aataggaaat
15121 cgagcaccgt atataggatc acggacagaa gacaagatcg gttatcctcc cttaagagta
15181 aattgtccat cagcggcact taaagaagcc attgagatgg tttctagatt gttgtgggtg
15241 actcaaggca ctgcagaccg agaaaaattg cttattcctc tcctcaattc gagggtaaat
15301 ctggactatc agacagtgct taactttta cctacacact actcaggcaa catagttcat
15361 agatataatg accaatatgg acaacattcc tttatggcaa acaggatgag taatacatct
15421 acacgtgcaa ttatatcaac taacacactg ggcaaatatg ctgggggggg tcaagctgct
15481 gttgatagta atataatctt ccaaaatact atcaatttag gagtggcagt tttagatatt
15541 gcattatctc ttgctaaatt gtcgtcagca tcaaatgtca ctttccgttt gatgttaaat
15601 aagtgctgca cgcggcatgt gccatctgaa tacctatttt ttgataaacc tttagatgtg
15661 gatttgaaca agtatatgga caatgagtta gtttatgaca atgaccctct ttgcagtggg
15721 attaaaggga gattaggcag agtatcccga tcaacactct cgttgagttt gaatgtcagt
15781 gacattggtt cttatgactt tccaactatt gctgcatgga cactaggaga aactatagtc
15841 ggaagcattt tttctgatga gtcttctcaa agtacagatc caataagttc aggttgcaca
15901 aaaactttcg tcacacattt ccttgtgtat ccagttgaga gtatttttta tgcattcggg
15961 gctaacttaa tagtagaaag tttaagtcta gtaggatca aatcaattaa gaacctctca
16021 gatttgacat tccttatatc atccacaatc aggaatttat cacatagatc acttcggatt
16081 cttcaatcta ccttccgaca tgaattggta ctcacccgac tagcccacca cataccgtta
16141 atttcttaa tgttagggggg ttctgcagga gagaaaagtt catcagatgc tgttcggcta
16201 ttcttacag caagttacca gaattcatc aacaacttca gttgtttgat gaaaaagggc
16261 cagtcatcac taccggtttg gctttactt cctagtgaag ggcaacaatt aaaacctata
16321 ttaaaaatct tacagagatt atcagacttg ttatcacctg acaaagttca aaagcatcaa
16381 atcttagctg acacctgttg tccaattgac agcttttggg tctatccaag caagtccaca
16441 aggactaacc actattatgc aagccttaat tattggagag acaaagctaa taaggtcaag
16501 aatactcctt tttcgcattt gataaattgt tcatttcttg aactttcttc acacaccagt
16561 tcggtctctt ctaatcaaca agtgaccaat tcgaaatata ttgttcatcc agagaatatc
16621 cctgaaataa atgcaagaac caaattaata gattatggat caacagctct acaggggatg
```

FIG. 18JJ 16681 gatatcaaga tgccactctc ggagcaaaat ctggttggaa attgtcgacc atcaaagggc
16741 attagattca aggacaatcc aaaaacaaca aaacatgacc agggatttgt ggggaaggac
16801 tcttcaccgc gaccaatgtc ccctgaagac aacatgcaga ctcctgcata catacatagt
16861 tcccccccat atcaaacccct tacaaaatca ccagatgtac atgaggactt tgatgcctcg
16921 aaggtaatct taaattctga aataaataac cttaacctta cggattgtac gcttaataca
16981 aagtcattga caactcctac cgggacagaa atcttaggta taagtccgtt cagatcctct
17041 agatattcat caacttccag ggaacggtct cgactatcta gagaacaagc ttcatatttg
17101 tatgttgatt gcagtaatat tccctctatc tctctagacc cgggttttca gaatatgtct
17161 gatcagaatc aagttcaaat gttaatcaat acctacaaac gtgatttaca tgcttgtttt
17221 gatagcaatc aattctgtcg gtttacaggg gtagtctcat caatgcatta caagctttat
17281 gatctcttgc ctccaggtga attgagaaag gcaatttgct tggccgaagg agaaggaagt
17341 ggtgctcggt tacttttgaa gtggaagaag acggattatt tattttcaa cactttggct
17401 acggattcac agcaagaagc agagatttta agtggccggg taataccgag aatgttatat
17461 aacatagata ggttaaatgc tttgcttgaa tcaagaagat taatattgaa caacctaact
17521 atccaaatta cagatattac aagtccacta tggctagatt ctgtaataca atacttacct
17581 gaagatagcg acattcttac aatggacgca gagaccacta aagatgaaac aagggaacag
17641 ctttataaga ctattgtgaa tatttggaca cgtacttctc ctaatattcc aaaaattagc
17701 atcatcaagg tattttatt agactatgaa gggactttgt tcttaatgag gaatgccatt
17761 cagtattatg ggcaggttca actcaagaaa ccatatagct caaatgcaaa aaactcagaa
17821 tggtacttgt gttgcggtaa acgaagaatt caacgactca aaattgattt ctcagaccag
17881 gtaggaattt ttctgatttg taaagcaatg tcgcgccaaa gacaagcaat tccttactgg
17941 ttaaaacata tagaaaagaa ttatcctgct tcattacata agttttttcct aacttgggt
18001 ttcccttctt tagagtcatc tttctgccat cgttatacta ttccattcag tgaaggaaag
18061 gctctttttc ataaggtcca atcttatgtt cgtcaaggca acaacatttt acattctctt
18121 atgttggatt atgaaaacaa ttcacctcta ctagacttga gaaatcactt tatttgctca
18181 ttgagggaaa agataactaa gtattacaat gatatattaa agttaaatct agttatcaag
18241 gcagtagaga aaggtaaaaa ttggtcacaa cttgttgaga cccttcctaa tatgcattca
18301 gtctgcatag tacacgtgga tcatgagtgc tttggatgtg agaaacggtt actactcaaa
18361 ttggatttta ttagaaacac aaagatcgca gaacaaaaat tacttaatag agtaatcggg
18421 tatatttttat tctttccgtt cggtctgttt aaatctgaat cattaacagc ataacttttaa
18481 caaagagaac ttcatttaat tcacgaaaat aatctatta aaaatgaggg ttacattttc
18541 tagagtattg tatgagaaat aataaaataa acaagaagaa gaaaaaacta ttagacagct
18601 tgctttacac aagataatct tatatcgtct caaaccgtac acaagtaggg aaatcacgcg
18661 cacaaattaa cttgtgattg aacgttcggt cacaccagtg gtaacttttc aatgttagtt
18721 actcaaatat tattgctcat aattggtatt gatattggta cattgggtga gtccttgagc
18781 tttatcctta atataatgta agaaattagg gaaatactga gatatactag ttgaattgag
18841 ttatgacata ccatatatca taaatataaa agaacgatct gctgtaatct ataagcatct

FIG. 18KK 18901 cttttacata tcattggggaa agaactaggt tatcgttgag attaaaaaga ctacgttacg
18961 ttttctctga tgacaagtga caaaatttcg tagttaaatt tctagaatgt caatgtgaat
19021 gtaaattaag aaaaaccaat atataaaatt aaaaaattaa aaaactttga tataagtaac
19081 acaaaacatt cttcatcttt tttgtgtgtc ca (SEQ ID NO:27)

AF086833, Zaire Ebola virus strain Mayinga, complete genome, 18959 bp, RNA, linear

| | |
|---|---|
| 5'UTR | 1 – 55, leader region, regulation or initiation of RNA replication |
| gene | 56 – 3026, NP |
| mRNA | 56 – 3026, NP |
| misc signal | 56 – 67, transcription start signal for NP |
| CDS | 470 – 2689, NP |

MDSRPQKIWMAPSLTESDMDYHKILTAGLSVQQGIVRQRVIPVYQVNNLEEICQLIIQAFEAGVDF
QESADSFLLMLCLHHAYQGDYKLFLESGAVKYLEGHGFRFEVKKRDGVKRLEELLPAVSSGKNI
KRTLAAMPEEETTEANAGQFLSFASLFLPKLVVGEKACLEKVQRQIQVHAEQGLIQYPTAWQSV
GHMMVIFRLMRTNFLIKFLLIHQGMHMVAGHDANDAVISNSVAQARFSGLLIVKTVLDHILQKTER
GVRLHPLARTAKVKNEVNSFKAALSSLAKHGEYAPFARLLNLSGVNNLEHGLFPQLSAIALGVAT
AHGSTLAGVNVGEQYQQLREAATEAEKQLQQYAESRELDHLGLDDQEKKILMNFHQKKNEISFQ
QTNAMVTLRKERLAKLTEAITAASLPKTSGHYDDDDDIPFPGPINDDDNPGHQDDDPTDSQDTTI
PDVVVDPDDGSYGEYQSYSENGMNAPDDLVLFDLDEDDEDTKPVPNRSTKGGQQKNSQKGQH
IEGRQTQSRPIQNVPGPHRTIHHASAPLTDNDRRNEPSGSTSPRMLTPINEEADPLDDADDETSS
LPPLESDDEEQDRDGTSNRTPTVAPPAPVYRDHSEKKELPQDEQQDQDHTQEARNQDSDNTQ
SEHSFEEMYRHILRSQGPFDAVLYYHMMKDEPVVFSTSDGKEYTYPDSLEEEYPPWLTEKEAM
NEENRFVTLDGQQFYWPVMNHKNKFMAILQHHQ (SEQ ID NO:28)

| | |
|---|---|
| polyA signal | 3015 – 3026, NP |
| misc feature | 3027 – 3031, intergenic region |
| gene | 3032 – 4407, VP35 |
| mRNA | 3032 – 4407, VP35 |
| misc signal | 3032 – 3043, transcription start signal for VP35 |
| CDS | 3129 – 4151, VP35 |

MTTRTKGRGHTAATTQNDRMPGPELSGWISEQLMTGRIPVSDIFCDIENNPGLCYASQMQQTKP
NPKTRNSQTQTDPICNHSFEEVVQTLASLATVVQQQTIASESLEQRITSLENGLKPVYDMAKTISS
LNRVCAEMVAKYDLLVMTTGRATATAAATEAYWAEHGQPPPGPSLYEESAIRGKIESRDETVPQ
SVREAFNNLNSTTSLTEENFGKPDISAKDLRNIMYDHLPGFGTAFHQLVQVICKLGKDSNSLDIIH

FIG. 18LL

AEFQASLAEGDSPQCALIQITKRVPIFQDAAPPVIHIRSRGDIPRACQKSLRPVPPSPKIDRGWVC
VFQLQDGKTLGLKI (SEQ ID NO:29)

| gene | 4390 – 5894, VP40 |
|---|---|
| mRNA | 4390 – 5894, VP40 |
| misc signal | 4390 – 4401, transcription start signal for VP40 |
| polyA signal | 4397 – 4407, VP35 |
| CDS | 4479 – 5459, VP40 |

MRRVILPTAPPEYMEAIYPVRSNSTIARGGNSNTGFLTPESVNGDTPSNPLRPIADDTIDHASHTP
GSVSSAFILEAMVNVISGPKVLMKQIPIWLPLGVADQKTYSFDSTTAAIMLASYTITHFGKATNPLV
RVNRLGPGIPDHPLRLLRIGNQAFLQEFVLPPVQLPQYFTFDLTALKLITQPLPAATWTDDTPTGS
NGALRPGISFHPKLRPILLPNKSGKKGNSADLTSPEKIQAIMTSLQDFKIVPIDPTKNIMGIEVPETL
VHKLTGKKVTSKNGQPIIPVLLPKYIGLDPVAPGDLTMVITQDCDTCHSPASLPAVIEK (SEQ ID
NO:30)

| polyA signal | 5883 – 5894, VP40 |
|---|---|
| misc feature | 5895 – 5899, intergenic region |
| gene | 5900 – 8305, GP |
| mRNA | 5900 – 8305, sGP |
| misc signal | 5900 – 5911, transcription start signal for GP |
| CDS | join(6039..6923,6923..8068), GP, an additional A residue is inserted during | transcription; encodes two disulfide linked subunits GP1 and GP2

MGVTGILQLPRDRFKRTSFFLWVIILFQRTFSIPLGVIHNSTLQVSDVDKLVCRDKLSSTNQLRSV
GLNLEGNGVATDVPSATKRWGFRSGVPPKVVNYEAGEWAENCYNLEIKKPDGSECLPAAPDGI
RGFPRCRYVHKVSGTGPCAGDFAFHKEGAFFLYDRLASTVIYRGTTFAEGVVAFLILPQAKKDFF
SSHPLREPVNATEDPSSGYYSTTIRYQATGFGTNETEYLFEVDNLTYVQLESRFTPQFLLQLNETI
YTSGKRSNTTGKLIWKVNPEIDTTIGEWAFWETKKNLTRKIRSEELSFTVVSNGAKNISGQSPART
SSDPGTNTTTEDHKIMASENSSAMVQVHSQGREAAVSHLTTLATISTSPQSLTTKPGPDNSTHN
TPVYKLDISEATQVEQHHRRTDNDSTASDTPSATTAAGPPKAENTNTSKSTDFLDPATTTSPQN
HSETAGNNNTHHQDTGEESASSGKLGLITNTIAGVAGLITGGRRTRREAIVNAQPKCNPNLHYW
TTQDEGAAIGLAWIPYFGPAAEGIYIEGLMHNQDGLICGLRQLANETTQALQLFLRATTELRTFSIL
NRKAIDFLLQRWGGTCHILGPDCCIEPHDWTKNITDKIDQIIHDFVDKTLPDQGDNDNWWTGWR
QWIPAGIGVTGVIIAVIALFCICKFVF (SEQ ID NO:31)

FIG. 18MM misc feature 7529 – 7540, encodes the GP cleavage site, precursor, GP is cleaved by subtilisin-like cellular protease furin into subunits GP1 and GP2 that are linked by a disulfide bond misc feature 7793 – 7870, immunosuppressive motif of GP misc feature 7988 – 8053, GP, transmembrane anchor; transmembrane-region site CDS 6039 – 7133, GP, small non-structural, secreted glycoprotein; sGP secreted as a anti-parallel oriented homodimer MGVTGILQLPRDRFKRTSFFLWVIILFQRTFSIPLGVIHNSTLQVSDVDKLVCRDKLSSTNQLRSV
GLNLEGNGVATDVPSATKRWGFRSGVPPKVVNYEAGEWAENCYNLEIKKPDGSECLPAAPDGI
RGFPRCRYVHKVSGTGPCAGDFAFHKEGAFFLYDRLASTVIYRGTTFAEGVVAFLILPQAKKDFF
SSHPLREPVNATEDPSSGYYSTTIRYQATGFGTNETEYLFEVDNLTYVQLESRFTPQFLLQLNETI
YTSGKRSNTTGKLIWKVNPEIDTTIGEWAFWETKKTSLEKFAVKSCLSQLYQTEPKTSVVRVRRE
LLPTQGPTQQLKTTKSWLQKIPLQWFKCTVKEGKLQCRI (SEQ ID NO:32)

CDS join(6039..6922,6924..6933), GP, second non-structural secreted glycoprotein; secreted in a monomeric form; one A residue is deleted or two additional A residues are inserted at the editing site during transcription of the GP gene MGVTGILQLPRDRFKRTSFFLWVIILFQRTFSIPLGVIHNSTLQVSDVDKLVCRDKLSSTNQLRSV
GLNLEGNGVATDVPSATKRWGFRSGVPPKVVNYEAGEWAENCYNLEIKKPDGSECLPAAPDGI
RGFPRCRYVHKVSGTGPCAGDFAFHKEGAFFLYDRLASTVIYRGTTFAEGVVAFLILPQAKKDFF
SSHPLREPVNATEDPSSGYYSTTIRYQATGFGTNETEYLFEVDNLTYVQLESRFTPQFLLQLNETI
YTSGKRSNTTGKLIWKVNPEIDTTIGEWAFWETKKPH (SEQ ID NO:33)

misc signal 6918 – 6924, GP, additional A residues are inserted or deleted during transcription of the GP gene by the viral polymerase for RNA editing gene 8288 – 9740, VP30 mRNA 8288 – 9740, VP30 misc signal 8288 – 8299, transcription start signal for VP30 polyA signal 8295 – 8305, GP

CDS 8509 – 9375, VP30

MEASYERGRPRAARQHSRDGHDHHVRARSSSRENYRGEYRQSRSASQVRVPTVFHKKRVEPL
TVPPAPKDICPTLKKGFLCDSSFCKKDHQLESLTDRELLLLIARKTCGSVEQQLNITAPKDSRLAN
PTADDFQQEEGPKITLLTLIKTAEHWARQDIRTIEDSKLRALLTLCAVMTRKFSKSQLSLLCETHLR
REGLGQDQAEPVLEVYQRLHSDKGGSFEAALWQQWDRQSLIMFITAFLNIALQLPCESSAVVVS
GLRTLVPQSDNEEASTNPGTCSWSDEGTP (SEQ ID NO:34)

FIG. 18NN

| | | |
|---|---|---|
| polyA signal | 9730 – 9740, | VP30 |
| misc feature | 9741 – 9884, | intergenic region |
| gene | 9885 – 11518, | VP24 |
| mRNA | 9885 – 11496, | VP24 |
| misc signal | 9885 – 9896, | transcription start signal for VP24 |
| CDS | 10345 – 11100, | VP24 |

MAKATGRYNLISPKKDLEKGVVLSDLCNFLVSQTIQGWKVYWAGIEFDVTHKGMALLHRLKTND
FAPAWSMTRNLFPHLFQNPNSTIESPLWALRVILAAGIQDQLIDQSLIEPLAGALGLISDWLLTTNT
NHFNMRTQRVKEQLSLKMLSLIRSNILKFINKLDALHVVNYNGLLSSIEIGTQNHTIITRTNMGFLV
ELQEPDKSAMNRMKPGPAKFSLLHESTLKAFTQGSSTRMQSLILEFNSSLAI (SEQ ID NO:35)

| | | |
|---|---|---|
| polyA signal | 11485 – 11496, | VP24 |
| misc feature | 11497 – 11500, | intergenic region |
| gene | 11501 – 18282, | L |
| mRNA | 11501 – 18282, | L |
| misc signal | 11501 – 11512, | transcription start signal for L |
| polyA signal | 11508 – 11518, | VP24 |
| CDS | 11581 – 18219, | L |

MATQHTQYPDARLSSPIVLDQCDLVTRACGLYSSYSLNPQLRNCKLPKHIYRLKYDVTVTKFLSD
VPVATLPIDFIVPVLLKALSGNGFCPVEPRCQQFLDEIIKYTMQDALFLKYYLKNVGAQEDCVDEH
FQEKILSSIQGNEFLHQMFFWYDLAILTRRGRLNRGNSRSTWFVHDDLIDILGYGDYVFWKIPISM
LPLNTQGIPHAAMDWYQASVFKEAVQGHTHIVSVSTADVLIMCKDLITCRFNTTLISKIAEIEDPVC
SDYPNFKIVSMLYQSGDYLLSILGSDGYKIIKFLEPLCLAKIQLCSKYTERKGRFLTQMHLAVNHTL
EEITEMRALKPSQAQKIREFHRTLIRLEMTPQQLCELFSIQKHWGHPVLHSETAIQKVKKHATVLK
ALRPIVIFETYCVFKYSIAKHYFDSQGSWYSVTSDRNLTPGLNSYIKRNQFPPLPMIKELLWEFYH
LDHPPLFSTKIISDLSIFIKDRATAVERTCWDAVFEPNVLGYNPPHKFSTKRVPEQFLEQENFSIEN
VLSYAQKLEYLLPQYRNFSFSLKEKELNVGRTFGKLPYPTRNVQTLCEALLADGLAKAFPSNMM
WTEREQKESLLHQASWHHTSDDFGEHATVRGSSFVTDLEKYNLAFRYEFTAPFIEYCNRCYGV
KNVFNWMHYTIPQCYMHVSDYYNPPHNLTLENRDNPPEGPSSYRGHMGGIEGLQQKLWTSISC
AQISLVEIKTGFKLRSAVMGDNQCITVLSVFPLETDADEQEQSAEDNAARVAASLAKVTSACGIFL
KPDETFVHSGFIYFGKKQYLNGVQLPQSLKTATRMAPLSDAIFDDLQGTLASIGTAFERSISETRHI
FPCRITAAFHTFFSVRILQYHHLGFNKGFDLGQLTLGKPLDFGTISLALAVPQVLGGLSFLNPEKC
FYRNLGDPVTSGLFQLKTYLRMIEMDDLFLPLIAKNPGNCTAIDFVLNPSGLNVPGSQDLTSFLRQ
IVRRTITLSAKNKLINTLFHASADFEDEMVCKWLLSSTPVMSRFAADIFSRTPSGKRLQILGYLEGT

FIG. 18OO

RTLLASKIINNNNTETPVLDRLRKITLQRWSLWFSYLDHCDNILAEALTQITCTVDLAQILREYSWAHI
LEGRPLIGATLPCMIEQFKVFWLKPYEQCPQCSNAKQPGGKPFVSVAVKKHIVSAWPNASRISW
TIGDGIPYIGSRTEDKIGQPAIKPKCPSAALREAIELASRLTWVTQGSSNSDLLIKPFLEARVNLSV
QEILQMTPSHYSGNIVHRYNDQYSPHSFMANRMSNSATRLIVSTNTLGEFSGGGQSARDSNIIFQ
NVINYAVALFDIKFRNTEATDIQYNRAHLHLTKCCTREVPAQYLTYTSTLDLDLTRYRENELIYDSN
PLKGGLNCNISFDNPFFQGKRLNIIEDDLIRLPHLSGWELAKTIMQSIISDSNNSSTDPISSGETRSF
TTHFLTYPKIGLLYSFGAFVSYYLGNTILRTKKLTLDNFLYYLTTQIHNLPHRSLRILKPTFKHASVM
SRLMSIDPHFSIYIGGAAGDRGLSDAARLFLRTSISSFLTFVKEWIINRGTIVPLWIVYPLEGQNPTP
VNNFLYQIVELLVHDSSRQQAFKTTISDHVHPHDNLVYTCKSTASNFFHASLAYWRSRHRNSNR
KYLARDSSTGSSTNNSDGHIERSQEQTTRDPHDGTERNLVLQMSHEIKRTTIPQENTHQGPSFQ
SFLSDSACGTANPKLNFDRSRHNVKFQDHNSASKREGHQIISHRLVLPFFTLSQGTRQLTSSNES
QTQDEISKYLRQLRSVIDTTVYCRFTGIVSSMHYKLDEVLWEIESFKSAVTLAEGEGAGALLLIQK
YQVKTLFFNTLATESSIESEIVSGMTTPRMLLPVMSKFHNDQIEIILNNSASQITDITNPTWFKDQR
ARLPKQVEVITMDAETTENINRSKLYEAVYKLILHHIDPSVLKAVVLKVFLSDTEGMLWLNDNLAPF
FATGYLIKPITSSARSSEWYLCLTNFLSTTRKMPHQNHLSCKQVILTALQLQIQRSPYWLSHLTQY
ADCELHLSYIRLGFPSLEKVLYHRYNLVDSKRGPLVSITQHLAHLRAEIRELTNDYNQQRQSRTQ
TYHFIRTAKGRITKLVNDYLKFFLIVQALKHNGTWQAEFKKLPELISVCNRFYHIRDCNCEERFLVQ
TLYLHRMQDSEVKLIERLTGLLSLFPDGLYRFD (SEQ ID NO:36)

polyA signal   18272 – 18282, L
3'UTR          18283 – 18959, trailer region

```
  1 cggacacaca aaaagaaaga agaatttta ggatcttttg tgtgcgaata actatgagga
 61 agattaataa ttttcctctc attgaaattt atatcggaat ttaaattgaa attgttactg
121 taatcacacc tggtttgttt cagagccaca tcacaaagat agagaacaac ctaggtctcc
181 gaagggagca agggcatcag tgtgctcagt tgaaaatccc ttgtcaacac ctaggtctta
241 tcacatcaca agttccacct cagactctgc agggtgatcc aacaaccta atagaaacat
301 tattgttaaa ggacagcatt agttcacagt caaacaagca agattgagaa ttaaccttgg
361 ttttgaactt gaacacttag gggattgaag attcaacaac cctaaagctt ggggtaaaac
421 attggaaata gttaaaagac aaattgctcg gaatcacaaa attccgagta tggattctcg
481 tcctcagaaa atctggatgg cgccgagtct cactgaatct gacatggatt accacaagat
541 cttgacagca ggtctgtccg ttcaacaggg gattgttcgg caaagagtca tcccagtgta
601 tcaagtaaac aatcttgaag aaatttgcca acttatcata caggcctttg aagcaggtgt
661 tgatttttcaa gagagtgcgg acagtttcct tctcatgctt tgtcttcatc atgcgtacca
721 gggagattac aaacttttct tggaaagtgg cgcagtcaag tatttggaag ggcacgggtt
781 ccgttttgaa gtcaagaagc gtgatggagt gaagcgcctt gaggaattgc tgccagcagt
841 atctagtgga aaaacatta agagaacact tgctgccatg ccggaagagg agacaactga
```

FIG. 18PP 901 agctaatgcc ggtcagtttc tctcctttgc aagtctattc cttccgaaat tggtagtagg 961 agaaaaggct tgccttgaga aggttcaaag gcaaattcaa gtacatgcag agcaaggact 1021 gatacaatat ccaacagctt ggcaatcagt aggacacatg atggtgattt tccgtttgat 1081 gcgaacaaat tttctgatca aatttctcct aatacaccaa gggatgcaca tggttgccgg 1141 gcatgatgcc aacgatgctg tgatttcaaa ttcagtggct caagctcgtt tttcaggctt 1201 attgattgtc aaaacagtac ttgatcatat cctacaaaag acagaacgag gagttcgtct 1261 ccatcctctt gcaaggaccg ccaaggtaaa aaatgaggtg aactccttta aggctgcact 1321 cagctccctg gccaagcatg gagagtatgc tcctttcgcc cgactttga accttctgg 1381 agtaaataat cttgagcatg gtcttttccc tcaactatcg gcaattgcac tcggagtcgc 1441 cacagcacac gggagtaccc tcgcaggagt aaatgttgga gaacagtatc aacaactcag 1501 agaggctgcc actgaggctg agaagcaact ccaacaatat gcagagtctc gcgaacttga 1561 ccatcttgga cttgatgatc aggaaaagaa aattcttatg aacttccatc agaaaaagaa 1621 cgaaatcagc ttccagcaaa caaacgctat ggtaactcta agaaaagagc gcctggccaa 1681 gctgacagaa gctatcactg ctgcgtcact gcccaaaaca agtggacatt acgatgatga 1741 tgacgacatt cccttccag gacccatcaa tgatgacgac aatcctggcc atcaagatga 1801 tgatccgact gactcacagg atacgaccat tcccgatgtg gtggttgatc ccgatgatgg 1861 aagctacggc gaataccaga gttactcgga aaacggcatg aatgcaccag atgacttggt 1921 cctattcgat ctagacgagg acgacgagga cactaagcca gtgcctaata gatcgaccaa 1981 gggtggacaa cagaagaaca gtcaaaaggg ccagcatata gagggcagac agacacaatc 2041 caggccaatt caaaatgtcc caggccctca cagaacaatc caccacgcca gtgcgccact 2101 cacggacaat gacagaagaa atgaaccctc cggctcaacc agccctcgca tgctgacacc 2161 aattaacgaa gaggcagacc cactggacga tgccgacgac gagacgtcta gccttccgcc 2221 cttggagtca gatgatgaag agcaggacag ggacggaact tccaaccgca cacccactgt 2281 cgccccaccg gctcccgtat acagagatca ctctgaaaag aaagaactcc cgcaagacga 2341 gcaacaagat caggaccaca ctcaagaggc caggaaccag gacagtgaca cacccagtc 2401 agaacactct tttgaggaga tgtatcgcca cattctaaga tcacaggggc catttgatgc 2461 tgttttgtat tatcatatga tgaaggatga gcctgtagtt ttcagtacca gtgatggcaa 2521 agagtacacg tatccagact cccttgaaga ggaatatcca ccatggctca ctgaaaaaga 2581 ggctatgaat gaagagaata gatttgttac attggatggt caacaatttt attggccggt 2641 gatgaatcac aagaataaat tcatggcaat cctgcaacat catcagtgaa tgagcatgga 2701 acaatgggat gattcaaccg acaaatagct aacattaagt agtcaaggaa cgaaaacagg 2761 aagaattttt gatgtctaag gtgtgaatta ttatcacaat aaaagtgatt cttattttg 2821 aatttaaagc tagcttatta ttactagccg tttttcaaag ttcaattga gtcttaatgc 2881 aaataggcgt taagccacag ttatagccat aattgtaact caatattcta actagcgatt 2941 tatctaaatt aaattacatt atgcttttat aacttaccta ctagcctgcc caacatttac 3001 acgatcgttt tataattaag aaaaaactaa tgatgaagat taaaaccttc atcatcctta 3061 cgtcaattga attctctagc actcgaagct tattgtcttc aatgtaaaag aaaagctggt

FIG. 18QQ 3121 ctaacaagat gacaactaga acaaagggca ggggccatac tgcggccacg actcaaaacg
3181 acagaatgcc aggccctgag ctttcgggct ggatctctga gcagctaatg accggaagaa
3241 ttcctgtaag cgacatcttc tgtgatattg agaacaatcc aggattatgc tacgcatccc
3301 aaatgcaaca aacgaagcca aacccgaaga cgcgcaacag tcaaacccaa acggacccaa
3361 tttgcaatca tagttttgag gaggtagtac aaacattggc ttcattggct actgttgtgc
3421 aacaacaaac catcgcatca gaatcattag aacaacgcat tacgagtctt gagaatggtc
3481 taaagccagt ttatgatatg gcaaaaacaa tctcctcatt gaacagggtt tgtgctgaga
3541 tggttgcaaa atatgatctt ctggtgatga caaccggtcg ggcaacagca accgctgcgg
3601 caactgaggc ttattgggcc gaacatggtc aaccaccacc tggaccatca ctttatgaag
3661 aaagtgcgat tcggggtaag attgaatcta gagatgagac cgtccctcaa agtgttaggg
3721 aggcattcaa caatctaaac agtaccactt cactaactga ggaaaatttt gggaaacctg
3781 acatttcggc aaaggatttg agaaacatta tgtatgatca cttgcctggt tttggaactg
3841 ctttccacca attagtacaa gtgatttgta aattgggaaa agatagcaac tcattggaca
3901 tcattcatgc tgagttccag gccagcctgg ctgaaggaga ctctcctcaa tgtgccctaa
3961 ttcaaattac aaaaagagtt ccaatcttcc aagatgctgc tccacctgtc atccacatcc
4021 gctctcgagg tgacattccc cgagcttgcc agaaaagctt gcgtccagtc ccaccatcgc
4081 ccaagattga tcgaggttgg gtatgtgttt ttcagcttca agatggtaaa acacttggac
4141 tcaaatttg agccaatctc ccttccctcc gaaagaggcg aataatagca gaggcttcaa
4201 ctgctgaact atagggtacg ttacattaat gatacacttg tgagtatcag ccctggataa
4261 tataagtcaa ttaaacgacc aagataaaat tgttcatatc tcgctagcag cttaaaatat
4321 aaatgtaata ggagctatat ctctgacagt attataatca attgttatta agtaacccaa
4381 accaaagtg atgaagatta agaaaaacct acctcggctg agagagtgtt ttttcattaa
4441 ccttcatctt gtaaacgttg agcaaaattg ttaaaaatat gaggcgggtt atattgccta
4501 ctgctcctcc tgaatatatg gaggccatat accctgtcag gtcaaattca acaattgcta
4561 gaggtggcaa cagcaataca ggcttcctga caccggagtc agtcaatggg gacactccat
4621 cgaatccact caggccaatt gccgatgaca ccatcgacca tgccagccac acaccaggca
4681 gtgtgtcatc agcattcatc cttgaagcta tgtgaatgt catatcgggc cccaaagtgc
4741 taatgaagca aattccaatt tggcttcctc taggtgtcgc tgatcaaaag acctacagct
4801 ttgactcaac tacggccgcc atcatgcttg cttcatacac tatcacccat ttcggcaagg
4861 caaccaatcc acttgtcaga gtcaatcggc tgggtcctgg aatcccggat catcccctca
4921 ggctcctgcg aattggaaac caggcttttcc tccaggagtt cgttcttccg ccagtccaac
4981 tacccagta tttcaccttt gatttgacag cactcaaact gatcacccaa ccactgcctg
5041 ctgcaacatg gaccgatgac actccaacag gatcaaatgg agcgttgcgt ccaggaattt
5101 catttcatcc aaaacttcgc cccattcttt tacccaacaa aagtgggaag aagggggaaca
5161 gtgccgatct aacatctccg gagaaaatcc aagcaataat gacttcactc caggacttta
5221 agatcgttcc aattgatcca accaaaaata tcatgggaat cgaagtgcca gaaactctgg
5281 tccacaagct gaccggtaag aaggtgactt ctaaaaatgg acaaccaatc atccctgttc

FIG. 18RR

```
5341 ttttgccaaa gtacattggg ttggacccgg tggctccagg agacctcacc atggtaatca
5401 cacaggattg tgacacgtgt cattctcctg caagtcttcc agctgtgatt gagaagtaat
5461 tgcaataatt gactcagatc cagttttata gaatcttctc agggatagtg ataacatcta
5521 tttagtaatc cgtccattag aggagacact tttaattgat caatatacta aaggtgcttt
5581 acaccattgt cttttttctc tcctaaatgt agaacttaac aaaagactca taatatactt
5641 gttttaaag gattgattga tgaaagatca taactaataa cattacaaat aatcctacta
5701 taatcaatac ggtgattcaa atgttaatct ttctcattgc acatactttt tgcccttatc
5761 ctcaaattgc ctgcatgctt acatctgagg atagccagtg tgacttggat tggaaatgtg
5821 gagaaaaaat cgggacccat ttctaggttg ttcacaatcc aagtacagac attgcccttc
5881 taattaagaa aaaatcggcg atgaagatta agccgacagt gagcgtaatc ttcatctctc
5941 ttagattatt tgttttccag agtaggggtc gtcaggtcct tttcaatcgt gtaaccaaaa
6001 taaactccac tagaaggata ttgtggggca acaacacaat gggcgttaca ggaatattgc
6061 agttacctcg tgatcgattc aagaggacat cattctttct ttgggtaatt atcctttcc
6121 aaagaacatt ttccatccca cttggagtca tccacaatag cacattacag gttagtgatg
6181 tcgacaaact agtttgtcgt gacaaactgt catccacaaa tcaattgaga tcagttggac
6241 tgaatctcga agggaatgga gtggcaactg acgtgccatc tgcaactaaa agatggggct
6301 tcaggtccgg tgtcccacca aaggtggtca attatgaagc tggtaatgg gctgaaaact
6361 gctacaatct tgaaatcaaa aaacctgacg ggagtgagtg tctaccagca gcgccagacg
6421 ggattcgggg cttcccccgg tgccggtatg tgcacaaagt atcaggaacg ggaccgtgtg
6481 ccggagactt tgccttccat aaagagggtg ctttcttcct gtatgatcga cttgcttcca
6541 cagttatcta ccgaggaacg actttcgctg aaggtgtcgt tgcatttctg atactgcccc
6601 aagctaagaa ggacttcttc agctcacacc ccttgagaga gccggtcaat gcaacggagg
6661 acccgtctag tggctactat tctaccacaa ttagatatca ggctaccggt tttggaacca
6721 atgagacaga gtacttgttc gaggttgaca atttgaccta cgtccaactt gaatcaagat
6781 tcacaccaca gtttctgctc cagctgaatg agacaatata tacaagtggg aaaaggagca
6841 ataccacggg aaaactaatt tggaaggtca accccgaaat tgatacaaca atcggggagt
6901 gggccttctg ggaaactaaa aaaacctcac tagaaaaatt cgcagtgaag agttgtcttt
6961 cacagttgta tcaaacgag ccaaaaaacat cagtggtcag agtccggcgc gaacttcttc
7021 cgacccaggg accaacacaa caactgaaga ccacaaaatc atggcttcag aaaattcctc
7081 tgcaatggtt caagtgcaca gtcaaggaag ggaagctgca gtgtcgcatc taacaaccct
7141 tgccacaatc tccacgagtc cccaatccct cacaaccaaa ccaggtccgg acaacagcac
7201 ccataataca cccgtgtata aacttgacat ctctgaggca actcaagttg aacaacatca
7261 ccgcagaaca gacaacgaca gcacagcctc cgacactccc tctgccacga ccgcagccgg
7321 acccccaaaa gcagagaaca ccaacacgag caagagcact gacttcctgg accccgccac
7381 cacaacaagt ccccaaaacc acagcgagac cgctggcaac aacaacactc atcaccaaga
7441 taccggagaa gagagtgcca gcagcgggaa gctaggctta attaccaata ctattgctgg
7501 agtcgcagga ctgatcacag gcgggagaag aactcgaaga gaagcaattg tcaatgctca
```

FIG. 18SS

```
7561 acccaaatgc aaccctaatt tacattactg gactactcag gatgaaggtg ctgcaatcgg
7621 actggcctgg ataccatatt tcgggccagc agccgaggga atttacatag aggggctaat
7681 gcacaatcaa gatggtttaa tctgtgggtt gagacagctg gccaacgaga cgactcaagc
7741 tcttcaactg ttcctgagag ccacaactga gctacgcacc ttttcaatcc tcaaccgtaa
7801 ggcaattgat ttcttgctgc agcgatgggg cggcacatgc cacattctgg gaccggactg
7861 ctgtatcgaa ccacatgatt ggaccaagaa cataacagac aaaattgatc agattattca
7921 tgattttgtt gataaaaccc ttccggacca gggggacaat gacaattggt ggacaggatg
7981 gagacaatgg ataccggcag gtattggagt tacaggcgtt ataattgcag ttatcgcttt
8041 attctgtata tgcaaatttg tcttttagtt tttcttcaga ttgcttcatg gaaaagctca
8101 gcctcaaatc aatgaaacca ggatttaatt atatggatta cttgaatcta agattacttg
8161 acaaatgata atataataca ctggagcttt aaacatagcc aatgtgattc taactccttt
8221 aaactcacag ttaatcataa acaaggtttg acatcaatct agttatctct ttgagaatga
8281 taaacttgat gaagattaag aaaaaggtaa tctttcgatt atctttaatc ttcatccttg
8341 attctacaat catgacagtt gtctttagtg acaagggaaa gaagcctttt tattaagttg
8401 taataatcag atctgcgaac cggtagagtt tagttgcaac ctaacacaca taaagcattg
8461 gtcaaaaagt caatagaaat ttaaacagtg agtggagaca acttttaaat ggaagcttca
8521 tatgagagag gacgcccacg agctgccaga cagcattcaa gggatggaca cgaccaccat
8581 gttcgagcac gatcatcatc cagagagaat tatcgaggtg agtaccgtca atcaaggagc
8641 gcctcacaag tgcgcgttcc tactgtattt cataagaaga gagttgaacc attaacagtt
8701 cctccagcac ctaaagacat atgtccgacc ttgaaaaaag gattttgtg tgacagtagt
8761 ttttgcaaaa aagatcacca gttggagagt ttaactgata gggaattact cctactaatc
8821 gcccgtaaga cttgtggatc agtagaacaa caattaaata taactgcacc caaggactcg
8881 cgcttagcaa atccaacggc tgatgatttc cagcaagagg aaggtccaaa aattaccttg
8941 ttgacactga tcaagacggc agaacactgg gcgagacaag acatcagaac catagaggat
9001 tcaaaattaa gagcattgtt gactctatgt gctgtgatga cgaggaaatt ctcaaaatcc
9061 cagctgagtc ttttatgtga gacacaccta aggcgcgagg ggcttgggca agatcaggca
9121 gaacccgttc tcgaagtata tcaacgatta cacagtgata aaggaggcag ttttgaagct
9181 gcactatggc aacaatggga ccgacaatcc ctaattatgt ttatcactgc attcttgaat
9241 attgctctcc agttaccgtg tgaaagttct gctgtcgttg tttcagggtt aagaacattg
9301 gttcctcaat cagataatga ggaagcttca accaacccgg ggacatgctc atggtctgat
9361 gagggtaccc cttaataagg ctgactaaaa cactatataa ccttctactt gatcacaata
9421 ctccgtatac ctatcatcat atatttaatc aagacgatat cctttaaaac ttattcagta
9481 ctataatcac tctcgtttca aattaataag atgtgcatga ttgccctaat atatgaagag
9541 gtatgataca accctaacag tgatcaaaga aaatcataat ctcgtatcgc tcgtaatata
9601 acctgccaag catacctctt gcacaaagtg attcttgtac acaaataatg ttttactcta
9661 caggaggtag caacgatcca tcccatcaaa aaataagtat ttcatgactt actaatgatc
9721 tcttaaaata ttaagaaaaa ctgacggaac ataaattctt tatgcttcaa gctgtggagg
```

FIG. 18TT 9781 aggtgtttgg tattggctat tgttatatta caatcaataa caagcttgta aaaatattgt
9841 tcttgtttca agaggtagat tgtgaccgga aatgctaaac taatgatgaa gattaatgcg
9901 gaggtctgat aagaataaac cttattattc agattaggcc ccaagaggca ttcttcatct
9961 ccttttagca aagtactatt tcagggtagt ccaattagtg gcacgtcttt tagctgtata
10021 tcagtcgccc ctgagatacg ccacaaaagt gtctctaagc taaattggtc tgtacacatc
10081 ccatacattg tattaggggc aataatatct aattgaactt agccgtttaa aatttagtgc
10141 ataaatctgg gctaacacca ccaggtcaac tccattggct gaaaagaagc ttacctacaa
10201 cgaacatcac tttgagcgcc ctcacaatta aaaaatagga acgtcgttcc aacaatcgag
10261 cgcaaggttt caaggttgaa ctgagagtgt ctagacaaca aaatattgat actccagaca
10321 ccaagcaaga cctgagaaaa aaccatggct aaagctacgg gacgatacaa tctaatatcg
10381 cccaaaaagg acctggagaa aggggttgtc ttaagcgacc tctgtaactt cttagttagc
10441 caaactattc aggggtggaa ggtttattgg gctggtattg agtttgatgt gactcacaaa
10501 ggaatggccc tattgcatag actgaaaact aatgactttg cccctgcatg gtcaatgaca
10561 aggaatctct ttcctcattt atttcaaaat ccgaattcca caattgaatc accgctgtgg
10621 gcattgagag tcatccttgc agcagggata caggaccagc tgattgacca gtctttgatt
10681 gaacccttag caggagccct tggtctgatc tctgattggc tgctaacaac caacactaac
10741 catttcaaca tgcgaacaca acgtgtcaag gaacaattga gcctaaaaat gctgtcgttg
10801 attcgatcca atattctcaa gtttattaac aaattggatg ctctacatgt cgtgaactac
10861 aacggattgt tgagcagtat tgaaattgga actcaaaatc atacaatcat cataactcga
10921 actaacatgg gttttctggt ggagctccaa gaacccgaca aatcggcaat gaaccgcatg
10981 aagcctgggc cggcgaaatt ttccctcctt catgagtcca cactgaaagc atttacacaa
11041 ggatcctcga cacgaatgca aagtttgatt cttgaattta atagctctct tgctatctaa
11101 ctaaggtaga atacttcata ttgagctaac tcatatatgc tgactcaata gttatcttga
11161 catctctgct ttcataatca gatatataag cataataaat aaatactcat atttcttgat
11221 aatttgttta accacagata aatcctcact gtaagccagc ttccaagttg acacccttac
11281 aaaaaccagg actcagaatc cctcaaacaa gagattccaa gacaacatca tagaattgct
11341 ttattatatg aataagcatt ttatcaccag aaatcctata tactaaatgg ttaattgtaa
11401 ctgaacccgc aggtcacatg tgttaggttt cacagattct atatattact aactctatac
11461 tcgtaattaa cattagataa gtagattaag aaaaaagcct gaggaagatt aagaaaaact
11521 gcttattggg tctttccgtg ttttagatga agcagttgaa attcttcctc ttgatattaa
11581 atggctacac aacataccca atacccagac gctaggttat catcaccaat tgtattggac
11641 caatgtgacc tagtcactag agcttgcggg ttatattcat catactccct taatccgcaa
11701 ctacgcaact gtaaactccc gaaacatatc taccgtttga aatacgatgt aactgttacc
11761 aagttcttga gtgatgtacc agtggcgaca ttgcccatag atttcatagt cccagttctt
11821 ctcaaggcac tgtcaggcaa tggattctgt cctgttgagc cgcggtgcca acagttctta
11881 gatgaaatca ttaagtacac aatgcaagat gctctcttct tgaaatatta tctcaaaaat
11941 gtgggtgctc aagaagactg tgttgatgaa cactttcaag agaaaatctt atcttcaatt

FIG. 18UU

```
12001 cagggcaatg aatttttaca tcaaatgttt ttctggtatg atctggctat tttaactcga
12061 aggggtagat taaatcgagg aaactctaga tcaacatggt ttgttcatga tgatttaata
12121 gacatcttag gctatgggga ctatgttttt tggaagatcc caatttcaat gttaccactg
12181 aacacacaag gaatccccca tgctgctatg gactggtatc aggcatcagt attcaaagaa
12241 gcggttcaag ggcatacaca cattgtttct gtttctactg ccgacgtctt gataatgtgc
12301 aaagatttaa ttacatgtcg attcaacaca actctaatct caaaaatagc agagattgag
12361 gatccagttt gttctgatta tcccaatttt aagattgtgt ctatgcttta ccagagcgga
12421 gattacttac tctccatatt agggtctgat gggtataaaa ttattaagtt cctcgaacca
12481 ttgtgcttgg ccaaaattca attatgctca aagtacactg agaggaaggg ccgattctta
12541 acacaaatgc atttagctgt aaatcacacc ctagaagaaa ttacagaaat gcgtgcacta
12601 aagccttcac aggctcaaaa gatccgtgaa ttccatagaa cattgataag gctggagatg
12661 acgccacaac aactttgtga gctatttttcc attcaaaaac actgggggca tcctgtgcta
12721 catagtgaaa cagcaatcca aaaagttaaa aaacatgcta cggtgctaaa agcattacgc
12781 cctatagtga ttttcgagac atactgtgtt tttaaatata gtattgccaa acattatttt
12841 gatagtcaag gatcttggta cagtgttact tcagatagga atctaacacc gggtcttaat
12901 tcttatatca aaagaaatca attccctccg ttgccaatga ttaaagaact actatgggaa
12961 ttttaccacc ttgaccaccc tccacttttc tcaaccaaaa ttattagtga cttaagtatt
13021 tttataaaag acagagctac cgcagtagaa aggacatgct gggatgcagt attcgagcct
13081 aatgttctag gatataatcc acctcacaaa tttagtacta aacgtgtacc ggaacaattt
13141 ttagagcaag aaaactttttc tattgagaat gttctttcct acgcacaaaa actcgagtat
13201 ctactaccac aatatcggaa cttttctttc tcattgaaag agaaagagtt gaatgtaggt
13261 agaaccttcg gaaaattgcc ttatccgact cgcaatgttc aaacactttg tgaagctctg
13321 ttagctgatg gtcttgctaa agcatttcct agcaatatga tggtagttac ggaacgtgag
13381 caaaaagaaa gcttattgca tcaagcatca tggcaccaca caagtgatga ttttggtgaa
13441 catgccacag ttagagggag tagctttgta actgatttag agaaatacaa tcttgcattt
13501 agatatgagt ttacagcacc tttatagaaa tattgcaacc gttgctatgg tgttaagaat
13561 gtttttaatt ggatgcatta tacaatccca cagtgttata tgcatgtcag tgattattat
13621 aatccaccac ataacctcac actggagaat cgagacaacc cccccgaagg gcctagttca
13681 tacaggggtc atatgggagg gattgaagga ctgcaacaaa aactctggac aagtatttca
13741 tgtgctcaaa tttcttttagt tgaaattaag actggtttta agttacgctc agctgtgatg
13801 ggtgacaatc agtgcattac tgtttatca gtcttcccct tagagactga cgcagacgag
13861 caggaacaga gcgccgaaga caatgcagcg agggtggccg ccagcctagc aaaagttaca
13921 agtgcctgtg gaatcttttt aaaacctgat gaaacatttg tacattcagg tttatctat
13981 tttggaaaaa aacaatattt gaatggggtc caattgcctc agtcccttaa aacggctaca
14041 agaatggcac cattgtctga tgcaattttt gatgatcttc aagggaccct ggctagtata
14101 ggcactgctt tgagcgatc catctctgag acacgacata tctttccttg caggataacc
14161 gcagctttcc atacgttttt ttcggtgaga atcttgcaat atcatcatct cgggttcaat
```

FIG. 18VV

```
14221 aaaggttttg accttggaca gttaacactc ggcaaacctc tggatttcgg aacaatatca
14281 ttggcactag cggtaccgca ggtgcttgga gggttatcct tcttgaatcc tgagaaatgt
14341 ttctaccgga atctaggaga tccagttacc tcaggcttat tccagttaaa aacttatctc
14401 cgaatgattg agatggatga tttattctta cctttaattg cgaagaaccc tgggaactgc
14461 actgccattg actttgtgct aaatcctagc ggattaaatg tccctgggtc gcaagactta
14521 acttcatttc tgcgccagat tgtacgcagg accatcaccc taagtgcgaa aaacaaactt
14581 attaatacct tatttcatgc gtcagctgac ttcgaagacg aaatggtttg taaatggcta
14641 ttatcatcaa ctcctgttat gagtcgtttt gcggccgata tcttttcacg cacgccgagc
14701 gggaagcgat tgcaaattct aggatacctg gaaggaacac gcacattatt agcctctaag
14761 atcatcaaca ataatacaga gacaccggtt ttggacagac tgaggaaaat aacattgcaa
14821 aggtggagcc tatggtttag ttatcttgat cattgtgata atatcctggc ggaggcttta
14881 acccaaataa cttgcacagt tgatttagca cagattctga gggaatattc atgggctcat
14941 attttagagg gaagacctct tattggagcc acactcccat gtatgattga gcaattcaaa
15001 gtgttttggc tgaaaccta cgaacaatgt ccgcagtgtt caaatgcaaa gcaaccaggt
15061 gggaaaccat tcgtgtcagt ggcagtcaag aaacatattg ttagtgcatg gccgaacgca
15121 tcccgaataa gctggactat cggggatgga atcccataca ttggatcaag gacagaagat
15181 aagataggac aacctgctat taaaccaaaa tgtccttccg cagccttaag agaggccatt
15241 gaattggcgt cccgtttaac atgggtaact caaggcagtt cgaacagtga cttgctaata
15301 aaaccatttt tggaagcacg agtaaattta agtgttcaag aaatacttca aatgaccccct
15361 tcacattact caggaaatat tgttcacagg tacaacgatc aatacagtcc tcattcttc
15421 atggccaatc gtatgagtaa ttcagcaacg cgattgattg tttctacaaa cactttaggt
15481 gagtttcag gaggtggcca gtctgcacgc gacagcaata ttatttcca gaatgttata
15541 aattatgcag ttgcactgtt cgatattaaa tttagaaaca ctgaggctac agatatccaa
15601 tataatcgtg ctcaccttca tctaactaag tgttgcaccc gggaagtacc agctcagtat
15661 ttaacataca catctacatt ggatttagat ttaacaagat accgagaaaa cgaattgatt
15721 tatgacagta atcctctaaa aggaggactc aattgcaata tctcattcga taatccatt
15781 ttccaaggta aacggctgaa cattatagaa gatgatctta ttcgactgcc tcacttatct
15841 ggatgggagc tagccaagac catcatgcaa tcaattattt cagatagcaa caattcatct
15901 acagacccaa ttagcagtgg agaaacaaga tcattcacta cccattctt aacttatccc
15961 aagataggac ttctgtacag ttttgggggcc tttgtaagtt attatcttgg caatacaatt
16021 cttcggacta agaaattaac acttgacaat tttttatatt acttaactac tcaaattcat
16081 aatctaccac atcgctcatt gcgaatactt aagccaacat tcaaacatgc aagcgttatg
16141 tcacggttaa tgagtattga tcctcatttt tctatttaca taggcggtgc tgcaggtgac
16201 agaggactct cagatgcggc caggttattt tgagaacgt ccatttcatc ttttcttaca
16261 tttgtaaaag aatggataat taatcgcgga acaattgtcc ctttatggat agtatatccg
16321 ctagagggtc aaaacccaac acctgtgaat aattttctct atcagatcgt agaactgctg
16381 gtgcatgatt catcaagaca acaggctttt aaaactacca taagtgatca tgtacatcct
```

FIG. 18WW

```
16441 cacgacaatc ttgtttacac atgtaagagt acagccagca atttcttcca tgcatcattg
16501 gcgtactgga ggagcagaca cagaaacagc aaccgaaaat acttggcaag agactcttca
16561 actggatcaa gcacaaacaa cagtgatggt catattgaga gaagtcaaga acaaaccacc
16621 agagatccac atgatggcac tgaacggaat ctagtcctac aaatgagcca tgaaataaaa
16681 agaacgacaa ttccacaaga aaacacgcac cagggtccgt cgttccagtc ctttctaagt
16741 gactctgctt gtggtacagc aaatccaaaa ctaaatttcg atcgatcgag acacaatgtg
16801 aaatttcagg atcataactc ggcatccaag agggaaggtc atcaaataat ctcacaccgt
16861 ctagtcctac ctttctttac attatctcaa gggacacgcc aattaacgtc atccaatgag
16921 tcacaaaccc aagacgagat atcaaagtac ttacggcaat tgagatccgt cattgatacc
16981 acagtttatt gtagatttac cggtatagtc tcgtccatgc attacaaact tgatgaggtc
17041 ctttgggaaa tagagagttt caagtcggct gtgacgctag cagagggaga aggtgctggt
17101 gccttactat tgattcagaa ataccaagtt aagaccttat ttttcaacac gctagctact
17161 gagtccagta tagagtcaga aatagtatca ggaatgacta ctcctaggat gcttctacct
17221 gttatgtcaa aattccataa tgaccaaatt gagattattc ttaacaactc agcaagccaa
17281 ataacagaca taacaaatcc tacttggttt aaagaccaaa gagcaaggct acctaagcaa
17341 gtcgaggtta taaccatgga tgcagagaca acagagaata taaacagatc gaaattgtac
17401 gaagctgtat ataaattgat cttacaccat attgatccta gcgtattgaa agcagtggtc
17461 cttaaagtct ttctaagtga tactgagggt atgttatggc taaatgataa tttagccccg
17521 tttttgcca ctggttattt aattaagcca ataacgtcaa gtgctagatc tagtgagtgg
17581 tatctttgtc tgacgaactt cttatcaact acacgtaaga tgccacacca aaaccatctc
17641 agttgtaaac aggtaatact tacggcattg caactgcaaa ttcaacgaag cccatactgg
17701 ctaagtcatt taactcagta tgctgactgt gagttacatt taagttatat ccgccttggt
17761 tttccatcat tagagaaagt actataccac aggtataacc tcgtcgattc aaaaagaggt
17821 ccactagtct ctatcactca gcacttagca catcttagag cagagattcg agaattaact
17881 aatgattata atcaacagcg acaaagtcgg actcaaacat atcactttat tcgtactgca
17941 aaaggacgaa tcacaaaact agtcaatgat tatttaaaat tctttcttat tgtgcaagca
18001 ttaaaacata atgggacatg gcaagctgag tttaagaaat taccagagtt gattagtgtg
18061 tgcaataggt tctaccatat tagagattgc aattgtgaag aacgtttctt agttcaaacc
18121 ttatatttac atagaatgca ggattctgaa gttaagctta tcgaaaggct gacagggctt
18181 ctgagtttat ttccggatgg tctctacagg tttgattgaa ttaccgtgca tagtatcctg
18241 atacttgcaa aggttggtta ttaacataca gattataaaa aactcataaa ttgctctcat
18301 acatcatatt gatctaatct caataaacaa ctatttaaat aacgaaagga gtccctatat
18361 tatatactat atttagcctc tctccctgcg tgataatcaa aaaattcaca atgcagcatg
18421 tgtgacatat tactgccgca atgaatttaa cgcaacataa taaactctgc actctttata
18481 attaagcttt aacgaaaggt ctgggctcat attgttattg atataataat gttgtatcaa
18541 tatcctgtca gatggaatag tgttttggtt gataacacaa cttcttaaaa caaaattgat
18601 ctttaagatt aagttttta taattatcat tactttaatt tgtcgtttta aaacggtga
```

FIG. 18XX 18661 tagccttaat ctttgtgtaa aataagagat taggtgtaat aaccttaaca tttttgtcta
18721 gtaagctact atttcataca gaatgataaa attaaaagaa aaggcaggac tgtaaaatca
18781 gaaatacctt ctttacaata tagcagacta gataataatc ttcgtgttaa tgataattaa
18841 gacattgacc acgctcatca gaaggctcgc cagaataaac gttgcaaaaa ggattcctgg
18901 aaaaatggtc gcacacaaaa atttaaaaat aaatctattt cttcttttt gtgtgtcca (SEQ ID NO:37)

AF272001, Zaire Ebola virus strain Mayinga, complete genome, 18959 bp, RNA, linear

| | | |
|---|---|---|
| misc feature | 1 – 55, leader region | |
| gene | 56 – 3026, NP | |
| mRNA | 56 – 3026, NP | |
| misc feature | 56 – 67, transcription start signal for NP | |
| CDS | 470 – 2689, NP | |

MDSRPQKIWMAPSLTESDMDYHKILTAGLSVQQGIVRQRVIPVYQVNNLEEICQLIIQAFEAGVDF
QESADSFLLMLCLHHAYQGDYKLFLESGAVKYLEGHGFRFEVKKRDGVKRLEELLPAVSSGKNI
KRTLAAMPEEETTEANAGQFLSFASLFLPKLVVGEKACLEKVQRQIQVHAEQGLIQYPTAWQSV
GHMMVIFRLMRTNFLIKFLLIHQGMHMVAGHDANDAVISNSVAQARFSGLLIVKTVLDHILQKTER
GVRLHPLARTAKVKNEVNSFKAALSSLAKHGEYAPFARLLNLSGVNNLEHGLFPQLSAIALGVAT
AHGSTLAGVNVGEQYQQLREAATEAEKQLQQYAESRELDHLGLDDQEKKILMNFHQKKNEISFQ
QTNAMVTLRKERLAKLTEAITAASLPKTSGHYDDDDDIPFPGPINDDDNPGHQDDDPTDSQDTTI
PDVVVDPDDGSYGEYQSYSENGMNAPDDLVFDLDEDDEDTKPVPNRSTKGGQQKNSQKGQH
IEGRQTQFRPIQNVPGPHRTIHHASAPLTDNDRRNEPSGSTSPRMLTPINEEADPLDDADDETSS
LPPLESDDEEQDRDGTSNRTPTVAPPAPVYRDHSEKKELPQDEQQDQDHTQEARNQDSDNTQ
SEHSLEEMYRHILRSQGPFDAVLYYHMMKDEPVVFSTSDGKEYTYPDSLEEEYPPWLTEKEAM
NEENRFVTLDGQQFYWPVMNHKNKFMAILQHHQ (SEQ ID NO:38)

| | | |
|---|---|---|
| polyA signal | 3015 – 3026, NP | |
| misc feature | 3027 – 3031, intergenic region | |
| gene | 3032 – 4407, VP35 | |
| mRNA | 3032 – 4407, VP35 | |
| misc feature | 3032 – 3043, transcription start signal for VP35 | |
| CDS | 3129 – 4151, VP35 | |

MTTRTKGRGHTAATTQNDRMPGPELSGWISEQLMTGRIPVSDIFCDIENNPGLCYASQMQQTKP
NPKTRNSQTQTDPICNHSFEEVVQTLASLATVVQQQTIASESLEQRITSLENGLKPVYDMAKTISS
LNRVCAEMVAKYDLLVMTTGRATATAAATEAYWAEHGQPPPGPSLYEESAIRGKIESRDETVPQ

FIG. 18YY

SVREAFNNLNSTTSLTEENFGKPDISAKDLRNIMYDHLPGFGTAFHQLVQVICKLGKDSNSLDIIH
AEFQASLAEGDSPQCALIQITKRVPIFQDAAPPVIHIRSRGDIPRACQKSLRPVPPSPKIDRGWVC
VFQLQDGKTLGLKI (SEQ ID NO:39)

| | |
|---|---|
| gene | 4390 – 5894, VP40 |
| mRNA | 4390 – 5894, VP40 |
| misc feature | 4390 – 4401, transcription start signal for VP35 |
| polyA signal | 4397 – 4407, VP35 |
| CDS | 4479 – 5459, VP40 |

MRRVILPTAPPEYMEAIYPVRSNSTIARGGNSNTGFLTPESVNGDTPSNPLRPIADDTIDHASHTP
GSVSSAFILEAMVNVISGPKVLMKQIPIWLPLGVADQKTYSFDSTTAAIMLASYTITHFGKATNPLV
RVNRLGPGIPDHPLRLLRIGNQAFLQEFVLPPVQLPQYFTFDLTALKLITQPLPAATWTDDTPTGS
NGALRPGISFHPKLRPILLPNKSGKKGNSADLTSPEKIQAIMTSLQDFKIVPIDPTKNIMGIEVPETL
VHKLTGKKVTSKNGQPIIPVLLPKYIGLDPVAPGDLTMVITQDCDTCHSPASLPAVIEK (SEQ ID
NO:40)

| | |
|---|---|
| polyA signal | 5883 – 5894, VP40 |
| misc feature | 5895 – 5899, intergenic region |
| gene | 5900 – 8305, GP |
| mRNA | 5900 – 8305, GP |
| misc feature | 5900 – 5911, transcription start signal for GP |
| CDS | join(6039..6923,6923..8068), GP |

MGVTGILQLPRDRFKRTSFFLWVIILFQRTFSIPLGVIHNSTLQVSDVDKLVCRDKLSSTNQLRSV
GLNLEGNGVATDVPSATKRWGFRSGVPPKVVNYEAGEWAENCYNLEIKKPDGSECLPAAPDGI
RGFPRCRYVHKVSGTGPCAGDFAFHKEGAFFLYDRLASTVIYRGTTFAEGVVAFLILPQAKKDFF
SSHPLREPVNATEDPSSGYYSTTIRYQATGFGTNETEYLFEVDNLTYVQLESRFTPQFLLQLNETI
YTSGKRSNTTGKLIWKVNPEIDTTIGEWAFWETKKNLTRKIRSEELSFTVVSNGAKNISGQSPART
SSDPGTNTTTEDHKIMASENSSAMVQVHSQGREAAVSHLTTLATISTSPQSLTTKPGPDNSTHN
TPVYKLDISEATQVEQHHRRTDNDSTASDTPSATTAAGPPKAENTNTSKSTDFLDPATTTSPQN
HSETAGNNNTHHQDTGEESASSGKLGLITNTIAGVAGLITGGRRTRREAIVNAQPKCNPNLHYW
TTQDEGAAIGLAWIPYFGPAAEGIYIEGLMHNQDGLICGLRQLANETTQALQLFLRATTELRTFSIL
NRKAIDFLLQRWGGTCHILGPDCCIEPHDWTKNITDKIDQIIHDFVDKTLPDQGDNDNWWTGWR
QWIPAGIGVTGVIIAVIALFCICKFVF (SEQ ID NO:41)

| | |
|---|---|
| CDS | 6039 – 7133, GP |

FIG. 18ZZ

MGVTGILQLPRDRFKRTSFFLWVIILFQRTFSIPLGVIHNSTLQVSDVDKLVCRDKLSSTNQLRSV
GLNLEGNGVATDVPSATKRWGFRSGVPPKVVNYEAGEWAENCYNLEIKKPDGSECLPAAPDGI
RGFPRCRYVHKVSGTGPCAGDFAFHKEGAFFLYDRLASTVIYRGTTFAEGVVAFLILPQAKKDFF
SSHPLREPVNATEDPSSGYYSTTIRYQATGFGTNETEYLFEVDNLTYVQLESRFTPQFLLQLNETI
YTSGKRSNTTGKLIWKVNPEIDTTIGEWAFWETKKTSLEKFAVKSCLSQLYQTEPKTSVVRVRRE
LLPTQGPTQQLKTTKSWLQKIPLQWFKCTVKEGKLQCRI (SEQ ID NO:42)

misc feature    6918 – 6924, GP gene editing site; additional A residues are inserted or deleted during transcription of the GP gene by the viral polymerase that resulted in a reading frame shift misc feature    6999 – 7010, encodes the glycoprotein sGP cleavage site (RVRR), precursor sGP (presGP) is cleaved by subtilisin-like proteases into two distict subunits sGP and short carboxy terminal glycopeptide (Delta peptide)

misc feature    7529 – 7540, encodes the glycoprotein GP cleavage site (RTRR), precursor GP (preGP) is cleaved by subtilisin-like proteases into subunits GP1 and GP2 that are linked by a disulfide bond misc feature    7793 – 7870, immunosuppressive motif of GP
    gene    7988 – 9740, VP30
    misc feature    7988 – 8053, GP, transmembrane anchor
    mRNA    8288 – 9740, VP30
    misc feature    8288 – 8299, transcription start signal for VP30
    polyA signal    8295 – 8305, VP30
    CDS    8509 – 9375, VP30

MEASYERGRPRAARQHSRDGHDHHVRARSSSRENYRGEYRQSRSASQVRVPTVFHKKRVEPL
TVPPAPKDICPTLKKGFLCDSSFCKKDHQLESLTDRELLLLIARKTCGSVEQQLNITAPKDSRLAN
PTADDFQQEEGPKITLLTLIKTAEHWARQDIRTIEDSKLRALLTLCAVMTRKFSKSQLSLLCETHLR
REGLGQDQAEPVLEVYQRLHSDKGGSFEAALWQQWDRQSLIMFITAFLNIALQLPCESSAVVVS
GLRTLVPQSDNEEASTNPGTCSWSDEGTP (SEQ ID NO:43)

polyA signal    9730 – 9740, VP30
    misc feature    9884 – 9896, intergenic region
    gene    9885 – 11496, VP24
    mRNA    9885 – 11496, VP24
    CDS    10345 – 11100, VP24

FIG. 18AAA

MAKATGRYNLISPKKDLEKGVVLSDLCNFLVSQTIQGWKVYWAGIEFDVTHKGMALLHRLKTND
FAPAWSITRNLFPHLFQNPNSTIESPLWALRVILAAGIQDQLIDQSLIEPLAGALGLISDWLLTTNTN
HFNMRTQRVKEQLSPKMLSLIRSNILKFINKLDALHVVNYNGLLSSIEIGTQNHIIITRTNMGFLVEL
QEPDKSAMNRMKPGPAKFSLLHESTLKAFTQGSSTRMQSLILEFNSSLAI (SEQ ID NO:44)

| | |
|---|---|
| polyA signal | 11485 – 11496, VP24 |
| misc feature | 11497 – 11500, intergenic region |
| gene | 11501 – 18282, L |
| mRNA | 11501 – 18282, L |
| misc feature | 11501 – 11512, transcription start signal for L |
| polyA signal | 11508 – 11518, L |
| CDS | 11581 – 18219, L |

MATQHTQYPDARLSSPIVLDQCDLVTRACGLYSSYSLNPQLRNCKLPKHIYRLKYDVTVTKFLSD
VPVATLPIDFIVPVLLKALSGNGFCPVEPRCQQFLDEIIKYTMQDALFLKYYLKNVGAQEDCVDEH
FQEKILSSIQGNEFLHQMFFWYDLAILTRRGRLNRGNSRSTWFVHDDLIDILGYGDYVFWKIPISM
LPLNTQGIPHAAMDWYQASVFKEAVQGHTHIVSVSTADVLIMCKDLITCRFNTTLISKIAEIEDPVC
SDYPNFKIVSMLYQSGDYLLSILGSDGYKIIKFLEPLCLAKIQLCSKYTERKGRFLTQMHLAVNHTL
EEITEMRALKPSQAQKIREFHRTLIRLEMTPQQLCELFSIQKHWGHPVLHSETAIQKVKKHATVLK
ALRPIVIFETYCVFKYSIAKHYFDSQGSWYSVTSDRNLTPGLNSYIKRNQFPPLPMIKELLWEFYH
LDHPPLFSTKIISDLSIFIKDRATAVERTCWDAVFEPNVLGYNPPHKFSTKRVPEQFLEQENFSIEN
VLSYAQKLEYLLPQYRNFSFSLKEKELNVGRTFGKLPYPTRNVQTLCEALLADGLAKAFPSNMM
WTEREQKESLLHQASWHHTSDDFGEHATVRGSSFVTDLEKYNLAFRYEFTAPFIEYCNRCYGV
KNVFNWMHYTIPQCYMHVSDYYNPPHNLTLENRDNPPEGPSSYRGHMGGIEGLQQKLWTSISC
AQISLVEIKTGFKLRSAVMGDNQCITVLSVFPLETDADEQEQSAEDNAARVAASLAKVTSACGIFL
KPDETFVHSGFIYFGKKQYLNGVQLPQSLKTAARMAPLSDAIFDDLQGTLASIGTAFERSISETRH
IFPCRITAAFHTFFSVRILQYHHLGFNKGFDLGQLTLGKPLDFGTISLALAVPQVLGGLSFLNPEKC
FYRNLGDPVTSGLFQLKTYLRMIEMDDLFLPLIAKNPGNCTAIDFVLNPSGLNVPGSQDLTSFLRQ
IVRRTITLSAKNKLINTLFHASADFEDEMVCKWLLSSTPVMSRFAADIFSRTPSGKRLQILGYLEGT
RTLLASKIINNNTETPVLDRLRKITLQRWSLWFSYLDHCDNILAEALTQITCTVDLAQILREYSWAHI
LEGRPLIGATLPCMIEQFKVFWLKPYEQCPQCSNAKQPGGKPFVSVAVKKHIVSAWPNASRISW
TIGDGIPYIGSRTEDKIGQPAIKPKCPSAALREAIELASRLTWVTQGSSNSDLLIKPFLEARVNLSV
QEILQMTPSHYSGNIVHRYNDQYSPHSFMANRMSNSATRLIVSTNTLGEFSGGGQSARDSNIIFQ
NVINYAVALFDIKFRNTEATDIQYNRAHLHLTKCCTREVPAQYLTYTSTLDLDLTRYRENELIYDSN
PLKGGLNCNISFDNPFFQGKRLNIIEDDLIRLPHLSGWELAKTIMQSIISDSNNSSTDPISSGETRSF
TTHFLTYPKIGLLYSFGAFVSYYLGNTILRTKKLTLDNFLYYLTTQIHNLPHRSLRILKPTFKHASVM
SRLMSIDPHFSIYIGGAAGDRGLSDAARLFLRTSISSFLTFVKEWIINRGTIVPLWIVYPLEGQNPTP

FIG. 18BBB

VNNFLYQIVELLVHDSSRQQAFKTTISDHVHPHDNLVYTCKSTASNFFHASLAYWRSRHRNSNR
KYLARDSSTGSSTNNSDGHIERSQEQTTRDPHDGTERNLVLQMSHEIKRTTIPQENTHQGPSFQ
SFLSDSACGTANPKLNFDRSRHNVKFQDHNSASKREGHQIISHRLVLPFFTLSQGTRQLTSSNES
QTQDEISKYLRQLRSVIDTTVYCRFTGIVSSMHYKLDEVLWEIESFKSAVTLAEGEGAGALLLIQK
YQVKTLFFNTLATESSIESEIVSGMTTPRMLLPVMSKFHNDQIEIILNNSASQITDITNPTWFKDQR
ARLPKQVEVITMDAETTENINRSKLYEAVYKLILHHIDPSVLKAVVLKVFLSDTEGMLWLNDNLAPF
FATGYLIKPITSSARSSEWYLCLTNFLSTTRKMPHQNHLSCKQVILTALQLQIQRSPYWLSHLTQY
ADCELHLSYIRLGFPSLEKVLYHRYNLVDSKRGPLVSITQHLAHLRAEIRELTNDYNQQRQSRTQ
TYHFIRTAKGRITKLVNDYLKFFLIVQALKHNGTWQAEFKKLPELISVCNRFYHIRDCNCEERFLVQ
TLYLHRMQDSEVKLIERLTGLLSLFPDGLYRFD (SEQ ID NO:45)

polyA signal   18272 – 18282, L
misc feature   18283 – 18959, trailer region

```
   1 cggacacaca aaaagaaaga agaattttta ggatcttttg tgtgcgaata actatgagga
  61 agattaataa ttttcctctc attgaaattt atatcggaat ttaaattgaa attgttactg
 121 taatcacacc tggtttgttt cagagccaca tcacaaagat agagaacaac ctaggtctcc
 181 gaagggagca agggcatcag tgtgctcagt tgaaaatccc ttgtcaacac ctaggtctta
 241 tcacatcaca agttccacct cagactctgc agggtgatcc aacaaccta atagaaacat
 301 tattgttaaa ggacagcatt agttcacagt caaacaagca agattgagaa ttaaccttgg
 361 ttttgaactt gaacacttag gggattgaag attcaacaac cctaaagctt ggggtaaaac
 421 attggaaata gttaaaagac aaattgctcg gaatcacaaa attccgagta tggattctcg
 481 tcctcagaaa atctggatgg cgccgagtct cactgaatct gacatggatt accacaagat
 541 cttgacagca ggtctgtccg ttcaacaggg gattgttcgg caaagagtca tcccagtgta
 601 tcaagtaaac aatcttgaag aaatttgcca acttatcata caggcctttg aagcaggtgt
 661 tgattttcaa gagagtgcgg acagtttcct tctcatgctt tgtcttcatc atgcgtacca
 721 gggagattac aaactttttct tggaaagtgg cgcagtcaag tatttggaag ggcacgggtt
 781 ccgttttgaa gtcaagaagc gtgatggagt gaagcgcctt gaggaattgc tgccagcagt
 841 atctagtgga aaaaacatta agagaacact tgctgccatg ccggaagagg agacaactga
 901 agctaatgcc ggtcagtttc tctcctttgc aagtctattc cttccgaaat tggtagtagg
 961 agaaaaggct tgccttgaga aggttcaaag gcaaattcaa gtacatgcag agcaaggact
1021 gatacaatat ccaacagctt ggcaatcagt aggacacatg atggtgattt tccgtttgat
1081 gcgaacaaat tttctgatca aatttctcct aatacaccaa gggatgcaca tggttgccgg
1141 gcatgatgcc aacgatgctg tgatttcaaa ttcagtggct caagctcgtt tttcaggctt
1201 attgattgtc aaaacagtac ttgatcatat cctacaaaag acagaacgag gagttcgtct
1261 ccatcctctt gcaaggaccg ccaaggtaaa aatgaggtg aactccttta aggctgcact
1321 cagctccctg ccaagcatg gagagtatgc tccttttcgcc cgacttttga accttctctgg
```

FIG. 18CCC 1381 agtaaataat cttgagcatg gtcttttccc tcaactatcg gcaattgcac tcggagtcgc 1441 cacagcacac gggagtaccc tcgcaggagt aaatgttgga gaacagtatc aacaactcag 1501 agaggctgcc actgaggctg agaagcaact ccaacaatat gcagagtctc gcgaacttga 1561 ccatcttgga cttgatgatc aggaaaagaa aattcttatg aacttccatc agaaaaagaa 1621 cgaaatcagc ttccagcaaa caaacgctat ggtaactcta agaaaagagc gcctggccaa 1681 gctgacagaa gctatcactg ctgcgtcact gcccaaaaca agtggacatt acgatgatga 1741 tgacgacatt cccttttccag gacccatcaa tgatgacgac aatcctggcc atcaagatga 1801 tgatccgact gactcacagg atacgaccat tcccgatgtg gtggttgatc ctgatgatgg 1861 aagctacggc gaataccaga gttactcgga aaacggcatg aatgcaccag atgacttggt 1921 cctattcgat ctagacgagg acgacgagga cactaagcca gtgcctaata gatcgaccaa 1981 gggtggacaa cagaagaaca gtcaaaaggg ccagcatata gagggcagac agacacaatt 2041 caggccaatt caaaatgtcc caggccctca cagaacaatc caccacgcca gtgcgccact 2101 cacggacaat gacagaagaa atgaaccctc cggctcaacc agccctcgca tgctgacacc 2161 aattaacgaa gaggcagacc cactggacga tgccgacgac gagacgtcta gccttccgcc 2221 cttggagtca gatgatgaag agcaggacag ggacggaact tccaaccgca cacccactgt 2281 cgccccaccg gctcccgtat acagagatca ctctgaaaag aaagaactcc cgcaagacga 2341 gcaacaagat caggaccaca ctcaagaggc caggaaccag gacagtgaca acacccagtc 2401 agaacactcc cttgaggaga tgtatcgcca cattctaaga tcacaggggc catttgatgc 2461 tgttttgtat tatcatatga tgaaggatga gcctgtagtt ttcagtacca gtgatggcaa 2521 agagtacacg tatccagact cccttgaaga ggaatatcca ccatggctca ctgaaaaaga 2581 ggctatgaat gaagagaata gatttgttac attggatggt caacaatttt attggccggt 2641 gatgaatcac aagaataaat tcatggcaat cctgcaacat catcagtgaa tgagcatgga 2701 acaatgggat gattcaaccg acaaatagct aacattaagt agtcaaggaa cgaaaacagg 2761 aagaattttt gatgtctaag gtgtgaatta ttatcacaat aaaagtgatt cttatttttg 2821 aatttaaagc tagcttatta ttactagccg tttttcaaag ttcaatttga gtcttaatgc 2881 aaataggcgt taagccacag ttatagccat aattgtaact caatattcta actagcgatt 2941 tatctaaatt aaattacatt atgcttttat aacttaccta ctagcctgcc caacatttac 3001 acgatcgttt tataattaag aaaaaactaa tgatgaagat taaaaccttc atcatcctta 3061 cgtcaattga attctctagc actcgaagct tattgtcttc aatgtaaaag aaaagctggt 3121 ctaacaagat gacaactaga acaaagggca ggggccatac tgcggccacg actcaaaacg 3181 acagaatgcc aggccctgag ctttcgggct ggatctctga gcagctaatg accggaagaa 3241 ttcctgtaag cgacatcttc tgtgatattg agaacaatcc aggattatgc tacgcatccc 3301 aaatgcaaca aacgaagcca aacccgaaga cgcgcaacag tcaaacccaa acggacccaa 3361 tttgcaatca tagttttgag gaggtagtac aaacattggc ttcattggct actgttgtgc 3421 aacaacaaac catcgcatca gaatcattag acaacgcat tacgagtctt gagaatggtc 3481 taaagccagt ttatgatatg gcaaaaacaa tctcctcatt gaacagggtt tgtgctgaga 3541 tggttgcaaa atatgatctt ctggtgatga caaccggtcg ggcaacagca accgctgcgg

FIG. 18DDD 3601 caactgaggc ttattgggcc gaacatggtc aaccaccacc tggaccatca ctttatgaag 3661 aaagtgcgat tcggggtaag attgaatcta gagatgagac cgtccctcaa agtgttaggg 3721 aggcattcaa caatctaaac agtaccactt cactaactga ggaaaatttt gggaaacctg 3781 acatttcggc aaaggatttg agaaacatta tgtatgatca cttgcctggt tttggaactg 3841 ctttccacca attagtacaa gtgatttgta aattgggaaa agatagcaac tcattggaca 3901 tcattcatgc tgagttccag gccagcctgg ctgaaggaga ctctcctcaa tgtgccctaa 3961 ttcaaattac aaaaagagtt ccaatcttcc aagatgctgc tccacctgtc atccacatcc 4021 gctctcgagg tgacattccc cgagcttgcc agaaaagctt gcgtccagtc ccaccatcgc 4081 ccaagattga tcgaggttgg gtatgtgttt ttcagcttca agatggtaaa acacttggac 4141 tcaaaatttg agccaatctc ccttccctcc gaaagaggcg aataatagca gaggcttcaa 4201 ctgctgaact ataggggtacg ttacattaat gatacacttg tgagtatcag ccctggataa 4261 tataagtcaa ttaaacgacc aagataaaat tgttcatatc tcgctagcag cttaaaatat 4321 aaatgtaata ggagctatat ctctgacagt attataatca attgttatta agtaacccaa 4381 accaaaagtg atgaagatta agaaaaaacct acctcggctg agagagtgtt tttcattaa 4441 ccttcatctt gtaaacgttg agcaaaattg ttaaaaatat gaggcgggtt atattgccta 4501 ctgctcctcc tgaatatatg gaggccatat accctgtcag gtcaaattca acaattgcta 4561 gaggtggcaa cagcaataca ggcttcctga caccggagtc agtcaatggg gacactccat 4621 cgaatccact caggccaatt gccgatgaca ccatcgacca tgccagccac acaccaggca 4681 gtgtgtcatc agcattcatc cttgaagcta tggtgaatgt catatcgggc cccaaagtgc 4741 taatgaagca aattccaatt tggcttcctc taggtgtcgc tgatcaaaag acctacagct 4801 ttgactcaac tacggccgcc atcatgcttg cttcatacac tatcacccat ttcggcaagg 4861 caaccaatcc acttgtcaga gtcaatcggc tgggtcctgg aatcccggat catcccctca 4921 ggctcctgcg aattggaaac caggcttttcc tccaggagtt cgttcttccg ccagtccaac 4981 taccccagta tttcaccttt gatttgacag cactcaaact gatcacccaa ccactgcctg 5041 ctgcaacatg gaccgatgac actccaacag gatcaaatgg agcgttgcgt ccaggaattt 5101 catttcatcc aaaacttcgc cccattcttt tacccaacaa aagtgggaag aagggggaaca 5161 gtgccgatct aacatctccg gagaaaatcc aagcaataat gacttcactc caggacttta 5221 agatcgttcc aattgatcca accaaaaata tcatgggaat cgaagtgcca gaaactctgg 5281 tccacaagct gaccggtaag aaggtgactt ctaaaaatgg acaaccaatc atccctgttc 5341 ttttgccaaa gtacattggg ttggacccgg tggctccagg agacctcacc atggtaatca 5401 cacaggattg tgacacgtgt cattctcctg caagtcttcc agctgtgatt gagaagtaat 5461 tgcaataatt gactcagatc cagttttata gaatcttctc agggatagtg ataacatcta 5521 tttagtaatc cgtccattag aggagacact tttaattgat caatatacta aaggtgcttt 5581 acaccattgt ctttttctc tcctaaatgt agaacttaac aaaagactca taatatactt 5641 gtttttaaag gattgattga tgaaagatca taactaataa cattacaaat aatcctacta 5701 taatcaatac ggtgattcaa atgttaatct ttctcattgc acatactttt tgcccttatc 5761 ctcaaattgc ctgcatgctt acatctgagg atagccagtg tgacttggat tggaaatgtg

FIG. 18EEE

```
5821 gagaaaaaat cgggacccat ttctaggttg ttcacaatcc aagtacagac attgcccttc
5881 taattaagaa aaaatcggcg atgaagatta agccgacagt gagcgtaatc ttcatctctc
5941 ttagattatt tgttttccag agtaggggtc gtcaggtcct tttcaatcgt gtaaccaaaa
6001 taaactccac tagaaggata ttgtggggca acaacacaat gggcgttaca ggaatattgc
6061 agttacctcg tgatcgattc aagaggacat cattctttct ttgggtaatt atccttttcc
6121 aaagaatatt ttccatccca cttggagtca tccacaatag cacattacag gttagtgatg
6181 tcgacaaact agtttgtcgt gacaaactgt catccacaaa tcaattgaga tcagttggac
6241 tgaatctcga agggaatgga gtggcaactg acgtgccatc tgcaactaaa agatggggct
6301 tcaggtccgg tgtcccacca aaggtggtca attatgaagc tggtgaatgg gctgaaaact
6361 gctacaatct tgaaatcaaa aaacctgacg ggagtgagtg tctaccagca gcgccagacg
6421 ggattcgggg cttccccgg tgccggtatg tgcacaaagt atcaggaacg ggaccgtgtg
6481 ccggagactt tgccttccat aaagagggtg ctttcttcct gtatgatcga cttgcttcca
6541 cagttatcta ccgaggaacg actttcgctg aaggtgtcgt tgcatttctg atactgcccc
6601 aagctaagaa ggacttcttc agctcacacc ccttgagaga gccggtcaat gcaacggagg
6661 acccgtctag tggctactat tctaccacaa ttagatatca ggctaccggt tttggaacca
6721 atgagacaga gtacttgttc gaggttgaca atttgaccta cgtccaactt gaatcaagat
6781 tcacaccaca gtttctgctc cagctgaatg agacaatata tacaagtggg aaaaggagca
6841 ataccacggg aaaactaatt tggaaggtca accccgaaat tgatacaaca atcggggagt
6901 gggccttctg ggaaactaaa aaaacctcac tagaaaaatt cgcagtgaag agttgtcttt
6961 cacagttgta tcaaacggag ccaaaaacat cagtggtcag agtccggcgc gaacttcttc
7021 cgacccaggg accaacacaa caactgaaga ccacaaaatc atggcttcag aaaattcctc
7081 tgcaatggtt caagtgcaca gtcaaggaag ggaagctgca gtgtcgcatc taacaaccct
7141 tgccacaatc tccacgagtc cccaatccct cacaaccaaa ccaggtccgg acaacagcac
7201 ccataataca cccgtgtata aacttgacat ctctgaggca actcaagttg aacaacatca
7261 ccgcagaaca gacaacgaca gcacagcctc cgacactccc tctgccacga ccgcagccgg
7321 accccaaaa gcagagaaca ccaacacgag caagagcact gacttcctgg accccgccac
7381 cacaacaagt ccccaaaacc acagcgagac cgctggcaac aacaacactc atcaccaaga
7441 taccggagaa gagagtgcca gcagcgggaa gctaggctta attaccaata ctattgctgg
7501 agtcgcagga ctgatcacag gcgggagaag aactcgaaga gaagcaattg tcaatgctca
7561 acccaaatgc aaccctaatt tacattactg gactactcag gatgaaggtg ctgcaatcgg
7621 actggcctgg ataccatatt tcgggccagc agccgaggga atttacatag aggggctaat
7681 gcacaatcaa gatggtttaa tctgtgggt gagacagctg gccaacgaga cgactcaagc
7741 tcttcaactg ttcctgagag ccacaactga gctacgcacc ttttcaatcc tcaaccgtaa
7801 ggcaattgat ttcttgctgc agcgatgggg cggcacatgc cacattctgg gaccggactg
7861 ctgtatcgaa ccacatgatt ggaccaagaa cataacagac aaaattgatc agattattca
7921 tgatttgtt gataaaaccc ttccggacca gggggacaat gacaattggt ggacaggatg
7981 gagacaatgg ataccggcag gtattggagt tacaggcgtt ataattgcag ttatcgcttt
```

FIG. 18FFF 8041 attctgtata tgcaaatttg tcttttagtt tttcttcaga ttgcttcatg gaaaagctca
8101 gcctcaaatc aatgaaacca ggatttaatt atatggatta cttgaatcta agattacttg
8161 acaaatgata atataataca ctggagcttt aaacatagcc aatgtgattc taactccttt
8221 aaactcacag ttaatcataa acaaggtttg acatcaatct agttatctct ttgagaatga
8281 taaacttgat gaagattaag aaaaaggtaa tctttcgatt atctttaatc ttcatccttg
8341 attctacaat catgacagtt gtctttagtg acaagggaaa gaagccttt tattaagttg
8401 taataatcag atctgcgaac cggtagagtt tagttgcaac ctaacacaca taaagcattg
8461 gtcaaaaagt caatagaaat ttaaacagtg agtggagaca acttttaaat ggaagcttca
8521 tatgagagag gacgcccacg agctgccaga cagcattcaa gggatggaca cgaccaccat
8581 gttcgagcac gatcatcatc cagagagaat tatcgaggtg agtaccgtca atcaaggagc
8641 gcctcacaag tgcgcgttcc tactgtattt cataagaaga gagttgaacc attaacagtt
8701 cctccagcac ctaaagacat atgtccgacc ttgaaaaaag gattttgtg tgacagtagt
8761 ttttgcaaaa aagatcacca gttggagagt ttaactgata gggaattact cctactaatc
8821 gcccgtaaga cttgtggatc agtagaacaa caattaaata taactgcacc caaggactcg
8881 cgcttagcaa atccaacggc tgatgatttc cagcaagagg aaggtccaaa aattaccttg
8941 ttgacactga tcaagacggc agaacactgg gcgagacaag acatcagaac catagaggat
9001 tcaaaattaa gagcattgtt gactctatgt gctgtgatga cgaggaaatt ctcaaaatcc
9061 cagctgagtc ttttatgtga gacacaccta aggcgcgagg ggcttgggca agatcaggca
9121 gaacccgttc tcgaagtata tcaacgatta cacagtgata aaggaggcag ttttgaagct
9181 gcactatggc aacaatggga ccgacaatcc ctaattatgt ttatcactgc attcttgaat
9241 attgctctcc agttaccgtg tgaaagttct gctgtcgttg tttcagggtt aagaacattg
9301 gttcctcaat cagataatga ggaagcttca accaacccgg ggacatgctc atggtctgat
9361 gagggtaccc cttaataagg ctgactaaaa cactatataa ccttctactt gatcacaata
9421 ctccgtatac ctatcatcat atatttaatc aagacgatat cctttaaaac ttattcagta
9481 ctataatcac tctcgtttca aattaataag atgtgcatga ttgccctaat atatgaagag
9541 gtatgataca accctaacag tgatcaaaga aaatcataat ctcgtatcgc tcgaaatata
9601 acctgccaag cataccctctt gcacaaagtg attcttgtac acaaataatg ttttactcta
9661 caggaggtag caacgatcca tcccatcaaa aaataagtat ttcatgactt actaatgatc
9721 tcttaaaata ttaagaaaaa ctgacggaac ataaattctt tatgcttcaa gctgtggagg
9781 aggtgtttgg tattggctat tgttatatta caatcaataa caagcttgta aaaatattgt
9841 tcttgtttca agaggtagat tgtgaccgga aatgctaaac taatgatgaa gattaatgcg
9901 gaggtctgat aagaataaac cttattattc agattaggcc ccaagaggca ttcttcatct
9961 cctttagca aagtactatt tcagggtagt ccaattagtg gcacgtcttt tagctgtata
10021 tcagtcgccc ctgagatacg ccacaaaagt gtctctaagc taaattggtc tgtacacatc
10081 ccatacattg tattaggggc aataatatct aattgaactt agccgtttaa aatttagtgc
10141 ataaatctgg gctaacacca ccaggtcaac tccattggct gaaagaagc ttacctacaa
10201 cgaacatcac tttgagcgcc ctcacaatta aaaaatagga acgtcgttcc aacaatcgag

FIG. 18GGG

```
10261 cgcaaggttt caaggttgaa ctgagagtgt ctagacaaca aaatattgat actccagaca
10321 ccaagcaaga cctgagaaaa aaccatggct aaagctacgg gacgatacaa tctaatatcg
10381 cccaaaaagg acctggagaa agggttgtc ttaagcgacc tctgtaactt cttagttagc
10441 caaactattc aggggtggaa ggtttattgg gctggtattg agtttgatgt gactcacaaa
10501 ggaatggccc tattgcatag actgaaaact aatgactttg ccctgcatg gtcaataaca
10561 aggaatctct ttcctcattt atttcaaaat ccgaattcca caattgaatc accgctgtgg
10621 gcattgagag tcatccttgc agcagggata caggaccagc tgattgacca gtctttgatt
10681 gaaccctag caggagccct tggtctgatc tctgattggc tgctaacaac caacactaac
10741 catttcaaca tgcgaacaca acgtgtcaag gaacaattga gcccaaaaat gctgtcgttg
10801 attcgatcca atattctcaa gtttattaac aaattggatg ctctacatgt cgtgaactac
10861 aacggattgt tgagcagtat tgaaattgga actcaaaatc atataatcat cataactcga
10921 actaacatgg gttttctggt ggagctccaa gaacccgaca aatcggcaat gaaccgcatg
10981 aagcctgggc cggcgaaatt ttccctcctt catgagtcca cactgaaagc atttacacaa
11041 ggatcctcga cacgaatgca aagtttgatt cttgaattta atagctctct tgctatctaa
11101 ctaaggtaga atacttcata ttgagctaac tcatatatgc tgactcaata gttatcttga
11161 catctctgct ttcataatca gatatataag cataataaat aaatactcat atttcttgat
11221 aatttgttta accacagata aatcctcact gtaagccagc ttccaagttg acacccttac
11281 aaaaaccagg actcagaatc cctcaaacaa gagattccaa gacaacatca tagaattgct
11341 ttattatatg aataagcatt ttatcaccag aaatcctata tactaaatgg ttaattgtaa
11401 ctgaacccgc aggtcacatg tgttaggttt cacagattct atatattact aactctatac
11461 tcgtaattaa cattagataa gtagattaag aaaaaagcct gaggaagatt aagaaaaact
11521 gcttattggg tctttccgtg ttttagatga agcagttgaa attcttcctc ttgatattaa
11581 atggctacac aacatacca atacccagac gctaggttat catcaccaat tgtattggac
11641 caatgtgacc tagtcactag agcttgcggg ttatattcat catactccct taatccgcaa
11701 ctacgcaact gtaaactccc gaaacatatc taccgtttga aatacgatgt aactgttacc
11761 aagttcttga gtgatgtacc agtggcgaca ttgcccatag atttcatagt cccagttctt
11821 ctcaaggcac tgtcaggcaa tggattctgt cctgttgagc cgcggtgcca acagttctta
11881 gatgaaatca ttaagtacac aatgcaagat gctctcttct tgaaatatta tctcaaaaat
11941 gtgggtgctc aagaagactg tgttgatgaa cactttcaag agaaaatctt atcttcaatt
12001 cagggcaatg aattttaca tcaaatgttt ttctggtatg atctggctat tttaactcga
12061 agggtagat taaatcgagg aaactctaga tcaacatggt ttgttcatga tgatttaata
12121 gacatcttag gctatgggga ctatgttttt tggaagatcc caatttcaat gttaccactg
12181 aacacacaag gaatcccca tgctgctatg gactggtatc aggcatcagt attcaaagaa
12241 gcggttcaag ggcatacaca cattgtttct gtttctactg ccgacgtctt gataatgtgc
12301 aaagatttaa ttacatgtcg attcaacaca actctaatct caaaatagc agagattgag
12361 gatccagttt gttctgatta tcccaatttt aagattgtgt ctatgcttta ccagagcgga
12421 gattacttac tctccatatt agggtctgat gggtataaaa ttattaagtt cctcgaacca
```

FIG. 18HHH

```
12481 ttgtgcttgg ccaaaattca attatgctca aagtacactg agaggaaggg ccgattctta
12541 acacaaatgc atttagctgt aaatcacacc ctagaagaaa ttacagaaat gcgtgcacta
12601 aagccttcac aggctcaaaa gatccgtgaa ttccatagaa cattgataag gctggagatg
12661 acgccacaac aactttgtga gctattttcc attcaaaaac actgggggca tcctgtgcta
12721 catagtgaaa cagcaatcca aaaagttaaa aaacatgcta cggtgctaaa agcattacgc
12781 cctatagtga ttttcgagac atactgtgtt tttaaatata gtattgccaa acattatttt
12841 gatagtcaag gatcttggta cagtgttact tcagatagga atctaacacc gggtcttaat
12901 tcttatatca aaagaaatca attccctccg ttgccaatga ttaaagaact actatgggaa
12961 ttttaccacc ttgaccaccc tccactttc tcaaccaaaa ttattagtga cttaagtatt
13021 tttataaaag acagagctac cgcagtagaa aggacatgct gggatgcagt attcgagcct
13081 aatgttctag gatataatcc acctcacaaa tttagtacta aacgtgtacc ggaacaattt
13141 ttagagcaag aaaacttttc tattgagaat gttctttcct acgcacaaaa actcgagtat
13201 ctactaccac aatatcggaa ctttcttttc tcattgaaag agaaagagtt gaatgtaggt
13261 agaaccttcg gaaaattgcc ttatccgact cgcaatgttc aaacactttg tgaagctctg
13321 ttagctgatg gtcttgctaa agcatttcct agcaatatga tggtagttac ggaacgtgag
13381 caaaaagaaa gcttattgca tcaagcatca tggcaccaca caagtgatga ttttggtgaa
13441 catgccacag ttagagggag tagctttgta actgatttag agaaatacaa tcttgcattt
13501 agatatgagt ttacagcacc ttttatagaa tattgcaacc gttgctatgg tgttaagaat
13561 gtttttaatt ggatgcatta tacaatccca cagtgttata tgcatgtcag tgattattat
13621 aatccaccac ataacctcac actggagaat cgagacaacc cccccgaagg gcctagttca
13681 tacaggggtc atatgggagg gattgaagga ctgcaacaaa aactctggac aagtatttca
13741 tgtgctcaaa tttctttagt tgaaattaag actggtttta agttacgctc agctgtgatg
13801 ggtgacaatc agtgcattac tgttttatca gtcttccct tagagactga cgcagacgag
13861 caggaacaga gcgccgaaga caatgcagcg aggggtggccg ccagcctagc aaaagttaca
13921 agtgcctgtg gaatctttt aaaacctgat gaaacatttg tacattcagg ttttatctat
13981 tttggaaaaa aacaatattt gaatggggtc caattgcctc agtcccttaa aacggctgca
14041 agaatggcac cattgtctga tgcaattttt gatgatcttc aagggaccct ggctagtata
14101 ggcactgctt ttgagcgatc catctctgag acacgacata tcttttcttg caggataacc
14161 gcagctttcc atacgttttt ttcggtgaga atcttgcaat atcatcatct cgggttcaat
14221 aaaggttttg accttggaca gttaacactc ggcaaaacctc tggatttcgg aacaatatca
14281 ttggcactag cggtaccgca ggtgcttgga gggttatcct tcttgaatcc tgagaaatgt
14341 ttctaccgga atctaggaga tccagttacc tcaggcttat tccagttaaa aacttatctc
14401 cgaatgattg agatggatga tttattctta cctttaattg cgaagaaccc tgggaactgc
14461 actgccattg actttgtgct aaatcctagc ggattaaatg tccctgggtc gcaagactta
14521 acttcatttc tgcgccagat tgtacgcagg accatcaccc taagtgcgaa aaacaaactt
14581 attaatacct tatttcatgc gtcagctgac ttcgaagacg aaatggttgt taaatggcta
14641 ttatcatcaa ctcctgttat gagtcgtttt gcggccgata tcttttcacg cacgccgagc
```

FIG. 18III

```
14701 gggaagcgat tgcaaattct aggatacctg gaaggaacac gcacattatt agcctctaag
14761 atcatcaaca ataatacaga gacaccggtt ttggacagac tgaggaaaat aacattgcaa
14821 aggtggagcc tatggtttag ttatcttgat cattgtgata atatcctggc ggaggcttta
14881 acccaaataa cttgcacagt tgatttagca cagattctga gggaatattc atgggctcat
14941 attttagagg gaagacctct tattggagcc acactcccat gtatgattga gcaattcaaa
15001 gtgttttggc tgaaaccta cgaacaatgt ccgcagtgtt caaatgcaaa gcaaccaggt
15061 gggaaaccat tcgtgtcagt ggcagtcaag aaacatattg ttagtgcatg gccgaacgca
15121 tcccgaataa gctggactat cggggatgga atcccataca ttggatcaag gacagaagat
15181 aagataggac aacctgctat taaaccaaaa tgtccttccg cagccttaag agaggccatt
15241 gaattggcgt cccgtttaac atgggtaact caaggcagtt cgaacagtga cttgctaata
15301 aaaccatttt tggaagcacg agtaaattta agtgttcaag aaatacttca aatgaccct
15361 tcacattact caggaaatat tgttcacagg tacaacgatc aatacagtcc tcattctttc
15421 atggccaatc gtatgagtaa ttcagcaacg cgattgattg tttctacaaa cactttaggt
15481 gagttttcag gaggtggcca gtctgcacgc gacagcaata ttattttcca gaatgttata
15541 aattatgcag ttgcactgtt cgatattaaa tttagaaaca ctgaggctac agatatccaa
15601 tataatcgtg ctcaccttca tctaactaag tgttgcaccc gggaagtacc agctcagtat
15661 ttaacataca catctacatt ggatttagat ttaacaagat accgagaaaa cgaattgatt
15721 tatgacagta atcctctaaa aggaggactc aattgcaata tctcattcga taatccattt
15781 ttccaaggta aacggctgaa cattatagaa gatgatctta ttcgactgcc tcacttatct
15841 ggatgggagc tagccaagac catcatgcaa tcaattattt cagatagcaa caattcatct
15901 acagacccaa ttagcagtgg agaaacaaga tcattcacta cccatttctt aacttatccc
15961 aagataggac ttctgtacag ttttgggggcc tttgtaagtt attatcttgg caatacaatt
16021 cttcggacta agaaattaac acttgacaat ttttatatt acttaactac tcaaattcat
16081 aatctaccac atcgctcatt gcgaatactt aagccaacat tcaaacatgc aagcgttatg
16141 tcacggttaa tgagtattga tcctcattt tctatttaca taggcggtgc tgcaggtgac
16201 agaggactct cagatgcggc caggttattt ttgagaacgt ccatttcatc tttcttaca
16261 tttgtaaaag aatggatata taatcgcgga acaattgtcc ctttatggat agtatatccg
16321 ctagagggtc aaaacccaac acctgtgaat aattttctct atcagatcgt agaactgctg
16381 gtgcatgatt catcaagaca acaggctttt aaaactacca taagtgatca tgtacatcct
16441 cacgacaatc ttgtttacac atgtaagagt acagccagca atttcttcca tgcatcattg
16501 gcgtactgga ggagcagaca cagaaacagc aaccgaaaat acttggcaag agactcttca
16561 actggatcaa gcacaaacaa cagtgatggt catattgaga gaagtcaaga acaaaccacc
16621 agagatccac atgatggcac tgaacggaat ctagtcctac aaatgagcca tgaaataaaa
16681 agaacgacaa ttccacaaga aaacacgcac cagggtccgt cgttccagtc ctttctaagt
16741 gactctgctt gtggtacagc aaatccaaaa ctaaatttcg atcgatcgag acacaatgtg
16801 aaatttcagg atcataactc ggcatccaag agggaaggtc atcaaataat ctcacaccgt
16861 ctagtcctac ctttctttac attatctcaa gggacacgcc aattaacgtc atccaatgag
```

FIG. 18JJJ 16921 tcacaaacoc aagacgagat atcaaagtac ttacggcaat tgagatccgt cattgatacc
16981 acagtttatt gtagatttac cggtatagtc tcgtccatgc attacaaact tgatgaggtc
17041 ctttgggaaa tagagagttt caagtcggct gtgacgctag cagagggaga aggtgctggt
17101 gccttactat tgattcagaa ataccaagtt aagaccttat ttttcaacac gctagctact
17161 gagtccagta tagagtcaga aatagtatca ggaatgacta ctcctaggat gcttctacct
17221 gttatgtcaa aattccataa tgaccaaatt gagattattc ttaacaactc agcaagccaa
17281 ataacagaca taacaaatcc tacttggttt aaagaccaaa gagcaaggct acctaagcaa
17341 gtcgaggtta taaccatgga tgcagagaca acagagaata taaacagatc gaaattgtac
17401 gaagctgtat ataaattgat cttacaccat attgatccta gcgtattgaa agcagtggtc
17461 cttaaagtct ttctaagtga tactgagggt atgttatggc taaatgataa tttagccccg
17521 ttttttgcca ctggttattt aattaagcca ataacgtcaa gtgctagatc tagtgagtgg
17581 tatctttgtc tgacgaactt cttatcaact acacgtaaga tgccacacca aaaccatctc
17641 agttgtaaac aggtaatact tacggcattg caactgcaaa ttcaacgaag cccatactgg
17701 ctaagtcatt taactcagta tgctgactgt gagttacatt taagttatat ccgccttggt
17761 tttccatcat tagagaaagt actataccac aggtataacc tcgtcgattc aaaaagaggt
17821 ccactagtct ctatcactca gcacttagca catcttagag cagagattcg agaattaact
17881 aatgattata atcaacagcg acaaagtcgg actcaaacat atcactttat tcgtactgca
17941 aaaggacgaa tcacaaaact agtcaatgat tatttaaaat tctttcttat tgtgcaagca
18001 ttaaaacata atgggacatg gcaagctgag tttaagaaat taccagagtt gattagtgtg
18061 tgcaataggt tctaccatat tagagattgc aattgtgaag aacgtttctt agttcaaacc
18121 ttatatttac atagaatgca ggattctgaa gttaagctta tcgaaaggct gacagggctt
18181 ctgagtttat ttccggatgg tctctacagg tttgattgaa ttaccgtgca tagtatcctg
18241 atacttgcaa aggttggtta ttaacataca gattataaaa aactcataaa ttgctctcat
18301 acatcatatt gatctaatct caataaacaa ctattaaat aacgaaagga gtccctatat
18361 tatatactat atttagcctc tctccctgcg tgataatcaa aaaattcaca atgcagcatg
18421 tgtgacatat tactgccgca atgaatttaa cgcaacataa taaactctgc actctttata
18481 attaagcttt aacgaaaggt ctgggctcat attgttattg atataataat gttgtatcaa
18541 tatcctgtca gatggaatag tgttttggtt gataacacaa cttcttaaaa caaaattgat
18601 ctttaagatt aagttttta taattatcat tactttaatt tgtcgtttta aaaacggtga
18661 tagccttaat ctttgtgtaa aataagagat taggtgtaat aaccttaaca tttttgtcta
18721 gtaagctact atttcataca gaatgataaa attaaaagaa aaggcaggac tgtaaaatca
18781 gaaataccctt ctttacaata tagcagacta gataataatc ttcgtgttaa tgataattaa
18841 gacattgacc acgctcatca gaaggctcgc cagaataaac gttgcaaaaa ggattcctgg
18901 aaaaatggtc gcacacaaaa atttaaaaat aaatctattt cttctttttt gtgtgtcca (SEQ ID NO:46)

FIG. 18KKK

SEQUENCE LISTING

```
<160> NUMBER OF SEQ ID NOS: 58

<210> SEQ ID NO 1
<211> LENGTH: 739
<212> TYPE: PRT
<213> ORGANISM: Reston Ebola virus

<400> SEQUENCE: 1

Met Asp Arg Gly Thr Arg Arg Ile Trp Val Ser Gln Asn Gln Gly Asp
1               5                   10                  15

Thr Asp Leu Asp Tyr His Lys Ile Leu Thr Ala Gly Leu Thr Val Gln
            20                  25                  30

Gln Gly Ile Val Arg Gln Lys Ile Ile Ser Val Tyr Leu Val Asp Asn
        35                  40                  45

Leu Glu Ala Met Cys Gln Leu Val Ile Gln Ala Phe Glu Ala Gly Ile
    50                  55                  60

Asp Phe Gln Glu Asn Ala Asp Ser Phe Leu Leu Met Leu Cys Leu His
65                  70                  75                  80

His Ala Tyr Gln Gly Asp Tyr Lys Leu Phe Leu Glu Ser Asn Ala Val
                85                  90                  95

Gln Tyr Leu Glu Gly His Gly Phe Lys Phe Glu Leu Arg Lys Lys Asp
            100                 105                 110

Gly Val Asn Arg Leu Glu Glu Leu Leu Pro Ala Ala Thr Ser Gly Lys
        115                 120                 125

Asn Ile Arg Arg Thr Leu Ala Ala Leu Pro Glu Glu Glu Thr Thr Glu
    130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ala Glu Gln Gly Leu Ile Gln Tyr Pro Thr Ala Trp Gln
            180                 185                 190

Ser Val Gly His Met Met Val Ile Phe Arg Leu Met Arg Thr Asn Phe
```

-continued

```
                195                 200                 205
Leu Ile Lys Tyr Leu Leu Ile His Gln Gly Met His Met Val Ala Gly
210                 215                 220

His Asp Ala Asn Asp Ala Val Ile Ala Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Asp Gln Gly Val Arg Leu His Pro Leu Ala Arg Thr Ala Lys
                260                 265                 270

Val Arg Asn Glu Val Asn Ala Phe Lys Ala Ala Leu Ser Ser Leu Ala
                275                 280                 285

Lys His Gly Glu Tyr Ala Pro Phe Ala Arg Leu Leu Asn Leu Ser Gly
                290                 295                 300

Val Asn Asn Leu Glu His Gly Leu Tyr Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Gln Leu Arg Glu Ala Ala Thr Glu Ala Glu Lys
                340                 345                 350

Gln Leu Gln Gln Tyr Ala Glu Ser Arg Glu Leu Asp Ser Leu Gly Leu
                355                 360                 365

Asp Asp Gln Glu Arg Arg Ile Leu Met Asn Phe His Gln Lys Lys Asn
370                 375                 380

Glu Ile Ser Phe Gln Gln Thr Asn Ala Met Val Thr Leu Arg Lys Glu
385                 390                 395                 400

Arg Leu Ala Lys Leu Thr Glu Ala Ile Thr Leu Ala Ser Arg Pro Asn
                405                 410                 415

Leu Gly Ser Arg Gln Asp Asp Asn Glu Ile Pro Phe Pro Gly Pro
                420                 425                 430

Ile Ser Asn Asn Pro Asp Gln Asp His Leu Glu Asp Pro Arg Asp
                435                 440                 445

Ser Arg Asp Thr Ile Ile Pro Asn Ser Ala Ile Asp Pro Glu Asp Gly
                450                 455                 460

Asp Phe Glu Asn Tyr Asn Gly Tyr His Asp Glu Val Gly Thr Ala
465                 470                 475                 480

Gly Asp Leu Val Leu Phe Asp Leu Asp Asp His Glu Asp Asp Asn Lys
                485                 490                 495

Ala Phe Glu Leu Gln Asp Ser Ser Pro Gln Ser Gln Arg Glu Ile Glu
                500                 505                 510

Arg Glu Arg Leu Ile His Pro Pro Gly Asn Asn Lys Asp Asp Asn
                515                 520                 525

Arg Ala Ser Asp Asn Asn Gln Gln Ser Ala Asp Ser Glu Glu Gln Glu
530                 535                 540

Gly Gln Tyr Asn Arg His Arg Gly Pro Glu Arg Thr Thr Ala Asn Arg
545                 550                 555                 560

Arg Leu Ser Pro Val His Glu Glu Asp Thr Pro Ile Asp Gln Gly Asp
                565                 570                 575

Asp Asp Pro Ser Ser Pro Pro Leu Glu Ser Asp Asp Asp Ala
                580                 585                 590

Ser Ser Ser Gln Gln Asp Pro Asp Tyr Thr Ala Val Ala Pro Pro Ala
                595                 600                 605

Pro Val Tyr Arg Ser Ala Glu Ala His Glu Pro Pro His Lys Ser Ser
                610                 615                 620
```

-continued

```
Asn Glu Pro Ala Glu Thr Ser Gln Leu Asn Glu Asp Pro Asp Ile Gly
625                 630                 635                 640

Gln Ser Lys Ser Met Gln Lys Leu Gly Glu Thr Tyr His His Leu Leu
            645                 650                 655

Arg Thr Gln Gly Pro Phe Glu Ala Ile Asn Tyr Tyr His Met Met Lys
            660                 665                 670

Asp Glu Pro Val Ile Phe Ser Thr Asp Asp Gly Lys Glu Tyr Thr Tyr
            675                 680                 685

Pro Asp Ser Leu Glu Glu Ala Tyr Pro Pro Trp Leu Thr Glu Lys Glu
            690                 695                 700

Arg Leu Asp Asn Glu Asn Arg Tyr Ile Tyr Ile Asn Asn Gln Gln Phe
705                 710                 715                 720

Phe Trp Pro Val Met Ser Pro Arg Asp Lys Phe Leu Ala Ile Leu Gln
                725                 730                 735

His His Gln

<210> SEQ ID NO 2
<211> LENGTH: 329
<212> TYPE: PRT
<213> ORGANISM: Reston Ebola virus

<400> SEQUENCE: 2

Met Tyr Asn Asp Lys Leu Lys Ile Cys Ser Gly Pro Glu Thr Thr Gly
1               5                   10                  15

Trp Ile Ser Glu Gln Leu Met Thr Gly Lys Ile Pro Val Thr Asp Ile
            20                  25                  30

Phe Ile Asp Ile Asp Asn Lys Pro Asp Gln Met Glu Val Arg Leu Lys
        35                  40                  45

Pro Ser Ser Arg Ser Ser Thr Arg Thr Cys Thr Ser Ser Ser Gln Thr
50                  55                  60

Glu Val Asn Tyr Val Pro Leu Leu Lys Lys Val Glu Asp Thr Leu Thr
65                  70                  75                  80

Met Leu Val Ser Ala Thr Ser Arg Gln Asn Ala Ala Ile Glu Ala Leu
                85                  90                  95

Glu Asn Arg Leu Ser Thr Leu Glu Ser Ser Leu Lys Pro Ile Gln Asp
            100                 105                 110

Met Gly Lys Val Ile Ser Ser Leu Asn Arg Ser Cys Ala Glu Met Val
        115                 120                 125

Ala Lys Tyr Asp Leu Leu Val Met Thr Thr Gly Arg Ala Thr Ser Thr
130                 135                 140

Ala Ala Ala Val Asp Ala Tyr Trp Lys Glu His Lys Gln Pro Pro Pro
145                 150                 155                 160

Gly Pro Ala Leu Tyr Glu Glu Asn Ala Leu Lys Gly Lys Ile Asp Asp
                165                 170                 175

Pro Asn Ser Tyr Val Pro Asp Ala Val Gln Glu Ala Tyr Lys Asn Leu
            180                 185                 190

Asp Ser Thr Ser Thr Leu Thr Glu Glu Asn Phe Gly Lys Pro Tyr Ile
        195                 200                 205

Ser Ala Lys Asp Leu Lys Glu Ile Met Tyr Asp His Leu Pro Gly Phe
210                 215                 220

Gly Thr Ala Phe His Gln Leu Val Gln Val Ile Cys Lys Ile Gly Lys
225                 230                 235                 240

Asp Asn Asn Leu Leu Asp Thr Ile His Ala Glu Phe Gln Ala Ser Leu
                245                 250                 255
```

```
Ala Asp Gly Asp Ser Pro Gln Cys Ala Leu Ile Gln Ile Thr Lys Arg
            260                 265                 270

Val Pro Ile Phe Gln Asp Val Pro Pro Thr Ile His Ile Arg Ser
            275                 280                 285

Arg Gly Asp Ile Pro Arg Ala Cys Gln Lys Ser Leu Arg Pro Ala Pro
            290                 295                 300

Pro Ser Pro Lys Ile Asp Arg Gly Trp Val Cys Leu Phe Lys Met Gln
305                 310                 315                 320

Asp Gly Lys Thr Leu Gly Leu Lys Ile
                325

<210> SEQ ID NO 3
<211> LENGTH: 331
<212> TYPE: PRT
<213> ORGANISM: Reston Ebola virus

<400> SEQUENCE: 3

Met Arg Arg Gly Val Leu Pro Thr Ala Pro Ala Tyr Asn Asp Ile
1               5                   10                  15

Ala Tyr Ser Met Ser Ile Leu Pro Thr Arg Pro Ser Val Ile Val Asn
            20                  25                  30

Glu Thr Lys Ser Asp Val Leu Ala Val Pro Gly Ala Asp Val Pro Ser
            35                  40                  45

Asn Ser Met Arg Pro Val Ala Asp Asp Asn Ile Asp His Ser Ser His
50                  55                  60

Thr Pro Ser Gly Val Ala Ser Ala Phe Ile Leu Glu Ala Lys Val Asn
65                  70                  75                  80

Val Ile Ser Gly Thr Lys Val Leu Met Lys Gln Ile Pro Ile Trp Leu
            85                  90                  95

Pro Leu Gly Val Ala Asp Gln Lys Ile Tyr Ser Phe Asp Ser Thr Thr
            100                 105                 110

Ala Ala Ile Met Leu Ala Ser Tyr Thr Val Thr His Phe Gly Lys Ile
            115                 120                 125

Ser Asn Pro Leu Val Arg Val Asn Arg Leu Gly Pro Gly Ile Pro Asp
            130                 135                 140

His Pro Leu Arg Leu Leu Arg Leu Gly Asn Gln Ala Phe Leu Gln Glu
145                 150                 155                 160

Phe Val Leu Pro Pro Val Gln Leu Pro Gln Tyr Phe Thr Phe Asp Leu
            165                 170                 175

Thr Ala Leu Lys Leu Ile Thr Gln Pro Leu Pro Ala Ala Thr Trp Thr
            180                 185                 190

Asp Glu Thr Pro Ala Gly Ala Val Asn Ala Leu Arg Pro Gly Leu Ser
            195                 200                 205

Leu His Pro Lys Leu Arg Pro Ile Leu Leu Pro Gly Lys Ile Gly Lys
            210                 215                 220

Lys Gly His Ala Ser Asp Leu Thr Ser Pro Asp Lys Ile Gln Thr Ile
225                 230                 235                 240

Met Asn Ala Ile Pro Asp Leu Lys Ile Val Pro Ile Asp Pro Ile Lys
            245                 250                 255

Asn Ile Val Gly Ile Glu Val Pro Glu Leu Leu Val Gln Arg Leu Thr
            260                 265                 270

Gly Lys Lys Pro Gln Pro Lys Asn Gly Gln Pro Ile Ile Pro Val Leu
            275                 280                 285

Leu Pro Lys Tyr Val Gly Leu Asp Pro Ile Ser Pro Gly Asp Leu Thr
```

-continued

```
                290                 295                 300
Met Val Ile Thr Gln Asp Cys Asp Ser Cys His Ser Pro Ala Ser His
305                 310                 315                 320

Pro Tyr His Met Asp Lys Gln Asp Ser Tyr Gln
                325                 330

<210> SEQ ID NO 4
<211> LENGTH: 677
<212> TYPE: PRT
<213> ORGANISM: Reston Ebola virus

<400> SEQUENCE: 4

Met Gly Ser Gly Tyr Gln Leu Leu Gln Leu Pro Arg Glu Arg Phe Arg
  1               5                  10                  15

Lys Thr Ser Phe Leu Val Trp Val Ile Leu Phe Gln Arg Ala Ile
                 20                  25                  30

Ser Met Pro Leu Gly Ile Val Thr Asn Ser Thr Leu Lys Ala Thr Glu
                 35                  40                  45

Ile Asp Gln Leu Val Cys Arg Asp Lys Leu Ser Ser Thr Ser Gln Leu
 50                  55                  60

Lys Ser Val Gly Leu Asn Leu Glu Gly Asn Gly Ile Ala Thr Asp Val
 65                  70                  75                  80

Pro Ser Ala Thr Lys Arg Trp Gly Phe Arg Ser Gly Val Pro Pro Lys
                 85                  90                  95

Val Val Ser Tyr Glu Ala Gly Glu Trp Ala Glu Asn Cys Tyr Asn Leu
                100                 105                 110

Glu Ile Lys Lys Ser Asp Gly Ser Glu Cys Leu Pro Leu Pro Pro Asp
                115                 120                 125

Gly Val Arg Gly Phe Pro Arg Cys Arg Tyr Val His Lys Val Gln Gly
            130                 135                 140

Thr Gly Pro Cys Pro Gly Asp Leu Ala Phe His Lys Asn Gly Ala Phe
145                 150                 155                 160

Phe Leu Tyr Asp Arg Leu Ala Ser Thr Val Ile Tyr Arg Gly Thr Thr
                165                 170                 175

Phe Ala Glu Gly Val Ile Ala Phe Leu Ile Leu Ser Glu Pro Lys Lys
                180                 185                 190

His Phe Trp Lys Ala Thr Pro Ala His Glu Pro Val Asn Thr Thr Asp
                195                 200                 205

Asp Ser Thr Ser Tyr Tyr Met Thr Leu Thr Leu Ser Tyr Glu Met Ser
            210                 215                 220

Asn Phe Gly Gly Glu Glu Ser Asn Thr Leu Phe Lys Val Asp Asn His
225                 230                 235                 240

Thr Tyr Val Gln Leu Asp Arg Pro His Thr Pro Gln Phe Leu Val Gln
                245                 250                 255

Leu Asn Glu Thr Leu Arg Arg Asn Asn Arg Leu Ser Asn Ser Thr Gly
                260                 265                 270

Arg Leu Thr Trp Thr Val Asp Pro Lys Ile Glu Pro Asp Val Gly Glu
            275                 280                 285

Trp Ala Phe Trp Glu Thr Lys Lys Asn Phe Ser Gln Gln Leu His Gly
            290                 295                 300

Glu Asn Leu His Phe Gln Ile Leu Ser Thr His Thr Asn Asn Ser Ser
305                 310                 315                 320

Asp Gln Ser Pro Ala Gly Thr Val Gln Gly Lys Ile Ser Tyr His Pro
                325                 330                 335
```

-continued

```
Pro Thr Asn Asn Ser Glu Leu Val Pro Thr Asp Ser Pro Pro Val Val
                340                 345                 350

Ser Val Leu Thr Ala Gly Arg Thr Glu Glu Met Ser Thr Gln Gly Leu
            355                 360                 365

Thr Asn Gly Glu Thr Ile Thr Gly Phe Thr Ala Asn Pro Met Thr Thr
        370                 375                 380

Thr Ile Ala Pro Ser Pro Thr Met Thr Ser Glu Val Asp Asn Asn Val
385                 390                 395                 400

Pro Ser Glu Gln Pro Asn Asn Thr Ala Ser Ile Glu Asp Ser Pro Pro
                405                 410                 415

Ser Ala Ser Asn Glu Thr Ile Asp His Ser Glu Met Asn Ser Ile Gln
            420                 425                 430

Gly Ser Asn Asn Ser Ala Gln Ser Pro Gln Thr Lys Ala Thr Pro Ala
        435                 440                 445

Pro Thr Ala Ser Pro Met Thr Leu Asp Pro Gln Glu Thr Ala Asn Ile
    450                 455                 460

Ser Lys Pro Gly Thr Ser Pro Gly Ser Ala Ala Gly Pro Ser Gln Pro
465                 470                 475                 480

Gly Leu Thr Ile Asn Thr Ile Ser Lys Val Ala Asp Ser Leu Ser Pro
                485                 490                 495

Thr Arg Lys Gln Lys Arg Ser Val Arg Gln Asn Thr Ala Asn Lys Cys
            500                 505                 510

Asn Pro Asp Leu His Tyr Trp Thr Ala Val Asp Glu Gly Ala Ala Ala
        515                 520                 525

Gly Leu Ala Trp Ile Pro Tyr Phe Gly Pro Ala Ala Glu Gly Ile Tyr
    530                 535                 540

Ile Glu Gly Val Met His Asn Gln Asn Gly Leu Ile Cys Gly Leu Arg
545                 550                 555                 560

Gln Leu Ala Asn Glu Thr Thr Gln Ala Leu Gln Leu Phe Leu Arg Ala
                565                 570                 575

Thr Thr Glu Leu Arg Thr Tyr Ser Leu Leu Asn Arg Lys Ala Ile Asp
            580                 585                 590

Phe Leu Leu Gln Arg Trp Gly Gly Thr Cys Arg Ile Leu Gly Pro Ser
        595                 600                 605

Cys Cys Ile Glu Pro His Asp Trp Thr Lys Asn Ile Thr Asp Glu Ile
    610                 615                 620

Asn Gln Ile Lys His Asp Phe Ile Asp Asn Pro Leu Pro Asp His Gly
625                 630                 635                 640

Asp Asp Leu Asn Leu Trp Thr Gly Trp Arg Gln Trp Ile Pro Ala Gly
                645                 650                 655

Ile Gly Ile Ile Gly Val Ile Ile Ala Ile Ile Ala Leu Leu Cys Ile
            660                 665                 670

Cys Lys Ile Leu Cys
        675

<210> SEQ ID NO 5
<211> LENGTH: 367
<212> TYPE: PRT
<213> ORGANISM: Reston Ebola virus

<400> SEQUENCE: 5

Met Gly Ser Gly Tyr Gln Leu Leu Gln Leu Pro Arg Glu Arg Phe Arg
1               5                   10                  15

Lys Thr Ser Phe Leu Val Trp Val Ile Ile Leu Phe Gln Arg Ala Ile
            20                  25                  30
```

Ser Met Pro Leu Gly Ile Val Thr Asn Ser Thr Leu Lys Ala Thr Glu
            35                  40                  45

Ile Asp Gln Leu Val Cys Arg Asp Lys Leu Ser Ser Thr Ser Gln Leu
    50                  55                  60

Lys Ser Val Gly Leu Asn Leu Glu Gly Asn Gly Ile Ala Thr Asp Val
65                  70                  75                  80

Pro Ser Ala Thr Lys Arg Trp Gly Phe Arg Ser Gly Val Pro Pro Lys
                85                  90                  95

Val Val Ser Tyr Glu Ala Gly Glu Trp Ala Glu Asn Cys Tyr Asn Leu
            100                 105                 110

Glu Ile Lys Lys Ser Asp Gly Ser Glu Cys Leu Pro Leu Pro Pro Asp
        115                 120                 125

Gly Val Arg Gly Phe Pro Arg Cys Arg Tyr Val His Lys Val Gln Gly
    130                 135                 140

Thr Gly Pro Cys Pro Gly Asp Leu Ala Phe His Lys Asn Gly Ala Phe
145                 150                 155                 160

Phe Leu Tyr Asp Arg Leu Ala Ser Thr Val Ile Tyr Arg Gly Thr Thr
                165                 170                 175

Phe Ala Glu Gly Val Ile Ala Phe Leu Ile Leu Ser Glu Pro Lys Lys
            180                 185                 190

His Phe Trp Lys Ala Thr Pro Ala His Glu Pro Val Asn Thr Thr Asp
        195                 200                 205

Asp Ser Thr Ser Tyr Tyr Met Thr Leu Thr Leu Ser Tyr Glu Met Ser
    210                 215                 220

Asn Phe Gly Gly Glu Ser Asn Thr Leu Phe Lys Val Asp Asn His
225                 230                 235                 240

Thr Tyr Val Gln Leu Asp Arg Pro His Thr Pro Gln Phe Leu Val Gln
                245                 250                 255

Leu Asn Glu Thr Leu Arg Arg Asn Asn Arg Leu Ser Asn Ser Thr Gly
            260                 265                 270

Arg Leu Thr Trp Thr Val Asp Pro Lys Ile Glu Pro Asp Val Gly Glu
        275                 280                 285

Trp Ala Phe Trp Glu Thr Lys Lys Thr Phe Pro Asn Asn Phe Met Glu
    290                 295                 300

Lys Thr Cys Ile Ser Lys Phe Tyr Gln Pro Thr Pro Thr Thr Pro Gln
305                 310                 315                 320

Ile Arg Ala Arg Arg Glu Leu Ser Lys Glu Lys Leu Ala Thr Thr His
                325                 330                 335

Pro Pro Thr Thr Pro Ser Trp Phe Gln Arg Ile Pro Leu Gln Trp Phe
            340                 345                 350

Gln Cys Ser Leu Gln Asp Gly Gln Arg Lys Cys Arg Pro Lys Val
        355                 360                 365

<210> SEQ ID NO 6
<211> LENGTH: 287
<212> TYPE: PRT
<213> ORGANISM: Reston Ebola virus

<400> SEQUENCE: 6

Met Glu His Ser Arg Glu Arg Gly Arg Ser Ser Asn Met Arg His Asn
1               5                   10                  15

Ser Arg Glu Pro Tyr Glu Asn Pro Ser Arg Ser Arg Ser Leu Ser Arg
            20                  25                  30

Asp Pro Asn Gln Val Asp Arg Arg Gln Pro Arg Ser Ala Ser Gln Ile

```
            35                  40                  45
Arg Val Pro Asn Leu Phe His Arg Lys Lys Thr Asp Ala Leu Ile Val
 50                  55                  60

Pro Pro Ala Pro Lys Asp Ile Cys Pro Thr Leu Lys Lys Gly Phe Leu
 65                  70                  75                  80

Cys Asp Ser Lys Phe Cys Lys Lys Asp His Gln Leu Asp Ser Leu Asn
                     85                  90                  95

Asp His Glu Leu Leu Leu Leu Ile Ala Arg Arg Thr Cys Gly Ile Ile
                    100                 105                 110

Glu Ser Asn Ser Gln Ile Thr Ser Pro Lys Asp Met Arg Leu Ala Asn
                    115                 120                 125

Pro Thr Ala Glu Asp Phe Ser Gln Gly Asn Ser Pro Lys Leu Thr Leu
                    130                 135                 140

Ala Val Leu Leu Gln Ile Ala Glu His Trp Ala Thr Arg Asp Leu Arg
145                 150                 155                 160

Gln Ile Glu Asp Ser Lys Leu Arg Ala Leu Leu Thr Leu Cys Ala Val
                    165                 170                 175

Leu Thr Arg Lys Phe Ser Lys Ser Gln Leu Gly Leu Leu Cys Glu Thr
                    180                 185                 190

His Leu Arg His Glu Gly Leu Gly Gln Asp Gln Ala Asp Ser Val Leu
                    195                 200                 205

Glu Val Tyr Gln Arg Leu His Ser Asp Lys Gly Gly Asn Phe Glu Ala
                    210                 215                 220

Ala Leu Trp Gln Gln Trp Asp Arg Gln Ser Leu Ile Met Phe Ile Ser
225                 230                 235                 240

Ala Phe Leu Asn Ile Ala Leu Gln Thr Pro Cys Glu Ser Ser Ser Val
                    245                 250                 255

Val Val Ser Gly Leu Ala Thr Leu Tyr Pro Ala Gln Asp Asn Ser Thr
                    260                 265                 270

Pro Ser Glu Ala Thr Asn Asp Thr Thr Trp Ser Ser Thr Val Glu
                    275                 280                 285

<210> SEQ ID NO 7
<211> LENGTH: 251
<212> TYPE: PRT
<213> ORGANISM: Reston Ebola virus

<400> SEQUENCE: 7

Met Ala Lys Ala Thr Gly Arg Tyr Asn Leu Val Pro Pro Lys Lys Asp
 1                   5                  10                  15

Met Glu Lys Gly Val Ile Phe Ser Asp Leu Cys Asn Phe Leu Ile Thr
                     20                  25                  30

Gln Thr Leu Gln Gly Trp Lys Val Tyr Trp Ala Gly Ile Glu Phe Asp
                     35                  40                  45

Val Ser Gln Lys Gly Met Ala Leu Leu Thr Arg Leu Lys Thr Asn Asp
 50                  55                  60

Phe Ala Pro Ala Trp Ala Met Thr Arg Asn Leu Phe Pro His Leu Phe
 65                  70                  75                  80

Gln Asn Pro Asn Ser Val Ile Gln Ser Pro Ile Trp Ala Leu Arg Val
                     85                  90                  95

Ile Leu Ala Ala Gly Leu Gln Asp Gln Leu Leu Asp His Ser Leu Val
                    100                 105                 110

Glu Pro Leu Thr Gly Ala Leu Gly Leu Ile Ser Asp Trp Leu Leu Thr
                    115                 120                 125
```

```
Thr Thr Ser Thr His Phe Asn Leu Arg Thr Arg Ser Val Lys Asp Gln
    130                 135                 140

Leu Ser Leu Arg Met Leu Ser Leu Ile Arg Ser Asn Ile Leu Gln Phe
145                 150                 155                 160

Ile Asn Lys Leu Asp Ala Leu His Val Val Asn Tyr Asn Gly Leu Leu
                165                 170                 175

Ser Ser Ile Glu Ile Gly Thr Ser Thr His Thr Ile Ile Thr Arg
                180                 185                 190

Thr Asn Met Gly Phe Leu Val Glu Val Gln Pro Asp Lys Ser Ala
                195                 200                 205

Met Asn Ser Lys Arg Pro Gly Pro Val Lys Phe Ser Leu Leu His Glu
    210                 215                 220

Ser Ala Phe Lys Pro Phe Thr Arg Val Pro Gln Ser Gly Met Gln Ser
225                 230                 235                 240

Leu Ile Met Glu Phe Asn Ser Leu Leu Ala Ile
                245                 250

<210> SEQ ID NO 8
<211> LENGTH: 2212
<212> TYPE: PRT
<213> ORGANISM: Reston Ebola virus

<400> SEQUENCE: 8

Met Ala Thr Gln His Thr Gln Tyr Pro Asp Ala Arg Leu Ser Ser Pro
1               5                   10                  15

Ile Val Leu Asp Gln Cys Asp Leu Val Thr Arg Ala Cys Gly Leu Tyr
                20                  25                  30

Ser Ser Tyr Ser Leu Asn Pro Gln Leu Arg Gln Cys Lys Leu Pro Lys
            35                  40                  45

His Ile Tyr Arg Leu Lys Phe Asp Thr Ile Val Ser Lys Phe Leu Ser
        50                  55                  60

Asp Thr Pro Val Ala Thr Leu Pro Ile Asp Tyr Leu Val Pro Ile Leu
65                  70                  75                  80

Leu Arg Ser Leu Thr Gly His Gly Asp Arg Pro Leu Thr Pro Thr Cys
                85                  90                  95

Asn Gln Phe Leu Asp Gly Ile Ile Asn Tyr Thr Leu His Asp Ala Ala
                100                 105                 110

Phe Leu Asp Tyr Tyr Leu Lys Ala Thr Gly Ala Gln Asp His Leu Thr
            115                 120                 125

Asn Ile Thr Thr Arg Glu Lys Leu Lys Asn Glu Ile Leu Asn Asn Asp
        130                 135                 140

Tyr Val His Gln Leu Phe Phe Trp His Asp Leu Ser Ile Leu Ala Arg
145                 150                 155                 160

Arg Gly Arg Leu Asn Arg Gly Asn Asn Arg Ser Thr Trp Phe Val His
                165                 170                 175

Asp Glu Phe Ile Asp Ile Leu Gly Tyr Gly Asp Tyr Ile Phe Trp Lys
                180                 185                 190

Ile Pro Leu Ser Leu Leu Pro Val Thr Ile Asp Gly Val Pro His Ala
            195                 200                 205

Ala Thr Asp Trp Tyr Gln Pro Thr Leu Phe Lys Glu Ser Ile Leu Gly
        210                 215                 220

His Ser Gln Ile Leu Ser Val Ser Thr Ala Glu Ile Leu Ile Met Cys
225                 230                 235                 240

Lys Asp Ile Ile Thr Cys Arg Phe Asn Thr Ser Leu Ile Ala Ser Ile
                245                 250                 255
```

```
Ala Lys Leu Glu Asp Val Asp Val Ser Asp Tyr Pro Asp Pro Ser Asp
            260                 265                 270
Ile Leu Lys Ile Tyr Asn Ala Gly Asp Tyr Val Ile Ser Ile Leu Gly
            275                 280                 285
Ser Glu Gly Tyr Lys Ile Ile Lys Tyr Leu Pro Leu Cys Leu Ala
    290                 295                 300
Lys Ile Gln Leu Cys Ser Lys Phe Thr Glu Arg Lys Gly Arg Phe Leu
305                 310                 315                 320
Thr Gln Met His Leu Ser Val Ile Asn Asp Leu Arg Glu Leu Ile Ser
                325                 330                 335
Asn Arg Arg Leu Lys Asp Tyr Gln Gln Glu Lys Ile Arg Asp Phe His
                340                 345                 350
Lys Ile Leu Leu Gln Leu Gln Leu Ser Pro Gln Gln Phe Cys Glu Leu
            355                 360                 365
Phe Ser Val Gln Lys His Trp Gly His Pro Ile Leu His Ser Glu Lys
    370                 375                 380
Ala Ile Gln Lys Val Lys Arg His Ala Thr Ile Leu Lys Ala Leu Arg
385                 390                 395                 400
Pro Asn Val Ile Phe Glu Thr Tyr Cys Val Phe Lys Tyr Asn Ile Ala
                405                 410                 415
Lys His Tyr Phe Asp Ser Gln Gly Thr Trp Tyr Ser Val Ile Ser Asp
            420                 425                 430
Arg Asn Leu Thr Pro Gly Leu Asn Ser Phe Ile Lys Arg Asn His Phe
    435                 440                 445
Pro Ser Leu Pro Met Ile Lys Asp Leu Leu Trp Glu Phe Tyr His Leu
450                 455                 460
Asn His Pro Pro Leu Phe Ser Thr Lys Val Ile Ser Asp Leu Ser Ile
465                 470                 475                 480
Phe Ile Lys Asp Arg Ala Thr Ala Val Glu Gln Thr Cys Trp Asp Ala
                485                 490                 495
Val Phe Glu Pro Asn Val Leu Gly Tyr Asn Pro Pro Asn Lys Phe Ser
            500                 505                 510
Thr Lys Arg Val Pro Glu Gln Phe Leu Glu Gln Glu Asp Phe Ser Ile
    515                 520                 525
Glu Ser Val Leu Asn Tyr Ala Gln Glu Leu His Tyr Leu Leu Pro Gln
    530                 535                 540
Asn Arg Asn Phe Ser Phe Ser Leu Lys Glu Lys Glu Leu Asn Ile Gly
545                 550                 555                 560
Arg Thr Phe Gly Lys Leu Pro Tyr Leu Thr Arg Asn Val Gln Thr Leu
                565                 570                 575
Cys Glu Ala Leu Leu Ala Asp Gly Leu Ala Lys Ala Phe Pro Ser Asn
            580                 585                 590
Met Met Val Val Thr Glu Arg Glu Gln Lys Glu Ser Leu Leu His Gln
            595                 600                 605
Ala Ser Trp His His Thr Ser Asp Asp Phe Gly Glu Asn Ala Thr Val
            610                 615                 620
Arg Gly Ser Ser Phe Val Thr Asp Leu Glu Lys Tyr Asn Leu Ala Phe
625                 630                 635                 640
Arg Tyr Glu Phe Thr Ala Pro Phe Ile Glu Tyr Cys Asn His Cys Tyr
                645                 650                 655
Gly Val Arg Asn Val Phe Asn Trp Met His Tyr Leu Ile Pro Gln Cys
            660                 665                 670
```

```
Tyr Met His Val Ser Asp Tyr Asn Pro Pro His Asn Val Asn Leu
            675                 680                 685

Ser Asn Arg Glu Tyr Pro Pro Glu Gly Pro Ser Ser Tyr Arg Gly His
        690                 695                 700

Leu Gly Gly Ile Glu Gly Leu Gln Gln Lys Leu Trp Thr Ser Ile Ser
705                 710                 715                 720

Cys Ala Gln Ile Ser Leu Val Glu Ile Lys Thr Gly Phe Lys Leu Arg
                725                 730                 735

Ser Ala Val Met Gly Asp Asn Gln Cys Ile Thr Val Leu Ser Val Phe
            740                 745                 750

Pro Leu Glu Thr Asp Pro Glu Glu Gln Glu Gln Ser Ala Glu Asp Asn
        755                 760                 765

Ala Ala Arg Val Ala Ala Ser Leu Ala Lys Val Thr Ser Ala Cys Gly
    770                 775                 780

Ile Phe Leu Lys Pro Glu Glu Thr Phe Val His Ser Gly Phe Ile Tyr
785                 790                 795                 800

Phe Gly Lys Lys Gln Tyr Leu Asn Gly Val Gln Leu Pro Gln Ser Leu
                805                 810                 815

Lys Thr Ala Ala Arg Met Ala Pro Leu Ser Asp Ala Ile Phe Asp Asp
            820                 825                 830

Leu Gln Gly Thr Leu Ala Ser Ile Gly Thr Ala Phe Glu Arg Ala Ile
        835                 840                 845

Ser Glu Thr Arg His Ile Leu Pro Cys Arg Ile Val Ala Ala Phe His
    850                 855                 860

Thr Tyr Phe Ala Val Arg Ile Leu Gln Tyr His His Leu Gly Phe Asn
865                 870                 875                 880

Lys Gly Ile Asp Leu Gly Gln Leu Ser Leu Ser Lys Pro Leu Asp Tyr
                885                 890                 895

Gly Thr Ile Thr Leu Thr Leu Ala Val Pro Gln Val Leu Gly Gly Leu
            900                 905                 910

Ser Phe Leu Asn Pro Glu Lys Cys Phe Tyr Arg Asn Phe Gly Asp Pro
        915                 920                 925

Val Thr Ser Gly Leu Phe Gln Leu Arg Val Tyr Leu Glu Met Val Asn
    930                 935                 940

Met Lys Asp Leu Phe Tyr Pro Leu Ile Ser Lys Asn Pro Gly Asn Cys
945                 950                 955                 960

Ser Ala Ile Asp Phe Val Leu Asn Pro Ser Gly Leu Asn Val Pro Gly
                965                 970                 975

Ser Gln Asp Leu Thr Ser Phe Leu Arg Gln Ile Val Arg Ser Ile
            980                 985                 990

Thr Leu Thr Ala Arg Asn Lys Leu Ile Asn Thr Leu Phe His Ala Ser
        995                 1000                1005

Ala Asp Leu Glu Asp Glu Met Val Cys Lys Trp Leu Leu Ser Ser Asn
    1010                1015                1020

Pro Val Met Ser Arg Phe Ala Asp Ile Phe Ser Thr Pro Ser
1025                1030                1035                1040

Gly Lys Arg Leu Gln Ile Leu Gly Tyr Leu Glu Gly Thr Arg Thr Leu
                1045                1050                1055

Leu Ala Ser Lys Ile Ile Asn Asn Ser Glu Thr Pro Val Leu Asp
            1060                1065                1070

Lys Leu Arg Lys Ile Thr Leu Gln Arg Trp Asn Leu Trp Phe Ser Tyr
        1075                1080                1085

Leu Asp His Cys Asp Gln Leu Leu Ala Asp Ala Leu Gln Lys Ile Ser
```

```
                1090                1095                1100
Cys Thr Val Asp Leu Ala Gln Ile Leu Arg Glu Tyr Thr Trp Ser His
1105                1110                1115                1120

Ile Leu Glu Gly Arg Pro Leu Ile Gly Ala Thr Leu Pro Cys Met Val
                1125                1130                1135

Glu Gln Phe Lys Val Lys Trp Leu Arg Gln Tyr Glu Pro Cys Pro Glu
                1140                1145                1150

Cys Leu Asn Lys Lys Gly Ser Asn Ala Tyr Val Ser Val Ala Val Lys
                1155                1160                1165

Asp Gln Val Val Ser Ala Trp Pro Asn Thr Ser Arg Ile Ser Trp Thr
                1170                1175                1180

Ile Gly Ser Gly Val Pro Tyr Ile Gly Ser Arg Thr Glu Asp Lys Ile
1185                1190                1195                1200

Gly Gln Pro Ala Ile Lys Pro Arg Cys Pro Ser Ser Ala Leu Lys Glu
                1205                1210                1215

Ala Ile Glu Leu Ala Ser Arg Leu Thr Trp Val Thr Gln Gly Ser Ser
                1220                1225                1230

Asn Ser Glu Gln Leu Ile Arg Pro Phe Leu Glu Ala Arg Val Asn Leu
                1235                1240                1245

Ser Val Ser Glu Val Leu Gln Met Thr Pro Ser His Tyr Ser Gly Asn
                1250                1255                1260

Ile Val His Arg Tyr Asn Asp Gln Tyr Ser Pro His Ser Phe Met Ala
1265                1270                1275                1280

Asn Arg Met Ser Asn Thr Ala Thr Arg Leu Ile Val Ser Thr Asn Thr
                1285                1290                1295

Leu Gly Glu Phe Ser Gly Gly Gly Gln Ala Ala Arg Asp Ser Asn Ile
                1300                1305                1310

Ile Phe Gln Asn Val Ile Asn Leu Ala Val Ala Leu Tyr Asp Ile Arg
                1315                1320                1325

Phe Arg Asn Thr Asn Thr Ser Asp Ile Arg His Asn Arg Ala His Leu
                1330                1335                1340

His Leu Thr Glu Cys Cys Thr Lys Glu Val Pro Ala Gln Tyr Leu Thr
1345                1350                1355                1360

Tyr Thr Ser Ala Leu Asn Leu Asp Leu Ser Arg Tyr Arg Asp Asn Glu
                1365                1370                1375

Leu Ile Tyr Asp Ser Asn Pro Leu Arg Gly Gly Leu Asn Cys Asn Leu
                1380                1385                1390

Thr Met Asp Ser Pro Leu Val Lys Gly Pro Arg Leu Asn Met Ile Glu
                1395                1400                1405

Asp Asp Leu Leu Arg Phe Pro His Leu Ser Gly Trp Glu Leu Ala Lys
                1410                1415                1420

Thr Val Val Gln Ser Ile Ile Ser Asp Asn Ser Asn Ser Ser Thr Asp
1425                1430                1435                1440

Pro Ile Ser Ser Gly Glu Thr Arg Ser Phe Thr Thr His Phe Leu Thr
                1445                1450                1455

Tyr Pro Gln Ile Gly Leu Leu Tyr Ser Phe Gly Ala Val Leu Cys Phe
                1460                1465                1470

Tyr Leu Gly Asn Thr Ile Leu Trp Thr Lys Lys Leu Asp Tyr Glu Gln
                1475                1480                1485

Phe Leu Tyr Tyr Leu His Asn Gln Leu His Asn Leu Pro His Arg Ala
                1490                1495                1500

Leu Arg Val Phe Lys Pro Thr Phe Lys His Ala Ser Val Met Ser Arg
1505                1510                1515                1520
```

```
Leu Met Glu Ile Asp Ser Asn Phe Ser Ile Tyr Ile Gly Gly Thr Ser
            1525                1530                1535

Gly Asp Arg Gly Leu Ser Asp Ala Ala Arg Leu Phe Leu Arg Thr Ala
            1540                1545                1550

Ile Ala Ser Phe Leu Gln Phe Leu Lys Ser Trp Ile Ile Asp Arg Gln
            1555                1560                1565

Lys Ala Ile Pro Leu Trp Ile Val Tyr Pro Leu Glu Gly Gln Gln Pro
            1570                1575                1580

Glu Ser Ile Asn Glu Phe Leu His Lys Ile Phe Gly Leu Leu Lys Gln
1585                1590                1595                1600

Gly Pro Lys Asn Ile Pro Lys Glu Val Ser Ile Gln Asn Asp Gly His
            1605                1610                1615

Leu Asp Leu Ala Glu Asn Asn Tyr Val Tyr Asn Ser Lys Ser Thr Ala
            1620                1625                1630

Ser Asn Phe Phe His Ala Ser Leu Ala Tyr Trp Arg Ser Arg Lys Ser
            1635                1640                1645

Arg Lys Thr Gln Asp His Asn Asp Phe Ser Arg Gly Asp Gly Thr Leu
            1650                1655                1660

Thr Glu Pro Val Cys Lys Phe Ser Ser Asn His Gln Ser Asp Glu Lys
1665                1670                1675                1680

Tyr Tyr Asn Val Thr Cys Gly Lys Ser Pro Lys Pro Gln Glu Arg Lys
            1685                1690                1695

Asp Phe Ser Gln Tyr Arg Leu Ser Asn Asn Gly Gln Thr Met Ser Asn
            1700                1705                1710

His Arg Lys Lys Gly Lys Phe His Lys Trp Asn Pro Cys Lys Val Leu
            1715                1720                1725

Met Glu Ser Gln Arg Gly Thr Val Leu Lys Glu Gly Asp Tyr Phe Gln
            1730                1735                1740

Asn Asn Thr Pro Pro Thr Asp Val Ser Ser Pro His Arg Leu Ile
1745                1750                1755                1760

Leu Pro Phe Phe Lys Leu Gly Asn His Asn His Ala His Asp Gln Asp
            1765                1770                1775

Ala Gln Glu Leu Ile Asn Gln Asn Ile Lys Gln Tyr Leu His Gln Leu
            1780                1785                1790

Arg Ser Met Leu Asp Thr Thr Ile Tyr Cys Arg Phe Thr Gly Ile Val
            1795                1800                1805

Ser Ser Met His Tyr Lys Leu Asp Glu Val Leu Leu Glu Tyr Asn Ser
            1810                1815                1820

Phe Asp Ser Ala Ile Thr Leu Ala Glu Gly Glu Gly Ser Gly Ala Leu
1825                1830                1835                1840

Leu Leu Leu Gln Lys Tyr Ser Thr Arg Leu Leu Phe Leu Asn Thr Leu
            1845                1850                1855

Ala Thr Glu His Ser Ile Glu Ser Glu Val Val Ser Gly Phe Ser Thr
            1860                1865                1870

Pro Arg Met Leu Leu Pro Ile Met Gln Lys Val His Glu Gly Gln Val
            1875                1880                1885

Thr Val Ile Leu Asn Asn Ser Ala Ser Gln Ile Thr Asp Ile Thr Ser
            1890                1895                1900

Ser Met Trp Leu Ser Asn Gln Lys Tyr Asn Leu Pro Cys Gln Val Glu
1905                1910                1915                1920

Ile Ile Thr Met Asp Ala Glu Thr Thr Glu Asn Leu Asn Arg Ser Gln
            1925                1930                1935
```

Leu Tyr Arg Ala Val Tyr Asn Leu Ile Leu Asp His Ile Asp Pro Gln
            1940                1945                1950

Tyr Leu Lys Val Val Leu Lys Val Phe Leu Ser Asp Ile Glu Gly
        1955                1960                1965

Ile Leu Trp Ile Asn Asp Tyr Leu Ala Pro Leu Phe Gly Ala Gly Tyr
    1970                1975                1980

Leu Ile Lys Pro Ile Thr Ser Ser Ala Arg Ser Ser Glu Trp Tyr Leu
1985                1990                1995                2000

Cys Leu Ser Asn Leu Ile Ser Thr Asn Arg Arg Ser Ala His Gln Thr
            2005                2010                2015

His Lys Ala Cys Leu Gly Val Ile Arg Asp Ala Leu Gln Ala Gln Val
        2020                2025                2030

Gln Arg Gly Val Tyr Trp Leu Ser His Ile Ala Gln Tyr Ala Thr Lys
        2035                2040                2045

Asn Leu His Cys Glu Tyr Ile Cys Leu Gly Phe Pro Pro Leu Glu Lys
    2050                2055                2060

Val Leu Tyr His Arg Tyr Asn Leu Val Asp Thr Gly Leu Gly Pro Leu
2065                2070                2075                2080

Ser Ser Val Ile Arg His Leu Thr Asn Leu Gln Ala Glu Ile Arg Asp
            2085                2090                2095

Leu Val Leu Asp Tyr Thr Leu Met Arg Glu Ser Arg Thr Gln Thr Tyr
        2100                2105                2110

His Phe Ile Lys Thr Ala Lys Gly Arg Ile Thr Lys Leu Val Asn Asp
        2115                2120                2125

Phe Leu Lys Phe Ser Leu Ile Val Gln Ala Leu Lys Asn Asn Ser Ser
    2130                2135                2140

Trp Tyr Thr Glu Leu Lys Lys Leu Pro Glu Val Ile Asn Val Cys Asn
2145                2150                2155                2160

Arg Phe Tyr His Thr His Ser Cys Glu Cys Gln Glu Lys Phe Phe Val
            2165                2170                2175

Gln Thr Leu Tyr Leu Gln Arg Leu Arg Asp Ala Glu Ile Lys Leu Ile
        2180                2185                2190

Glu Arg Leu Thr Gly Leu Met Arg Phe Tyr Pro Glu Gly Leu Ile Tyr
        2195                2200                2205

Ser Asn His Thr
    2210

<210> SEQ ID NO 9
<211> LENGTH: 18890
<212> TYPE: DNA
<213> ORGANISM: Reston Ebola virus

<400> SEQUENCE: 9
gggacacaca aaagaaaaag gttttttaag attttttgtg tgcgagtaac tatgaggaag      60
attaacagtt ttcctcagtt taaggtatac actgaaattg agattgagat tctcctcttt     120
gctattctgt aactttccct ggttgtgaca attgaatcag ttttatctat taccaattac     180
catcaacatg gtatgtctag tgatcttggg actcttcttc atctggtttt tcctagagct     240
ctgaatctat tttgtgagaa gttcatccaa acgacccagt gtctgaaaat acaagaggtt     300
cccctttccg tcaagtttaa ggggttgttt tgattgtgtg tagattttat aatcctagag     360
tgccaaggag ttgcgtgtca tcattaattg ggaagatcaa ggaaacaatt tgttccaata     420
atatcgtaca tcttgactaa gtcgaacaag gggaagtcga tatggatcgt gggaccagaa     480
gaatctgggt gtcgcaaaat caaggtgata ctgatttaga ttatcataaa attttgacag     540

```
ctggccttac tgttcaacag ggaattgtca ggcagaaaat aatttctgta tatcttgttg      600
ataacttgga ggctatgtgt caattggtaa tacaagcctt tgaggccgga attgatttcc      660
aagaaaatgc cgacagcttc cttctgatgc tttgcctaca tcatgcttac caaggtgact      720
ataaattgtt cttggagagc aatgctgtac agtatttgga aggtcatgga ttcaaatttg      780
agctccggaa gaaggacggt gtcaatcggc tcgaggaatt gcttcctgct gcaacgagtg      840
gaaaaaacat caggcgtacg ttggccgcac tgcctgaaga ggagactaca gaagcaaatg      900
cagggcaatt tctctcattt gcgagtttgt tcttcccaa actggttgtg ggagagaagg       960
cttgcttgga aaaagtccag cgacaaattc aggttcatgc agaacagggt ttaattcaat     1020
atcccactgc atggcaatca gttggacaca tgatggtaat cttcagattg atgaggacta     1080
atttcttgat taaatatttta ctgatccacc agggtatgca tatggtagct ggccacgatg    1140
ccaatgatgc tgtcattgct aattcagttg ctcaggctcg cttttcagga ctcctaattg     1200
tcaaaaccgt tcttgatcat attctgcaga aaaccgacca aggagtaaga cttcacccctt    1260 tggcccgaac agccaaagtg cgtaatgagg ttaatgcatt taaggccgcc ctaagctcac     1320
ttgctaagca tggggagtat gcccctttg ctcgccttct caatctctcg ggagttaaca      1380
acctagaaca tggtctctac ccacagttat cagcaattgc tcttggagtt gccacagcac     1440
atggtagcac ccttgcagga gttaatgttg gtgagcagta tcagcagctt agagaggctg     1500
ccactgaagc tgagaagcaa ctccaacaat atgctgagtc cagagaactc gacagcctag     1560
gcctagcgaa tcaggaaaga agaatactaa tgaacttcca tcagaagaaa atgaaatta      1620 gtttccagca gaccaatgca atggtaaccc ttaggaaaga gcgactggct aaattaacag     1680
aagctataac gctggcctca agacctaacc tcgggtctag acaagacgac gacaatgaaa     1740
taccgttccc tgggcctata agcaacaacc cagaccaaga tcatctggag gatgatccta     1800
gagactccag agacactatc attcctaata gtgcaattga ccccgaggat ggtgattttg     1860
aaaattacaa tggctatcat gatgatgaag ttgggacggc aggtgacttg gtcttgttcg     1920
atcttgacga tcatgaggat gacaataaag cttttgagct acaggacagc tcaccacaat     1980
cccaaaggga aatagagaga gaaagattaa ttcatccacc cccaggcaac aacaaggacg     2040
acaatcgggc ctcagacaac aatcaacaat cagcagattc tgaggaacaa gaaggtcaat     2100
acaacaggca ccgaggccca gaacgtacga ccgccaatcg aagactctca ccagtgcacg     2160
aagaggacac ccctatagat caaggcgatg atgatccctc aagcccacct ccgctggaat     2220
ctgatgatga cgatgcatca agtagccaac aagatcccga ttatacagct gttgcccctc     2280
ctgctcctgt ataccgcagt gcagaagccc acgagcctcc ccacaaatcc tcgaacgagc     2340
cagctgaaac atcacaattg aatgaagacc ctgatatcgg tcaatcaaag tctatgcaaa     2400
aattaggaga gacatatcac catctgctga gaactcaagg tccatttgaa gctatcaatt     2460
attatcacat gatgaaggat gagccggtaa tatttagcac tgatgatggg aaggaataca     2520
cctacccgga ttcacttgag gaagcctatc ctccatggct caccgagaaa gaacgactgg     2580
acaatgaaaa tcgatacatt tacataaata atcaacagtt cttctggcct gtcatgagtc     2640
ccagagacaa atttcttgca atcttgcagc accatcagta accacagcac aaagcgcggt     2700
ccacttcgta aagctaaata cacttaaagc ttgaccgatt catctacaaa aactaatcca     2760
ttataactta ttagtgctac ttttctataa gtgattctca atctaaggcc attaagagtt     2820
taagcaatat acatatacac ttacaccggt ctatccaaga tgtggctcaa tgttcttaat     2880
```

```
ttgaacatag tcataagggg ataaataata ctttatatt  ctgattgtgg actgacccat   2940
tctgcttaaa atgcttcgcc cattaaaaat gtgatctaat agatagccct gactagacca   3000
attaagaaaa acatttgatg aagattaaaa ccttcatcgc cagtaaatga ttatattgtc   3060
tgtaggcagg tgtttactcc accttaaagt cggaaatatc ctaccttagg accattgtta   3120
agaggtgcat aggcattacc atccttgaga acatgtataa tgataaattg aagatatgtt   3180
caggcccaga aacaactgga tggatttctg agcaactaat gacaggtaag attccagtaa   3240
ctgatatatt cattgatatt gataacaagc cagatcaaat ggaagtccgg ctcaaaccat   3300
catcaaggag ctcaaccaga acttgtacaa gtagcagtca gacggaggtc aactatgtac   3360
ctctccttaa aaaggttgag gatacattaa ctatgctagt gagtgcaacc agtcgtcaga   3420
atgctgcaat cgaggccctt gaaaaccgcc tcagcacact tgagagtagc ttaaagccaa   3480
tccaagacat gggtaaagtg atttcatcat tgaatcgcag ttgtgccgaa atggtggcaa   3540
aatatgatct tctagttatg acaactggac gggctacttc aaccgcagct gcagtagatg   3600
cgtactggaa agagcacaaa cagccaccac cagggccagc gttgtatgaa gagaatgcgc   3660
ttaaaggaaa aatcgatgat ccaaacagct atgtaccaga tgctgtgcag gaggcttaca   3720
agaaccttga cagtacatcg accctgaccg aggaaaattt tgggaaacct tatatatctg   3780
ctaaagatct gaaggagatc atgtatgatc atctacctgg ttttgggact gcctttcacc   3840
aacttgttca agtgatttgt aaaataggaa aggataacaa cctcttggac acaatccatg   3900
ctgagttcca ggcaagtcta gcagatggtg actctcccca atgtgcactc atacagataa   3960
ccaaaagagt cccaatcttt caggatgtgc cgccccgac  aatccacatt agatcccgtg   4020
gtgatatccc acgagcatgc caaaagagtc tccgaccagc accaccatca cccaaaattg   4080
atcgtggttg ggtttgtttg tttaagatgc aagatggtaa aacgcttgga cttaagatct   4140
aaggatcaag atttatttaa caaggcaagc cacaaccta  gatagaacct cagccagact   4200
attgaactat tgacgctgtt gatgataata taattaat   ggtcatattt gaatatgaca   4260
acatcttgct tcttgttttg ccttgtatct ctttgagttg gaagatcatt ccaaacttac   4320
aaacatgcac aagatgttat ggtttagcaa agaattgata ggagtactgg tatataatgt   4380
aaatataaca agtgatgaag attaagaaaa accagtcggt attttccaga cttggcattt   4440
cttatcttca tcttctaaag tgagatattt tatcatcaaa aaatgagacg cggagtgtta   4500
ccaacggctc ctccagcata taatgatatt gcatactcta tgagcatact cccaacccga   4560
ccaagtgtca tagtcaatga gaccaaatca gatgtactgg cagtgccagg agcagatgtt   4620
ccatcaaact ccatgagacc agtggctgat gataacattg atcactcaag ccatactcca   4680
agcggagtag cttctgcctt tatattggaa gctaaagtga atgtaatttc gggaacaaaa   4740
gtcctgatga agcaaatacc tatttggctt ccactgggtg tagctgatca aagagatatac  4800 agctttgatt caacaacagc cgcaattatg ttggcttcct acacagtgac acacttcggg   4860
aagatatcta acccgctggt acgtgtcaac aggctaggcc caggaatacc cgatcatccg   4920
ctacgactcc taaggttggg caatcaggca ttccttcaag agtttgttct tccaccagtc   4980
cagcttcccc agtatttcac atttgatcta acagctctaa agctcatcac tcaaccattg   5040
ccagctgcaa cctggacaga cgaaactcca gcaggagcag tcaatgctct tcgtcctggg   5100
ctctcactcc atcccaagct tcgtccaatt cttctaccgg ggaagatagg aaagaaaggt   5160
catgcttcag acttaacatc acctgacaaa attcaaacaa tcatgaatgc aataccggac   5220
ctcaaaattg tcccgattga tccaatcaag aacatagttg gaattgaggt tccagaatta   5280
```

```
ctagttcaaa ggctgaccgg caaaaaacca cacccaaaa atggccaacc aattattcca    5340
gttcttcttc cgaaatatgt tggacttgat cctatatcgc caggggactt aactatggtt    5400
atcacccagg attgtgattc atgccactct ccagccagcc atccgtatca catggacaag    5460
caggatagtt accaataatt taaattccat tcgagctatt attctgctag taattccgac    5520
gggatcaata gactaaaaat ctgattgtat agaattataa agaatcaag cagaggcaac     5580 agactcacag cttacgccta gatgactaat attaaggagt tttttaatct aattttccag    5640
tcttaagtaa taatcatttc ttttgtaatt aattatgcat tgttaactt atcggtgcga     5700 gatttccttg agaacccggc ggggcttcta ctatctgtag taaccagaag agaagttcaa    5760
cccagtcaaa actaaaccaa gcaatattct gaatgctcta tagtctattc taatcagagg    5820
tataacaatg ctaagatttt caatgactcg ttaacaatcg ctagtaattt taatctccag    5880
attaagaaaa agatatacga tgaagattaa ggcgacaacg agccgaaact tcatctcttt    5940
taaagatcta acattatctg ttccaaagtc atacaaggac acattcaaat cagggattgt    6000
aagctgctat ttcttacctc cccaaatcac ctatacaaca tggggtcagg atatcaactt    6060
ctccaattgc ctcgggaacg ttttcgtaaa acttcgttct tagtatgggt aatcatcctc    6120
ttccagcgag caatctccat gccgcttggt atagtgacaa atagcactct caaagcaaca    6180
gaaattgatc aattggtttg tcgggacaaa ctgtcatcaa ccagtcagct caagtctgtg    6240
gggctgaatc tggaaggaaa tggaattgca accgatgtcc catcagcaac aaaacgctgg    6300
ggattccgtt caggtgtgcc tcccaaggtg gtcagctatg aagccggaga atgggcagaa    6360
aattgctaca atctggagat caaaaagtca gacggaagtg agtgcctccc tctccctccc    6420
gacggtgtac ggggattccc tagatgtcgc tatgtccaca aagttcaagg aacaggtcct    6480
tgtcccggtg acttagcttt ccataaaaat ggggcttttt tcttgtatga tagattggcc    6540
tcaactgtca tctaccgtgg gacaactttt gctgaaggtg tcatagcttt tttaattctg    6600
tcagagccca agaagcattt ttggaaggct acaccagctc atgaaccggt gaacacaaca    6660
gatgattcca caagctacta catgacccctg acactcagct acgagatgtc aaattttgga    6720
ggcgaggaaa gtaacaccct ttttaaggta gacaaccaca catatgtgca actagatcgt    6780
ccacacactc cgcagttcct tgttcagctc aatgaaacac ttcgaagaaa taatcgcctt    6840
agcaacagta cagggagatt gacttggaca gtggatccca aaattgaacc agatgttggt    6900
gagtgggcct tctgggaaac taaaaaaact tttcccaaca acttcatgga gaaaacttgc    6960
atttccaaat tctatcaacc cacaccaaca actcctcaga tcagagcccg gcggaactg    7020 tccaaggaaa aattagctac cacccaccca ccaacaactc cgagctggtt ccaacggatt    7080
cccctccagt ggtttcagtg ctcactgcag gacggacaga ggaaatgtcg acccaaggtc    7140
taactaacgg agagacaatc acaggtttca ccgcgaaccc aatgacaacc accattgccc    7200
caagtccaac catgacaagc gaggttgata acaatgtacc aagtgaacaa ccgaacaaca    7260
cagcatccat tgaagactcc cccccatcgg caagcaacga cacaattgac cactccgaaa    7320
tgaattcgat ccaaggctcg aacaactccg cccagagccc acagaccaag gccacgccag    7380
cgcccacagc atccccgatg accctggacc cgcaagagac ggccaacatc agcaaaccag    7440
gaaccagccc aggaagcgca gccggaccaa gtcagcccgg actcactata aatacaataa    7500
gtaaggtagc tgattcactg agtcccacca ggaaacaaaa gcgatcggtt cgacaaaaca    7560
ccgctaataa atgtaaccca gatcttcact attggacagc tgttgatgag ggggcagcag    7620
```

-continued

```
caggattggc atggattcca tattttggac ctgcagcaga aggcatctac attgagggtg      7680
taatgcataa tcagaatggg cttatttgcg ggctacgtca gctagccaat gaaactaccc      7740
aggctcttca attatttctg cgggccacaa cagaactgag gacttactca cttcttaaca      7800
gaaaagctat tgattttctt cttcaacgat ggggaggtac ctgtcgaatc ctaggaccat      7860
cttgttgcat tgagccacat gattggacaa aaaatattac tgatgaaatt aaccaaatta      7920
aacatgactt tattgacaat cccctaccag accacggaga tgatcttaat ctatggacag      7980
gttggagaca atggatcccg gctggaattg ggattattgg agttataatt gctataatag      8040
ccctactttg tatatgtaag attttgtgtt gatttattct gagatctgag agaaaaaaat      8100
ctcagggtta ctctaaggag aaatattatt tttaaaattt acttaaatgc tgaccactta      8160
tcttaaatga gcaattaata atatgttttt ctgcttcttt gcttgattta caatatgata      8220
tttctcttaa taatgattaa tatattaaga aaaacttatg acgaagatta aaggggagga      8280
tcgttaacgg gaaaatctcc catctcgttc gtcgaagcca cgttggtggt gcttgcagct      8340
gagaacaact ccagagattg taggtagaaa ggaccagcat ttataggtag gggtcagaaa      8400
gcaacaatag cctaaaaagg agagcctgac attgctattt aatatcctag aacctgattt      8460
ctaggttcta gttgtacaat ccggatgatg gagcattcaa gagaacgggg tagatctagc      8520
aacatgcgac ataatagccg ggaaccatac gaaaatccat caaggtctcg ctcattatct      8580
cgggacccta atcaggttga tcgtaggcag cctcgaagtg catcccaaat tcgtgttccg      8640
aatctgttcc atcggaaaaa gactgatgca ctcatagttc ctccggctcc caaagatata      8700
tgcccaacac tcaaaaaagg attcctctgc gatagtaaat tttgcaaaaa agatcaccaa      8760
ttggatagct taaatgatca tgaattacta ctgctaattg caagaagaac atgtggaatt      8820
atcgagagca attcgcagat tacatcccca aaagatatgc ggttagcgaa tccaacagct      8880
gaagacttct cacaaggtaa tagtcctaaa ttaacacttg cagtccttct tcaaattgct      8940
gaacattggg caaccagaga cctaaggcaa attgaggact ctaaacttag agctctttta      9000
acccttcgtg ccgtattaac aaggaaattt ctaaatcccc aactgggtct tctatgtgag      9060
acccacctac ggcatgaggg cctcggacag gaccaagctg attctgtatt agaggtctac      9120
caaagactcc acagtgataa aggagggaat tttgaggctg ccctgtggca acaatgggac      9180
cgacagtcgt taataatgtt catctctgct tttctcaaca ttgctctcca gacaccttgt      9240
gaaagttcta gtgtcgtagt ctcaggtctt gccacattgt acccagcaca agacaattct      9300
acaccgtccg aggcaactaa tgataccacc tggtcaagta cagttgaata gaaaaccact      9360
ggagctattt ttccacgatt gctctcagtc aataaattaa tatagatata atacgacttc      9420
ggtgtgcaat tgtcaagggt tccatttggt aataatgatt cttaaaacaa tctactatcg      9480
taattatcga tggatctacc ctatttgacg gtacatgact tgaatgtaat aaggtaagtt      9540
ggtatctgag gtattttgtc tagagtatac tcaaaatcgt atgtctagca aattatcaat      9600
agcaaagtta aattctccta acctcatatt ttgatcaagt aatcatgatt ttatggtaat      9660 tcttttgcaga ttatcggttt aatctttatt aagaaaaaat catgattgta gacaatttac      9720
tggtagtccc tgggtatcca agtttatgaa cagagctaga gagaatttgc tacttccgag      9780
gtataacttt attatttgct acttcgaatg cctaaaacca gtaatgcagg atgaagatta      9840
attgcggagg aatcaggaat tcaactttag ttccttaagg cctcgtctga atcttcatca      9900
gttagtaagt tcttttatag aagtcattag cttctaaggt gattatattt tagtattaaa      9960
ttttgttaat tgcttgctat aaagttgaaa tgtctaatgc ttaaatgaac atttctttga     10020
```

```
agctgacata cgaatacatc atatcatatg aaaacatcgc aattagagcg tccttgaagt   10080
ctggcattga cagtcaccag gctgttctca gtagtctgtc cttggaagct cttggggaga   10140
caagaagagg tcccagagag tcccaacagg ttggcataag gtcattaaca ccagcatagt   10200
cagctcgatc aagactgtaa gcgagtcgat tgcaactaaa aagattattt cttgttgttt   10260
aaacaaattc cttttgtgtg agacaccctc aaggcacaag atggctaaag ccacaggccg   10320
atacaatctc gtgcccccaa agaaagatat ggaaaaggga gtgattttta gtgatctttg   10380
taatttcttg attactcaaa ccctgcaagg ttggaaggtt tattgggcag gaattgagtt   10440
tgatgtaagt caaaaaggca tggctcttct gacaagactc aaaacaaatg actttgctcc   10500
tgcctgggcg atgacaagaa atctcttccc acatctgttc caaacccaa attcggttat   10560
tcaatctccc atctgggctt tgagggtgat tttggcagcc ggattgcagg atcagttgtt   10620
agaccattca ttggttgagc cattgacagg ggctctcggt ctaatttctg attggctcct   10680
aactacaacg tcaacacatt tcaatcttcg tactagaagc gtaaaggacc agcttagtct   10740
tcgtatgtta tctttgatca ggtcaaacat cttgcagttc atcaacaagc ttgacgccct   10800
gcatgttgtc aattacaatg gtttactcag tagtattgag atcgggactt ctacacacac   10860
aatcattata actcgtacaa atatgggttt tctcgtggaa gttcaggagc ctgacaaatc   10920
agctatgaat tctaagcgcc caggaccagt caagttctca ttacttcatg agtctgcctt   10980
caaacctttc actcgtgttc cacaatctgg gatgcaatca ttaataatgg agttcaacag   11040
tttgttggca atttaacaag gtgatcttaa aataagtaca tgaatgagaa ttagttgtgg   11100
gtcttaccta gcattgttga gttagctatc taatctattt tcactaattg cattgagcac   11160
tgctagtagg tttgcaccac gttaaagatt cagagtgtat gaattgtgca gatttaaact   11220
tgggttttgc cttatgcttc acaggtggtc ttttttaaaat ggagattatc agcatttctt   11280
caatgggagg agttagcaat cagaaattgg agataaatgg acatcgggat agaacaatgc   11340
ctaactattg ggcggctttc atttttaaat gtgtatataa ccaatctttt cctatctttg   11400
cttatattgg tgtaacttta ctttaataac atgtcaatgc tatactgtta agagaaggtc   11460
tgaggaagat taagaaaaag gtctcgtgtt cacttggttg ccgtcaagta tcctgtggtt   11520
ttttctacc taacttcctc atgccatatg gctacccagc ataccagta cccggatgca   11580
cgtttatctt cacctatagt cctggatcaa tgtgatttgg taactcgagc atgtgggtta   11640
tattcatctt attctctaaa tcctcagcta aggcaatgta aattaccaaa acatatatat   11700
cgacttaagt tcgacacaat agtatccaaa ttcctaagtg atacacctgt agcaacactg   11760
ccgatagact atttagtacc aattctcctg cgttccctaa cggggcacgg tgataggccg   11820
ttgaccccga cttgtaatca attccttgat ggaattatta attacactct tcatgatgca   11880
gcctttcttg attactatct caaggcaaca ggtgcacagg accatttgac aaacattaca   11940
actagagaga agcttaaaaa cgaaattcta acaatgatt atgtccatca attgttcttc   12000
tggcatgacc tgtctatttt ggctcgacgt gggcgtctga atcgcgggaa caaccgttca   12060
acctggtttg ttcatgatga attcattgat attttaggat atggcgatta tattttttgg   12120
aaaatacctt tatcattatt accagttact atagacgggg tccacacgc ggcaactgac   12180
tggtatcaac cgactctttt taaagaatcc atcctagggc acagccaaat cctatctgtg   12240
tcgacagctg aaatactaat tatgtgtaaa gatattatca cctgtaggtt taatacatca   12300
ctgattgcat ccattgcaaa attagaggat gtagatgtgt ctgattatcc tgacccgagt   12360
```

```
gatattctta agatatacaa tgctggagac tatgtaatat ctattcttgg ctcagaaggt    12420
tataagataa taaagtacct tgaaccactt tgtttggcca aaatccaact ttgctctaaa    12480
ttcacagaaa gaaaaggtcg tttcctcaca cagatgcatt tatcagtaat aaatgatctt    12540
cgggagttga tttctaaccg caggttaaag gactatcagc aagagaagat tagggatttt    12600
cacaaaatat tattacaatt gcaattatct cctcaacagt tttgtgaatt attctctgtt    12660
caaaaacatt gggggcatcc aattttacat agtgagaaag ctatacaaaa agtaaaacgg    12720
catgcaacca tccttaaggc tctcagacct aatgtcattt ttgagacata ttgtgtattc    12780
aagtacaata ttgccaagca ctatttcgac agccaaggaa cttggtacag tgtaatctca    12840
gacaggaatt taactccagg actcaactcc ttcataaaac gtaatcactt tccttcacta    12900
cccatgatta aggatcttct atgggaattc tatcatctta atcaccctcc gttattctct    12960
acaaaggtga ttagtgactt aagtattttc atcaaggata gggccacagc tgttgaacag    13020
acatgttggg atgcagtctt tgaacccaat gtgctaggtt acaatcctcc aaacaaattc    13080
tccactaaaa gggtgccgga acaatttcta gaacaggagg atttttcaat cgaaagtgtc    13140
ctgaattatg cacaggaatt acattattta ttaccacaga ataggaattt ttccttttct    13200
cttaaagaaa agaattaaaa tattggacga acatttggta agctaccata tctcacacgg    13260
aatgtccaaa ctttatgtga ggctctgtta gcagatggac tggctaaggc cttccccagt    13320
aacatgatgg tagtaactga acgtgaacaa aaagagagcc ttcttcatca ggcatcatgg    13380
caccacacca gtgatgattt tggagagaat gctaccgttc gagggagtag ttttgtaact    13440
gatttagaga agtacaatct tgcatttcgc tatgagttca ctgcaccatt tattgagtac    13500
tgcaaccatt gctatggtgt gcgtaatgtc tttaattgga tgcattattt aatcccgcag    13560
tgttacatgc atgtaagtga ttattataat ccgcctcaca atgttaatct tagcaatcga    13620
gaatatcctc ctgaaggccc gagttcgtac cgagggcact taggaggcat agagggatta    13680
caacaaaaac tgtggacgag tatatcctgt gcacaaatct ccttagtgga aattaaaact    13740
ggttttaagt tacgatcagc ggtcatggga gacaatcagt gtataaccgt attgtctgtt    13800
tttccacttg aaacagaccc tgaagagcag gagcaaagcg ccgaagacaa tgctgcaaga    13860
gtagcagcaa gtcttgcaaa agtaaccagt gcatgtggga tctttcttaa accagaagag    13920
acattcgtac actcaggttt catttatttc ggaaaaaaac aatatctcaa tggtgtacaa    13980
ttaccgcaat cactcaaaac agcagcaaga atggcgccac tctctgatgc tatattcgat    14040
gatctacaag gaacacttgc cagtattgga actgccttcg aacgtgctat atcggaaacg    14100
cgacatatcc tcccatgtcg tattgtagca gcttttccata cgtatttcgc cgttcggatt    14160
ttacaatatc accatcttgg atttaataaa ggcatcgatt tagggcagtt gtcacttagt    14220
aaaccattag actatgggac tattactcta acattggcgg ttccacaagt ccttggggga    14280
ttgtcttttc taaatccaga aaagtgtttt tatcgaaact tcggagatcc tgtgacttct    14340
ggacttttcc agctacgggt gtacctagaa atggttaaca tgaaagacct attttatcca    14400
ttaatatcga aaaatccagg aaattgtagt gccattgatt ttgtcttaaa tccatccgga    14460
ttaaatgttc caggatcaca agacttgaca tccttttttgc gacagatcgt taggcgtagt    14520
attacactaa ctgcaagaaa taagttaatt aacactctct tccatgcctc tgctgatttg    14580
gaagatgaga tggtttgtaa atggctcctt tcatcaaacc ctgtcatgag tcgctttgca    14640
gcggatattt tttccaggac acctagtggt aaacgtctcc aaatattagg ttatcttgaa    14700
gggaccagga ctctattggc ctccaaaatc ataaacaaca acagtgagac acctgtactt    14760
```

```
gataagctga ggaagatcac cctacaaaga tggaatctgt ggttcagtta tttggaccat   14820
tgtgaccaat tactagcaga tgctctacag aaaattagtt gcacggtgga tttggcccag   14880
attttgcgtg agtatacatg gtcacacatc ttagagggta gaccattgat cggagcgaca   14940
ttaccatgta tggtggagca attcaaagtt aagtggctaa gacaatatga accttgtcca   15000
gaatgcctca acaaaaaagg ctcaaatgct tatgtctcag ttgcagtcaa agatcaagtg   15060
gtcagtgctt ggcctaatac ttctcgaata agttggacaa tagggagtgg tgtcccctat   15120
atagggtcaa gaaccgagga taaaatcgga cagcctgcaa tcaagccgcg atgcccttca   15180
tctgccctca aggaggctat agaattagca tcaaggctca cttgggttac acaaggaagt   15240
tctaatagtg aacaattaat ccggcctttc ttagaagcga gagtcaacct tagtgtcagt   15300
gaagtcctgc aaatgacacc atcacattat tcaggaaata ttgtccatcg atataacgac   15360
caatatagcc cgcactcatt tatggcgaat cgcatgagca atactgcgac ccgtctcata   15420
gtgtcaacta atacacttgg agaattttca ggtggagggc aggccgccag ggatagcaat   15480
ataattttcc agaatgttat aaatttagca gttgcccttt atgatattag attccggaat   15540
acgaacacct ctgatataag gcataatagg gctcatcttc acctgacaga gtgctgtact   15600
aaagaggtcc cggcccagta tttgacatat acaagtgcac tcaatctgga tttaagccgt   15660
tatcgtgata tgaactaat atatgactca aatccactga ggggaggatt gaactgcaat   15720
ttaacaatgg atagtccttt agtgaagggt cctaggctta acatgattga agatgatctt   15780
ctccgctttc cacaccttc tggatgggag ttagcgaaaa cggtggtaca atccatcatc   15840
tcagacaata gcaactcatc aacagatcca atcagtagcg gagaaacacg ctctttcaca   15900
actcattttc tcacttaccc tcagattggc cttctttaca gtttcggggc agtattatgc   15960
ttttatctag gcaatactat cctatggact aaaaaacttg attatgaaca gtttctatat   16020
tatttgcata accagctgca caacttacct catcgagcac tccgtgtttt taaaccaaca   16080
tttaagcatg ccagtgtgat gtcccgatta atggaaattg attccaactt ctcaatttat   16140
attggcggga catctggaga tcgagggctg tctgatgctg ctcgactgtt tcttcggaca   16200
gcaatcgcga gtttttttaca atttcttaaa agctggatca tcgatcgcca aaaggcaatt   16260
cctttatgga tagtatatcc gcttgaaggt caacagccgg aatccatcaa tgaatttcta   16320
cataaaattt ttggtctgct caaacaaggc cccaaaaata ttccaaagga ggtcagcatt   16380
caaaatgatg gacatttgga tttggcagaa aataattatg tttacaatag taagagcact   16440
gctagtaatt tcttccatgc atccttagct tactggagaa gtaggaaatc tcggaaaact   16500
caagaccata atgatttctc aagagggat ggaacactta cagaacccgt gtgtaagttc   16560
tcaagcaatc atcagtcaga tgaaaagtac tacaatgtga catgtggaaa gtcaccgaag   16620
ccgcaagaac gcaaagactt ctcgcaatac agactcagca ataacgggca aacaatgagt   16680
aatcatcgta agaagggaa gttccacaag tggaatccct gcaaagtgtt aatggagagt   16740 caaagggaa ctgttctaaa agagggtgac tactttcaaa acaatactcc accaacagat   16800
gatgtatcaa gtcctcaccg actcattcta ccatttttta aattgggaaa tcacaaccat   16860
gcacatgatc aagatgccca agaattgata aatcaaaata ttaaacagta cctacatcag   16920
ctaaggtcta tgttggacac cactatatat tgtagattca cagggattgt ctcatccatg   16980
cattacaaat tggacgaagt tcttctagaa tacaatagtt tcgattcagc tatcacatta   17040
gctgaaggtg aggggtcagg ggctctatta ctttttgcaga aatatagtac aaggttatta   17100
```

-continued

```
ttttgaaca cattggcaac agaacacagt atagagtcag aagttgtatc aggttttct    17160
actccgagaa tgttgttacc aataatgcaa aaggttcatg aaggacaagt cactgttatc    17220
ttaaataatt cagcaagtca gataactgac ataactagct caatgtggtt aagtaatcaa    17280
aaatataatc taccttgtca agttgaaatc attacgatgg atgctgaaac aacagagaac    17340
ttaaacaggt cccaactcta ccgagcagta tataacttaa tacttgatca cattgatccg    17400
cagtatctca aggtggtggt actcaaagta tttctgagtg atatagaagg aatattatgg    17460
attaatgatt acttggctcc attattcggg gctggttact tgattaaacc gattacatca    17520
agtgcccggt caagtgaatg gtacctttgc ttatcaaatt tgatatctac taacaggaga    17580
tcggcccatc agactcacaa ggcatgtctt ggtgttatca gagatgcttt gcaagcacaa    17640
gtccagcgag gcgtgtactg gttgagtcac atcgcacagt atgctacaaa gaatctccat    17700
tgtgaataca tatgccttgg tttcccacct ctagaaaagg tcctatatca caggtataat    17760
ctagttgata ctggactcgg tccattgtcg tcagttatta gacatttaac taacctccag    17820
gcagagatac gagacttagt attagattat accctgatga gagagagtcg cactcaaacg    17880
taccatttta ttaagactgc aaaaggcaga atcacaaagt tagtcaatga ctttctgaag    17940
ttttctttaa ttgtccaggc actcaaaaat aattcttctt ggtatactga gcttaaaaaa    18000
ttacctgagg tgattaatgt gtgtaatcga ttttatcata ctcacagttg cgaatgtcag    18060
gaaaaattct ttgtccagac gctttattta caacgcctac gcgatgcaga aatcaagcta    18120
attgaacgcc ttaccgggtt aatgcgattt tatccagaag ggttaatata ttccaatcac    18180
acataggtac taaatcatca tagtatgagg aataaaataa tgataattcc tgacgacagt    18240
tttagttccg attctaagta tatcggaaga gagtatgcca atcttaatta ttaaaggtaa    18300
caagctatta gttattactt attgataaga ataaactta tcatagcgta acacatcata    18360
actttatagc gattttgcat ttctaatcct agtatttatt agaatgtact atcagagaaa    18420
tgaccccagt tcctatcttt aaataatgat tgtgtgtatt aaattattag tttattaggt    18480
ttatgagttg gttacacagt gagtattagt aattgaggat tatgtagata ggtaatctaa    18540
cactgaatca cccatctgat gtcaccatat ccaaatattg tgctagtcgc atttaaacat    18600
gctatcttca gttaagtaac atagactgaa aatgctaaga agagattgga gtaaaagtat    18660
aaaataaatt taattaaact tcaaagtgat taaatgataa tgatcttggg aactcgatat    18720
gacctcaagt caaaaataat gtcaatataa ttgtttagta atatgagtta taatgtgaat    18780
tttgataact aactagcttt agtagttaag atcaaatgca aacattctaa gaatgttaag    18840
cgcacacaaa aacattataa aaaaccaatt ttttcctttt tgtgtgtccc                18890
```

<210> SEQ ID NO 10
<211> LENGTH: 739
<212> TYPE: PRT
<213> ORGANISM: Zaire Ebola virus

<400> SEQUENCE: 10

Met Asp Ser Arg Pro Gln Lys Ile Trp Met Ala Pro Ser Leu Thr Glu
1               5                   10                  15

Ser Asp Met Asp Tyr His Lys Ile Leu Thr Ala Gly Leu Ser Val Gln
                20                  25                  30

Gln Gly Ile Val Arg Gln Arg Val Ile Pro Val Tyr Gln Val Asn Asn
        35                  40                  45

Leu Glu Glu Ile Cys Gln Leu Ile Ile Gln Ala Phe Glu Ala Gly Val
    50                  55                  60

```
Asp Phe Gln Glu Ser Ala Asp Ser Phe Leu Leu Met Leu Cys Leu His
 65                  70                  75                  80

His Ala Tyr Gln Gly Asp Tyr Lys Leu Phe Leu Glu Ser Gly Ala Val
             85                  90                  95

Lys Tyr Leu Glu Gly His Gly Phe Arg Phe Glu Val Lys Lys Arg Asp
            100                 105                 110

Gly Val Lys Arg Leu Glu Glu Leu Pro Ala Val Ser Ser Gly Lys
            115                 120                 125

Asn Ile Lys Arg Thr Leu Ala Ala Met Pro Glu Glu Thr Thr Glu
130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ala Glu Gln Gly Leu Ile Gln Tyr Pro Thr Ala Trp Gln
            180                 185                 190

Ser Val Gly His Met Met Val Ile Phe Arg Leu Met Arg Thr Asn Phe
            195                 200                 205

Leu Ile Lys Phe Leu Leu Ile His Gln Gly Met His Met Val Ala Gly
210                 215                 220

His Asp Ala Asn Asp Ala Val Ile Ser Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Glu Arg Gly Val Arg Leu His Pro Leu Ala Arg Thr Ala Lys
            260                 265                 270

Val Lys Asn Glu Val Asn Ser Phe Lys Ala Ala Leu Ser Ser Leu Ala
            275                 280                 285

Lys His Gly Glu Tyr Ala Pro Phe Ala Arg Leu Leu Asn Leu Ser Gly
            290                 295                 300

Val Asn Asn Leu Glu His Gly Leu Phe Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Gln Leu Arg Glu Ala Ala Thr Glu Ala Glu Lys
            340                 345                 350

Gln Leu Gln Gln Tyr Ala Glu Ser Arg Glu Leu Asp His Leu Gly Leu
            355                 360                 365

Asp Asp Gln Glu Lys Lys Ile Leu Met Asn Phe His Gln Lys Lys Asn
            370                 375                 380

Glu Ile Ser Phe Gln Gln Thr Asn Ala Met Val Thr Leu Arg Lys Glu
385                 390                 395                 400

Arg Leu Ala Lys Leu Thr Glu Ala Ile Thr Ala Ala Ser Leu Pro Lys
                405                 410                 415

Thr Ser Gly His Tyr Asp Asp Asp Asp Ile Pro Phe Pro Gly Pro
            420                 425                 430

Ile Asn Asp Asp Asn Pro Gly His Gln Asp Asp Pro Thr Asp
            435                 440                 445

Ser Gln Asp Thr Thr Ile Pro Asp Val Val Asp Pro Asp Gly
            450                 455                 460

Ser Tyr Gly Glu Tyr Gln Ser Tyr Ser Glu Asn Gly Met Asn Ala Pro
465                 470                 475                 480
```

```
Asp Asp Leu Val Leu Phe Asp Leu Asp Glu Asp Glu Asp Thr Lys
                485                 490                 495
Pro Val Pro Asn Arg Ser Thr Lys Gly Gly Gln Gln Lys Asn Ser Gln
            500                 505                 510
Lys Gly Gln His Ile Glu Gly Arg Gln Thr Gln Ser Arg Pro Ile Gln
            515                 520                 525
Asn Val Pro Gly Pro His Arg Thr Ile His His Ala Ser Ala Pro Leu
            530                 535                 540
Thr Asp Asn Asp Arg Arg Asn Glu Pro Ser Gly Ser Thr Ser Pro Arg
545                 550                 555                 560
Met Leu Thr Pro Ile Asn Glu Glu Ala Asp Pro Leu Asp Asp Ala Asp
                565                 570                 575
Asp Glu Thr Ser Ser Leu Pro Pro Leu Glu Ser Asp Asp Glu Glu Gln
            580                 585                 590
Asp Arg Asp Gly Thr Ser Asn Arg Thr Pro Thr Val Ala Pro Pro Ala
            595                 600                 605
Pro Val Tyr Arg Asp His Ser Glu Lys Lys Glu Leu Pro Gln Asp Glu
            610                 615                 620
Gln Gln Asp Gln Asp His Thr Gln Glu Ala Arg Asn Gln Asp Ser Asp
625                 630                 635                 640
Asn Thr Gln Ser Glu His Ser Phe Glu Glu Met Tyr Arg His Ile Leu
                645                 650                 655
Arg Ser Gln Gly Pro Phe Asp Ala Val Leu Tyr Tyr His Met Met Lys
            660                 665                 670
Asp Glu Pro Val Val Phe Ser Thr Ser Asp Gly Lys Glu Tyr Thr Tyr
            675                 680                 685
Pro Asp Ser Leu Glu Glu Glu Tyr Pro Pro Trp Leu Thr Glu Lys Glu
            690                 695                 700
Ala Met Asn Glu Glu Asn Arg Phe Val Thr Leu Asp Gly Gln Gln Phe
705                 710                 715                 720
Tyr Trp Pro Val Met Asn His Lys Asn Lys Phe Met Ala Ile Leu Gln
                725                 730                 735
His His Gln

<210> SEQ ID NO 11
<211> LENGTH: 340
<212> TYPE: PRT
<213> ORGANISM: Zaire Ebola virus

<400> SEQUENCE: 11

Met Thr Thr Arg Thr Lys Gly Arg Gly His Thr Ala Ala Thr Thr Gln
1               5                   10                  15
Asn Asp Arg Met Pro Gly Pro Glu Leu Ser Gly Trp Ile Ser Glu Gln
            20                  25                  30
Leu Met Thr Gly Arg Ile Pro Val Ser Asp Ile Phe Cys Asp Ile Glu
            35                  40                  45
Asn Asn Pro Gly Leu Cys Tyr Ala Ser Gln Met Gln Gln Thr Lys Pro
            50                  55                  60
Asn Pro Lys Thr Arg Asn Ser Gln Thr Gln Thr Asp Pro Ile Cys Asn
65                  70                  75                  80
His Ser Phe Glu Glu Val Val Gln Thr Leu Ala Ser Leu Ala Thr Val
                85                  90                  95
Val Gln Gln Gln Thr Ile Ala Ser Glu Ser Leu Glu Gln Arg Ile Thr
            100                 105                 110
```

Ser Leu Glu Asn Gly Leu Lys Pro Val Tyr Asp Met Ala Lys Thr Ile
            115                 120                 125

Ser Ser Leu Asn Arg Val Cys Ala Glu Met Val Ala Lys Tyr Asp Leu
        130                 135                 140

Leu Val Met Thr Thr Gly Arg Ala Thr Ala Thr Ala Ala Ala Thr Glu
145                 150                 155                 160

Ala Tyr Trp Ala Glu His Gly Gln Pro Pro Gly Pro Ser Leu Tyr
            165                 170                 175

Glu Glu Ser Ala Ile Arg Gly Lys Ile Glu Ser Arg Asp Glu Thr Val
                180                 185                 190

Pro Gln Ser Val Arg Glu Ala Phe Asn Asn Leu Asn Ser Thr Thr Ser
        195                 200                 205

Leu Thr Glu Glu Asn Phe Gly Lys Pro Asp Ile Ser Ala Lys Asp Leu
    210                 215                 220

Arg Asn Ile Met Tyr Asp His Leu Pro Gly Phe Gly Thr Ala Phe His
225                 230                 235                 240

Gln Leu Val Gln Val Ile Cys Lys Leu Gly Lys Asp Ser Asn Ser Leu
                245                 250                 255

Asp Ile Ile His Ala Glu Phe Gln Ala Ser Leu Ala Glu Gly Asp Ser
            260                 265                 270

Pro Gln Cys Ala Leu Ile Gln Ile Thr Lys Arg Val Pro Ile Phe Gln
        275                 280                 285

Asp Ala Ala Pro Pro Val Ile His Ile Arg Ser Arg Gly Asp Ile Pro
    290                 295                 300

Arg Ala Cys Gln Lys Ser Leu Arg Pro Val Pro Pro Ser Pro Lys Ile
305                 310                 315                 320

Asp Arg Gly Trp Val Cys Val Phe Gln Leu Gln Asp Gly Lys Thr Leu
                325                 330                 335

Gly Leu Lys Ile
            340

<210> SEQ ID NO 12
<211> LENGTH: 326
<212> TYPE: PRT
<213> ORGANISM: Zaire Ebola virus

<400> SEQUENCE: 12

Met Arg Arg Val Ile Leu Pro Thr Ala Pro Pro Glu Tyr Met Glu Ala
1               5                   10                  15

Ile Tyr Pro Val Arg Ser Asn Ser Thr Ile Ala Arg Gly Gly Asn Ser
            20                  25                  30

Asn Thr Gly Phe Leu Thr Pro Glu Ser Val Asn Gly Asp Thr Pro Ser
        35                  40                  45

Asn Pro Leu Arg Pro Ile Ala Asp Asp Thr Ile Asp His Ala Ser His
    50                  55                  60

Thr Pro Gly Ser Val Ser Ser Ala Phe Ile Leu Glu Ala Met Val Asn
65                  70                  75                  80

Val Ile Ser Gly Pro Lys Val Leu Met Lys Gln Ile Pro Ile Trp Leu
                85                  90                  95

Pro Leu Gly Val Ala Asp Gln Lys Thr Tyr Ser Phe Asp Ser Thr Thr
            100                 105                 110

Ala Ala Ile Met Leu Ala Ser Tyr Thr Ile Thr His Phe Gly Lys Ala
        115                 120                 125

Thr Asn Pro Leu Val Arg Val Asn Arg Leu Gly Pro Gly Ile Pro Asp
    130                 135                 140

His Pro Leu Arg Leu Leu Arg Ile Gly Asn Gln Ala Phe Leu Gln Glu
145                 150                 155                 160

Phe Val Leu Pro Pro Val Gln Leu Pro Gln Tyr Phe Thr Phe Asp Leu
                165                 170                 175

Thr Ala Leu Lys Leu Ile Thr Gln Pro Leu Pro Ala Ala Thr Trp Thr
            180                 185                 190

Asp Asp Thr Pro Thr Gly Ser Asn Gly Ala Leu Arg Pro Gly Ile Ser
            195                 200                 205

Phe His Pro Lys Leu Arg Pro Ile Leu Leu Pro Asn Lys Ser Gly Lys
210                 215                 220

Lys Gly Asn Ser Ala Asp Leu Thr Ser Pro Glu Lys Ile Gln Ala Ile
225                 230                 235                 240

Met Thr Ser Leu Gln Asp Phe Lys Ile Val Pro Ile Asp Pro Thr Lys
                245                 250                 255

Asn Ile Met Gly Ile Glu Val Pro Glu Thr Leu Val His Lys Leu Thr
            260                 265                 270

Gly Lys Lys Val Thr Ser Lys Asn Gly Gln Pro Ile Ile Pro Val Leu
        275                 280                 285

Leu Pro Lys Tyr Ile Gly Leu Asp Pro Val Ala Pro Gly Asp Leu Thr
290                 295                 300

Met Val Ile Thr Gln Asp Cys Asp Thr Cys His Ser Pro Ala Ser Leu
305                 310                 315                 320

Pro Ala Val Ile Glu Lys
                325

<210> SEQ ID NO 13
<211> LENGTH: 676
<212> TYPE: PRT
<213> ORGANISM: Zaire Ebola virus

<400> SEQUENCE: 13

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp

```
            180                 185                 190
Phe Phe Ser Ser His Pro Leu Arg Glu Pro Val Asn Ala Thr Glu Asp
            195                 200                 205
Pro Ser Ser Gly Tyr Tyr Ser Thr Thr Ile Arg Tyr Gln Ala Thr Gly
            210                 215                 220
Phe Gly Thr Asn Glu Thr Glu Tyr Leu Phe Glu Val Asp Asn Leu Thr
225                 230                 235                 240
Tyr Val Gln Leu Glu Ser Arg Phe Thr Pro Gln Phe Leu Leu Gln Leu
            245                 250                 255
Asn Glu Thr Ile Tyr Thr Ser Gly Lys Arg Ser Asn Thr Thr Gly Lys
            260                 265                 270
Leu Ile Trp Lys Val Asn Pro Glu Ile Asp Thr Thr Ile Gly Glu Trp
            275                 280                 285
Ala Phe Trp Glu Thr Lys Lys Asn Leu Thr Arg Lys Ile Arg Ser Glu
            290                 295                 300
Glu Leu Ser Phe Thr Val Val Ser Asn Gly Ala Lys Asn Ile Ser Gly
305                 310                 315                 320
Gln Ser Pro Ala Arg Thr Ser Ser Asp Pro Gly Thr Asn Thr Thr Thr
            325                 330                 335
Glu Asp His Lys Ile Met Ala Ser Glu Asn Ser Ser Ala Met Val Gln
            340                 345                 350
Val His Ser Gln Gly Arg Glu Ala Ala Val Ser His Leu Thr Thr Leu
            355                 360                 365
Ala Thr Ile Ser Thr Ser Pro Gln Ser Leu Thr Thr Lys Pro Gly Pro
            370                 375                 380
Asp Asn Ser Thr His Asn Thr Pro Val Tyr Lys Leu Asp Ile Ser Glu
385                 390                 395                 400
Ala Thr Gln Val Glu Gln His Arg Arg Thr Asp Asn Asp Ser Thr
            405                 410                 415
Ala Ser Asp Thr Pro Ser Ala Thr Thr Ala Ala Gly Pro Pro Lys Ala
            420                 425                 430
Glu Asn Thr Asn Thr Ser Lys Ser Thr Asp Phe Leu Asp Pro Ala Thr
            435                 440                 445
Thr Thr Ser Pro Gln Asn His Ser Glu Thr Ala Gly Asn Asn Asn Thr
            450                 455                 460
His His Gln Asp Thr Gly Glu Glu Ser Ala Ser Ser Gly Lys Leu Gly
465                 470                 475                 480
Leu Ile Thr Asn Thr Ile Ala Gly Val Ala Gly Leu Ile Thr Gly Gly
            485                 490                 495
Arg Arg Thr Arg Arg Glu Ala Ile Val Asn Ala Gln Pro Lys Cys Asn
            500                 505                 510
Pro Asn Leu His Tyr Trp Thr Thr Gln Asp Glu Gly Ala Ala Ile Gly
            515                 520                 525
Leu Ala Trp Ile Pro Tyr Phe Gly Pro Ala Ala Glu Gly Ile Tyr Ile
            530                 535                 540
Glu Gly Leu Met His Asn Gln Asp Gly Leu Ile Cys Gly Leu Arg Gln
545                 550                 555                 560
Leu Ala Asn Glu Thr Thr Gln Ala Leu Gln Leu Phe Leu Arg Ala Thr
            565                 570                 575
Thr Glu Leu Arg Thr Phe Ser Ile Leu Asn Arg Lys Ala Ile Asp Phe
            580                 585                 590
Leu Leu Gln Arg Trp Gly Gly Thr Cys His Ile Leu Gly Pro Asp Cys
            595                 600                 605
```

Cys Ile Glu Pro His Asp Trp Thr Lys Asn Ile Thr Asp Lys Ile Asp
610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
            675

<210> SEQ ID NO 14
<211> LENGTH: 364
<212> TYPE: PRT
<213> ORGANISM: Zaire Ebola virus

<400> SEQUENCE: 14

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
            35                  40                  45

Asp Lys Leu Val Cys Arg Asp Lys Leu Ser Ser Thr Asn Gln Leu Arg
50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Thr Ser Leu Glu Lys Phe Ala Val Lys

```
            290                 295                 300
Ser Cys Leu Ser Gln Leu Tyr Gln Thr Glu Pro Lys Thr Ser Val Val
305                 310                 315                 320

Arg Val Arg Arg Glu Leu Leu Pro Thr Gln Gly Pro Thr Gln Gln Leu
                325                 330                 335

Lys Thr Thr Lys Ser Trp Leu Gln Lys Ile Pro Leu Gln Trp Phe Lys
                340                 345                 350

Cys Thr Val Lys Glu Gly Lys Leu Gln Cys Arg Ile
                355                 360

<210> SEQ ID NO 15
<211> LENGTH: 297
<212> TYPE: PRT
<213> ORGANISM: Zaire Ebola virus

<400> SEQUENCE: 15

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
            35                  40                  45

Asp Lys Leu Val Cys Arg Asp Lys Leu Ser Ser Thr Asn Gln Leu Arg
 50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Pro His
    290                 295
```

<210> SEQ ID NO 16
<211> LENGTH: 288
<212> TYPE: PRT
<213> ORGANISM: Zaire Ebola virus

<400> SEQUENCE: 16

Met Glu Ala Ser Tyr Glu Arg Gly Arg Pro Arg Ala Ala Arg Gln His
1               5                   10                  15

Ser Arg Asp Gly His Asp His Val Arg Ala Arg Ser Ser Ser Arg
            20                  25                  30

Glu Asn Tyr Arg Gly Glu Tyr Arg Gln Ser Arg Ser Ala Ser Gln Val
            35                  40                  45

Arg Val Pro Thr Val Phe His Lys Lys Arg Val Glu Pro Leu Thr Val
50                  55                  60

Pro Pro Ala Pro Lys Asp Ile Cys Pro Thr Leu Lys Lys Gly Phe Leu
65                  70                  75                  80

Cys Asp Ser Ser Phe Cys Lys Lys Asp His Gln Leu Glu Ser Leu Thr
                85                  90                  95

Asp Arg Glu Leu Leu Leu Ile Ala Arg Lys Thr Cys Gly Ser Val
            100                 105                 110

Glu Gln Gln Leu Asn Ile Thr Ala Pro Lys Asp Ser Arg Leu Ala Asn
        115                 120                 125

Pro Thr Ala Asp Asp Phe Gln Gln Glu Gly Pro Lys Ile Thr Leu
    130                 135                 140

Leu Thr Leu Ile Lys Thr Ala Glu His Trp Ala Arg Gln Asp Ile Arg
145                 150                 155                 160

Thr Ile Glu Asp Ser Lys Leu Arg Ala Leu Leu Thr Leu Cys Ala Val
                165                 170                 175

Met Thr Arg Lys Phe Ser Lys Ser Gln Leu Ser Leu Leu Cys Glu Thr
            180                 185                 190

His Leu Arg Arg Glu Gly Leu Gly Gln Asp Gln Ala Glu Pro Val Leu
        195                 200                 205

Glu Val Tyr Gln Arg Leu His Ser Asp Lys Gly Gly Ser Phe Glu Ala
    210                 215                 220

Ala Leu Trp Gln Gln Trp Asp Arg Gln Ser Leu Ile Met Phe Ile Thr
225                 230                 235                 240

Ala Phe Leu Asn Ile Ala Leu Gln Leu Pro Cys Glu Ser Ser Ala Val
                245                 250                 255

Val Val Ser Gly Leu Arg Thr Leu Val Pro Gln Ser Asp Asn Glu Glu
            260                 265                 270

Ala Ser Thr Asn Pro Gly Thr Cys Ser Trp Ser Asp Glu Gly Thr Pro
        275                 280                 285

<210> SEQ ID NO 17
<211> LENGTH: 251
<212> TYPE: PRT
<213> ORGANISM: Zaire Ebola virus

<400> SEQUENCE: 17

Met Ala Lys Ala Thr Gly Arg Tyr Asn Leu Ile Ser Pro Lys Lys Asp
1               5                   10                  15

Leu Glu Lys Gly Val Val Leu Ser Asp Leu Cys Asn Phe Leu Val Ser
            20                  25                  30

Gln Thr Ile Gln Gly Trp Lys Val Tyr Trp Ala Gly Ile Glu Phe Asp
        35                  40                  45

```
Val Thr His Lys Gly Met Ala Leu Leu His Arg Leu Lys Thr Asn Asp
 50                  55                  60

Phe Ala Pro Ala Trp Ser Met Thr Arg Asn Leu Phe Pro His Leu Phe
 65                  70                  75                  80

Gln Asn Pro Asn Ser Thr Ile Glu Ser Pro Leu Trp Ala Leu Arg Val
                 85                  90                  95

Ile Leu Ala Ala Gly Ile Gln Asp Gln Leu Ile Asp Gln Ser Leu Ile
            100                 105                 110

Glu Pro Leu Ala Gly Ala Leu Gly Leu Ile Ser Asp Trp Leu Leu Thr
        115                 120                 125

Thr Asn Thr Asn His Phe Asn Met Arg Thr Gln Arg Val Lys Glu Gln
130                 135                 140

Leu Ser Leu Lys Met Leu Ser Leu Ile Arg Ser Asn Ile Leu Lys Phe
145                 150                 155                 160

Ile Asn Lys Leu Asp Ala Leu His Val Val Asn Tyr Asn Gly Leu Leu
                165                 170                 175

Ser Ser Ile Glu Ile Gly Thr Gln Asn His Thr Ile Ile Ile Thr Arg
            180                 185                 190

Thr Asn Met Gly Phe Leu Val Glu Leu Gln Glu Pro Asp Lys Ser Ala
        195                 200                 205

Met Asn Arg Met Lys Pro Gly Pro Ala Lys Phe Ser Leu Leu His Glu
    210                 215                 220

Ser Thr Leu Lys Ala Phe Thr Gln Gly Ser Ser Thr Arg Met Gln Ser
225                 230                 235                 240

Leu Ile Leu Glu Phe Asn Ser Ser Leu Ala Ile
                245                 250

<210> SEQ ID NO 18
<211> LENGTH: 2212
<212> TYPE: PRT
<213> ORGANISM: Zaire Ebola virus

<400> SEQUENCE: 18

Met Ala Thr Gln His Thr Gln Tyr Pro Asp Ala Arg Leu Ser Ser Pro
  1               5                  10                  15

Ile Val Leu Asp Gln Cys Asp Leu Val Thr Arg Ala Cys Gly Leu Tyr
             20                  25                  30

Ser Ser Tyr Ser Leu Asn Pro Gln Leu Arg Asn Cys Lys Leu Pro Lys
         35                  40                  45

His Ile Tyr Arg Leu Lys Tyr Asp Val Thr Val Thr Lys Phe Leu Ser
 50                  55                  60

Asp Val Pro Val Ala Thr Leu Pro Ile Asp Phe Ile Val Pro Val Leu
 65                  70                  75                  80

Leu Lys Ala Leu Ser Gly Asn Gly Phe Cys Pro Val Glu Pro Arg Cys
                 85                  90                  95

Gln Gln Phe Leu Asp Glu Ile Ile Lys Tyr Thr Met Gln Asp Ala Leu
            100                 105                 110

Phe Leu Lys Tyr Tyr Leu Lys Asn Val Gly Ala Gln Glu Asp Cys Val
        115                 120                 125

Asp Glu His Phe Gln Glu Lys Ile Leu Ser Ser Ile Gln Gly Asn Glu
130                 135                 140

Phe Leu His Gln Met Phe Phe Trp Tyr Asp Leu Ala Ile Leu Thr Arg
145                 150                 155                 160

Arg Gly Arg Leu Asn Arg Gly Asn Ser Arg Ser Thr Trp Phe Val His
                165                 170                 175
```

```
Asp Asp Leu Ile Asp Ile Leu Gly Tyr Gly Asp Tyr Val Phe Trp Lys
            180                 185                 190

Ile Pro Ile Ser Met Leu Pro Leu Asn Thr Gln Gly Ile Pro His Ala
        195                 200                 205

Ala Met Asp Trp Tyr Gln Ala Ser Val Phe Lys Glu Ala Val Gln Gly
    210                 215                 220

His Thr His Ile Val Ser Val Ser Thr Ala Asp Val Leu Ile Met Cys
225                 230                 235                 240

Lys Asp Leu Ile Thr Cys Arg Phe Asn Thr Thr Leu Ile Ser Lys Ile
                245                 250                 255

Ala Glu Ile Glu Asp Pro Val Cys Ser Asp Tyr Pro Asn Phe Lys Ile
            260                 265                 270

Val Ser Met Leu Tyr Gln Ser Gly Asp Tyr Leu Leu Ser Ile Leu Gly
        275                 280                 285

Ser Asp Gly Tyr Lys Ile Ile Lys Phe Leu Glu Pro Leu Cys Leu Ala
    290                 295                 300

Lys Ile Gln Leu Cys Ser Lys Tyr Thr Glu Arg Lys Gly Arg Phe Leu
305                 310                 315                 320

Thr Gln Met His Leu Ala Val Asn His Thr Leu Glu Glu Ile Thr Glu
                325                 330                 335

Met Arg Ala Leu Lys Pro Ser Gln Ala Gln Lys Ile Arg Glu Phe His
            340                 345                 350

Arg Thr Leu Ile Arg Leu Glu Met Thr Pro Gln Gln Leu Cys Glu Leu
        355                 360                 365

Phe Ser Ile Gln Lys His Trp Gly His Pro Val Leu His Ser Glu Thr
    370                 375                 380

Ala Ile Gln Lys Val Lys Lys His Ala Thr Val Leu Lys Ala Leu Arg
385                 390                 395                 400

Pro Ile Val Ile Phe Glu Thr Tyr Cys Val Phe Lys Tyr Ser Ile Ala
                405                 410                 415

Lys His Tyr Phe Asp Ser Gln Gly Ser Trp Tyr Ser Val Thr Ser Asp
            420                 425                 430

Arg Asn Leu Thr Pro Gly Leu Asn Ser Tyr Ile Lys Arg Asn Gln Phe
        435                 440                 445

Pro Pro Leu Pro Met Ile Lys Glu Leu Leu Trp Glu Phe Tyr His Leu
    450                 455                 460

Asp His Pro Pro Leu Phe Ser Thr Lys Ile Ile Ser Asp Leu Ser Ile
465                 470                 475                 480

Phe Ile Lys Asp Arg Ala Thr Ala Val Glu Arg Thr Cys Trp Asp Ala
                485                 490                 495

Val Phe Glu Pro Asn Val Leu Gly Tyr Asn Pro Pro His Lys Phe Ser
            500                 505                 510

Thr Lys Arg Val Pro Glu Gln Phe Leu Glu Gln Glu Asn Phe Ser Ile
        515                 520                 525

Glu Asn Val Leu Ser Tyr Ala Gln Lys Leu Glu Tyr Leu Leu Pro Gln
    530                 535                 540

Tyr Arg Asn Phe Ser Phe Ser Leu Lys Glu Lys Glu Leu Asn Val Gly
545                 550                 555                 560

Arg Thr Phe Gly Lys Leu Pro Tyr Pro Thr Arg Asn Val Gln Thr Leu
                565                 570                 575

Cys Glu Ala Leu Leu Ala Asp Gly Leu Ala Lys Ala Phe Pro Ser Asn
            580                 585                 590
```

-continued

```
Met Met Val Val Thr Glu Arg Glu Gln Lys Glu Ser Leu Leu His Gln
            595                 600                 605

Ala Ser Trp His His Thr Ser Asp Asp Phe Gly Glu His Ala Thr Val
            610                 615                 620

Arg Gly Ser Ser Phe Val Thr Asp Leu Glu Lys Tyr Asn Leu Ala Phe
625                 630                 635                 640

Arg Tyr Glu Phe Thr Ala Pro Phe Ile Glu Tyr Cys Asn Arg Cys Tyr
                645                 650                 655

Gly Val Lys Asn Val Phe Asn Trp Met His Tyr Thr Ile Pro Gln Cys
                660                 665                 670

Tyr Met His Val Ser Asp Tyr Tyr Asn Pro Pro His Asn Leu Thr Leu
            675                 680                 685

Glu Asn Arg Asp Asn Pro Pro Glu Gly Pro Ser Ser Tyr Arg Gly His
            690                 695                 700

Met Gly Gly Ile Glu Gly Leu Gln Gln Lys Leu Trp Thr Ser Ile Ser
705                 710                 715                 720

Cys Ala Gln Ile Ser Leu Val Glu Ile Lys Thr Gly Phe Lys Leu Arg
                725                 730                 735

Ser Ala Val Met Gly Asp Asn Gln Cys Ile Thr Val Leu Ser Val Phe
            740                 745                 750

Pro Leu Glu Thr Asp Ala Asp Glu Gln Glu Gln Ser Ala Glu Asp Asn
            755                 760                 765

Ala Ala Arg Val Ala Ala Ser Leu Ala Lys Val Thr Ser Ala Cys Gly
            770                 775                 780

Ile Phe Leu Lys Pro Asp Glu Thr Phe Val His Ser Gly Phe Ile Tyr
785                 790                 795                 800

Phe Gly Lys Lys Gln Tyr Leu Asn Gly Val Gln Leu Pro Gln Ser Leu
                805                 810                 815

Lys Thr Ala Thr Arg Met Ala Pro Leu Ser Asp Ala Ile Phe Asp Asp
            820                 825                 830

Leu Gln Gly Thr Leu Ala Ser Ile Gly Thr Ala Phe Glu Arg Ser Ile
            835                 840                 845

Ser Glu Thr Arg His Ile Phe Pro Cys Arg Ile Thr Ala Ala Phe His
850                 855                 860

Thr Phe Phe Ser Val Arg Ile Leu Gln Tyr His His Leu Gly Phe Asn
865                 870                 875                 880

Lys Gly Phe Asp Leu Gly Gln Leu Thr Leu Gly Lys Pro Leu Asp Phe
                885                 890                 895

Gly Thr Ile Ser Leu Ala Leu Ala Val Pro Gln Val Leu Gly Gly Leu
            900                 905                 910

Ser Phe Leu Asn Pro Glu Lys Cys Phe Tyr Arg Asn Leu Gly Asp Pro
            915                 920                 925

Val Thr Ser Gly Leu Phe Gln Leu Lys Thr Tyr Leu Arg Met Ile Glu
            930                 935                 940

Met Asp Asp Leu Phe Leu Pro Leu Ile Ala Lys Asn Pro Gly Asn Cys
945                 950                 955                 960

Thr Ala Ile Asp Phe Val Leu Asn Pro Ser Gly Leu Asn Val Pro Gly
                965                 970                 975

Ser Gln Asp Leu Thr Ser Phe Leu Arg Gln Ile Val Arg Arg Thr Ile
            980                 985                 990

Thr Leu Ser Ala Lys Asn Lys Leu Ile Asn Thr Leu Phe His Ala Ser
            995                 1000                1005

Ala Asp Phe Glu Asp Glu Met Val Cys Lys Trp Leu Leu Ser Ser Thr
```

```
               1010                1015                1020
Pro Val Met Ser Arg Phe Ala Ala Asp Ile Phe Ser Arg Thr Pro Ser
1025                1030                1035                1040

Gly Lys Arg Leu Gln Ile Leu Gly Tyr Leu Glu Gly Thr Arg Thr Leu
               1045                1050                1055

Leu Ala Ser Lys Ile Ile Asn Asn Asn Thr Glu Thr Pro Val Leu Asp
               1060                1065                1070

Arg Leu Arg Lys Ile Thr Leu Gln Arg Trp Ser Leu Trp Phe Ser Tyr
               1075                1080                1085

Leu Asp His Cys Asp Asn Ile Leu Ala Glu Ala Leu Thr Gln Ile Thr
               1090                1095                1100

Cys Thr Val Asp Leu Ala Gln Ile Leu Arg Glu Tyr Ser Trp Ala His
1105                1110                1115                1120

Ile Leu Glu Gly Arg Pro Leu Ile Gly Ala Thr Leu Pro Cys Met Ile
               1125                1130                1135

Glu Gln Phe Lys Val Phe Trp Leu Lys Pro Tyr Glu Gln Cys Pro Gln
               1140                1145                1150

Cys Ser Asn Ala Lys Gln Pro Gly Gly Lys Pro Phe Val Ser Val Ala
               1155                1160                1165

Val Lys Lys His Ile Val Ser Ala Trp Pro Asn Ala Ser Arg Ile Ser
               1170                1175                1180

Trp Thr Ile Gly Asp Gly Ile Pro Tyr Ile Gly Ser Arg Thr Glu Asp
1185                1190                1195                1200

Lys Ile Gly Gln Pro Ala Ile Lys Pro Lys Cys Pro Ser Ala Ala Leu
               1205                1210                1215

Arg Glu Ala Ile Glu Leu Ala Ser Arg Leu Thr Trp Val Thr Gln Gly
               1220                1225                1230

Ser Ser Asn Ser Asp Leu Leu Ile Lys Pro Phe Leu Glu Ala Arg Val
               1235                1240                1245

Asn Leu Ser Val Gln Glu Ile Leu Gln Met Thr Pro Ser His Tyr Ser
               1250                1255                1260

Gly Asn Ile Val His Arg Tyr Asn Asp Gln Tyr Ser Pro His Ser Phe
1265                1270                1275                1280

Met Ala Asn Arg Met Ser Asn Ser Ala Thr Arg Leu Ile Val Ser Thr
               1285                1290                1295

Asn Thr Leu Gly Glu Phe Ser Gly Gly Gly Gln Ser Ala Arg Asp Ser
               1300                1305                1310

Asn Ile Ile Phe Gln Asn Val Ile Asn Tyr Ala Val Ala Leu Phe Asp
               1315                1320                1325

Ile Lys Phe Arg Asn Thr Glu Ala Thr Asp Ile Gln Tyr Asn Arg Ala
               1330                1335                1340

His Leu His Leu Thr Lys Cys Cys Thr Arg Glu Val Pro Ala Gln Tyr
1345                1350                1355                1360

Leu Thr Tyr Thr Ser Thr Leu Asp Leu Asp Leu Thr Arg Tyr Arg Glu
               1365                1370                1375

Asn Glu Leu Ile Tyr Asp Ser Asn Pro Leu Lys Gly Gly Leu Asn Cys
               1380                1385                1390

Asn Ile Ser Phe Asp Asn Pro Phe Phe Gln Gly Lys Arg Leu Asn Ile
               1395                1400                1405

Ile Glu Asp Asp Leu Ile Arg Leu Pro His Leu Ser Gly Trp Glu Leu
               1410                1415                1420

Ala Lys Thr Ile Met Gln Ser Ile Ile Ser Asp Ser Asn Asn Ser Ser
1425                1430                1435                1440
```

```
Thr Asp Pro Ile Ser Ser Gly Glu Thr Arg Ser Phe Thr Thr His Phe
            1445                1450                1455

Leu Thr Tyr Pro Lys Ile Gly Leu Leu Tyr Ser Phe Gly Ala Phe Val
            1460                1465                1470

Ser Tyr Tyr Leu Gly Asn Thr Ile Leu Arg Thr Lys Lys Leu Thr Leu
            1475                1480                1485

Asp Asn Phe Leu Tyr Tyr Leu Thr Thr Gln Ile His Asn Leu Pro His
            1490                1495                1500

Arg Ser Leu Arg Ile Leu Lys Pro Thr Phe Lys His Ala Ser Val Met
1505                1510                1515                1520

Ser Arg Leu Met Ser Ile Asp Pro His Phe Ser Ile Tyr Ile Gly Gly
            1525                1530                1535

Ala Ala Gly Asp Arg Gly Leu Ser Asp Ala Ala Arg Leu Phe Leu Arg
            1540                1545                1550

Thr Ser Ile Ser Ser Phe Leu Thr Phe Val Lys Glu Trp Ile Ile Asn
            1555                1560                1565

Arg Gly Thr Ile Val Pro Leu Trp Ile Val Tyr Pro Leu Glu Gly Gln
            1570                1575                1580

Asn Pro Thr Pro Val Asn Asn Phe Leu Tyr Gln Ile Val Glu Leu Leu
1585                1590                1595                1600

Val His Asp Ser Ser Arg Gln Gln Ala Phe Lys Thr Thr Ile Ser Asp
            1605                1610                1615

His Val His Pro His Asp Asn Leu Val Tyr Thr Cys Lys Ser Thr Ala
            1620                1625                1630

Ser Asn Phe Phe His Ala Ser Leu Ala Tyr Trp Arg Ser Arg His Arg
            1635                1640                1645

Asn Ser Asn Arg Lys Tyr Leu Ala Arg Asp Ser Ser Thr Gly Ser Ser
            1650                1655                1660

Thr Asn Asn Ser Asp Gly His Ile Glu Arg Ser Gln Glu Thr Thr
1665                1670                1675                1680

Arg Asp Pro His Asp Gly Thr Glu Arg Asn Leu Val Leu Gln Met Ser
            1685                1690                1695

His Glu Ile Lys Arg Thr Thr Ile Pro Gln Glu Asn Thr His Gln Gly
            1700                1705                1710

Pro Ser Phe Gln Ser Phe Leu Ser Asp Ser Ala Cys Gly Thr Ala Asn
            1715                1720                1725

Pro Lys Leu Asn Phe Asp Arg Ser Arg His Asn Val Lys Phe Gln Asp
            1730                1735                1740

His Asn Ser Ala Ser Lys Arg Glu Gly His Gln Ile Ile Ser His Arg
1745                1750                1755                1760

Leu Val Leu Pro Phe Phe Thr Leu Ser Gln Gly Thr Arg Gln Leu Thr
            1765                1770                1775

Ser Ser Asn Glu Ser Gln Thr Gln Asp Glu Ile Ser Lys Tyr Leu Arg
            1780                1785                1790

Gln Leu Arg Ser Val Ile Asp Thr Thr Val Tyr Cys Arg Phe Thr Gly
            1795                1800                1805

Ile Val Ser Ser Met His Tyr Lys Leu Asp Glu Val Leu Trp Glu Ile
            1810                1815                1820

Glu Ser Phe Lys Ser Ala Val Thr Leu Ala Glu Gly Glu Gly Ala Gly
1825                1830                1835                1840

Ala Leu Leu Leu Ile Gln Lys Tyr Gln Val Lys Thr Leu Phe Phe Asn
            1845                1850                1855
```

```
Thr Leu Ala Thr Glu Ser Ser Ile Glu Ser Glu Ile Val Ser Gly Met
            1860                1865                1870

Thr Thr Pro Arg Met Leu Leu Pro Val Met Ser Lys Phe His Asn Asp
        1875                1880                1885

Gln Ile Glu Ile Ile Leu Asn Asn Ser Ala Ser Gln Ile Thr Asp Ile
        1890                1895                1900

Thr Asn Pro Thr Trp Phe Lys Asp Gln Arg Ala Arg Leu Pro Lys Gln
1905                1910                1915                1920

Val Glu Val Ile Thr Met Asp Ala Glu Thr Thr Glu Asn Ile Asn Arg
                1925                1930                1935

Ser Lys Leu Tyr Glu Ala Val Tyr Lys Leu Ile Leu His His Ile Asp
            1940                1945                1950

Pro Ser Val Leu Lys Ala Val Val Leu Lys Val Phe Leu Ser Asp Thr
            1955                1960                1965

Glu Gly Met Leu Trp Leu Asn Asp Asn Leu Ala Pro Phe Phe Ala Thr
        1970                1975                1980

Gly Tyr Leu Ile Lys Pro Ile Thr Ser Ser Ala Arg Ser Ser Glu Trp
1985                1990                1995                2000

Tyr Leu Cys Leu Thr Asn Phe Leu Ser Thr Thr Arg Lys Met Pro His
            2005                2010                2015

Gln Asn His Leu Ser Cys Lys Gln Val Ile Leu Thr Ala Leu Gln Leu
            2020                2025                2030

Gln Ile Gln Arg Ser Pro Tyr Trp Leu Ser His Leu Thr Gln Tyr Ala
            2035                2040                2045

Asp Cys Glu Leu His Leu Ser Tyr Ile Arg Leu Gly Phe Pro Ser Leu
            2050                2055                2060

Glu Lys Val Leu Tyr His Arg Tyr Asn Leu Val Asp Ser Lys Arg Gly
2065                2070                2075                2080

Pro Leu Val Ser Ile Thr Gln His Leu Ala His Leu Arg Ala Glu Ile
            2085                2090                2095

Arg Glu Leu Thr Asn Asp Tyr Asn Gln Gln Arg Gln Ser Arg Thr Gln
            2100                2105                2110

Thr Tyr His Phe Ile Arg Thr Ala Lys Gly Arg Ile Thr Lys Leu Val
            2115                2120                2125

Asn Asp Tyr Leu Lys Phe Phe Leu Ile Val Gln Ala Leu Lys His Asn
2130                2135                2140

Gly Thr Trp Gln Ala Glu Phe Lys Lys Leu Pro Glu Leu Ile Ser Val
2145                2150                2155                2160

Cys Asn Arg Phe Tyr His Ile Arg Asp Cys Asn Cys Glu Glu Arg Phe
            2165                2170                2175

Leu Val Gln Thr Leu Tyr Leu His Arg Met Gln Asp Ser Glu Val Lys
            2180                2185                2190

Leu Ile Glu Arg Leu Thr Gly Leu Leu Ser Leu Phe Pro Asp Gly Leu
            2195                2200                2205

Tyr Arg Phe Asp
    2210

<210> SEQ ID NO 19
<211> LENGTH: 18959
<212> TYPE: DNA
<213> ORGANISM: Zaire Ebola virus

<400> SEQUENCE: 19
cggacacaca aaagaaaga agaatttta ggatcttttg tgtgcgaata actatgagga    60
```

| | |
|---|---|
| agattaataa ttttcctctc attgaaattt atatcggaat ttaaattgaa attgttactg | 120 |
| taatcacacc tggtttgttt cagagccaca tcacaaagat agagaacaac ctaggtctcc | 180 |
| gaagggagca agggcatcag tgtgctcagt tgaaaatccc ttgtcaacac ctaggtctta | 240 |
| tcacatcaca agttccacct cagactctgc agggtgatcc aacaaccttg atagaaacat | 300 |
| tattgttaaa ggacagcatt agttcacagt caaacaagca agattgagaa ttaaccttgg | 360 |
| ttttgaactt gaacacttag gggattgaag attcaacaac cctaaagctt ggggtaaaac | 420 |
| attggaaata gttaaaagac aaattgctcg gaatcacaaa attccgagta tggattctcg | 480 |
| tcctcagaaa atctggatgg cgccgagtct cactgaatct gacatggatt accacaagat | 540 |
| cttgacagca ggtctgtccg ttcaacaggg gattgttcgg caaagagtca tcccagtgta | 600 |
| tcaagtaaac aatcttgaag aaatttgcca acttatcata caggcctttg aagcaggtgt | 660 |
| tgattttcaa gagagtgcgg acagtttcct tctcatgctt tgtcttcatc atgcgtacca | 720 |
| gggagattac aaacttttct tggaaagtgg cgcagtcaag tatttggaag ggcacgggtt | 780 |
| ccgttttgaa gtcaagaagc gtgatggagt gaagcgcctt gaggaattgc tgccagcagt | 840 |
| atctagtgga aaaaacatta agagaacact tgctgccatg ccggaagagg agacaactga | 900 |
| agctaatgcc ggtcagtttc tctcctttgc aagtctattc cttccgaaat tggtagtagg | 960 |
| agaaaaggct tgccttgaga aggttcaaag gcaaattcaa gtacatgcag agcaaggact | 1020 |
| gatacaatat ccaacagctt ggcaatcagt aggacacatg atggtgattt ccgtttgat | 1080 |
| gcgaacaaat tttctgatca aatttctcct aatacaccaa gggatgcaca tggttgccgg | 1140 |
| gcatgatgcc aacgatgctg tgatttcaaa ttcagtggct caagctcgtt tttcaggctt | 1200 |
| attgattgtc aaaacagtac ttgatcatat cctacaaaag acagaacgag gagttcgtct | 1260 |
| ccatcctctt gcaaggaccg ccaaggtaaa aaatgaggtg aactcccttta aggctgcact | 1320 |
| cagctccctg gccaagcatg gagagtatgc tcctttcgcc cgacttttga acctttctgg | 1380 |
| agtaaataat cttgagcatg gtcttttccc tcaactatcg gcaattgcac tcggagtcgc | 1440 |
| cacagcacac gggagtaccc tcgcaggagt aaatgttgga gaacagtatc aacaactcag | 1500 |
| agaggctgcc actgaggctg agaagcaact ccaacaatat gcagagtctc gcgaacttga | 1560 |
| ccatcttgga cttgatgatc aggaaaagaa aattcttatg aacttccatc agaaaaagaa | 1620 |
| cgaaatcagc ttccagcaaa caaacgctat ggtaactcta agaaaagagc gcctggccaa | 1680 |
| gctgacagaa gctatcactg ctgcgtcact gcccaaaaca agtggacatt acgatgatga | 1740 |
| tgacgacatt ccctttccag gacccatcaa tgatgacgac aatcctggcc atcaagatga | 1800 |
| tgatccgact gactcacagg atacgaccat tcccgatgtg gtggttgatc ccgatgatgg | 1860 |
| aagctacggc gaataccaga gttactcgga aaacggcatg aatgcaccag atgacttggt | 1920 |
| cctattcgat ctagacgagg acgacgagga cactaagcca gtgcctaata gatcgaccaa | 1980 |
| gggtggacaa cagaagaaca gtcaaaaggg ccagcatata gagggcagac agacacaatc | 2040 |
| caggccaatt caaaatgtcc caggccctca cagaacaatc caccacgcca gtgcgccact | 2100 |
| cacggacaat gacagaagaa atgaaccctc cggctcaacc agccctcgca tgctgacacc | 2160 |
| aattaacgaa gaggcagacc cactggacga tgccgacgac gagacgtcta gccttccgcc | 2220 |
| cttggagtca gatgatgaag agcaggacag ggacggaact tccaaccgca cacccactgt | 2280 |
| cgccccaccg gctcccgtat acagagatca ctctgaaaag aaagaactcc cgcaagacga | 2340 |
| gcaacaagat caggaccaca ctcaagaggc caggaaccag gacagtgaca acacccagtc | 2400 |
| agaacactct tttgaggaga tgtatcgcca cattctaaga tcacagggggc catttgatgc | 2460 |

```
tgttttgtat tatcatatga tgaaggatga gcctgtagtt ttcagtacca gtgatggcaa    2520
agagtacacg tatccagact cccttgaaga ggaatatcca ccatggctca ctgaaaaaga    2580
ggctatgaat gaagagaata gatttgttac attggatggt caacaatttt attggccggt    2640
gatgaatcac aagaataaat tcatggcaat cctgcaacat catcagtgaa tgagcatgga    2700
acaatgggat gattcaaccg acaaatagct aacattaagt agtcaaggaa cgaaaacagg    2760
aagaattttt gatgtctaag gtgtgaatta ttatcacaat aaaagtgatt cttattttg     2820
aatttaaagc tagcttatta ttactagccg ttttcaaag ttcaatttga gtcttaatgc     2880
aaataggcgt taagccacag ttatagccat aattgtaact caatattcta actagcgatt    2940
tatctaaatt aaattacatt atgcttttat aacttaccta ctagcctgcc caacatttac    3000
acgatcgttt tataattaag aaaaaactaa tgatgaagat taaaaccttc atcatcctta    3060
cgtcaattga attctctagc actcgaagct tattgtcttc aatgtaaaag aaaagctggt    3120
ctaacaagat gacaactaga acaaagggca ggggccatac tgcggccacg actcaaaacg    3180
acagaatgcc aggccctgag ctttcgggct ggatctctga gcagctaatg accggaagaa    3240
ttcctgtaag cgacatcttc tgtgatattg agaacaatcc aggattatgc tacgcatccc    3300
aaatgcaaca aacgaagcca aacccgaaga cgcgcaacag tcaaacccaa acggacccaa    3360
tttgcaatca tagttttgag gaggtagtac aaacattggc ttcattggct actgttgtgc    3420
aacaacaaac catcgcatca gaatcattag aacaacgcat tacgagtctt gagaatggtc    3480
taaagccagt ttatgatatg gcaaaaacaa tctcctcatt gaacagggtt tgtgctgaga    3540
tggttgcaaa atatgatctt ctggtgatga caaccggtcg ggcaacagca accgctgcgg    3600
caactgaggc ttattgggcc gaacatggtc aaccaccacc tggaccatca ctttatgaag    3660
aaagtgcgat tcggggtaag attgaatcta gagatgagac cgtccctcaa agtgttaggg    3720
aggcattcaa caatctaaac agtaccactt cactaactga ggaaaatttt gggaaacctg    3780
acatttcggc aaaggatttg agaaacatta tgtatgatca cttgcctggt tttggaactg    3840
cttttccacca attagtacaa gtgatttgta aattgggaaa agatagcaac tcattggaca    3900
tcattcatgc tgagttccag gccagcctgg ctgaaggaga ctctcctcaa tgtgccctaa    3960
ttcaaattac aaaaagagtt ccaatcttcc aagatgctgc tccacctgtc atccacatcc    4020
gctctcgagg tgacattccc cgagcttgcc agaaaagctt gcgtccagtc ccaccatcgc    4080
ccaagattga tcgaggttgg gtatgtgttt ttcagcttca agatggtaaa acacttggac    4140
tcaaaatttg agccaatctc ccttccctcc gaaagaggcg aataatagca gaggcttcaa    4200
ctgctgaact atagggtacg ttacattaat gatacacttg tgagtatcag ccctggataa    4260
tataagtcaa ttaaacgacc aagataaaat tgttcatatc tcgctagcag cttaaaatat    4320
aaatgtaata ggagctatat ctctgacagt attataatca attgttatta agtaacccaa    4380
accaaaagtg atgaagatta agaaaaacct acctcggctg agagagtgtt ttttcattaa    4440
ccttcatctt gtaaacgttg agcaaaattg ttaaaaatat gaggcgggtt atattgccta    4500
ctgctcctcc tgaatatatg gaggccatat accctgtcag gtcaaattca acaattgcta    4560
gaggtggcaa cagcaataca ggcttcctga caccggagtc agtcaatggg gacactccat    4620
cgaatccact caggccaatt gccgatgaca ccatcgacca tgccagccac acaccaggca    4680
gtgtgtcatc agcattcatc cttgaagcta tggtgaatgt catatcgggc cccaaagtgc    4740
taatgaagca aattccaatt tggcttcctc taggtgtcgc tgatcaaaag acctacagct    4800
```

```
ttgactcaac tacggccgcc atcatgcttg cttcatacac tatcacccat ttcggcaagg    4860
caaccaatcc acttgtcaga gtcaatcggc tgggtcctgg aatcccggat catcccctca    4920
ggctcctgcg aattggaaac caggctttcc tccaggagtt cgttcttccg ccagtccaac    4980
taccccagta tttcaccttt gatttgacag cactcaaact gatcacccaa ccactgcctg    5040
ctgcaacatg gaccgatgac actccaacag gatcaaatgg agcgttgcgt ccaggaattt    5100
catttcatcc aaaacttcgc cccattcttt tacccaacaa aagtgggaag aaggggaaca    5160
gtgccgatct aacatctccg gagaaaatcc aagcaataat gacttcactc caggacttta    5220
agatcgttcc aattgatcca accaaaaata tcatgggaat cgaagtgcca gaaactctgg    5280
tccacaagct gaccggtaag aaggtgactt ctaaaaatgg acaaccaatc atccctgttc    5340
ttttgccaaa gtacattggg ttggacccgg tggctccagg agacctcacc atggtaatca    5400
cacaggattg tgacacgtgt cattctcctg caagtcttcc agctgtgatt gagaagtaat    5460
tgcaataatt gactcagatc cagttttata gaatcttctc agggatagtg ataacatcta    5520
tttagtaatc cgtccattag aggagacact tttaattgat caatatacta aaggtgcttt    5580
acaccattgt cttttttctc tcctaaatgt agaacttaac aaaagactca taatatactt    5640
gtttttaaag gattgattga tgaaagatca taactaataa cattacaaat aatcctacta    5700
taatcaatac ggtgattcaa atgttaatct ttctcattgc acatactttt tgcccttatc    5760
ctcaaattgc ctgcatgctt acatctgagg atagccagtg tgacttggat tggaaatgtg    5820
gagaaaaaat cgggacccat ttctaggttg ttcacaatcc aagtacagac attgcccttc    5880
taattaagaa aaaatcggcg atgaagatta agccgacagt gagcgtaatc ttcatctctc    5940
ttagattatt tgttttccag agtaggggtc gtcaggtcct tttcaatcgt gtaaccaaaa    6000
taaactccac tagaaggata ttgtgggggca acaacacaat gggcgttaca ggaatattgc    6060
agttacctcg tgatcgattc aagaggacat cattctttct ttgggtaatt atccttttcc    6120
aaagaacatt ttccatccca cttggagtca tccacaatag cacattacag gttagtgatg    6180
tcgacaaact agtttgtcgt gacaaactgt catccacaaa tcaattgaga tcagttggac    6240
tgaatctcga agggaatgga gtggcaactg acgtgccatc tgcaactaaa agatggggct    6300
tcaggtccgg tgtcccacca aaggtggtca attatgaagc tggtgaatgg gctgaaaact    6360
gctacaatct tgaaatcaaa aaacctgacg ggagtgagtg tctaccagca gcgccagacg    6420
ggattcgggg cttccccgg tgccggtatg tgcacaaagt atcaggaacg ggaccgtgtg    6480
ccggagactt tgccttccat aaagagggtg ctttcttcct gtatgatcga cttgcttcca    6540
cagttatcta ccgaggaacg actttcgctg aaggtgtcgt tgcatttctg atactgcccc    6600
aagctaagaa ggacttcttc agctcacacc ccttgagaga gccggtcaat gcaacgcgagg   6660
acccgtctag tggctactat tctaccacaa ttagatatca ggctaccggt tttggaacca    6720
atgagacaga gtacttgttc gaggttgaca atttgaccta cgtccaactt gaatcaagat    6780
tcacaccaca gtttctgctc cagctgaatg agacaatata tacaagtggg aaaaggagca    6840
ataccacggg aaaactaatt tggaaggtca accccgaaat tgatacaaca atcggggagt    6900
gggccttctg gaaactaaa aaaacctcac tagaaaaatt cgcagtgaag agttgtcttt    6960
cacagttgta tcaaacggag ccaaaaacat cagtggtcag agtccggcgc gaacttcttc    7020
cgacccaggg accaacacaa caactgaaga ccacaaaatc atggcttcag aaaattcctc    7080
tgcaatggtt caagtgcaca gtcaaggaag ggaagctgca gtgtcgcatc taacaaccct    7140
tgccacaatc tccacgagtc cccaatccct cacaaccaaa ccaggtccgg acaacagcac    7200
```

```
ccataataca cccgtgtata aacttgacat ctctgaggca actcaagttg aacaacatca    7260
ccgcagaaca gacaacgaca gcacagcctc cgacactccc tctgccacga ccgcagccgg    7320 accccccaaaa gcagagaaca ccaacacgag caagagcact gacttcctgg accccgccac   7380
cacaacaagt ccccaaaacc acagcgagac cgctggcaac aacaacactc atcaccaaga    7440
taccggagaa gagagtgcca gcagcgggaa gctaggctta attaccaata ctattgctgg    7500
agtcgcagga ctgatcacag gcgggagaag aactcgaaga gaagcaattg tcaatgctca    7560
acccaaatgc aaccctaatt tacattactg gactactcag gatgaaggtg ctgcaatcgg    7620
actggcctgg ataccatatt tcgggccagc agccgaggga atttacatag agggctaat    7680 gcacaatcaa gatggtttaa tctgtgggtt gagacagctg gccaacgaga cgactcaagc    7740
tcttcaactg ttcctgagag ccacaactga gctacgcacc ttttcaatcc tcaaccgtaa    7800
ggcaattgat ttcttgctgc agcgatgggg cggcacatgc acattctgg gaccggactg     7860 ctgtatcgaa ccacatgatt ggaccaagaa cataacagaa aaaattgatc agattattca    7920
tgattttgtt gataaaaccc ttccggacca ggggggacaat gacaattggt ggacaggatg   7980
gagacaatgg ataccggcag gtattggagt tacaggcgtt ataattgcag ttatcgcttt    8040
attctgtata tgcaaatttg tcttttagtt tttcttcaga ttgcttcatg gaaaagctca    8100
gcctcaaatc aatgaaacca ggatttaatt atatggatta cttgaatcta agattacttg    8160
acaaatgata atataataca ctggagcttt aaacatagcc aatgtgattc taactccttt    8220
aaactcacag ttaatcataa acaaggtttg acatcaatct agttatctct ttgagaatga    8280
taaacttgat gaagattaag aaaaaggtaa tctttcgatt atctttaatc ttcatccttg    8340
attctacaat catgacagtt gtctttagtg acaagggaaa gaagccttttt tattaagttg    8400 taataatcag atctgcgaac cggtagagtt tagttgcaac ctaacacaca taaagcattg    8460
gtcaaaaagt caatagaaat ttaaacagtg agtggagaca acttttaaat ggaagcttca    8520
tatgagagag gacgcccacg agctgccaga cagcattcaa gggatggaca cgaccaccat    8580
gttcgagcac gatcatcatc cagagagaat tatcgaggtg agtaccgtca atcaaggagc    8640
gcctcacaag tgcgcgttcc tactgtattt cataagaaga gagttgaacc attaacagtt    8700
cctccagcac ctaaagacat atgtccgacc ttgaaaaaag gattttttgtg tgacagtagt    8760 ttttgcaaaa aagatcacca gttggagagt ttaactgata gggaattact cctactaatc    8820
gcccgtaaga cttgtggatc agtagaacaa caattaaata taactgcacc caaggactcg    8880
cgcttagcaa atccaacggc tgatgatttc cagcaagagg aaggtccaaa aattaccttg    8940
ttgacactga tcaagacggc agaacactgg gcgagacaag acatcagaac catagaggat    9000
tcaaaattaa gagcattgtt gactctatgt gctgtgatga cgaggaaatt ctcaaaatcc    9060
cagctgagtc ttttatgtga gacacaccta aggcgcgagg ggcttgggca agatcaggca    9120
gaacccgttc tcgaagtata tcaacgatta cacagtgata aaggaggcag ttttgaagct    9180
gcactatggc aacaatggga ccgacaatcc ctaattatgt ttatcactgc attcttgaat    9240
attgctctcc agttaccgtg tgaaagttct gctgtcgttg tttcagggtt aagaacattg    9300
gttcctcaat cagataatga ggaagcttca accaacccgg ggacatgctc atggtctgat    9360
gagggtaccc cttaataagg ctgactaaaa cactatataa ccttctactt gatcacaata    9420
ctccgtatac ctatcatcat atatttaatc aagacgatat cctttaaaac ttattcagta    9480
ctataatcac tctcgtttca aattaataag atgtgcatga ttgccctaat atatgaagag    9540
```

```
gtatgataca accctaacag tgatcaaaga aaatcataat ctcgtatcgc tcgtaatata   9600
acctgccaag catacctctt gcacaaagtg attcttgtac acaaataatg ttttactcta   9660
caggaggtag caacgatcca tcccatcaaa aaataagtat ttcatgactt actaatgatc   9720
tcttaaaata ttaagaaaaa ctgacggaac ataaattctt tatgcttcaa gctgtggagg   9780
aggtgtttgg tattggctat tgttatatta caatcaataa caagcttgta aaaatattgt   9840
tcttgtttca agaggtagat tgtgaccgga atgctaaac  taatgatgaa gattaatgcg   9900
gaggtctgat aagaataaac cttattattc agattaggcc ccaagaggca ttcttcatct   9960 cctttttagca aagtactatt tcagggtagt ccaattagtg gcacgtcttt tagctgtata  10020
tcagtcgccc ctgagatacg ccacaaaagt gtctctaagc taaattggtc tgtacacatc  10080
ccatacattg tattagggggc aataatatct aattgaactt agccgtttaa aatttagtgc  10140
ataaatctgg gctaacacca ccaggtcaac tccattggct gaaaagaagc ttacctacaa  10200
cgaacatcac tttgagcgcc ctcacaatta aaaatagga acgtcgttcc aacaatcgag  10260
cgcaaggttt caaggttgaa ctgagagtgt ctagacaaca aatattgat  actccagaca  10320 ccaagcaaga cctgagaaaa aaccatggct aaagctacgg gacgatacaa tctaatatcg  10380
cccaaaaagg acctggagaa aggggttgtc ttaagcgacc tctgtaactt cttagttagc  10440
caaactattc aggggtggaa ggtttattgg gctggtattg agtttgatgt gactcacaaa  10500
ggaatggccc tattgcatag actgaaaact aatgactttg cccctgcatg gtcaatgaca  10560
aggaatctct ttcctcattt atttcaaaat ccgaattcca caattgaatc accgctgtgg  10620
gcattgagag tcatccttgc agcagggata caggaccagc tgattgacca gtctttgatt  10680
gaacccttag caggagccct tggtctgatc tctgattggc tgctaacaac caacactaac  10740
catttcaaca tgcgaacaca acgtgtcaag gaacaattga gcctaaaaat gctgtcgttg  10800
attcgatcca atattctcaa gtttattaac aaattggatg ctctacatgt cgtgaactac  10860
aacggattgt tgagcagtat tgaaattgga actcaaaatc atacaatcat cataactcga  10920
actaacatgg gttttctggt ggagctccaa gaacccgaca aatcggcaat gaaccgcatg  10980
aagcctgggc cggcgaaatt ttccctcctt catgagtcca cactgaaagc atttacacaa  11040
ggatcctcga cacgaatgca agtttgatt  cttgaattta atagctctct tgctatctaa  11100
ctaaggtaga atacttcata ttgagctaac tcatatatgc tgactcaata gttatcttga  11160
catctctgct ttcataatca gatatataag cataataaat aaatactcat atttcttgat  11220
aatttgttta accacagata aatcctcact gtaagccagc ttccaagttg acacccttac  11280
aaaaaccagg actcagaatc cctcaaacaa gagattccaa gacaacatca tagaattgct  11340
ttattatatg aataagcatt ttatcaccag aaatcctata tactaaatgg ttaattgtaa  11400
ctgaacccgc aggtcacatg tgttaggttt cacagattct atatattact aactctatac  11460
tcgtaattaa cattagataa gtagattaag aaaaaagcct gaggaagatt aagaaaaact  11520
gcttattggg tctttccgtg ttttagatga agcagttgaa attcttcctc ttgatattaa  11580
atggctacac aacataccca atacccagac gctaggttat catcaccaat tgtattggac  11640
caatgtgacc tagtcactag agcttgcggg ttatattcat catactccct taatccgcaa  11700
ctacgcaact gtaaactccc gaaacatatc taccgtttga aatacgatgt aactgttacc  11760
aagttcttga gtgatgtacc agtggcgaca ttgcccatag atttcatagt cccagttctt  11820
ctcaaggcac tgtcaggcaa tggattctgt cctgttgagc cgcggtgcca acagttctta  11880
gatgaaatca ttaagtacac aatgcaagat gctctcttct tgaaatatta tctcaaaaat  11940
```

```
gtgggtgctc aagaagactg tgttgatgaa cactttcaag agaaaatctt atcttcaatt    12000
cagggcaatg aattttttaca tcaaatgttt ttctggtatg atctggctat tttaactcga    12060
aggggtagat taaatcgagg aaactctaga tcaacatggt ttgttcatga tgatttaata    12120
gacatcttag gctatgggga ctatgttttt tggaagatcc caatttcaat gttaccactg    12180
aacacacaag gaatccccca tgctgctatg gactggtatc aggcatcagt attcaaagaa    12240
gcggttcaag ggcatacaca cattgtttct gtttctactg ccgacgtctt gataatgtgc    12300
aaagatttaa ttacatgtcg attcaacaca actctaatct caaaaatagc agagattgag    12360
gatccagttt gttctgatta tcccaatttt aagattgtgt ctatgctttta ccagagcgga    12420 gattacttac tctccatatt agggtctgat gggtataaaa ttattaagtt cctcgaacca    12480
ttgtgcttgg ccaaaattca attatgctca agtacactg agaggaaggg ccgattctta    12540
acacaaatgc atttagctgt aaatcacacc ctagaagaaa ttacagaaat gcgtgcacta    12600
aagccttcac aggctcaaaa gatccgtgaa ttccatagaa cattgataag gctggagatg    12660
acgccacaac aactttgtga gctatttttcc attcaaaaac actgggggca tcctgtgcta    12720
catagtgaaa cagcaatcca aaaagttaaa aaacatgcta cggtgctaaa agcattacgc    12780
cctatagtga ttttcgagac atactgtgtt tttaaatata gtattgccaa acattatttt    12840
gatagtcaag gatcttggta cagtgttact tcagatagga atctaacacc gggtcttaat    12900
tcttatatca aagaaatca attccctccg ttgccaatga ttaaagaact actatgggaa    12960
ttttaccacc ttgaccaccc tccactttc tcaaccaaaa ttattagtga cttaagtatt    13020
tttataaaag acagagctac cgcagtagaa aggacatgct gggatgcagt attcgagcct    13080
aatgttctag gatataatcc acctcacaaa tttagtacta aacgtgtacc ggaacaattt    13140
ttagagcaag aaaacttttc tattgagaat gttctttcct acgcacaaaa actcgagtat    13200
ctactaccac aatatcggaa cttttctttc tcattgaaag agaaagagtt gaatgtaggt    13260
agaaccttcg gaaaattgcc ttatccgact cgcaatgttc aaacactttg tgaagctctg    13320
ttagctgatg gtcttgctaa agcatttcct agcaatatga tggtagttac ggaacgtgag    13380
caaaaagaaa gcttattgca tcaagcatca tggcaccaca caagtgatga ttttggtgaa    13440
catgccacag ttagagggag tagctttgta actgatttag agaaatacaa tcttgcattt    13500
agatatgagt ttacagcacc ttttatagaa tattgcaacc gttgctatgg tgttaagaat    13560 gttttttaatt ggatgcatta tacaatccca cagtgttata tgcatgtcag tgattattat    13620
aatccaccac ataacctcac actggagaat cgagacaacc cccccgaagg gcctagttca    13680
tacaggggtc atatgggagg gattgaagga ctgcaacaaa aactctggac aagtatttca    13740
tgtgctcaaa tttctttagt tgaaattaag actggtttta agttacgctc agctgtgatg    13800
ggtgacaatc agtgcattac tgtttttatca gtcttcccct tagagactga cgcagacgag    13860
caggaacaga gcgccgaaga caatgcagcg agggtggccg ccagcctagc aaaagttaca    13920
agtgcctgtg gaatctttttt aaaacctgat gaaacatttg tacattcagg ttttatctat    13980
tttgaaaaaa aacaatattt gaatggggtc caattgcctc agtcccttaa aacggctaca    14040
agaatggcac cattgtctga tgcaattttt gatgatcttc aagggaccct ggctagtata    14100
ggcactgctt ttgagcgatc catctctgag acacgacata tctttccttg caggataacc    14160
gcagctttcc atacgttttt ttcggtgaga atcttgcaat atcatcatct cgggttcaat    14220
aaaggttttg accttggaca gttaacactc ggcaaacctc tggattcgg aacaatatca    14280
```

```
ttggcactag cggtaccgca ggtgcttgga gggttatcct tcttgaatcc tgagaaatgt   14340
ttctaccgga atctaggaga tccagttacc tcaggcttat tccagttaaa aacttatctc   14400
cgaatgattg agatggatga tttattctta cctttaattg cgaagaaccc tgggaactgc   14460
actgccattg actttgtgct aaatcctagc ggattaaatg tccctgggtc gcaagactta   14520
acttcatttc tgcgccagat tgtacgcagg accatcaccc taagtgcgaa aaacaaactt   14580
attaatacct tatttcatgc gtcagctgac ttcgaagacg aaatggtttg taaatggcta   14640
ttatcatcaa ctcctgttat gagtcgtttt gcggccgata tcttttcacg cacgccgagc   14700
gggaagcgat tgcaaattct aggatacctg gaaggaacac gcacattatt agcctctaag   14760
atcatcaaca ataatacaga gacaccggtt ttggacagac tgaggaaaat aacattgcaa   14820
aggtggagcc tatggtttag ttatcttgat cattgtgata atatcctggc ggaggcttta   14880
acccaaataa cttgcacagt tgatttagca cagattctga gggaatattc atgggctcat   14940
attttagagg gaagacctct tattggagcc acactcccat gtatgattga gcaattcaaa   15000
gtgttttggc tgaaacccta cgaacaatgt ccgcagtgtt caaatgcaaa gcaaccaggt   15060
gggaaaccat tcgtgtcagt ggcagtcaag aaacatattg ttagtgcatg gccgaacgca   15120
tcccgaataa gctggactat cggggatgga atcccataca ttggatcaag gacagaagat   15180
aagataggac aacctgctat taaaccaaaa tgtccttccg cagccttaag agaggccatt   15240
gaattggcgt cccgtttaac atgggtaact caaggcagtt cgaacagtga cttgctaata   15300
aaaccatttt tggaagcacg agtaaattta agtgttcaag aaatacttca aatgaccect   15360
tcacattact caggaaatat tgttcacagg tacaacgatc aatacagtcc tcattctttc   15420
atggccaatc gtatgagtaa ttcagcaacg cgattgattg tttctacaaa cactttaggt   15480
gagttttcag gaggtggcca gtctgcacgc gacagcaata ttattttcca gaatgttata   15540
aattatgcag ttgcactgtt cgatattaaa tttagaaaca ctgaggctac agatatccaa   15600
tataatcgtg ctcaccttca tctaactaag tgttgcaccc gggaagtacc agctcagtat   15660
ttaacataca catctacatt ggatttagat ttaacaagat accgagaaaa cgaattgatt   15720
tatgacagta atcctctaaa aggaggactc aattgcaata tctcattcga taatccattt   15780
ttccaaggta aacggctgaa cattatagaa gatgatctta ttcgactgcc tcacttatct   15840
ggatgggagc tagccaagac catcatgcaa tcaattattt cagatagcaa caattcatct   15900
acagacccaa ttagcagtgg agaaacaaga tcattcacta cccatttctt aacttatccc   15960
aagataggac ttctgtacag ttttgggggcc tttgtaagtt attatcttgg caatacaatt   16020
cttcggacta agaaattaac acttgacaat ttttatatt acttaactac tcaaattcat   16080
aatctaccac atcgctcatt gcgaatactt aagccaacat tcaaacatgc aagcgttatg   16140
tcacggttaa tgagtattga tcctcatttt tctatttaca taggcggtgc tgcaggtgac   16200
agaggactct cagatgcggc caggttattt ttgagaacgt ccatttcatc ttttcttaca   16260
tttgtaaaag aatggataat taatcgcgga acaattgtcc ctttatggat agtatatccg   16320
ctagagggtc aaaacccaac acctgtgaat aattttctct atcagatcgt agaactgctg   16380
gtgcatgatt catcaagaca acaggctttt aaaactacca taagtgatca tgtacatcct   16440
cacgacaatc ttgtttacac atgtaagagt acagccagca atttcttcca tgcatcattg   16500
gcgtactgga ggagcagaca cagaaacagc aaccgaaaat acttggcaag agactcttca   16560
actggatcaa gcacaaacaa cagtgatggt catattgaga gaagtcaaga acaaaccacc   16620
agagatccac atgatggcac tgaacggaat ctagtcctac aaatgagcca tgaaataaaa   16680
```

```
agaacgacaa ttccacaaga aaacacgcac cagggtccgt cgttccagtc ctttctaagt    16740
gactctgctt gtggtacagc aaatccaaaa ctaaatttcg atcgatcgag acacaatgtg    16800
aaatttcagg atcataactc ggcatccaag agggaaggtc atcaaataat ctcacaccgt    16860
ctagtcctac ctttctttac attatctcaa gggacacgcc aattaacgtc atccaatgag    16920
tcacaaaccc aagacgagat atcaaagtac ttacggcaat tgagatccgt cattgatacc    16980
acagtttatt gtagatttac cggtatagtc tcgtccatgc attacaaact tgatgaggtc    17040
ctttgggaaa tagagagttt caagtcggct gtgacgctag cagagggaga aggtgctggt    17100
gccttactat tgattcagaa ataccaagtt aagaccttat ttttcaacac gctagctact    17160
gagtccagta tagagtcaga aatagtatca ggaatgacta ctcctaggat gcttctacct    17220
gttatgtcaa aattccataa tgaccaaatt gagattattc ttaacaactc agcaagccaa    17280
ataacagaca taacaaatcc tacttggttt aaagaccaaa gagcaaggct acctaagcaa    17340
gtcgaggtta taaccatgga tgcagagaca acagagaata taaacagatc gaaattgtac    17400
gaagctgtat ataaattgat cttacaccat attgatccta gcgtattgaa agcagtggtc    17460
cttaaagtct ttctaagtga tactgagggt atgttatggc taaatgataa tttagccccg    17520 tttttttgcca ctggttattt aattaagcca ataacgtcaa gtgctagatc tagtgagtgg    17580
tatctttgtc tgacgaactt cttatcaact acacgtaaga tgccacacca aaaccatctc    17640
agttgtaaac aggtaatact tacggcattg caactgcaaa ttcaacgaag cccatactgg    17700
ctaagtcatt taactcagta tgctgactgt gagttacatt taagttatat ccgccttggt    17760
tttccatcat tagagaaagt actataccac aggtataacc tcgtcgattc aaaaagaggt    17820
ccactagtct ctatcactca gcacttagca catcttagag cagagattcg agaattaact    17880
aatgattata atcaacagcg acaaagtcgg actcaaacat atcactttat tcgtactgca    17940
aaaggacgaa tcacaaaact agtcaatgat tatttaaaat tctttcttat tgtgcaagca    18000
ttaaaacata atgggacatg gcaagctgag tttaagaaat taccagagtt gattagtgtg    18060
tgcaataggt tctaccatat tagagattgc aattgtgaag aacgtttctt agttcaaacc    18120
ttatatttac atagaatgca ggattctgaa gttaagctta tcgaaaggct gacagggctt    18180
ctgagtttat ttccggatgg tctctacagg tttgattgaa ttaccgtgca tagtatcctg    18240
atacttgcaa aggttggtta ttaacataca gattataaaa aactcataaa ttgctctcat    18300
acatcatatt gatctaatct caataaacaa ctatttaaat aacgaaagga gtccctatat    18360
tatatactat atttagcctc tctccctgcg tgataatcaa aaaattcaca atgcagcatg    18420
tgtgacatat tactgccgca atgaatttaa cgcaacataa taaactctgc actctttata    18480
attaagcttt aacgaaaggt ctgggctcat attgttattg atataataat gttgtatcaa    18540
tatcctgtca gatggaatag tgttttggtt gataacacaa cttcttaaaa caaaattgat    18600
ctttaagatt aagtttttta taattatcat tactttaatt tgtcgtttta aaacggtga     18660 tagccttaat ctttgtgtaa aataagagat taggtgtaat aaccttaaca tttttgtcta    18720
gtaagctact atttcataca gaatgataaa attaaaagaa aaggcaggac tgtaaaatca    18780
gaaatacctt ctttacaata tagcagacta gataataatc ttcgtgttaa tgataattaa    18840
gacattgacc acgctcatca gaaggctcgc cagaataaac gttgcaaaaa ggattcctgg    18900
aaaaatggtc gcacacaaaa atttaaaaat aaatctattt cttcttttt gtgtgtcca      18959
```

<210> SEQ ID NO 20

```
<211> LENGTH: 695
<212> TYPE: PRT
<213> ORGANISM: Marburg virus

<400> SEQUENCE: 20
```

| | | | | | | | | | | | | | | |
|---|---|---|---|---|---|---|---|---|---|---|---|---|---|---|
|Met|Asp|Leu|His|Ser|Leu|Leu|Glu|Leu|Gly|Thr|Lys|Pro|Thr|Ala|Pro|
|1| | | |5| | | | |10| | | | |15|
|His|Val|Arg|Asn|Lys|Lys|Val|Ile|Leu|Phe|Asp|Thr|Asn|His|Gln|Val|
| | | |20| | | | |25| | | | |30| | |
|Ser|Ile|Cys|Asn|Gln|Ile|Ile|Asp|Ala|Ile|Asn|Ser|Gly|Ile|Asp|Leu|
| | |35| | | | |40| | | | |45| | | |
|Gly|Asp|Leu|Leu|Glu|Gly|Gly|Leu|Leu|Thr|Leu|Cys|Val|Glu|His|Tyr|
| |50| | | | |55| | | | |60| | | | |
|Tyr|Asn|Ser|Asp|Lys|Asp|Lys|Phe|Asn|Thr|Ser|Pro|Ile|Ala|Lys|Tyr|
|65| | | |70| | | | |75| | | | |80| |
|Leu|Arg|Asp|Ala|Gly|Tyr|Glu|Phe|Asp|Val|Val|Lys|Asn|Ala|Asp|Ala|
| | | | |85| | | | |90| | | | |95| |
|Thr|Arg|Phe|Leu|Asp|Val|Ile|Pro|Asn|Glu|Pro|His|Tyr|Ser|Pro|Leu|
| | | |100| | | | |105| | | | |110| | |
|Ile|Leu|Ala|Leu|Lys|Thr|Leu|Glu|Ser|Thr|Glu|Ser|Gln|Arg|Gly|Arg|
| | |115| | | | |120| | | | |125| | | |
|Ile|Gly|Leu|Phe|Leu|Ser|Phe|Cys|Ser|Leu|Phe|Leu|Pro|Lys|Leu|Val|
| |130| | | | |135| | | | |140| | | | |
|Val|Gly|Asp|Arg|Ala|Ser|Ile|Glu|Lys|Ala|Leu|Arg|Gln|Val|Thr|Val|
|145| | | | |150| | | | |155| | | | |160|
|His|Gln|Glu|Gln|Gly|Ile|Val|Thr|Tyr|Pro|Asn|His|Trp|Leu|Thr|Thr|
| | | | |165| | | | |170| | | | |175| |
|Gly|His|Met|Lys|Val|Ile|Phe|Gly|Ile|Leu|Arg|Ser|Ser|Phe|Ile|Leu|
| | | |180| | | | |185| | | | |190| | |
|Lys|Phe|Val|Leu|Ile|His|Gln|Gly|Val|Asn|Leu|Val|Thr|Gly|His|Asp|
| | |195| | | | |200| | | | |205| | | |
|Ala|Tyr|Asp|Ser|Ile|Ile|Ser|Asn|Ser|Val|Gly|Gln|Thr|Arg|Phe|Ser|
| |210| | | | |215| | | | |220| | | | |
|Gly|Leu|Leu|Ile|Val|Lys|Thr|Val|Leu|Glu|Phe|Ile|Leu|Gln|Lys|Thr|
|225| | | | |230| | | | |235| | | | |240|
|Asp|Ser|Gly|Val|Thr|Leu|His|Pro|Leu|Val|Arg|Thr|Ser|Lys|Val|Lys|
| | | | |245| | | | |250| | | | |255| |
|Asn|Glu|Val|Ala|Ser|Phe|Lys|Gln|Ala|Leu|Ser|Asn|Leu|Ala|Arg|His|
| | | |260| | | | |265| | | | |270| | |
|Gly|Glu|Tyr|Ala|Pro|Phe|Ala|Arg|Val|Leu|Asn|Leu|Ser|Gly|Ile|Asn|
| | |275| | | | |280| | | | |285| | | |
|Asn|Leu|Glu|His|Gly|Leu|Tyr|Pro|Gln|Leu|Ser|Ala|Ile|Ala|Leu|Gly|
| |290| | | | |295| | | | |300| | | | |
|Val|Ala|Thr|Ala|His|Gly|Ser|Thr|Leu|Ala|Gly|Val|Asn|Val|Gly|Glu|
|305| | | | |310| | | | |315| | | | |320|
|Gln|Tyr|Gln|Gln|Leu|Arg|Glu|Ala|Ala|His|Asp|Ala|Glu|Ile|Lys|Leu|
| | | | |325| | | | |330| | | | |335| |
|Gln|Arg|Arg|His|Glu|His|Gln|Glu|Ile|Gln|Ala|Ile|Ala|Glu|Asp|Asp|
| | | | |340| | | | |345| | | | |350| |
|Glu|Glu|Arg|Lys|Ile|Leu|Glu|Gln|Phe|His|Leu|Gln|Lys|Thr|Glu|Ile|
| | | |355| | | | |360| | | | |365| | |
|Thr|His|Ser|Gln|Thr|Leu|Ala|Val|Leu|Ser|Gln|Lys|Arg|Glu|Lys|Leu|
| | |370| | | | |375| | | | |380| | | |
|Ala|Arg|Leu|Ala|Ala|Glu|Ile|Glu|Asn|Asn|Ile|Val|Glu|Asp|Gln|Gly|

```
                385                 390                 395                 400
        Phe Lys Gln Ser Gln Asn Gln Val Ser Gln Ser Phe Leu Asn Asp Pro
                        405                 410                 415

Thr Pro Val Glu Val Thr Val Gln Ala Arg Pro Ile Asn Arg Pro Thr
                        420                 425                 430

Ala Leu Pro Pro Val Asp Asn Lys Ile Glu His Glu Ser Thr Glu
                        435                 440                 445

Asp Ser Ser Ser Ser Ser Phe Val Asp Leu Asn Asp Pro Phe Ala
            450                 455                 460

Leu Leu Asn Glu Asp Glu Asp Thr Leu Asp Asp Ser Val Met Ile Pro
        465                 470                 475                 480

Ser Thr Thr Ser Arg Glu Phe Gln Gly Ile Pro Ala Pro Pro Arg Gln
                        485                 490                 495

Ser Gln Asp Leu Asn Asn Ser Gln Gly Lys Gln Glu Asp Glu Ser Thr
                        500                 505                 510

Asn Pro Ile Lys Lys Gln Phe Leu Arg Tyr Gln Glu Leu Pro Pro Val
                        515                 520                 525

Gln Glu Asp Asp Glu Ser Glu Tyr Thr Thr Asp Ser Gln Glu Ser Ile
                        530                 535                 540

Asp Gln Pro Gly Ser Asp Asn Glu Gln Gly Val Asp Leu Pro Pro Pro
        545                 550                 555                 560

Pro Leu Tyr Ala Gln Glu Lys Arg Gln Asp Pro Ile Gln His Pro Ala
                        565                 570                 575

Val Ser Ser Gln Asp Pro Phe Gly Ser Ile Gly Asp Val Asn Gly Asp
                        580                 585                 590

Ile Leu Glu Pro Ile Arg Ser Pro Ser Ser Pro Ser Ala Pro Gln Glu
                        595                 600                 605

Asp Thr Arg Ala Arg Glu Ala Tyr Glu Leu Ser Pro Asp Phe Thr Asn
                        610                 615                 620

Tyr Glu Asp Asn Gln Gln Asn Trp Pro Gln Arg Val Val Thr Lys Lys
        625                 630                 635                 640

Gly Arg Thr Phe Leu Tyr Pro Asn Asp Leu Leu Gln Thr Asn Pro Pro
                        645                 650                 655

Glu Ser Leu Ile Thr Ala Leu Val Glu Glu Tyr Gln Asn Pro Val Ser
                        660                 665                 670

Ala Lys Glu Leu Gln Ala Asp Trp Pro Asp Met Ser Phe Asp Glu Arg
                        675                 680                 685

Arg His Val Ala Met Asn Leu
                        690                 695

<210> SEQ ID NO 21
<211> LENGTH: 329
<212> TYPE: PRT
<213> ORGANISM: Marburg virus

<400> SEQUENCE: 21

Met Trp Asp Ser Ser Tyr Met Gln Gln Val Ser Glu Gly Leu Met Thr
        1               5                   10                  15

Gly Lys Val Pro Ile Asp Gln Val Phe Gly Ala Asn Pro Ser Glu Lys
                        20                  25                  30

Leu His Lys Arg Arg Lys Pro Lys Gly Thr Val Gly Leu Gln Cys Ser
                        35                  40                  45

Pro Cys Leu Met Ser Lys Ala Thr Ser Thr Asp Ile Val Trp Asp
        50                  55                  60
```

```
Gln Leu Ile Val Lys Lys Thr Leu Ala Asp Leu Ile Pro Ile Asn
 65                  70                  75                  80

Arg Gln Ile Ser Asp Ile Gln Ser Thr Leu Asn Glu Val Thr Thr Arg
                 85                  90                  95

Val His Glu Ile Glu Arg Gln Leu His Glu Ile Thr Pro Val Leu Lys
            100                 105                 110

Met Gly Arg Thr Leu Glu Ala Ile Ser Lys Gly Met Ser Glu Met Leu
        115                 120                 125

Ala Lys Tyr Asp His Leu Val Ile Ser Thr Gly Arg Thr Thr Ala Pro
    130                 135                 140

Ala Ala Ala Phe Asp Ala Tyr Leu Asn Glu His Gly Val Pro Pro Pro
145                 150                 155                 160

Gln Pro Ala Ile Phe Lys Asp Leu Gly Val Ala Gln Gln Ala Cys Ser
                165                 170                 175

Lys Gly Thr Met Val Lys Asn Glu Thr Thr Asp Ala Ala Asp Lys Met
            180                 185                 190

Ser Lys Val Leu Glu Leu Ser Glu Glu Thr Phe Ser Lys Pro Asn Leu
        195                 200                 205

Ser Ala Lys Asp Leu Ala Leu Leu Leu Phe Thr His Leu Pro Gly Asn
    210                 215                 220

Asn Thr Pro Phe His Ile Leu Ala Gln Val Leu Ser Lys Ile Ala Tyr
225                 230                 235                 240

Lys Ser Gly Lys Ser Gly Ala Phe Leu Asp Ala Phe His Gln Ile Leu
                245                 250                 255

Ser Glu Gly Glu Asn Ala Gln Ala Ala Leu Thr Arg Leu Ser Arg Thr
            260                 265                 270

Phe Asp Ala Phe Leu Gly Val Val Pro Pro Val Ile Arg Val Lys Asn
        275                 280                 285

Phe Gln Thr Val Pro Arg Pro Cys Gln Lys Ser Leu Arg Ala Val Pro
    290                 295                 300

Pro Asn Pro Thr Ile Asp Lys Gly Trp Val Cys Val Tyr Ser Ser Glu
305                 310                 315                 320

Gln Gly Glu Thr Arg Ala Leu Lys Ile
                325

<210> SEQ ID NO 22
<211> LENGTH: 303
<212> TYPE: PRT
<213> ORGANISM: Marburg virus

<400> SEQUENCE: 22

Met Ala Ser Ser Ser Asn Tyr Asn Thr Tyr Met Gln Tyr Leu Asn Pro
  1               5                  10                  15

Pro Pro Tyr Ala Asp His Gly Ala Asn Gln Leu Ile Pro Ala Asp Gln
             20                  25                  30

Leu Ser Asn Gln Gln Gly Ile Thr Pro Asn Tyr Val Gly Asp Leu Asn
         35                  40                  45

Leu Asp Asp Gln Phe Lys Gly Asn Val Cys His Ala Phe Thr Leu Glu
    50                  55                  60

Ala Ile Ile Asp Ile Ser Ala Tyr Asn Glu Pro Thr Val Lys Gly Val
 65                  70                  75                  80

Pro Ala Trp Leu Pro Leu Gly Ile Met Ser Asn Phe Glu Tyr Pro Leu
                 85                  90                  95

Ala His Thr Val Ala Ala Leu Leu Thr Gly Ser Tyr Thr Ile Thr Gln
            100                 105                 110
```

```
Phe Thr His Asn Gly Gln Lys Phe Val Arg Val Asn Arg Leu Gly Thr
            115                 120                 125

Gly Ile Pro Ala His Pro Leu Arg Met Leu Arg Glu Gly Asn Gln Ala
        130                 135                 140

Phe Ile Gln Asn Met Val Ile Pro Arg Asn Phe Ser Thr Asn Gln Phe
145                 150                 155                 160

Thr Tyr Asn Leu Thr Asn Leu Val Leu Ser Val Gln Lys Leu Pro Asp
                165                 170                 175

Asp Ala Trp Arg Pro Ser Lys Asp Lys Leu Ile Gly Asn Thr Met His
            180                 185                 190

Pro Ala Val Ser Ile His Pro Asn Leu Pro Pro Ile Val Leu Pro Thr
        195                 200                 205

Val Lys Lys Gln Ala Tyr Arg Gln His Lys Asn Pro Asn Asn Gly Pro
    210                 215                 220

Leu Leu Ala Ile Ser Gly Ile Leu His Gln Leu Arg Val Glu Lys Val
225                 230                 235                 240

Pro Glu Lys Thr Ser Leu Phe Arg Ile Ser Leu Pro Ala Asp Met Phe
                245                 250                 255

Ser Val Lys Glu Gly Met Met Lys Lys Arg Gly Glu Asn Ser Pro Val
            260                 265                 270

Val Tyr Phe Gln Ala Pro Glu Asn Phe Pro Leu Asn Gly Phe Asn Asn
        275                 280                 285

Arg Gln Val Val Leu Ala Tyr Ala Asn Pro Thr Leu Ser Ala Val
    290                 295                 300

<210> SEQ ID NO 23
<211> LENGTH: 681
<212> TYPE: PRT
<213> ORGANISM: Marburg virus

<400> SEQUENCE: 23

Met Lys Thr Thr Cys Leu Phe Ile Ser Leu Ile Leu Ile Gln Gly Ile
1               5                   10                  15

Lys Thr Leu Pro Ile Leu Glu Ile Ala Ser Asn Asn Gln Pro Gln Asn
            20                  25                  30

Val Asp Ser Val Cys Ser Gly Thr Leu Gln Lys Thr Glu Asp Val His
        35                  40                  45

Leu Met Gly Phe Thr Leu Ser Gly Gln Lys Val Ala Asp Ser Pro Leu
    50                  55                  60

Glu Ala Ser Lys Arg Trp Ala Phe Arg Thr Gly Val Pro Pro Lys Asn
65                  70                  75                  80

Val Glu Tyr Thr Glu Gly Glu Glu Ala Lys Thr Cys Tyr Asn Ile Ser
                85                  90                  95

Val Thr Asp Pro Ser Gly Lys Ser Leu Leu Leu Asp Pro Pro Thr Asn
            100                 105                 110

Ile Arg Asp Tyr Pro Lys Cys Lys Thr Ile His His Ile Gln Gly Gln
        115                 120                 125

Asn Pro His Ala Gln Gly Ile Ala Leu His Leu Trp Gly Ala Phe Phe
    130                 135                 140

Leu Tyr Asp Arg Ile Ala Ser Thr Thr Met Tyr Arg Gly Arg Val Phe
145                 150                 155                 160

Thr Glu Gly Asn Ile Ala Ala Met Ile Val Asn Lys Thr Val His Lys
                165                 170                 175

Met Ile Phe Ser Arg Gln Gly Gln Gly Tyr Arg His Met Asn Leu Thr
```

```
                    180                 185                 190
        Ser Thr Asn Lys Tyr Trp Thr Ser Asn Gly Thr Gln Thr Asn Asp
                    195                 200                 205

Thr Gly Cys Phe Gly Ala Leu Gln Glu Tyr Asn Ser Thr Lys Asn Gln
                    210                 215                 220

Thr Cys Ala Pro Ser Lys Ile Pro Ser Pro Leu Pro Thr Ala Arg Pro
        225                 230                 235                 240

Glu Ile Lys Pro Thr Ser Thr Pro Thr Asp Ala Thr Thr Leu Asn Thr
                            245                 250                 255

Thr Asp Pro Asn Asn Asp Asp Glu Asp Leu Ile Thr Ser Gly Ser Gly
                        260                 265                 270

Ser Gly Glu Gln Glu Pro Tyr Thr Thr Ser Asp Ala Val Thr Lys Gln
                    275                 280                 285

Gly Leu Ser Ser Thr Met Pro Pro Thr Pro Ser Pro Gln Pro Ser Thr
                    290                 295                 300

Pro Gln Gln Glu Gly Asn Asn Thr Asp His Ser Gln Gly Thr Val Thr
        305                 310                 315                 320

Glu Pro Asn Lys Thr Asn Thr Thr Ala Gln Pro Ser Met Pro Pro His
                            325                 330                 335

Asn Thr Thr Ala Ile Ser Thr Asn Asn Thr Ser Lys Asn Asn Phe Ser
                        340                 345                 350

Thr Leu Ser Val Ser Leu Gln Asn Thr Thr Asn Tyr Asp Thr Gln Ser
                    355                 360                 365

Thr Ala Thr Glu Asn Glu Gln Thr Ser Ala Pro Ser Lys Thr Thr Leu
                    370                 375                 380

Pro Pro Thr Gly Asn Leu Thr Thr Ala Lys Ser Thr Asn Asn Thr Lys
        385                 390                 395                 400

Gly Pro Thr Thr Thr Ala Pro Asn Met Thr Asn Gly His Leu Thr Ser
                            405                 410                 415

Pro Ser Pro Thr Pro Asn Pro Thr Thr Gln His Leu Val Tyr Phe Arg
                        420                 425                 430

Lys Lys Arg Ser Ile Leu Trp Arg Glu Gly Asp Met Phe Pro Phe Leu
                    435                 440                 445

Asp Gly Leu Ile Asn Ala Pro Ile Asp Phe Asp Pro Val Pro Asn Thr
                    450                 455                 460

Lys Thr Ile Phe Asp Glu Ser Ser Ser Gly Ala Ser Ala Glu Glu
        465                 470                 475                 480

Asp Gln His Ala Ser Pro Asn Ile Ser Leu Thr Leu Ser Tyr Phe Pro
                            485                 490                 495

Asn Ile Asn Glu Asn Thr Ala Tyr Ser Gly Glu Asn Glu Asn Asp Cys
                        500                 505                 510

Asp Ala Glu Leu Arg Ile Trp Ser Val Gln Glu Asp Asp Leu Ala Ala
                    515                 520                 525

Gly Leu Ser Trp Ile Pro Phe Phe Gly Pro Gly Ile Glu Gly Leu Tyr
                    530                 535                 540

Thr Ala Gly Leu Ile Lys Asn Gln Asn Asn Leu Val Cys Arg Leu Arg
        545                 550                 555                 560

Arg Leu Ala Asn Gln Thr Ala Lys Ser Leu Glu Leu Leu Leu Arg Val
                            565                 570                 575

Thr Thr Glu Glu Arg Thr Phe Ser Leu Ile Asn Arg His Ala Ile Asp
                        580                 585                 590

Phe Leu Leu Thr Arg Trp Gly Gly Thr Cys Lys Val Leu Gly Pro Asp
                    595                 600                 605
```

```
Cys Cys Ile Gly Ile Glu Asp Leu Ser Arg Asn Ile Ser Glu Gln Ile
        610                 615                 620
Asp Gln Ile Lys Lys Asp Glu Gln Lys Glu Gly Thr Gly Trp Gly Leu
625                 630                 635                 640
Gly Gly Lys Trp Trp Thr Ser Asp Trp Gly Val Leu Thr Asn Leu Gly
                645                 650                 655
Ile Leu Leu Leu Leu Ser Ile Ala Val Leu Ile Ala Leu Ser Cys Ile
        660                 665                 670
Cys Arg Ile Phe Thr Lys Tyr Ile Gly
        675                 680

<210> SEQ ID NO 24
<211> LENGTH: 281
<212> TYPE: PRT
<213> ORGANISM: Marburg virus

<400> SEQUENCE: 24

Met Gln Gln Pro Arg Gly Arg Ser Arg Thr Arg Asn His Gln Thr Ala
1               5                   10                  15
Ser Ser Ile Tyr His Glu Thr Gln Leu Pro Ser Lys Pro His Tyr Thr
            20                  25                  30
Asn His His Pro Arg Ala Arg Ser Met Ser Ser Thr Arg Ser Ser Ala
        35                  40                  45
Glu Ser Ser Pro Thr Asn His Ile Pro Arg Ala Arg Pro Pro Pro Thr
50                  55                  60
Phe Asn Leu Ser Lys Pro Pro Pro Lys Asp Met Cys Arg Asn
65                  70                  75                  80
Met Lys Ile Gly Leu Pro Cys Thr Asp Pro Thr Cys Asn Arg Asp His
                85                  90                  95
Asp Leu Asp Asn Leu Thr Asn Arg Glu Leu Leu Leu Leu Met Ala Arg
            100                 105                 110
Lys Met Leu Pro Asn Thr Asp Lys Thr Phe Arg Ser Leu Gln Asp Cys
        115                 120                 125
Gly Ser Pro Ser Leu Ser Lys Gly Leu Ser Lys Asp Lys Gln Glu Gln
130                 135                 140
Thr Lys Asp Val Leu Thr Leu Glu Asn Leu Gly His Ile Leu Asn Tyr
145                 150                 155                 160
Leu His Arg Ser Asp Ile Gly Lys Leu Asp Glu Thr Ser Leu Arg Ala
                165                 170                 175
Ala Leu Ser Leu Thr Cys Ala Gly Ile Arg Lys Thr Asn Arg Ser Leu
            180                 185                 190
Ile Asn Thr Met Thr Glu Leu His Ile Asn His Glu Asn Leu Pro Gln
        195                 200                 205
Asp Gln Asn Gly Val Ile Lys Gln Thr Tyr Thr Gly Ile His Leu Asp
210                 215                 220
Lys Gly Gly Gln Phe Glu Ala Ala Leu Trp Gln Gly Trp Asp Lys Arg
225                 230                 235                 240
Ser Ile Ser Leu Phe Val Gln Ala Ala Leu Tyr Val Met Asn Asn Ile
                245                 250                 255
Pro Cys Glu Ser Ser Thr Ser Val Gln Ala Ser Tyr Asp His Phe Ile
            260                 265                 270
Leu Pro Gln Ser Gln Ser Lys Gly Gln
        275                 280
```

<210> SEQ ID NO 25
<211> LENGTH: 253
<212> TYPE: PRT
<213> ORGANISM: Marburg virus

<400> SEQUENCE: 25

Met Ala Glu Leu Ser Thr Arg Tyr Asn Leu Pro Ala Asn Val Thr Glu
 1               5                  10                  15

Lys Ser Ile Asn Leu Asp Leu Asn Ser Thr Ala Arg Trp Ile Lys Glu
            20                  25                  30

Pro Ser Val Gly Gly Trp Thr Val Lys Trp Gly Asn Phe Val Phe His
        35                  40                  45

Ile Pro Asn Thr Gly Met Ala Leu Leu His His Leu Lys Ser Asn Phe
    50                  55                  60

Val Val Pro Glu Trp Gln Gln Thr Arg Asn Leu Phe Ser His Leu Phe
65                  70                  75                  80

Lys Asn Pro Lys Ser Thr Ile Ile Glu Pro Phe Leu Ala Leu Arg Ile
                85                  90                  95

Leu Leu Gly Val Ala Leu Lys Asp Gln Glu Leu Gln Gln Ser Leu Ile
            100                 105                 110

Pro Gly Phe Arg Ser Ile Val His Met Leu Ser Glu Trp Leu Leu Leu
        115                 120                 125

Glu Val Thr Ser Ala Ile His Ile Ser Pro Asn Leu Leu Gly Ile Tyr
    130                 135                 140

Leu Thr Ser Asp Met Phe Lys Ile Leu Met Ala Gly Val Lys Asn Phe
145                 150                 155                 160

Phe Asn Lys Met Phe Thr Leu His Val Val Asn Asp His Gly Lys Pro
                165                 170                 175

Ser Ser Ile Glu Ile Lys Leu Thr Gly Gln Gln Ile Ile Ile Thr Arg
            180                 185                 190

Val Asn Met Gly Phe Leu Val Glu Val Arg Arg Ile Asp Ile Glu Pro
        195                 200                 205

Cys Cys Gly Glu Thr Val Leu Ser Glu Ser Val Val Phe Gly Leu Val
    210                 215                 220

Ala Glu Ala Val Leu Arg Glu His Ser Gln Met Glu Lys Gly Gln Pro
225                 230                 235                 240

Leu Asp Leu Thr Gln Tyr Met Asn Ser Lys Ile Ala Ile
                245                 250

<210> SEQ ID NO 26
<211> LENGTH: 2331
<212> TYPE: PRT
<213> ORGANISM: Marburg virus

<400> SEQUENCE: 26

Met Gln His Pro Thr Gln Tyr Pro Asp Ala Arg Leu Ser Ser Pro Ile
 1               5                  10                  15

Ile Leu Asp Gln Cys Asp Leu Leu Ala Arg Ser Leu Gly Leu Tyr Ser
            20                  25                  30

His Tyr Ser His Asn Pro Lys Leu Arg Asn Cys Arg Ile Pro His His
        35                  40                  45

Ile Tyr Arg Leu Arg Asn Ser Thr Ala Leu Lys Thr Phe Leu Gln Asn
    50                  55                  60

Cys Ser Ile Leu Thr Val Pro Phe His Ser Ile Trp Asp His Ile Leu
65                  70                  75                  80

Thr Ser Ile Gln Tyr Asp Ala Ile Asn His Val Asp Asp Phe Lys Tyr

```
                        85                  90                  95
Leu Leu Pro Ser Glu Leu Val Lys Tyr Ala Asn Trp Asp Asn Glu Phe
            100                 105                 110

Leu Lys Ala Tyr Leu Asn Lys Ile Leu Gly Leu Asp His Val Phe Pro
            115                 120                 125

Ala Ser Ala Arg Ser Gln Trp Glu Asp Phe Ser Pro Lys Glu Asn Pro
            130                 135                 140

Tyr Tyr Trp Gly Met Leu Leu Val His Leu Ser Gln Leu Ala Arg
145                 150                 155                 160

Arg Ile Lys Gly Gln Arg Gly Ser Leu Arg Ser Asn Trp Lys Phe Ile
                165                 170                 175

Gly Thr Asp Leu Glu Leu Phe Gly Ile Ala Asp Phe Ile Ile Phe Lys
            180                 185                 190

Val Pro Val Lys Thr Ile Ile Arg Asn Ala Val Ser Leu Gln Ala Ser
            195                 200                 205

Lys Pro Gly Leu Arg Val Trp Tyr Arg Asp Gln Asn Leu Thr Pro Tyr
            210                 215                 220

Leu Cys Asp Asp Glu Phe Ile Val Ser Val Ala Ser Tyr Glu Cys Phe
225                 230                 235                 240

Ile Met Ile Lys Asp Val Phe Ile Glu Arg Tyr Asn Thr Trp Glu Ile
                245                 250                 255

Cys Ala Arg Ala Trp Leu Glu Asp Ser Asp Gly Ala Asp Tyr Leu Pro
            260                 265                 270

Leu Asp Val Leu Gly Glu Leu Tyr Asn Gln Gly Asp Gln Ile Ile Ala
            275                 280                 285

Met Tyr Leu Glu Asp Gly Phe Lys Leu Ile Lys His Leu Glu Pro Leu
            290                 295                 300

Cys Val Ser Cys Ile Gln Thr His Gly Ile Phe Thr Pro Gly Lys Tyr
305                 310                 315                 320

Trp Phe Gln Ser Gln Arg Ile Glu Ser Tyr Tyr Glu Glu Leu Cys Ser
                325                 330                 335

Leu Asn Trp Lys Phe Lys Ile Ser Gly Asn Lys Ala Glu Cys Ala Gln
            340                 345                 350

Asn Phe Ile Lys Thr Ile Ile Gln Gly Lys Leu Thr Pro Gln Gln Tyr
            355                 360                 365

Cys Glu Leu Phe Ser Leu Gln Lys His Trp Gly His Pro Val Leu Tyr
            370                 375                 380

Ile Asp Val Ala Leu Asp Lys Val Lys Lys His Ala Gln Ser Val Lys
385                 390                 395                 400

Ile Leu Lys Pro Lys Val Met Phe Glu Thr Phe Cys Val Phe Lys Phe
                405                 410                 415

Ile Val Ala Lys Asn His Tyr His Ser Gln Gly Ser Trp Tyr Lys Thr
            420                 425                 430

Thr Met Asp Leu His Leu Thr Pro Tyr Leu Arg Gln His Ile Val Ser
            435                 440                 445

Asn Ser Phe Pro Ser Gln Ala Glu Ile Tyr Gln His Leu Trp Glu Trp
            450                 455                 460

Tyr Phe Val Glu His Glu Pro Leu Phe Ser Thr Lys Ile Ile Ser Asp
465                 470                 475                 480

Leu Ser Ile Phe Ile Lys Asp Arg Ala Thr Ala Val Asn Gln Glu Cys
                485                 490                 495

Trp Asp Ser Val Phe Asp Arg Ser Val Leu Gly Tyr Asn Pro Pro Val
            500                 505                 510
```

```
Arg Phe Gln Ser Lys Arg Val Pro Glu Gln Phe Leu Gly Gln Ala Asp
            515                 520                 525

Phe Ser Leu Asn Gln Ile Leu Asp Phe Ala Glu Lys Leu Glu Tyr Leu
            530                 535                 540

Ala Pro Ser Tyr Arg Asn Phe Ser Phe Ser Leu Lys Glu Lys Glu Leu
545                 550                 555                 560

Asn Ile Gly Arg Thr Phe Gly Lys Leu Pro Tyr Arg Val Arg Asn Val
            565                 570                 575

Gln Thr Leu Ala Glu Ala Leu Leu Ala Asp Gly Leu Ala Lys Ala Phe
            580                 585                 590

Pro Ser Asn Met Met Val Val Thr Glu Arg Glu Gln Lys Glu Ala Leu
            595                 600                 605

Leu His Gln Ala Ser Trp His His Asn Ser Ala Ser Ile Gly Glu Asn
            610                 615                 620

Ala Ile Val Arg Gly Ala Ser Phe Val Thr Asp Leu Glu Lys Tyr Asn
625                 630                 635                 640

Leu Ala Phe Arg Tyr Glu Phe Thr Arg His Phe Ile Asp Tyr Cys Asn
            645                 650                 655

Arg Cys Tyr Gly Val Lys Asn Leu Phe Asp Trp Met His Phe Leu Ile
            660                 665                 670

Pro Leu Cys Tyr Met His Val Ser Asp Phe Tyr Ser Pro Pro His Cys
            675                 680                 685

Val Thr Glu Asp Asn Arg Asn Asn Pro Pro Asp Cys Ala Asn Ala Tyr
            690                 695                 700

His Tyr His Leu Gly Gly Ile Glu Gly Leu Gln Gln Lys Leu Trp Thr
705                 710                 715                 720

Cys Ile Ser Cys Ala Gln Ile Thr Leu Val Glu Leu Lys Thr Lys Leu
            725                 730                 735

Lys Leu Lys Ser Ser Val Met Gly Asp Asn Gln Cys Ile Thr Thr Leu
            740                 745                 750

Ser Leu Phe Pro Ile Asp Ala Pro Asp Asp Tyr Gln Glu Asn Glu Ala
            755                 760                 765

Glu Leu Asn Ala Ala Arg Val Ala Val Glu Leu Ala Ile Thr Thr Gly
            770                 775                 780

Tyr Asp Gly Ile Phe Leu Lys Pro Glu Glu Thr Phe Val His Ser Gly
785                 790                 795                 800

Phe Ile Tyr Phe Gly Lys Lys Gln Tyr Leu Asn Gly Val Gln Leu Pro
            805                 810                 815

Gln Ser Leu Lys Thr Met Ala Arg Cys Gly Pro Leu Ser Asp Ser Ile
            820                 825                 830

Phe Asp Asp Leu Gln Gly Ser Leu Ala Ser Ile Gly Thr Ser Phe Glu
            835                 840                 845

Arg Gly Thr Ser Glu Thr Arg His Ile Phe Pro Ser Arg Trp Ile Ala
850                 855                 860

Ser Phe His Ser Met Leu Ala Ile Asn Leu Leu Asn Gln Asn His Leu
865                 870                 875                 880

Gly Phe Pro Leu Gly Phe Ser Ile Asp Ile Ser Cys Phe Lys Lys Pro
            885                 890                 895

Leu Thr Phe Ser Glu Lys Leu Ile Ala Leu Ile Thr Pro Gln Val Leu
            900                 905                 910

Gly Gly Leu Ser Phe Leu Asn Pro Glu Lys Leu Phe Tyr Arg Asn Ile
            915                 920                 925
```

```
Ser Asp Pro Leu Thr Ser Gly Leu Phe Gln Leu Lys Asn Ala Leu Glu
    930                 935                 940

Phe Leu Glu Lys Glu Glu Leu Phe Tyr Ile Leu Ile Ala Lys Lys Pro
945                 950                 955                 960

Gly Leu Ala Asp Ala Ser Asp Phe Val Met Asn Pro Leu Gly Leu Asn
                965                 970                 975

Val Pro Gly Ser Arg Glu Ile Ile Thr Phe Leu Arg Gln Thr Val Arg
            980                 985                 990

Glu Asn Ile Thr Ile Thr Ser Gln Asn Arg Ile Ile Asn Ser Leu Phe
        995                 1000                1005

His Ile Gly Ser Asp Leu Glu Asp Gln Arg Val Cys Glu Trp Leu Leu
    1010                1015                1020

Ser Ser Asn Pro Val Met Ser Arg Phe Ala Ala Asp Ile Phe Ser Arg
1025                1030                1035                1040

Thr Pro Ser Gly Lys Arg Leu Gln Val Leu Gly Tyr Leu Glu Gly Thr
                1045                1050                1055

Arg Thr Leu Leu Ala Ser Arg Thr Ile Ser Leu Thr Thr Glu Gly Thr
            1060                1065                1070

Met Leu Met Lys Leu Arg Glu Leu Thr Arg Asn Arg Trp Lys Ser Trp
        1075                1080                1085

Phe Ser Tyr Ile Asp Ala Leu Asp Asp Leu Ser Glu Ser Leu Glu
    1090                1095                1100

Lys Phe Thr Cys Thr Val Asp Ile Ala Asn Phe Leu Arg Ala Tyr Ser
1105                1110                1115                1120

Trp Leu Asp Val Leu Lys Gly Lys Arg Leu Ile Gly Ala Thr Leu Pro
                1125                1130                1135

Cys Leu Leu Glu Gln Phe Lys Val Lys Trp Ile Asn Leu Ser Glu Asp
            1140                1145                1150

Leu Arg Glu Gln Phe Asn Met Ser Ser Glu Ser Glu Ser Thr Ile Asn
        1155                1160                1165

Leu Leu Pro Tyr Asp Cys Lys Glu Leu Arg Leu Gly Arg Ser Asn Asp
    1170                1175                1180

Thr Glu Leu Asn Tyr Val Ser Cys Ala Leu Asp Arg Lys Val Val Gln
1185                1190                1195                1200

Lys His Pro Ser Val Asn Arg Leu Ala Trp Thr Ile Gly Asn Arg Ala
                1205                1210                1215

Pro Tyr Ile Gly Ser Arg Thr Glu Asp Lys Ile Gly Tyr Pro Pro Leu
            1220                1225                1230

Arg Val Asn Cys Pro Ser Ala Ala Leu Lys Glu Ala Ile Glu Met Val
        1235                1240                1245

Ser Arg Leu Leu Trp Val Thr Gln Gly Thr Ala Asp Arg Glu Lys Leu
    1250                1255                1260

Leu Ile Pro Leu Leu Asn Ser Arg Val Asn Leu Asp Tyr Gln Thr Val
1265                1270                1275                1280

Leu Asn Phe Leu Pro Thr His Tyr Ser Gly Asn Ile Val His Arg Tyr
                1285                1290                1295

Asn Asp Gln Tyr Gly Gln His Ser Phe Met Ala Asn Arg Met Ser Asn
            1300                1305                1310

Thr Ser Thr Arg Ala Ile Ile Ser Thr Asn Thr Leu Gly Lys Tyr Ala
        1315                1320                1325

Gly Gly Gly Gln Ala Ala Val Asp Ser Asn Ile Ile Phe Gln Asn Thr
    1330                1335                1340

Ile Asn Leu Gly Val Ala Val Leu Asp Ile Ala Leu Ser Leu Ala Lys
```

```
                1345                1350                1355                1360
Leu Ser Ser Ala Ser Asn Val Thr Phe Arg Leu Met Leu Asn Lys Cys
                    1365                1370                1375
Cys Thr Arg His Val Pro Ser Glu Tyr Leu Phe Phe Asp Lys Pro Leu
                    1380                1385                1390
Asp Val Asp Leu Asn Lys Tyr Met Asp Asn Glu Leu Val Tyr Asp Asn
                    1395                1400                1405
Asp Pro Leu Cys Ser Gly Ile Lys Gly Arg Leu Gly Arg Val Ser Arg
        1410                1415                1420
Ser Thr Leu Ser Leu Ser Leu Asn Val Ser Asp Ile Gly Ser Tyr Asp
1425                1430                1435                1440
Phe Pro Thr Ile Ala Ala Trp Thr Leu Gly Glu Thr Ile Val Gly Ser
                    1445                1450                1455
Ile Phe Ser Asp Glu Ser Ser Gln Ser Thr Asp Pro Ile Ser Ser Gly
                    1460                1465                1470
Cys Thr Lys Thr Phe Val Thr His Phe Leu Val Tyr Pro Val Glu Ser
                    1475                1480                1485
Ile Phe Tyr Ala Phe Gly Ala Asn Leu Ile Val Glu Ser Leu Ser Leu
            1490                1495                1500
Ser Arg Ile Lys Ser Ile Lys Asn Leu Ser Asp Leu Thr Phe Leu Ile
1505                1510                1515                1520
Ser Ser Thr Ile Arg Asn Leu Ser His Arg Ser Leu Arg Ile Leu Gln
                    1525                1530                1535
Ser Thr Phe Arg His Glu Leu Val Leu Thr Arg Leu Ala His His Ile
                    1540                1545                1550
Pro Leu Ile Ser Leu Met Leu Gly Gly Ser Ala Gly Glu Lys Ser Ser
            1555                1560                1565
Ser Asp Ala Val Arg Leu Phe Leu Thr Ala Ser Tyr Gln Asn Phe Ile
        1570                1575                1580
Asn Asn Phe Ser Cys Leu Met Lys Lys Gly Gln Ser Ser Leu Pro Val
1585                1590                1595                1600
Trp Leu Tyr Phe Pro Ser Glu Gly Gln Gln Leu Lys Pro Ile Leu Lys
                    1605                1610                1615
Ile Leu Gln Arg Leu Ser Asp Leu Leu Ser Pro Asp Lys Val Gln Lys
                    1620                1625                1630
His Gln Ile Leu Ala Asp Thr Cys Cys Pro Ile Asp Ser Phe Trp Val
            1635                1640                1645
Tyr Pro Ser Lys Ser Thr Arg Thr Asn His Tyr Tyr Ala Ser Leu Asn
        1650                1655                1660
Tyr Trp Arg Asp Lys Ala Asn Lys Val Lys Asn Thr Pro Phe Ser His
1665                1670                1675                1680
Leu Ile Asn Cys Ser Phe Leu Glu Leu Ser Ser His Thr Ser Ser Val
                    1685                1690                1695
Ser Ser Asn Gln Gln Val Thr Asn Ser Lys Tyr Ile Val His Pro Glu
                    1700                1705                1710
Asn Ile Pro Glu Ile Asn Ala Arg Thr Lys Leu Ile Asp Tyr Gly Ser
            1715                1720                1725
Thr Ala Leu Gln Gly Met Asp Ile Lys Met Pro Leu Ser Glu Gln Asn
        1730                1735                1740
Leu Val Gly Asn Cys Arg Pro Ser Lys Gly Ile Arg Phe Lys Asp Asn
1745                1750                1755                1760
Pro Lys Thr Thr Lys His Asp Gln Gly Phe Val Gly Lys Asp Ser Ser
                    1765                1770                1775
```

```
Pro Arg Pro Met Ser Pro Glu Asp Asn Met Gln Thr Pro Ala Tyr Ile
            1780                1785                1790

His Ser Ser Pro Pro Tyr Gln Thr Leu Thr Lys Ser Pro Asp Val His
            1795                1800                1805

Glu Asp Phe Asp Ala Ser Lys Val Ile Leu Asn Ser Glu Ile Asn Asn
            1810                1815                1820

Leu Asn Leu Thr Asp Cys Thr Leu Asn Thr Lys Ser Leu Thr Thr Pro
1825                1830                1835                1840

Thr Gly Thr Glu Ile Leu Gly Ile Ser Pro Phe Arg Ser Ser Arg Tyr
            1845                1850                1855

Ser Ser Thr Ser Arg Glu Arg Ser Arg Leu Ser Arg Glu Gln Ala Ser
            1860                1865                1870

Tyr Leu Tyr Val Asp Cys Ser Asn Ile Pro Ser Ile Ser Leu Asp Pro
            1875                1880                1885

Gly Phe Gln Asn Met Ser Asp Gln Asn Gln Val Gln Met Leu Ile Asn
            1890                1895                1900

Thr Tyr Lys Arg Asp Leu His Ala Cys Phe Asp Ser Asn Gln Phe Cys
1905                1910                1915                1920

Arg Phe Thr Gly Val Val Ser Ser Met His Tyr Lys Leu Tyr Asp Leu
            1925                1930                1935

Leu Pro Pro Gly Glu Leu Arg Lys Ala Ile Cys Leu Ala Glu Gly Glu
            1940                1945                1950

Gly Ser Gly Ala Arg Leu Leu Leu Lys Trp Lys Lys Thr Asp Tyr Leu
            1955                1960                1965

Phe Phe Asn Thr Leu Ala Thr Asp Ser Gln Gln Glu Ala Glu Ile Leu
            1970                1975                1980

Ser Gly Arg Val Ile Pro Arg Met Leu Tyr Asn Ile Asp Arg Leu Asn
1985                1990                1995                2000

Ala Leu Leu Glu Ser Arg Arg Leu Ile Leu Asn Asn Leu Thr Ile Gln
            2005                2010                2015

Ile Thr Asp Ile Thr Ser Pro Leu Trp Leu Asp Ser Val Ile Gln Tyr
            2020                2025                2030

Leu Pro Glu Asp Ser Asp Ile Leu Thr Met Asp Ala Glu Thr Thr Lys
            2035                2040                2045

Asp Glu Thr Arg Glu Gln Leu Tyr Lys Thr Ile Val Asn Ile Trp Thr
            2050                2055                2060

Arg Thr Ser Pro Asn Ile Pro Lys Ile Ser Ile Ile Lys Val Phe Leu
2065                2070                2075                2080

Leu Asp Tyr Glu Gly Thr Leu Phe Leu Met Arg Asn Ala Ile Gln Tyr
            2085                2090                2095

Tyr Gly Gln Val Gln Leu Lys Lys Pro Tyr Ser Ser Asn Ala Lys Asn
            2100                2105                2110

Ser Glu Trp Tyr Leu Cys Cys Gly Lys Arg Arg Ile Gln Arg Leu Lys
            2115                2120                2125

Ile Asp Phe Ser Asp Gln Val Gly Ile Phe Leu Ile Cys Lys Ala Met
            2130                2135                2140

Ser Arg Gln Arg Gln Ala Ile Pro Tyr Trp Leu Lys His Ile Glu Lys
2145                2150                2155                2160

Asn Tyr Pro Ala Ser Leu His Lys Phe Phe Leu Thr Leu Gly Phe Pro
            2165                2170                2175

Ser Leu Glu Ser Ser Phe Cys His Arg Tyr Thr Ile Pro Phe Ser Glu
            2180                2185                2190
```

```
Gly Lys Ala Leu Phe His Lys Val Gln Ser Tyr Val Arg Gln Gly Lys
        2195                2200                2205

Gln His Leu His Ser Leu Met Leu Asp Tyr Glu Asn Asn Ser Pro Leu
        2210                2215                2220

Leu Asp Leu Arg Asn His Phe Ile Cys Ser Leu Arg Gly Lys Ile Thr
2225                2230                2235                2240

Lys Tyr Tyr Asn Asp Ile Leu Lys Leu Asn Leu Val Ile Lys Ala Val
            2245                2250                2255

Glu Lys Gly Lys Asn Trp Ser Gln Leu Val Glu Thr Leu Pro Asn Met
        2260                2265                2270

His Ser Val Cys Ile Val His Val Asp His Glu Cys Phe Gly Cys Glu
        2275                2280                2285

Lys Arg Leu Leu Leu Lys Leu Asp Phe Ile Arg Asn Thr Lys Ile Ala
        2290                2295                2300

Glu Gln Lys Leu Leu Asn Arg Val Ile Gly Tyr Ile Leu Phe Phe Pro
2305                2310                2315                2320

Phe Gly Leu Phe Lys Ser Glu Ser Leu Thr Ala
            2325                2330

<210> SEQ ID NO 27
<211> LENGTH: 19112
<212> TYPE: DNA
<213> ORGANISM: Marburg virus

<400> SEQUENCE: 27
gacacacaaa aacaagagat gatgattttg tgtatcatat aaataaagaa gaatattaac      60
attgacattg agacttgtca gtctgttaat attcttgaaa agatggattt acatagcttg     120
ttagagttgg gtacaaaacc cactgcccct catgttcgta ataagaaggt gatattattt     180
gacacaaatc atcaggttag tatctgtaat cagataatag atgcaataaa ctcagggatt     240
gatcttggag atcttctaga aggggtttg ctgacgttgt gtgttgaaca ttactataat      300
tccgataaag ataaattcaa cacaagtcct atcgcaaaat acttgcgtga tgcgggctat     360
gagtttgatg tcgtcaagaa tgcagatgca acccgctttc tggatgtgat tcctaacgaa     420
cctcattaca gtcctttaat tttggcccctt aagacattgg aaagtactga atctcagagg     480
gggagaattg gctctttttt gtcatttttgc agtctttttc tcccgaaact tgttgtcgga     540
gatcgggcta gtatcgaaaa ggctttaaga caagtaacag tacatcaaga acaggggatc     600
gtcacatacc ctaatcactg gcttactaca ggccatatga agtaattttt gggattttg      660 aggtctagct ttatcttaaa atttgtgtta attcatcaag gagtaaattt ggtgacaggt     720
catgatgcct atgacagtat cattagtaat tcagtaggtc aaactagatt ctcaggactt     780
cttattgtga aaacagttct tgagttcatc ttgcaaaaaa ctgattcagg ggtgacacta     840 catccttgg tgcggacctc caaagtaaaa aatgaagttg ctagtttcaa gcaggcgttg      900
agcaacctag cccgacatgg agaatacgca ccgttcgcac gggttctgaa tttatcaggg     960
attaacaacc tcgaacatgg actctatcct cagctttcgg cgattgcgct gggtgttgca    1020
acagcacacg gcagtacatt ggctggtgtc aatgttggcg aacagtatca acagctacga    1080
gaggcggcac atgatgcgga aataaaacta caaaggcgac atgaacatca ggaaattcaa    1140
gctattgcag aggatgatga ggagaggaag atattagaac aattccacct tcagaaaact    1200
gaaatcacac acagtcagac actagccgtc tcagccaga aacgagaaaa attagctcgt     1260
cttgctgcag aaattgaaaa caatattgtg gaagatcagg gatttaaaca atcacagaat    1320
```

-continued

```
caggtgtcac agtcgttttt gaatgaccct acacctgtgg aagtaacggt tcaagccagg    1380
cccataaatc gaccaactgc tctgcctccc ccagttgaca acaaaattga gcacgaatct    1440
acagaagata gctcttcttc aagcagcttt gttgatctta atgatccatt tgcgctgctg    1500
aatgaggacg aagacactct tgacgacagt gtcatgatcc cgagcacaac atcgagagaa    1560
tttcaaggga ttccagcacc accaagacaa tctcaggacc tcaacaacag ccaaggaaag    1620
caggaagatg aatcaacaaa tccgattaag aaacagtttc tgagatatca agaactgcct    1680
ccggttcaag aggatgatga atcggaatac acaaccgact ctcaggagag tatcgaccaa    1740
ccaggatctg acaatgaaca aggagttgat cttccacctc ctccattgta cgctcaggaa    1800
aaaaggcaag atccaataca gcacccagca gtaagctctc aggatccctt tggcagtatt    1860
ggtgatgtaa atggtgatat cttagaaccc ataagatcac cttcttcacc atctgctcct    1920
caggaagaca caagggcaag agaagcctat gaattgtcgc ctgatttcac aaattatgag    1980
gacaatcagc agaattggcc acaaagagtg gtgacaaaga agggtaggac tttcctttat    2040
cctaatgatc ttctgcagac aaatcctcca gaatcactta aacagccct cgtagaggaa    2100 taccaaaatc ctgtctcagc taaggagctc aagcagatt ggcccgacat gtcatttgat    2160
gaaaggagac atgttgctat gaacttgtag tccagataac acagcacggt tacctactta    2220
tctactttga tccgattcgt cctcagatca cagtaatcaa atttatttga atattcaaac    2280 tacttttttag gatcctatta cttgttacta ttgtgtgaga acacataagc tatcaaataa    2340
caatcacggg caagaaccgg gcatactatg gtgatgcgag ggcattattc agtgctacaa    2400 attcttttt caattgctat aatgatacaa ctacgaacct ccatacattt gccgcaaatac    2460 tgtaatcaac actgctgtat ctctccttca agccatctga tttaacttaa taaacatgac    2520
ttgattcaga gagtgtgctg aaaatgttat tgattgagct tctcaaatgg tgcactatcc    2580
tactgttttg ctcagcctag tatactgtaa catataagtg gactctccac ttctcttctc    2640
gagtattccc tataagtgat ttacttgata gaatgtcaag tccactggtt tggagtttcc    2700
ttactctaat gattgtaata attaactgtt ggcttagatg ataacagata cgaggttata    2760
taattactca tagtataaag tataattctt gcctctgttt cttctgtttt ctctttcctt    2820
tgtaatatgc caattaagaa aaactaaaaa tcgaagaata ttaaaggttt tctttaatat    2880
tcagaaaagg ttttttattc tcttctttct ttttgcaaac atattgaaat aataattttc    2940
acaatgtggg actcatcata tatgcaacaa gtcagtgagg ggttgatgac tggaaaagtt    3000
cccatagatc aagtgtttgg tgccaatccc tcagagaagt tacacaagag aaggaaacca    3060
aaaggcacag ttggactaca atgcagccct tgtctaatgt caaaggcgac aagcactgat    3120
gatattgttt gggaccaact gatcgtgaag aaaacactag ctgatctact tataccgata    3180
aataggcaga tatcggacat tcaaagcact ctaaacgaag taacaacaag agtccatgaa    3240
attgagcggc aattacatga gataaccca gtgttaaaaa tgggaaggac actgaagca    3300 atttccaagg ggatgtcaga aatgttagcc aaatacgacc acctcgtaat ttcaactgga    3360
agaaccactg caccagctgc tgcctttgat gcttacttaa atgagcatgg tgtccctccc    3420
ccccaacctg cgattttcaa agatcttggg gttgctcaac aagcttgtag taagggacc    3480 atggttaaaa atgaaacaac agatgcagcc gacaagatgt cgaaagttct tgaactcagt    3540
gaggagacgt tctccaagcc aaatctttca gctaaggatt tagcccttt gttgtttacc    3600 catctacccg gcaacaacac tccattccat atcctagctc aagtcctttc aaaaattgct    3660
tacaagtcag gaaagtccgg agcattttttg gatgcatttc accagattct aagtgaagga    3720
```

```
gagaatgctc aggcagcatt gactcgacta agcagaacat ttgatgcttt cctcggagta    3780
gttcctccag tgataagagt caaaaacttc caaacagtcc ctcgcccatg tcaaaaaagt    3840
cttcgggctg ttcctcccaa cccaacaatt gacaaaggat gggtctgtgt ttattcatct    3900
gagcaaggtg agacacgggc cctgaaaatc taattctcat tgttaacagt tgcaggggga    3960
gtgatctttc cgagttgata caaagacact aaacatttca aaagcatata tgtgggcaaa    4020
acgtgactag accatcttaa tagaagtagt aatttatttc tgtcttaagt gtgattttca    4080
ccttgaaaga gttaaatggt gatagattaa tccttgaagt aacttttta tatattatag     4140 aggaactaat attactaaca aaaggggtct acctaacagg tatgactgag tgatcagtat    4200
attttataaa ccaagcaatt gacttctcac tttttaagaa tcaactaaca acatagaaaa    4260
catatttatc cttgtgtaat tctcggctta gttggaatta acttttgttg caattcaaga    4320
cgcttattca tagtagatta tatgattttt tataagttta agatatctta aattataccc    4380
acaagagata ctgttttaat taagaaaaac tatgaagaac attaagaaga tctttctctc    4440
gtagtgttct tttactggaa ggagtatccc aatctcagct tgttgaatta attgttactt    4500
aagtcattct tttaaaatt aattcacaca aggtagtttg ggtttatatc tagaacaaat     4560
tttaatatgg ccagttccag caattacaac acatacatgc aatacttgaa ccccccctcct   4620 tatgctgatc acggtgcaaa ccagttgatc ccggcggatc agctatcaaa tcagcagggt    4680
ataactccaa attatgtggg tgacttaaac ctagatgatc agttcaaagg gaatgtctgc    4740
catgctttca ctttagaggc aataattgac atatctgcgt ataatgaacc aacagtcaaa    4800
ggtgttccag catggctgcc tctcgggatt atgagcaatt ttgaatatcc tttagctcat    4860
actgtggctg cgttgctcac aggcagctat acaatcaccc aatttactca taatgggcaa    4920
aaattcgtcc gtgtaaatcg actcggtaca ggaatcccag cacacccact cagaatgttg    4980
cgtgaaggaa atcaagcttt tattcagaat atggtgatcc ccagaaattt ttccactaat    5040
caattcacct acaatctcac taacttagta ttgagtgtgc aaaagcttcc tgatgatgcc    5100
tggcgcccat ccaaggacaa attaattggg aacaccatgc atcccgcagt ctccatacac    5160
ccgaatttgc cacccattgt tctaccaaca gtcaagaagc aggcttatcg tcagcataaa    5220
aatcccaaca atggaccact gctggccata tctggcatcc ttcaccaact gagggtcgag    5280
aaagtcccag agaagacaag cctgtttagg atttcacttc ctgccgatat gttctcagta    5340
aaagaaggta tgatgaagaa aaggggagaa aattccccgg tggtttattt tcaagcacct    5400
gagaacttcc ctttgaatgg cttcaacaac agacaagttg tactagcgta tgcgaatcca    5460
acgctcagtg ccgtttgaaa taatgctcaa atgagacagg agtccatctg cataagaagc    5520
atggcctaaa tgggtgtctg ttaagttctc acaagattag tttgtattga tttcaataat    5580
gctttaacct tacattgctg ctttaaatgg ttaattaagc tgatcagctt gcaagatgta    5640
atctcttttg ggtcatcaga tctataatgg gtttactaga ttatataaaa gaaatagtaa    5700
tgttttataa acaattcttg cttagtttta ctttgattta ctaacatata tcattgtgcc    5760
cttcattgct aagtaaactc aactgatgat gatattcctt ctgaaatagt aagaaaaact    5820
aatgaagaac attaattgcc gggtaagagt gattaagttc tttaaatttg accaaagtaa    5880
tgttttgtta gtgaatacat tcttatattg cttgattaaa aacaagaaat tatcctaaca    5940
tgaagaccac atgtctcttt atcagtctta tcttaatcca agggataaaa actctcccta    6000
ttttagagat agctagtaac aatcaacccc aaaatgtgga ttcggtatgc tccggaactc    6060
```

```
tccagaagac agaagatgtc catctgatgg gattcacact gagtgggcaa aaagttgctg    6120
attccccttt ggaggcatcc aagcgatggg ctttcaggac aggtgtacct cccaagaatg    6180
ttgagtatac agaaggggag gaagccaaaa catgctacaa tataagtgta acggatccct    6240
ctggaaaatc cttgctgttg gatcctccta ccaacatccg tgactatcct aaatgcaaaa    6300
ctatccatca tattcaaggt caaaaccctc atgcgcaagg gatcgccctc catttgtggg    6360
gagcattttt cctgtatgat cgcattgcct ccacaacaat gtaccgaggc agagtcttca    6420
ctgaagggaa catagcagct atgattgtca ataagacagt gcacaaaatg attttctcga    6480
ggcaaggaca ggggtaccgt cacatgaatc tgacttctac taataaaatat tggacaagta    6540
acaatggaac acaaacgaat gacactggat gcttcggtgc tcttcaagaa tacaactcca    6600
cgaagaatca acatgtgct ccgtccaaaa taccctcacc actgcccaca gcccgtccag    6660
agatcaaacc cacaagcacc ccaactgatg ccaccacact caacaccaca gacccaaaca    6720
atgatgatga ggacctcata acatccggtt cagggtccgg agaacaggaa ccctatacaa    6780
cttcagatgc ggtcactaag caagggcttt catcaacaat gccacccact ccctcaccac    6840
aaccaagcac gccacagcaa gaaggaaaca acacagacca ttcccaaggt actgtgactg    6900
aacccaacaa aaccaacaca acggcacaac cgtccatgcc cccccacaac accactgcaa    6960
tctctactaa caaacctcc aagaacaact cagcaccct ctctgtatca ctacaaaaca    7020
ccaccaatta cgacacacag agcacagcca ctgaaaatga acaaaccagt gcccctcga    7080
aaacaaccct gcctccaaca ggaaatctta ccacagcaaa gagcactaac aacacgaaag    7140
gccccaccac aacggcacca aatatgacaa atgggcattt aaccagtccc tcccccaccc    7200
ccaacccgac cacacaacat cttgtatatt tcagaaagaa acgaagtatc ctctggaggg    7260
aaggcgacat gtttcctttt ctggacgggt taataaatgc tccaattgat tttgatccag    7320
ttccaaatac aaagacgatc tttgatgaat cttctagttc tggtgcttcg gctgaggaag    7380
atcaacatgc ctccccaat atcagtttaa ctttatccta ttttcctaat ataaatgaaa    7440
acactgccta ctctggagaa aatgagaacg attgtgatgc agagttaaga atttggagcg    7500
ttcaggagga tgacctggca gcagggctca gttggatacc gttttttggc cctggaatcg    7560
aaggacttta tactgctggt ttaattaaaa accaaaacaa tttggtctgc aggttgaggc    7620
gtctagccaa tcaaactgcc aaatccttgg aactcttatt aagagtcaca accgaggaaa    7680
ggacattttc cttaattaat agacatgcca ttgactttct actcacaagg tggggaggaa    7740
catgcaaagt gcttggacct gattgttgca ttggaataga agacttgtcc aggaatattt    7800
cggaacaaat tgaccaaatc aaaaaagatg aacaaaaaga ggggactggt tggggtctag    7860
gtggtaaatg gtggacatcc gactggggtg ttcttactaa cttgggcatt ttgctactat    7920
tatccatagc tgtcttgatt gctctatcct gtatttgtcg tatctttacc aaatatatcg    7980
ggtaatatta agtgtgtatt gattaaagct ttaggacaat tgctactgag cccttcttct    8040
aatctactga aatcaacttg ggagattttt aagaagctga taatttaatg tgaatcagta    8100
gtttacgtat tgttgattgt tatggtttga tattcaattg ttatcatagt caagagtaac    8160
cttttctatt tgatgcatta atgttttaaa ctacctctta agcttttgtg gatggtttca    8220
atatgtgcgt agaggttaat ttaaagagat ttcttgttgc acagtttttt gtattactta    8280
cttgggcttg aagacatagt taagactggc cgaaaatgct ctccagtcaa ctccattccc    8340
cctcagaaga gacgtgccgt tcaaagagtc ttgatttata actaaccatt gtaagaatta    8400
atttactctt tccgttatac ttatctacat taattccttg aatgtccagc atcattaacg    8460
```

```
acttgtctta attcaatctt ttggatgcaa accataagga aaaatgagcc actttccctc    8520
tactctgaac taaggaaatt tctcttatca gcctaaaatc tgatccgtta ggtcatgggc    8580
ccttcataat ctgtttgagc atgaatgttg atcaaatgac caaataatag tgcatttgta    8640
tagattcaat tatcctttat taagaaaaag atagacagaa cacaagaat tgataaaata    8700 ttactttgat caattttgcg aggaattata aaaatcttga gggacaaatt attgtaacgt    8760
agagtcgaag aacattaagt gttctttgtt agaattattc atccaagttg ttttgagtat    8820
actcgcttca atacaacttc ccttcatatt tgattcaaga tttaaaatgc aacaaccccg    8880
tggaaggagt cgaactcgca accaccaaac cgcatcatct atatatcatg aaactcagtt    8940
gccctccaaa cctcactaca ccaatcatca tccacgtgca agatcgatga gctcaacccg    9000
cagtagtgca gaaagcagtc ccaccaatca tattccccgt gctcgaccac ccccaacatt    9060
caacttatcg aaaccccctc ctcctccaaa agacatgtgt aggaacatga aaattggatt    9120
gccgtgcact gatcccactt gtaatagaga tcatgaccttt gataatctaa caaatcgtga    9180
acttttgcta ttgatggccc gaaaaatgct ccccaataca gacaagactt ttagaagtct    9240
gcaggattgt gggtcaccgt ctcttttctaa agggctctca aaagataaac aggagcaaac    9300
gaaagatgtg ttgaccttgg aaaatctagg acacattctg aactacctcc acagatcaga    9360
tattgggaaa ttggatgaga catcactccg tgcagcatta agtttgacgt gcgctgaat    9420 tcgaaagacg aatagatcct tgatcaacac catgaccgaa ttacacatta accatgaaaa    9480
tctcccgcaa gaccaaaacg gtgttatcaa acagacatat acaggtattc accttgacaa    9540
aggaggtcaa ttcgaagccg ccttatggca aggttgggat aagagatcga tatctttatt    9600
cgtacaagca gctttatatg taatgaacaa tatcccttgt gaatcatcaa ccagtgtgca    9660
agcctcatac gatcatttta ttcttcctca aagtcaaagt aaaggacaat gattattgtt    9720
tgaaagttga caatcaaatc actttcagtt tttagtttca actcttattg cgagacttga    9780
acacaattct actaacttca ataagtgacc ccaaattcaa gtttactgaa gactacgacg    9840
ataataatca ccaattcatt gtaaattact cgattaaaat attcttaagc tatcttaaac    9900
ttgatgatgc agctctgttt cacctttctg ttgatttcaa tgttacagct atatctaagt    9960
gtctaattaa caacttgtac ctctaaggaa aatcatgaag aacattaaga aaaaggatgt    10020 tcttatttt caactaaact tgcatatcct ttgttgatac ccttgagaga caacttttga    10080
cactagatca cggatcaagc atatttcatt caaacacccc aaattttcaa tcatacacat    10140
aataaccatt ttagtagcgt tacctttcaa tacaatctag gtgattgtga aaagacttcc    10200
aaacatggca gaattatcaa cgcgttacaa cttgcctgca aatgttacgg aaaaaagcat    10260
aaatcttgac cttaattcca cagcacgatg gataaaagaa cccagtgttg ggggctggac    10320
agtgaagtgg ggaaactttg ttttccacat accaaatact gggatggcat tgttgcatca    10380
tttaaagtct aacttcgttg ttccagagtg gcaacaaaca aggaatctat tctcccacct    10440
ctttaaaaac ccaaagtcaa caattataga accgttcttg gctttgagga tcttgcttgg    10500
agttgctttg aaggatcaag aattacagca atcattaatt cctggattta gatctattgt    10560
tcatatgctt tcagaatggt tgctcctaga ggtaacgtcg gcaatccata ttagccccaa    10620
tctgttggga atctatttga cctcagacat gtttaagatt ctgatggcag gtgtgaaaaa    10680 tttcttttaat aagatgttca ctcttcatgt tgtaaatgac cacggaaaac ccagcagtat    10740
tgaaataaag ttaactggac aacagatcat tatcactcgt gttaatatgg ggtttctagt    10800
```

```
ggaagtcagg aggattgata ttgaaccttg ttgtggtgag acagtcctct cagaatcagt    10860
tgtttttggg ctagtggctg aggcagttct aagagaacac agtcaaatgg agaagggcca    10920
accccctcgat ctgacacaat acatgaacag caaaattgct atataagtgg cttaaattag   10980
catggatatt catagtttaa ccacataata atgttggagg cacagtacat tatagttaat    11040
tatcctgtat aacaaagaat atacctaccc tgatttatat ttactggtat aaaatagtgg    11100
tatcatctta ttaaatagtt gtcatataac aggctgttcc tataatctga ttgtgagatt    11160
ataaacttgt agaattaccg tggatcacaa ctgttgcata tcttccaaaa tatatctttt    11220
gcaagcgatg tgtgcttgaa tacgtcgata ataacatac taataacgat tgattaagaa      11280
aaaccaatga tggatattaa atatccatca agcaggtgtc gcagaatacc aggggtttca    11340
tatgctgcca tatttactaa atcttacata ggattatatc attctcttcg atacacgtta    11400
tatctttagc aaagtaatga aaatagcctt gtcatgttag acgccagtta ccatcttaa     11460
gtgaatcctt tcttcaatat gcagcatcca actcaatatc ctgatgcaag gttgtcctcc    11520
cctataatcc tagaccagtg tgacttatta gccagaagtt tagggttgta tagtcattat    11580
tcacataatc cgaaattgcg taattgtagg attccacatc atatttaccg tttaaggaat    11640
tcgacagcat taaaaacatt tcttcagaac tgttcaatac tcaccgtccc tttcattca     11700
atctgggatc atattttaac ttccattcaa tatgatgcaa ttaatcatgt tgatgatttt    11760
aaatacctat tgccctctga gctagtcaag tatgcaaatt gggacaacga gttcttgaag    11820
gcatatctta ataagatctt aggacttgac catgtttttc cagcttctgc aaggtcacaa    11880
tgggaggatt tttctcctaa ggaaaatcct tattattggg ggatgctgtt actcgtgcat    11940
ttatctcaac ttgccaggag gataaaagga caagagggt cattaagaag taactggaag     12000
tttataggaa cagatttaga gctgtttgga atagcagatt ttattatttt taagttcca    12060
gtaaaaacaa taatccgaaa tgctgtaagc ttacaagctt caaaaccagg gttaagagta    12120
tggtaccgtg accaaaaactt gaccccttat ctatgcgatg atgagtttat tgtaagcgtc   12180
gctagttatg aatgttttat catgattaaa gacgtcttca ttgagaggta taacacgtgg    12240
gaaatatgtg cccgcgcctg gctcgaagac agtgatggag ctgattatct ccctcttgat    12300
gtgttaggtg agttatacaa ccagggagat caaattattg ccatgtactt ggaagacggt    12360
ttcaaattga tcaaacactt ggaacccttg tgtgtcagct gtatacaaac acatggcatc    12420
tttacaccag gaaaatactg gttccaatca cagaggattg agtcatatta tgaggagctc    12480
tgtagtctca attggaaatt taaaatttca ggcaataaag ctgagtgtgc tcaaaacttt    12540
attaaaacta taattcaggg gaaattgact cctcaacaat actgtgaatt attctctcta    12600
caaaagcatt ggggtcaccc cgtttttatac attgatgttg cactagataa ggttaaaaaa    12660
catgcgcaat ctgtaaaaat cttaaaacct aaagtcatgt ttgaaacttt tgtgtttttc    12720
aaatttatag tagcaaagaa tcattatcat tctcaaggat catggtataa aaccacaatg    12780
gatttgcatt taactccata tcttagacaa catattgtgt caaattcatt tccgtcacaa    12840
gccgaaattt atcagcatct ttgggagtgg tatttcgtgg agcatgaacc tcttttctca    12900
actaaaataa taagtgattt aagtattttt ataaaagaca gggctactgc tgtgaaccag    12960
gagtgttggg acagtgtttt cgatagaagt gtattagggt ataaccctcc tgttagattt    13020
cagtcaaaga gagtgccaga gcaattttttg ggccaagcag actttccctt gaatcaaata    13080
ttggattttg ctgaaaagtt agaatatttg gctccttctt ataggaattt ttccttctca    13140
ttaaaagaaa aagagttgaa tataggaaga acttttggga aattaccata tcgtgtcaga    13200
```

```
aatgtccaaa cactcgcaga agccttgcta gcagatggac tagcaaaagc attccctagc   13260
aacatgatgg ttgttactga gagggaacag aaagaagcat tattgcatca ggcttcttgg   13320
caccacaatt cagcaagcat aggggaaaac gctatagtaa ggggtgcaag ttttgttact   13380
gatcttgaga aatacaacct tgccttccga tatgaattta cacgacattt catagactac   13440
tgtaatcgat gttatggtgt gaagaattta ttcgattgga tgcactttt aataccacta    13500 tgttatatgc atgtcagtga tttttatagc ccaccacatt gcgtaacaga agataaccga   13560
aataacccac cggattgtgc taatgcttat cattatcact taggggtat agagggactt     13620 caacagaaat tgtggacatg tatatcatgt gcccagatca cccttgtaga gttaaaaact   13680
aaattaaaat taaaatccag tgttatgggt gataatcaat gtataacaac tctaagtctt   13740
tttccaattg atgctcccga cgattatcaa gagaacgaag ctgaattaaa tgcggcacga   13800
gttgctgtcg aattagctat tactacgggt tatgatggta tattttgaa gcctgaagaa    13860 acatttgtcc attcagggtt catttatttt ggtaaaaagc aatacctcaa cggtgttcaa   13920
ctgccacaat cattgaaaac aatggcaaga tgtggaccct tatctgactc tattttgat    13980 gatcttcaag gttccctggc cagtattggt acatcctttg agagaggaac aagtgagaca   14040
cggcacattt ttccgagtcg ttggatagct tcatttcatt caatgttagc aataaattta   14100
ttaaatcaga atcaccttgg gtttccccta gggttcagta ttgatatttc ttgtttcaaa   14160
aagcctctta ccttttcgga aaaattaatt gctcttataa cgccccaagt tctaggaggg    14220
ttatcatttt tgaatccgga gaaattgttc taccggaaca taagtgatcc gctcacttcg   14280
ggtctatttc aacttaagaa tgcattagaa tttcttgaaa aggaagaatt attctatatc   14340
ttgattgcta aaaaacctgg tttagcagat gcctcagatt tcgtcatgaa tccattaggc   14400
ttaaatgtac caggatcaag ggaaataata acgttcctta gacaaacagt tcgtgaaaat   14460
atcacgatca cgtcacaaaa tagaataata aattcccttt tcacatagg ttctgattta    14520 gaggaccaaa gggtgtgtga gtggctttta tcatcaaacc ccgtaatgag tcgatttgct   14580
gctgacatct tttcaagaac gcctagtgga aaacggcttc aggtcttagg ctatctggaa    14640
ggaacaagaa cattactagc ttctcggaca ataagtttaa ctacagaagg gacaatgttg   14700
atgaaattaa gggaattaac aagaaaccga tggaaaagct ggttttctta tattgatgca   14760
ttggacgatg atttatctga gtccttagaa aaattcacat gtactgttga tatagctaat   14820
ttcttgaggg catattcatg gctcgacgtc ttaaaaggga aaaggctaat tggtgccaca   14880
ttgccatgtt tactagagca atttaaggta aagtggatta atttgtctga ggatttaagg   14940
gaacaattta atatgtcttc agaatcagaa tcaactataa atttattgcc gtatgactgc   15000
aaggaactgc gacttggaag aagcaatgac acagagttaa actatgtcag ttgtgctctc   15060
gaccggaaag ttgtccagaa acatccctct gttaatcgtc tggcttggac aataggaaat   15120
cgagcaccgt ataggatc acggacagaa gacaagatcg ttatcctcc cttaagagta     15180 aattgtccat cagcggcact taaagaagcc attgagatgg tttctagatt gttgtgggtg   15240
actcaaggca ctgcagaccg agaaaaattg cttattcctc tcctcaattc gagggtaaat   15300
ctggactatc agacagtgct taactttta cctacacact actcaggcaa catagttcat     15360
agatataatg accaatatgg acaacattcc tttatggcaa acaggatgag taatacatct   15420
acacgtgcaa ttatatcaac taacacactg ggcaaatatg ctgggggggg tcaagctgct   15480
gttgatagta atataatctt ccaaaatact atcaatttag gagtggcagt tttagatatt   15540
```

```
gcattatctc ttgctaaatt gtcgtcagca tcaaatgtca ctttccgttt gatgttaaat   15600
aagtgctgca cgcggcatgt gccatctgaa tacctatttt ttgataaacc tttagatgtg   15660
gatttgaaca agtatatgga caatgagtta gtttatgaca atgaccctct ttgcagtggg   15720
attaaaggga gattaggcag agtatcccga tcaacactct cgttgagttt gaatgtcagt   15780
gacattggtt cttatgactt tccaactatt gctgcatgga cactaggaga aactatagtc   15840
ggaagcattt tttctgatga gtcttctcaa agtacagatc caataagttc aggttgcaca   15900
aaaactttcg tcacacattt ccttgtgtat ccagttgaga gtatttttta tgcattcggg   15960
gctaacttaa tagtagaaag tttaagtcta agtaggatca aatcaattaa gaacctctca   16020
gatttgacat tccttatatc atccacaatc aggaatttat cacatagatc acttcggatt   16080
cttcaatcta ccttccgaca tgaattggta ctcacccgac tagcccacca cataccgtta   16140
atttctttaa tgttaggggg ttctgcagga gagaaaagtt catcagatgc tgttcggcta   16200
tttcttacag caagttacca gaatttcatc aacaacttca gttgtttgat gaaaaagggc   16260
cagtcatcac taccggtttg gctttacttt cctagtgaag ggcaacaatt aaaacctata   16320
ttaaaaatct tacagagatt atcagacttg ttatcacctg acaaagttca aaagcatcaa   16380
atcttagctg cacctgttg tccaattgac agcttttggg tctatccaag caagtccaca   16440
aggactaacc actattatgc aagccttaat tattggagag acaaagctaa taaggtcaag   16500
aatactcctt tttcgcattt gataaattgt tcatttcttg aacttcttc acacaccagt   16560 tcggtctctt ctaatcaaca agtgaccaat tcgaaatata ttgttcatcc agagaatatc   16620
cctgaaataa atgcaagaac caaattaata gattatggat caacagctct acaggggatg   16680
gatatcaaga tgccactctc ggagcaaaat ctggttggaa attgtcgacc atcaaagggc   16740
attagattca aggacaatcc aaaaacaaca aacatgacc agggatttgt ggggaaggac   16800
tcttcaccgc gaccaatgtc ccctgaagac aacatgcaga ctcctgcata catacatagt   16860 tccccccat atcaaaccct tacaaaatca ccagatgtac atgaggactt tgatgcctcg   16920
aaggtaatct taaattctga aataaataac cttaaccta cggattgtac gcttaataca   16980
aagtcattga caactcctac cgggacagaa atcttaggta taagtccgtt cagatcctct   17040
agatattcat caacttccag ggaacggtct cgactatcta gagaacaagc ttcatatttg   17100
tatgttgatt gcagtaatat tccctctatc tctctagacc cgggttttca gaatatgtct   17160
gatcagaatc aagttcaaat gttaatcaat acctacaaac gtgatttaca tgcttgtttt   17220
gatagcaatc aattctgtcg gtttacaggg gtagtctcat caatgcatta caagctttat   17280
gatctcttgc ctccaggtga attgagaaag gcaatttgct tggccgaagg agaaggaagt   17340
ggtgctcggt tactttttgaa gtggaagaag acgattatt tattttttcaa cactttggct   17400 acggattcac agcaagaagc agagatttta agtggccggg taataccgag aatgttatat   17460
aacatagata ggttaaatgc tttgcttgaa tcaagaagat taatattgaa caacctaact   17520
atccaaatta cagatattac aagtccacta tggctagatt ctgtaataca atacttacct   17580
gaagatagcg acattcttac aatggacgca gagaccacta agatgaaac aagggaacag   17640 ctttataaga ctattgtgaa tatttggaca cgtacttctc ctaatattcc aaaaattagc   17700
atcatcaagg tatttttatt agactatgaa gggactttgt tcttaatgag gaatgccatt   17760
cagtattatg gcaggttca actcaagaaa ccatatagct caaatgcaaa aaactcagaa   17820
tggtacttgt gttgcggtaa acgaagaatt caacgactca aaattgattt ctcagaccag   17880
gtaggaattt ttctgatttg taaagcaatg tcgcgccaaa gacaagcaat tccttactgg   17940
```

```
ttaaaacata tagaaaagaa ttatcctgct tcattacata agttttcct aactttgggt    18000
ttcccttctt tagagtcatc tttctgccat cgttatacta ttccattcag tgaaggaaag    18060
gctctttttc ataaggtcca atcttatgtt cgtcaaggca aacaacattt acattctctt    18120
atgttggatt atgaaaacaa ttcacctcta ctagacttga gaaatcactt tatttgctca    18180
ttgagggaa agataactaa gtattacaat gatatattaa agttaaatct agttatcaag     18240
gcagtagaga aaggtaaaaa ttggtcacaa cttgttgaga cccttcctaa tatgcattca    18300
gtctgcatag tacacgtgga tcatgagtgc tttggatgtg agaacggtt actactcaaa     18360
ttggatttta ttagaaacac aaagatcgca gaacaaaaat tacttaatag agtaatcggg    18420
tatatttat tctttccgtt cggtctgttt aaatctgaat cattaacagc ataactttaa    18480
caaagagaac ttcatttaat tcacgaaaat aatctattta aaaatgaggg ttacattttc    18540
tagagtattg tatgagaaat aataaaataa acaagaagaa gaaaaaacta ttagacagct    18600
tgctttacac aagataatct tatatcgtct caaaccgtac acaagtaggg aaatcacgcg    18660
cacaaattaa cttgtgattg aacgttcggt cacaccagtg gtaactttc aatgttagtt     18720
actcaaatat tattgctcat aattggtatt gatattggta cattgggtga gtccttgagc    18780
tttatcctta atataatgta agaaattagg gaaatactga gatatactag ttgaattgag    18840
ttatgacata ccatatatca taaatataaa agaacgatct gctgtaatct ataagcatct    18900
cttttacata cattggggaa agaactaggt tatcgttgag attaaaaaga ctacgttacg    18960
ttttctctga tgacaagtga caaaatttcg tagttaaatt tctagaatgt caatgtgaat    19020
gtaaattaag aaaaaccaat atataaaatt aaaaaattaa aaactttga tataagtaac     19080
acaaaacatt cttcatcttt tttgtgtgtc ca                                  19112
```

<210> SEQ ID NO 28
<211> LENGTH: 739
<212> TYPE: PRT
<213> ORGANISM: Zaire Ebola virus strain Mayinga

<400> SEQUENCE: 28

```
Met Asp Ser Arg Pro Gln Lys Ile Trp Met Ala Pro Ser Leu Thr Glu
 1               5                  10                  15

Ser Asp Met Asp Tyr His Lys Ile Leu Thr Ala Gly Leu Ser Val Gln
             20                  25                  30

Gln Gly Ile Val Arg Gln Arg Val Ile Pro Val Tyr Gln Val Asn Asn
         35                  40                  45

Leu Glu Glu Ile Cys Gln Leu Ile Ile Gln Ala Phe Glu Ala Gly Val
     50                  55                  60

Asp Phe Gln Glu Ser Ala Asp Ser Phe Leu Leu Met Leu Cys Leu His
 65                  70                  75                  80

His Ala Tyr Gln Gly Asp Tyr Lys Leu Phe Leu Glu Ser Gly Ala Val
                 85                  90                  95

Lys Tyr Leu Glu Gly His Gly Phe Arg Phe Glu Val Lys Lys Arg Asp
            100                 105                 110

Gly Val Lys Arg Leu Glu Glu Leu Leu Pro Ala Val Ser Ser Gly Lys
        115                 120                 125

Asn Ile Lys Arg Thr Leu Ala Ala Met Pro Glu Glu Thr Thr Glu
    130                 135                 140

Ala Asn Ala Gly Gln Phe Leu Ser Phe Ala Ser Leu Phe Leu Pro Lys
145                 150                 155                 160
```

```
Leu Val Val Gly Glu Lys Ala Cys Leu Glu Lys Val Gln Arg Gln Ile
            165                 170                 175
Gln Val His Ala Glu Gln Gly Leu Ile Gln Tyr Pro Thr Ala Trp Gln
            180                 185                 190
Ser Val Gly His Met Met Val Ile Phe Arg Leu Met Arg Thr Asn Phe
            195                 200                 205
Leu Ile Lys Phe Leu Leu Ile His Gln Gly Met His Met Val Ala Gly
            210                 215                 220
His Asp Ala Asn Asp Ala Val Ile Ser Asn Ser Val Ala Gln Ala Arg
225                 230                 235                 240
Phe Ser Gly Leu Leu Ile Val Lys Thr Val Leu Asp His Ile Leu Gln
            245                 250                 255
Lys Thr Glu Arg Gly Val Arg Leu His Pro Leu Ala Arg Thr Ala Lys
            260                 265                 270
Val Lys Asn Glu Val Asn Ser Phe Lys Ala Ala Leu Ser Ser Leu Ala
            275                 280                 285
Lys His Gly Glu Tyr Ala Pro Phe Ala Arg Leu Leu Asn Leu Ser Gly
            290                 295                 300
Val Asn Asn Leu Glu His Gly Leu Phe Pro Gln Leu Ser Ala Ile Ala
305                 310                 315                 320
Leu Gly Val Ala Thr Ala His Gly Ser Thr Leu Ala Gly Val Asn Val
            325                 330                 335
Gly Glu Gln Tyr Gln Gln Leu Arg Glu Ala Ala Thr Glu Ala Glu Lys
            340                 345                 350
Gln Leu Gln Gln Tyr Ala Glu Ser Arg Glu Leu Asp His Leu Gly Leu
            355                 360                 365
Asp Asp Gln Glu Lys Lys Ile Leu Met Asn Phe His Gln Lys Lys Asn
            370                 375                 380
Glu Ile Ser Phe Gln Gln Thr Asn Ala Met Val Thr Leu Arg Lys Glu
385                 390                 395                 400
Arg Leu Ala Lys Leu Thr Glu Ala Ile Thr Ala Ala Ser Leu Pro Lys
            405                 410                 415
Thr Ser Gly His Tyr Asp Asp Asp Asp Ile Pro Phe Pro Gly Pro
            420                 425                 430
Ile Asn Asp Asp Asp Asn Pro Gly His Gln Asp Asp Pro Thr Asp
            435                 440                 445
Ser Gln Asp Thr Thr Ile Pro Asp Val Val Val Asp Pro Asp Asp Gly
450                 455                 460
Ser Tyr Gly Glu Tyr Gln Ser Tyr Ser Glu Asn Gly Met Asn Ala Pro
465                 470                 475                 480
Asp Asp Leu Val Leu Phe Asp Leu Asp Glu Asp Glu Asp Thr Lys
            485                 490                 495
Pro Val Pro Asn Arg Ser Thr Lys Gly Gly Gln Gln Lys Asn Ser Gln
            500                 505                 510
Lys Gly Gln His Ile Glu Gly Arg Gln Thr Gln Ser Arg Pro Ile Gln
            515                 520                 525
Asn Val Pro Gly Pro His Arg Thr Ile His His Ala Ser Ala Pro Leu
            530                 535                 540
Thr Asp Asn Asp Arg Arg Asn Glu Pro Ser Gly Ser Thr Ser Pro Arg
545                 550                 555                 560
Met Leu Thr Pro Ile Asn Glu Glu Ala Asp Pro Leu Asp Asp Ala Asp
            565                 570                 575
Asp Glu Thr Ser Ser Leu Pro Pro Leu Glu Ser Asp Asp Glu Glu Gln
```

```
                580             585             590
Asp Arg Asp Gly Thr Ser Asn Arg Thr Pro Thr Val Ala Pro Pro Ala
            595                 600             605
Pro Val Tyr Arg Asp His Ser Glu Lys Lys Glu Leu Pro Gln Asp Glu
            610                 615             620
Gln Gln Asp Gln Asp His Thr Gln Glu Ala Arg Asn Gln Asp Ser Asp
625                 630                 635                 640
Asn Thr Gln Ser Glu His Ser Phe Glu Glu Met Tyr Arg His Ile Leu
                645                 650                 655
Arg Ser Gln Gly Pro Phe Asp Ala Val Leu Tyr Tyr His Met Met Lys
            660                 665                 670
Asp Glu Pro Val Val Phe Ser Thr Ser Asp Gly Lys Glu Tyr Thr Tyr
            675                 680                 685
Pro Asp Ser Leu Glu Glu Glu Tyr Pro Pro Trp Leu Thr Glu Lys Glu
            690                 695                 700
Ala Met Asn Glu Glu Asn Arg Phe Val Thr Leu Asp Gly Gln Gln Phe
705                 710                 715                 720
Tyr Trp Pro Val Met Asn His Lys Asn Lys Phe Met Ala Ile Leu Gln
                725                 730                 735
His His Gln

<210> SEQ ID NO 29
<211> LENGTH: 340
<212> TYPE: PRT
<213> ORGANISM: Zaire Ebola virus strain Mayinga

<400> SEQUENCE: 29

Met Thr Thr Arg Thr Lys Gly Arg Gly His Thr Ala Ala Thr Thr Gln
1               5                   10                  15
Asn Asp Arg Met Pro Gly Pro Glu Leu Ser Gly Trp Ile Ser Glu Gln
                20                  25                  30
Leu Met Thr Gly Arg Ile Pro Val Ser Asp Ile Phe Cys Asp Ile Glu
            35                  40                  45
Asn Asn Pro Gly Leu Cys Tyr Ala Ser Gln Met Gln Gln Thr Lys Pro
50                  55                  60
Asn Pro Lys Thr Arg Asn Ser Gln Thr Gln Thr Asp Pro Ile Cys Asn
65                  70                  75                  80
His Ser Phe Glu Glu Val Val Gln Thr Leu Ala Ser Leu Ala Thr Val
                85                  90                  95
Val Gln Gln Gln Thr Ile Ala Ser Glu Ser Leu Glu Gln Arg Ile Thr
            100                 105                 110
Ser Leu Glu Asn Gly Leu Lys Pro Val Tyr Asp Met Ala Lys Thr Ile
            115                 120                 125
Ser Ser Leu Asn Arg Val Cys Ala Glu Met Val Ala Lys Tyr Asp Leu
130                 135                 140
Leu Val Met Thr Thr Gly Arg Ala Thr Ala Ala Ala Thr Glu
145                 150                 155                 160
Ala Tyr Trp Ala Glu His Gly Gln Pro Pro Pro Gly Pro Ser Leu Tyr
                165                 170                 175
Glu Glu Ser Ala Ile Arg Gly Lys Ile Glu Ser Arg Asp Glu Thr Val
            180                 185                 190
Pro Gln Ser Val Arg Glu Ala Phe Asn Asn Leu Asn Ser Thr Thr Ser
            195                 200                 205
Leu Thr Glu Glu Asn Phe Gly Lys Pro Asp Ile Ser Ala Lys Asp Leu
```

```
              210                 215                 220
Arg Asn Ile Met Tyr Asp His Leu Pro Gly Phe Gly Thr Ala Phe His
225                 230                 235                 240

Gln Leu Val Gln Val Ile Cys Lys Leu Gly Lys Asp Ser Asn Ser Leu
                245                 250                 255

Asp Ile Ile His Ala Glu Phe Gln Ala Ser Leu Ala Glu Gly Asp Ser
            260                 265                 270

Pro Gln Cys Ala Leu Ile Gln Ile Thr Lys Arg Val Pro Ile Phe Gln
        275                 280                 285

Asp Ala Ala Pro Pro Val Ile His Ile Arg Ser Arg Gly Asp Ile Pro
    290                 295                 300

Arg Ala Cys Gln Lys Ser Leu Arg Pro Val Pro Pro Ser Pro Lys Ile
305                 310                 315                 320

Asp Arg Gly Trp Val Cys Val Phe Gln Leu Gln Asp Gly Lys Thr Leu
                325                 330                 335

Gly Leu Lys Ile
            340

<210> SEQ ID NO 30
<211> LENGTH: 326
<212> TYPE: PRT
<213> ORGANISM: Zaire Ebola virus strain Mayinga

<400> SEQUENCE: 30

Met Arg Arg Val Ile Leu Pro Thr Ala Pro Pro Glu Tyr Met Glu Ala
1               5                   10                  15

Ile Tyr Pro Val Arg Ser Asn Ser Thr Ile Ala Arg Gly Gly Asn Ser
                20                  25                  30

Asn Thr Gly Phe Leu Thr Pro Glu Ser Val Asn Gly Asp Thr Pro Ser
            35                  40                  45

Asn Pro Leu Arg Pro Ile Ala Asp Asp Thr Ile Asp His Ala Ser His
        50                  55                  60

Thr Pro Gly Ser Val Ser Ser Ala Phe Ile Leu Glu Ala Met Val Asn
65                  70                  75                  80

Val Ile Ser Gly Pro Lys Val Leu Met Lys Gln Ile Pro Ile Trp Leu
                85                  90                  95

Pro Leu Gly Val Ala Asp Gln Lys Thr Tyr Ser Phe Asp Ser Thr Thr
            100                 105                 110

Ala Ala Ile Met Leu Ala Ser Tyr Thr Ile Thr His Phe Gly Lys Ala
        115                 120                 125

Thr Asn Pro Leu Val Arg Val Asn Arg Leu Gly Pro Gly Ile Pro Asp
    130                 135                 140

His Pro Leu Arg Leu Leu Arg Ile Gly Asn Gln Ala Phe Leu Gln Glu
145                 150                 155                 160

Phe Val Leu Pro Pro Val Gln Leu Pro Gln Tyr Phe Thr Phe Asp Leu
                165                 170                 175

Thr Ala Leu Lys Leu Ile Thr Gln Pro Leu Pro Ala Ala Thr Trp Thr
            180                 185                 190

Asp Asp Thr Pro Thr Gly Ser Asn Gly Ala Leu Arg Pro Gly Ile Ser
        195                 200                 205

Phe His Pro Lys Leu Arg Pro Ile Leu Leu Pro Asn Lys Ser Gly Lys
    210                 215                 220

Lys Gly Asn Ser Ala Asp Leu Thr Ser Pro Glu Lys Ile Gln Ala Ile
225                 230                 235                 240
```

```
Met Thr Ser Leu Gln Asp Phe Lys Ile Val Pro Ile Asp Pro Thr Lys
                245                 250                 255

Asn Ile Met Gly Ile Glu Val Pro Glu Thr Leu Val His Lys Leu Thr
            260                 265                 270

Gly Lys Lys Val Thr Ser Lys Asn Gly Gln Pro Ile Ile Pro Val Leu
        275                 280                 285

Leu Pro Lys Tyr Ile Gly Leu Asp Pro Val Ala Pro Gly Asp Leu Thr
    290                 295                 300

Met Val Ile Thr Gln Asp Cys Asp Thr Cys His Ser Pro Ala Ser Leu
305                 310                 315                 320

Pro Ala Val Ile Glu Lys
                325

<210> SEQ ID NO 31
<211> LENGTH: 676
<212> TYPE: PRT
<213> ORGANISM: Zaire Ebola virus strain Mayinga

<400> SEQUENCE: 31

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
            35                  40                  45

Asp Lys Leu Val Cys Arg Asp Lys Leu Ser Ser Thr Asn Gln Leu Arg
        50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285
```

```
Ala Phe Trp Glu Thr Lys Lys Asn Leu Thr Arg Lys Ile Arg Ser Glu
290                 295                 300

Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
                340                 345                 350

Val His Ser Gln Gly Arg Glu Ala Ala Val Ser His Leu Thr Thr Leu
                355                 360                 365

Ala Thr Ile Ser Thr Ser Pro Gln Ser Leu Thr Thr Lys Pro Gly Pro
370                 375                 380

Asp Asn Ser Thr His Asn Thr Pro Val Tyr Lys Leu Asp Ile Ser Glu
385                 390                 395                 400

Ala Thr Gln Val Glu Gln His Arg Arg Thr Asp Asn Asp Ser Thr
                405                 410                 415

Ala Ser Asp Thr Pro Ser Ala Thr Thr Ala Ala Gly Pro Pro Lys Ala
                420                 425                 430

Glu Asn Thr Asn Thr Ser Lys Ser Thr Asp Phe Leu Asp Pro Ala Thr
                435                 440                 445

Thr Thr Ser Pro Gln Asn His Ser Glu Thr Ala Gly Asn Asn Asn Thr
450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
                500                 505                 510

Pro Asn Leu His Tyr Trp Thr Thr Gln Asp Glu Gly Ala Ala Ile Gly
                515                 520                 525

Leu Ala Trp Ile Pro Tyr Phe Gly Pro Ala Ala Glu Gly Ile Tyr Ile
530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
                580                 585                 590

Leu Leu Gln Arg Trp Gly Gly Thr Cys His Ile Leu Gly Pro Asp Cys
                595                 600                 605

Cys Ile Glu Pro His Asp Trp Thr Lys Asn Ile Thr Asp Lys Ile Asp
610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
                660                 665                 670

Lys Phe Val Phe
675

<210> SEQ ID NO 32
<211> LENGTH: 364
```

```
<212> TYPE: PRT
<213> ORGANISM: Zaire Ebola virus strain Mayinga

<400> SEQUENCE: 32

Met Gly Val Thr Gly Ile Leu Gln Leu Pro Arg Asp Arg Phe Lys Arg
  1               5                  10                  15

Thr Ser Phe Phe Leu Trp Val Ile Ile Leu Phe Gln Arg Thr Phe Ser
                 20                  25                  30

Ile Pro Leu Gly Val Ile His Asn Ser Thr Leu Gln Val Ser Asp Val
             35                  40                  45

Asp Lys Leu Val Cys Arg Asp Lys Leu Ser Ser Thr Asn Gln Leu Arg
 50                  55                  60

Ser Val Gly Leu Asn Leu Glu Gly Asn Gly Val Ala Thr Asp Val Pro
 65                  70                  75                  80

Ser Ala Thr Lys Arg Trp Gly Phe Arg Ser Gly Val Pro Pro Lys Val
                 85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
            115                 120                 125

Ile Arg Gly Phe Pro Arg Cys Arg Tyr Val His Lys Val Ser Gly Thr
130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
            195                 200                 205

Pro Ser Ser Gly Tyr Tyr Ser Thr Thr Ile Arg Tyr Gln Ala Thr Gly
210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
            275                 280                 285

Ala Phe Trp Glu Thr Lys Lys Thr Ser Leu Glu Lys Phe Ala Val Lys
            290                 295                 300

Ser Cys Leu Ser Gln Leu Tyr Gln Thr Glu Pro Lys Thr Ser Val Val
305                 310                 315                 320

Arg Val Arg Arg Glu Leu Leu Pro Thr Gln Gly Pro Thr Gln Gln Leu
                325                 330                 335

Lys Thr Thr Lys Ser Trp Leu Gln Lys Ile Pro Leu Gln Trp Phe Lys
            340                 345                 350

Cys Thr Val Lys Glu Gly Lys Leu Gln Cys Arg Ile
            355                 360

<210> SEQ ID NO 33
<211> LENGTH: 297
<212> TYPE: PRT
<213> ORGANISM: Zaire Ebola virus strain Mayinga
```

<400> SEQUENCE: 33

```
Met Gly Val Thr Gly Ile Leu Gln Leu Pro Arg Asp Arg Phe Lys Arg
 1               5                  10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
 50                  55                  60

Ser Val Gly Leu Asn Leu Glu Gly Asn Gly Val Ala Thr Asp Val Pro
 65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Pro His
290                 295
```

<210> SEQ ID NO 34
<211> LENGTH: 288
<212> TYPE: PRT
<213> ORGANISM: Zaire Ebola virus strain Mayinga

<400> SEQUENCE: 34

```
Met Glu Ala Ser Tyr Glu Arg Gly Arg Pro Arg Ala Ala Arg Gln His
 1               5                  10                  15

Ser Arg Asp Gly His Asp His His Val Arg Ala Arg Ser Ser Ser Arg
            20                  25                  30

Glu Asn Tyr Arg Gly Glu Tyr Arg Gln Ser Arg Ser Ala Ser Gln Val
        35                  40                  45

Arg Val Pro Thr Val Phe His Lys Lys Arg Val Glu Pro Leu Thr Val
 50                  55                  60
```

Pro Pro Ala Pro Lys Asp Ile Cys Pro Thr Leu Lys Lys Gly Phe Leu
65                  70                  75                  80

Cys Asp Ser Ser Phe Cys Lys Lys Asp His Gln Leu Glu Ser Leu Thr
                85                  90                  95

Asp Arg Glu Leu Leu Leu Leu Ile Ala Arg Lys Thr Cys Gly Ser Val
            100                 105                 110

Glu Gln Gln Leu Asn Ile Thr Ala Pro Lys Asp Ser Arg Leu Ala Asn
        115                 120                 125

Pro Thr Ala Asp Asp Phe Gln Gln Glu Glu Gly Pro Lys Ile Thr Leu
130                 135                 140

Leu Thr Leu Ile Lys Thr Ala Glu His Trp Ala Arg Gln Asp Ile Arg
145                 150                 155                 160

Thr Ile Glu Asp Ser Lys Leu Arg Ala Leu Leu Thr Leu Cys Ala Val
                165                 170                 175

Met Thr Arg Lys Phe Ser Lys Ser Gln Leu Ser Leu Leu Cys Glu Thr
            180                 185                 190

His Leu Arg Arg Glu Gly Leu Gly Gln Asp Gln Ala Glu Pro Val Leu
        195                 200                 205

Glu Val Tyr Gln Arg Leu His Ser Asp Lys Gly Gly Ser Phe Glu Ala
210                 215                 220

Ala Leu Trp Gln Gln Trp Asp Arg Gln Ser Leu Ile Met Phe Ile Thr
225                 230                 235                 240

Ala Phe Leu Asn Ile Ala Leu Gln Leu Pro Cys Glu Ser Ser Ala Val
                245                 250                 255

Val Val Ser Gly Leu Arg Thr Leu Val Pro Gln Ser Asp Asn Glu Glu
            260                 265                 270

Ala Ser Thr Asn Pro Gly Thr Cys Ser Trp Ser Asp Glu Gly Thr Pro
        275                 280                 285

<210> SEQ ID NO 35
<211> LENGTH: 251
<212> TYPE: PRT
<213> ORGANISM: Zaire Ebola virus strain Mayinga

<400> SEQUENCE: 35

Met Ala Lys Ala Thr Gly Arg Tyr Asn Leu Ile Ser Pro Lys Lys Asp
1               5                   10                  15

Leu Glu Lys Gly Val Val Leu Ser Asp Leu Cys Asn Phe Leu Val Ser
            20                  25                  30

Gln Thr Ile Gln Gly Trp Lys Val Tyr Trp Ala Gly Ile Glu Phe Asp
        35                  40                  45

Val Thr His Lys Gly Met Ala Leu Leu His Arg Leu Lys Thr Asn Asp
50                  55                  60

Phe Ala Pro Ala Trp Ser Met Thr Arg Asn Leu Phe Pro His Leu Phe
65                  70                  75                  80

Gln Asn Pro Asn Ser Thr Ile Glu Ser Pro Leu Trp Ala Leu Arg Val
                85                  90                  95

Ile Leu Ala Ala Gly Ile Gln Asp Gln Leu Ile Asp Gln Ser Leu Ile
            100                 105                 110

Glu Pro Leu Ala Gly Ala Leu Gly Leu Ile Ser Asp Trp Leu Leu Thr
        115                 120                 125

Thr Asn Thr Asn His Phe Asn Met Arg Thr Gln Arg Val Lys Glu Gln
130                 135                 140

Leu Ser Leu Lys Met Leu Ser Leu Ile Arg Ser Asn Ile Leu Lys Phe

-continued

```
               145                 150                 155                 160
         Ile Asn Lys Leu Asp Ala Leu His Val Val Asn Tyr Asn Gly Leu Leu
                         165                 170                 175

Ser Ser Ile Glu Ile Gly Thr Gln Asn His Thr Ile Ile Thr Arg
                     180                 185                 190

Thr Asn Met Gly Phe Leu Val Glu Leu Gln Glu Pro Asp Lys Ser Ala
                     195                 200                 205

Met Asn Arg Met Lys Pro Gly Pro Ala Lys Phe Ser Leu Leu His Glu
                     210                 215                 220

Ser Thr Leu Lys Ala Phe Thr Gln Gly Ser Ser Thr Arg Met Gln Ser
         225                 230                 235                 240

Leu Ile Leu Glu Phe Asn Ser Ser Leu Ala Ile
                         245                 250

<210> SEQ ID NO 36
<211> LENGTH: 2212
<212> TYPE: PRT
<213> ORGANISM: Zaire Ebola virus strain Mayinga

<400> SEQUENCE: 36

Met Ala Thr Gln His Thr Gln Tyr Pro Asp Ala Arg Leu Ser Ser Pro
         1               5                   10                  15

Ile Val Leu Asp Gln Cys Asp Leu Val Thr Arg Ala Cys Gly Leu Tyr
                         20                  25                  30

Ser Ser Tyr Ser Leu Asn Pro Gln Leu Arg Asn Cys Lys Leu Pro Lys
                     35                  40                  45

His Ile Tyr Arg Leu Lys Tyr Asp Val Thr Val Thr Lys Phe Leu Ser
                 50                  55                  60

Asp Val Pro Val Ala Thr Leu Pro Ile Asp Phe Ile Val Pro Val Leu
         65                  70                  75                  80

Leu Lys Ala Leu Ser Gly Asn Gly Phe Cys Pro Val Glu Pro Arg Cys
                             85                  90                  95

Gln Gln Phe Leu Asp Glu Ile Ile Lys Tyr Thr Met Gln Asp Ala Leu
                         100                 105                 110

Phe Leu Lys Tyr Tyr Leu Lys Asn Val Gly Ala Gln Glu Asp Cys Val
                     115                 120                 125

Asp Glu His Phe Gln Glu Lys Ile Leu Ser Ser Ile Gln Gly Asn Glu
                     130                 135                 140

Phe Leu His Gln Met Phe Phe Trp Tyr Asp Leu Ala Ile Leu Thr Arg
         145                 150                 155                 160

Arg Gly Arg Leu Asn Arg Gly Asn Ser Arg Ser Thr Trp Phe Val His
                             165                 170                 175

Asp Asp Leu Ile Asp Ile Leu Gly Tyr Gly Asp Tyr Val Phe Trp Lys
                         180                 185                 190

Ile Pro Ile Ser Met Leu Pro Leu Asn Thr Gln Gly Ile Pro His Ala
                     195                 200                 205

Ala Met Asp Trp Tyr Gln Ala Ser Val Phe Lys Glu Ala Val Gln Gly
                     210                 215                 220

His Thr His Ile Val Ser Val Ser Thr Ala Asp Val Leu Ile Met Cys
         225                 230                 235                 240

Lys Asp Leu Ile Thr Cys Arg Phe Asn Thr Thr Leu Ile Ser Lys Ile
                             245                 250                 255

Ala Glu Ile Glu Asp Pro Val Cys Ser Asp Tyr Pro Asn Phe Lys Ile
                         260                 265                 270
```

```
Val Ser Met Leu Tyr Gln Ser Gly Asp Tyr Leu Leu Ser Ile Leu Gly
            275                 280                 285

Ser Asp Gly Tyr Lys Ile Ile Lys Phe Leu Glu Pro Leu Cys Leu Ala
290                 295                 300

Lys Ile Gln Leu Cys Ser Lys Tyr Thr Glu Arg Lys Gly Arg Phe Leu
305                 310                 315                 320

Thr Gln Met His Leu Ala Val Asn His Thr Leu Glu Glu Ile Thr Glu
                325                 330                 335

Met Arg Ala Leu Lys Pro Ser Gln Ala Gln Lys Ile Arg Glu Phe His
            340                 345                 350

Arg Thr Leu Ile Arg Leu Glu Met Thr Pro Gln Gln Leu Cys Glu Leu
        355                 360                 365

Phe Ser Ile Gln Lys His Trp Gly His Pro Val Leu His Ser Glu Thr
370                 375                 380

Ala Ile Gln Lys Val Lys Lys His Ala Thr Val Leu Lys Ala Leu Arg
385                 390                 395                 400

Pro Ile Val Ile Phe Glu Thr Tyr Cys Val Phe Lys Tyr Ser Ile Ala
                405                 410                 415

Lys His Tyr Phe Asp Ser Gln Gly Ser Trp Tyr Ser Val Thr Ser Asp
            420                 425                 430

Arg Asn Leu Thr Pro Gly Leu Asn Ser Tyr Ile Lys Arg Asn Gln Phe
        435                 440                 445

Pro Pro Leu Pro Met Ile Lys Glu Leu Leu Trp Glu Phe Tyr His Leu
450                 455                 460

Asp His Pro Pro Leu Phe Ser Thr Lys Ile Ile Ser Asp Leu Ser Ile
465                 470                 475                 480

Phe Ile Lys Asp Arg Ala Thr Ala Val Glu Arg Thr Cys Trp Asp Ala
                485                 490                 495

Val Phe Glu Pro Asn Val Leu Gly Tyr Asn Pro Pro His Lys Phe Ser
            500                 505                 510

Thr Lys Arg Val Pro Glu Gln Phe Leu Glu Gln Glu Asn Phe Ser Ile
        515                 520                 525

Glu Asn Val Leu Ser Tyr Ala Gln Lys Leu Glu Tyr Leu Leu Pro Gln
530                 535                 540

Tyr Arg Asn Phe Ser Phe Ser Leu Lys Glu Lys Glu Leu Asn Val Gly
545                 550                 555                 560

Arg Thr Phe Gly Lys Leu Pro Tyr Pro Thr Arg Asn Val Gln Thr Leu
                565                 570                 575

Cys Glu Ala Leu Leu Ala Asp Gly Leu Ala Lys Ala Phe Pro Ser Asn
            580                 585                 590

Met Met Val Val Thr Glu Arg Glu Gln Lys Glu Ser Leu Leu His Gln
        595                 600                 605

Ala Ser Trp His His Thr Ser Asp Asp Phe Gly Glu His Ala Thr Val
610                 615                 620

Arg Gly Ser Ser Phe Val Thr Asp Leu Glu Lys Tyr Asn Leu Ala Phe
625                 630                 635                 640

Arg Tyr Glu Phe Thr Ala Pro Phe Ile Glu Tyr Cys Asn Arg Cys Tyr
                645                 650                 655

Gly Val Lys Asn Val Phe Asn Trp Met His Tyr Thr Ile Pro Gln Cys
            660                 665                 670

Tyr Met His Val Ser Asp Tyr Tyr Asn Pro Pro His Asn Leu Thr Leu
        675                 680                 685

Glu Asn Arg Asp Asn Pro Pro Glu Gly Pro Ser Ser Tyr Arg Gly His
```

-continued

```
            690                 695                 700
Met Gly Gly Ile Glu Gly Leu Gln Gln Lys Leu Trp Thr Ser Ile Ser
705                 710                 715                 720

Cys Ala Gln Ile Ser Leu Val Glu Ile Lys Thr Gly Phe Lys Leu Arg
                725                 730                 735

Ser Ala Val Met Gly Asp Asn Gln Cys Ile Thr Val Leu Ser Val Phe
            740                 745                 750

Pro Leu Glu Thr Asp Ala Asp Glu Gln Glu Gln Ser Ala Glu Asp Asn
                755                 760                 765

Ala Ala Arg Val Ala Ala Ser Leu Ala Lys Val Thr Ser Ala Cys Gly
        770                 775                 780

Ile Phe Leu Lys Pro Asp Glu Thr Phe Val His Ser Gly Phe Ile Tyr
785                 790                 795                 800

Phe Gly Lys Lys Gln Tyr Leu Asn Gly Val Gln Leu Pro Gln Ser Leu
                805                 810                 815

Lys Thr Ala Thr Arg Met Ala Pro Leu Ser Asp Ala Ile Phe Asp Asp
            820                 825                 830

Leu Gln Gly Thr Leu Ala Ser Ile Gly Thr Ala Phe Glu Arg Ser Ile
        835                 840                 845

Ser Glu Thr Arg His Ile Phe Pro Cys Arg Ile Thr Ala Ala Phe His
    850                 855                 860

Thr Phe Phe Ser Val Arg Ile Leu Gln Tyr His His Leu Gly Phe Asn
865                 870                 875                 880

Lys Gly Phe Asp Leu Gly Gln Leu Thr Leu Gly Lys Pro Leu Asp Phe
                885                 890                 895

Gly Thr Ile Ser Leu Ala Leu Ala Val Pro Gln Val Leu Gly Gly Leu
            900                 905                 910

Ser Phe Leu Asn Pro Glu Lys Cys Phe Tyr Arg Asn Leu Gly Asp Pro
        915                 920                 925

Val Thr Ser Gly Leu Phe Gln Leu Lys Thr Tyr Leu Arg Met Ile Glu
    930                 935                 940

Met Asp Asp Leu Phe Leu Pro Leu Ile Ala Lys Asn Pro Gly Asn Cys
945                 950                 955                 960

Thr Ala Ile Asp Phe Val Leu Asn Pro Ser Gly Leu Asn Val Pro Gly
                965                 970                 975

Ser Gln Asp Leu Thr Ser Phe Leu Arg Gln Ile Val Arg Thr Ile
            980                 985                 990

Thr Leu Ser Ala Lys Asn Lys Leu Ile Asn Thr Leu Phe His Ala Ser
        995                 1000                1005

Ala Asp Phe Glu Asp Glu Met Val Cys Lys Trp Leu Leu Ser Ser Thr
    1010                1015                1020

Pro Val Met Ser Arg Phe Ala Ala Asp Ile Phe Ser Arg Thr Pro Ser
1025                1030                1035                1040

Gly Lys Arg Leu Gln Ile Leu Gly Tyr Leu Glu Gly Thr Arg Thr Leu
                1045                1050                1055

Leu Ala Ser Lys Ile Ile Asn Asn Asn Thr Glu Thr Pro Val Leu Asp
            1060                1065                1070

Arg Leu Arg Lys Ile Thr Leu Gln Arg Trp Ser Leu Trp Phe Ser Tyr
        1075                1080                1085

Leu Asp His Cys Asp Asn Ile Leu Ala Glu Ala Leu Thr Gln Ile Thr
    1090                1095                1100

Cys Thr Val Asp Leu Ala Gln Ile Leu Arg Glu Tyr Ser Trp Ala His
1105                1110                1115                1120
```

```
Ile Leu Glu Gly Arg Pro Leu Ile Gly Ala Thr Leu Pro Cys Met Ile
            1125                1130                1135

Glu Gln Phe Lys Val Phe Trp Leu Lys Pro Tyr Glu Gln Cys Pro Gln
            1140                1145                1150

Cys Ser Asn Ala Lys Gln Pro Gly Gly Lys Pro Phe Val Ser Val Ala
            1155                1160                1165

Val Lys Lys His Ile Val Ser Ala Trp Pro Asn Ala Ser Arg Ile Ser
            1170                1175                1180

Trp Thr Ile Gly Asp Gly Ile Pro Tyr Ile Gly Ser Arg Thr Glu Asp
1185                1190                1195                1200

Lys Ile Gly Gln Pro Ala Ile Lys Pro Lys Cys Pro Ser Ala Ala Leu
            1205                1210                1215

Arg Glu Ala Ile Glu Leu Ala Ser Arg Leu Thr Trp Val Thr Gln Gly
            1220                1225                1230

Ser Ser Asn Ser Asp Leu Leu Ile Lys Pro Phe Leu Glu Ala Arg Val
            1235                1240                1245

Asn Leu Ser Val Gln Glu Ile Leu Gln Met Thr Pro Ser His Tyr Ser
            1250                1255                1260

Gly Asn Ile Val His Arg Tyr Asn Asp Gln Tyr Ser Pro His Ser Phe
1265                1270                1275                1280

Met Ala Asn Arg Met Ser Asn Ser Ala Thr Arg Leu Ile Val Ser Thr
            1285                1290                1295

Asn Thr Leu Gly Glu Phe Ser Gly Gly Gly Gln Ser Ala Arg Asp Ser
            1300                1305                1310

Asn Ile Ile Phe Gln Asn Val Ile Asn Tyr Ala Val Ala Leu Phe Asp
            1315                1320                1325

Ile Lys Phe Arg Asn Thr Glu Ala Thr Asp Ile Gln Tyr Asn Arg Ala
            1330                1335                1340

His Leu His Leu Thr Lys Cys Cys Thr Arg Glu Val Pro Ala Gln Tyr
1345                1350                1355                1360

Leu Thr Tyr Thr Ser Thr Leu Asp Leu Asp Leu Thr Arg Tyr Arg Glu
            1365                1370                1375

Asn Glu Leu Ile Tyr Asp Ser Asn Pro Leu Lys Gly Gly Leu Asn Cys
            1380                1385                1390

Asn Ile Ser Phe Asp Asn Pro Phe Phe Gln Gly Lys Arg Leu Asn Ile
            1395                1400                1405

Ile Glu Asp Asp Leu Ile Arg Leu Pro His Leu Ser Gly Trp Glu Leu
            1410                1415                1420

Ala Lys Thr Ile Met Gln Ser Ile Ile Ser Asp Ser Asn Asn Ser Ser
1425                1430                1435                1440

Thr Asp Pro Ile Ser Ser Gly Glu Thr Arg Ser Phe Thr Thr His Phe
            1445                1450                1455

Leu Thr Tyr Pro Lys Ile Gly Leu Leu Tyr Ser Phe Gly Ala Phe Val
            1460                1465                1470

Ser Tyr Tyr Leu Gly Asn Thr Ile Leu Arg Thr Lys Lys Leu Thr Leu
            1475                1480                1485

Asp Asn Phe Leu Tyr Tyr Leu Thr Thr Gln Ile His Asn Leu Pro His
            1490                1495                1500

Arg Ser Leu Arg Ile Leu Lys Pro Thr Phe Lys His Ala Ser Val Met
1505                1510                1515                1520

Ser Arg Leu Met Ser Ile Asp Pro His Phe Ser Ile Tyr Ile Gly Gly
            1525                1530                1535
```

-continued

Ala Ala Gly Asp Arg Gly Leu Ser Asp Ala Ala Arg Leu Phe Leu Arg
        1540                1545                1550

Thr Ser Ile Ser Ser Phe Leu Thr Phe Val Lys Glu Trp Ile Ile Asn
        1555                1560                1565

Arg Gly Thr Ile Val Pro Leu Trp Ile Val Tyr Pro Leu Glu Gly Gln
        1570                1575                1580

Asn Pro Thr Pro Val Asn Asn Phe Leu Tyr Gln Ile Val Glu Leu Leu
1585                1590                1595                1600

Val His Asp Ser Ser Arg Gln Gln Ala Phe Lys Thr Thr Ile Ser Asp
        1605                1610                1615

His Val His Pro His Asp Asn Leu Val Tyr Thr Cys Lys Ser Thr Ala
        1620                1625                1630

Ser Asn Phe Phe His Ala Ser Leu Ala Tyr Trp Arg Ser Arg His Arg
        1635                1640                1645

Asn Ser Asn Arg Lys Tyr Leu Ala Arg Asp Ser Ser Thr Gly Ser Ser
        1650                1655                1660

Thr Asn Asn Ser Asp Gly His Ile Glu Arg Ser Gln Glu Gln Thr Thr
1665                1670                1675                1680

Arg Asp Pro His Asp Gly Thr Glu Arg Asn Leu Val Leu Gln Met Ser
        1685                1690                1695

His Glu Ile Lys Arg Thr Thr Ile Pro Gln Glu Asn Thr His Gln Gly
        1700                1705                1710

Pro Ser Phe Gln Ser Phe Leu Ser Asp Ser Ala Cys Gly Thr Ala Asn
        1715                1720                1725

Pro Lys Leu Asn Phe Asp Arg Ser Arg His Asn Val Lys Phe Gln Asp
        1730                1735                1740

His Asn Ser Ala Ser Lys Arg Glu Gly His Gln Ile Ile Ser His Arg
1745                1750                1755                1760

Leu Val Leu Pro Phe Phe Thr Leu Ser Gln Gly Thr Arg Gln Leu Thr
        1765                1770                1775

Ser Ser Asn Glu Ser Gln Thr Gln Asp Glu Ile Ser Lys Tyr Leu Arg
        1780                1785                1790

Gln Leu Arg Ser Val Ile Asp Thr Thr Val Tyr Cys Arg Phe Thr Gly
        1795                1800                1805

Ile Val Ser Ser Met His Tyr Lys Leu Asp Glu Val Leu Trp Glu Ile
        1810                1815                1820

Glu Ser Phe Lys Ser Ala Val Thr Leu Ala Glu Gly Glu Gly Ala Gly
1825                1830                1835                1840

Ala Leu Leu Leu Ile Gln Lys Tyr Gln Val Lys Thr Leu Phe Phe Asn
        1845                1850                1855

Thr Leu Ala Thr Glu Ser Ser Ile Glu Ser Glu Ile Val Ser Gly Met
        1860                1865                1870

Thr Thr Pro Arg Met Leu Leu Pro Val Met Ser Lys Phe His Asn Asp
        1875                1880                1885

Gln Ile Glu Ile Ile Leu Asn Asn Ser Ala Ser Gln Ile Thr Asp Ile
        1890                1895                1900

Thr Asn Pro Thr Trp Phe Lys Asp Gln Arg Ala Arg Leu Pro Lys Gln
1905                1910                1915                1920

Val Glu Val Ile Thr Met Asp Ala Glu Thr Thr Glu Asn Ile Asn Arg
        1925                1930                1935

Ser Lys Leu Tyr Glu Ala Val Tyr Lys Leu Ile Leu His His Ile Asp
        1940                1945                1950

Pro Ser Val Leu Lys Ala Val Val Leu Lys Val Phe Leu Ser Asp Thr

```
                1955                1960                1965
Glu Gly Met Leu Trp Leu Asn Asp Asn Leu Ala Pro Phe Phe Ala Thr
        1970                1975                1980
Gly Tyr Leu Ile Lys Pro Ile Thr Ser Ser Ala Arg Ser Ser Glu Trp
1985                1990                1995                2000
Tyr Leu Cys Leu Thr Asn Phe Leu Ser Thr Thr Arg Lys Met Pro His
            2005                2010                2015
Gln Asn His Leu Ser Cys Lys Gln Val Ile Leu Thr Ala Leu Gln Leu
        2020                2025                2030
Gln Ile Gln Arg Ser Pro Tyr Trp Leu Ser His Leu Thr Gln Tyr Ala
            2035                2040                2045
Asp Cys Glu Leu His Leu Ser Tyr Ile Arg Leu Gly Phe Pro Ser Leu
        2050                2055                2060
Glu Lys Val Leu Tyr His Arg Tyr Asn Leu Val Asp Ser Lys Arg Gly
2065                2070                2075                2080
Pro Leu Val Ser Ile Thr Gln His Leu Ala His Leu Arg Ala Glu Ile
            2085                2090                2095
Arg Glu Leu Thr Asn Asp Tyr Asn Gln Gln Arg Gln Ser Arg Thr Gln
        2100                2105                2110
Thr Tyr His Phe Ile Arg Thr Ala Lys Gly Arg Ile Thr Lys Leu Val
            2115                2120                2125
Asn Asp Tyr Leu Lys Phe Phe Leu Ile Val Gln Ala Leu Lys His Asn
        2130                2135                2140
Gly Thr Trp Gln Ala Glu Phe Lys Lys Leu Pro Glu Leu Ile Ser Val
2145                2150                2155                2160
Cys Asn Arg Phe Tyr His Ile Arg Asp Cys Asn Cys Glu Glu Arg Phe
            2165                2170                2175
Leu Val Gln Thr Leu Tyr Leu His Arg Met Gln Asp Ser Glu Val Lys
        2180                2185                2190
Leu Ile Glu Arg Leu Thr Gly Leu Leu Ser Leu Phe Pro Asp Gly Leu
        2195                2200                2205
Tyr Arg Phe Asp
    2210

<210> SEQ ID NO 37
<211> LENGTH: 18959
<212> TYPE: DNA
<213> ORGANISM: Zaire Ebola virus strain Mayinga

<400> SEQUENCE: 37
cggacacaca aaagaaaga agaattttta ggatcttttg tgtgcgaata actatgagga    60
agattaataa ttttcctctc attgaaattt atatcggaat ttaaattgaa attgttactg   120
taatcacacc tggtttgttt cagagccaca tcacaaagat agagaacaac ctaggtctcc   180
gaagggagca agggcatcag tgtgctcagt tgaaaatccc ttgtcaacac ctaggtctta   240
tcacatcaca agttccacct cagactctgc agggtgatcc aacaacctta atagaaacat   300
tattgttaaa ggacagcatt agttcacagt caaacaagca agattgagaa ttaaccttgg   360
ttttgaactt gaacacttag gggattgaag attcaacaac cctaaagctt ggggtaaaac   420
attggaaata gttaaaagac aaattgctcg gaatcacaaa attccgagta tggattctcg   480
tcctcagaaa atctggatgg cgccgagtct cactgaatct gacatggatt accacaagat   540
cttgacagca ggtctgtccg ttcaacaggg gattgttcgg caaagagtca tcccagtgta   600
tcaagtaaac aatcttgaag aaatttgcca acttatcata caggcctttg aagcaggtgt   660
```

```
tgatttcaa gagagtgcgg acagtttcct tctcatgctt tgtcttcatc atgcgtacca    720
gggagattac aaactttct tggaaagtgg cgcagtcaag tatttggaag gcacgggtt     780 ccgttttgaa gtcaagaagc gtgatggagt gaagcgcctt gaggaattgc tgccagcagt   840
atctagtgga aaaaacatta agagaacact tgctgccatg ccggaagagg agacaactga   900
agctaatgcc ggtcagtttc tctcctttgc aagtctattc cttccgaaat tggtagtagg   960
agaaaaggct tgccttgaga aggttcaaag gcaaattcaa gtacatgcag agcaaggact  1020
gatacaatat ccaacagctt ggcaatcagt aggacacatg atggtgattt ccgtttgat   1080 gcgaacaaat tttctgatca aatttctcct aatacaccaa gggatgcaca tggttgccgg  1140
gcatgatgcc aacgatgctg tgatttcaaa ttcagtggct caagctcgtt tttcaggctt  1200
attgattgtc aaaacagtac ttgatcatat cctacaaaag acagaacgag gagttcgtct  1260
ccatcctctt gcaaggaccg ccaaggtaaa aaatgaggtg aactccttta aggctgcact  1320
cagctccctg gccaagcatg gagagtatgc tcctttcgcc cgacttttga acctttctgg  1380
agtaaataat cttgagcatg gtcttttccc tcaactatcg gcaattgcac tcggagtcgc  1440
cacagcacac gggagtaccc tcgcaggagt aaatgttgga gaacagtatc aacaactcag  1500
agaggctgcc actgaggctg agaagcaact ccaacaatat gcagagtctc gcgaacttga  1560
ccatcttgga cttgatgatc aggaaaagaa aattcttatg aacttccatc agaaaaagaa  1620
cgaaatcagc ttccagcaaa caaacgctat ggtaactcta agaaagagc gcctggccaa   1680 gctgacagaa gctatcactg ctgcgtcact gcccaaaaca agtggacatt acgatgatga  1740
tgacgacatt cccttttccag gacccatcaa tgatgacgac aatcctggcc atcaagatga  1800
tgatccgact gactcacagg atacgaccat tcccgatgtg gtggttgatc ccgatgatgg  1860
aagctacggc gaataccaga gttactcgga aaacggcatg aatgcaccag atgacttggt  1920
cctattcgat ctagcgagg acgacgagga cactaagcca gtgcctaata gatcgaccaa   1980
gggtggacaa cagaagaaca gtcaaaaggg ccagcatata gagggcagac agacacaatc  2040
caggccaatt caaaatgtcc caggccctca cagaacaatc caccacgcca gtgcgccact  2100
cacggacaat gacagaagaa atgaaccctc cggctcaacc agcccctgca tgctgacacc   2160
aattaacgaa gaggcagacc cactggacga tgccgacgac gagacgtcta gccttccgcc  2220
cttggagtca gatgatgaag agcaggacag ggacggaact tccaaccgca cacccactgt  2280
cgccccaccg gctcccgtat acagagatca ctctgaaaag aaagaactcc gcaagacga   2340 gcaacaagat caggaccaca ctcaagaggc caggaaccag gacagtgaca cacccagtc   2400 agaacactct tttgaggaga tgtatcgcca cattctaaga tcacaggggc catttgatgc  2460
tgttttgtat tatcatatga tgaaggatga gcctgtagtt ttcagtacca gtgatggcaa  2520
agagtacacg tatccagact cccttgaaga ggaatatcca ccatggctca ctgaaaaaga  2580
ggctatgaat gaagagaata gatttgttac attggatggt caacaatttt attggccggt  2640
gatgaatcac aagaataaat tcatggcaat cctgcaacat catcagtgaa tgagcatgga  2700
acaatgggat gattcaaccg acaaatagct aacattaagt agtcaaggaa cgaaaacagg  2760 aagaatttt gatgtctaag gtgtgaatta ttatcacaat aaaagtgatt cttattttg   2820 aatttaaagc tagcttatta ttactagccg ttttcaaag ttcaatttga gtcttaatgc   2880
aaataggcgt taagccacag ttatagccat aattgtaact caatattcta actagcgatt  2940
tatctaaatt aaattacatt atgctttat aacttaccta ctagcctgcc caacatttac    3000
```

```
acgatcgttt tataattaag aaaaaactaa tgatgaagat taaaaccttc atcatcctta    3060
cgtcaattga attctctagc actcgaagct tattgtcttc aatgtaaaag aaaagctggt    3120
ctaacaagat gacaactaga acaaagggca ggggccatac tgcggccacg actcaaaacg    3180
acagaatgcc aggccctgag ctttcgggct ggatctctga gcagctaatg accggaagaa    3240
ttcctgtaag cgacatcttc tgtgatattg agaacaatcc aggattatgc tacgcatccc    3300
aaatgcaaca aacgaagcca aacccgaaga cgcgcaacag tcaaacccaa acggacccaa    3360
tttgcaatca tagttttgag gaggtagtac aaacattggc ttcattggct actgttgtgc    3420
aacaacaaac catcgcatca gaatcattag aacaacgcat tacgagtctt gagaatggtc    3480
taaagccagt ttatgatatg caaaaacaa tctcctcatt gaacagggtt tgtgctgaga    3540
tggttgcaaa atatgatctt ctggtgatga caaccggtcg ggcaacagca accgctgcgg    3600
caactgaggc ttattgggcc gaacatggtc aaccaccacc tggaccatca ctttatgaag    3660
aaagtgcgat tcggggtaag attgaatcta gagatgagac cgtccctcaa agtgttaggg    3720
aggcattcaa caatctaaac agtaccactt cactaactga ggaaaatttt gggaaacctg    3780
acatttcggc aaaggatttg agaaacatta tgtatgatca cttgcctggt tttggaactg    3840
cttttccacca attagtacaa gtgatttgta aattgggaaa agatagcaac tcattggaca    3900
tcattcatgc tgagttccag gccagcctgg ctgaaggaga ctctcctcaa tgtgccctaa    3960
ttcaaattac aaaaagagtt ccaatcttcc aagatgctgc tccacctgtc atccacatcc    4020
gctctcgagg tgacattccc cgagcttgcc agaaaagctt gcgtccagtc ccaccatcgc    4080
ccaagattga tcgaggttgg gtatgtgttt ttcagcttca agatggtaaa acacttggac    4140
tcaaaatttg agccaatctc ccttccctcc gaaagaggcg aataatagca gaggcttcaa    4200
ctgctgaact atagggtacg ttacattaat gatacacttg tgagtatcag ccctggataa    4260
tataagtcaa ttaaacgacc aagataaaat tgttcatatc tcgctagcag cttaaaatat    4320
aaatgtaata ggagctatat ctctgacagt attataatca attgttatta agtaacccaa    4380
accaaaagtg atgaagatta agaaaaacct acctcggctg agagagtgtt ttttcattaa    4440
ccttcatctt gtaaacgttg agcaaaattg ttaaaaatat gaggcgggtt atattgccta    4500
ctgctcctcc tgaatatatg gaggccatat accctgtcag gtcaaattca acaattgcta    4560
gaggtggcaa cagcaataca ggcttcctga caccggagtc agtcaatggg gacactccat    4620
cgaatccact caggccaatt gccgatgaca ccatcgacca tgccagccac acaccaggca    4680
gtgtgtcatc agcattcatc cttgaagcta tggtgaatgt catatcgggc cccaaagtgc    4740
taatgaagca aattccaatt tggcttcctc taggtgtcgc tgatcaaaag acctacagct    4800
ttgactcaac tacggccgcc atcatgcttg cttcatacac tatcacccat ttcggcaagg    4860
caaccaatcc acttgtcaga gtcaatcggc tgggtcctgg aatcccggat catcccctca    4920
ggctcctgcg aattggaaac caggctttcc tccaggagtt cgttcttccg ccagtccaac    4980
taccccagta tttcaccttt gatttgacag cactcaaact gatcacccaa ccactgcctg    5040
ctgcaacatg gaccgatgac actccaacag gatcaaatgg agcgttgcgt ccaggaattt    5100
catttcatcc aaaacttcgc cccattcttt tacccaacaa agtgggaag aaggggaaca    5160
gtgccgatct aacatctccg gagaaaatcc aagcaataat gacttcactc caggacttta    5220
agatcgttcc aattgatcca accaaaaata tcatgggaat cgaagtgcca gaaactctgg    5280
tccacaagct gaccggtaag aaggtgactt ctaaaaatgg acaaccaatc atccctgttc    5340
ttttgccaaa gtacattggg ttggacccgg tggctccagg agacctcacc atggtaatca    5400
```

```
cacaggattg tgacacgtgt cattctcctg caagtcttcc agctgtgatt gagaagtaat   5460
tgcaataatt gactcagatc cagttttata gaatcttctc agggatagtg ataacatcta   5520
tttagtaatc cgtccattag aggagacact tttaattgat caatatacta aaggtgcttt   5580
acaccattgt cttttttctc tcctaaatgt agaacttaac aaaagactca taatatactt   5640 gttttaaag gattgattga tgaaagatca taactaataa cattacaaat aatcctacta   5700
taatcaatac ggtgattcaa atgttaatct ttctcattgc atacttttt tgcccttatc   5760 ctcaaattgc ctgcatgctt acatctgagg atagccagtg tgacttggat tggaaatgtg   5820
gagaaaaaat cgggacccat ttctaggttg ttcacaatcc aagtacagac attgcccttc   5880
taattaagaa aaaatcggcg atgaagatta agccgacagt gagcgtaatc ttcatctctc   5940
ttagattatt tgttttccag gtaggggtc gtcaggtcct tttcaatcgt gtaaccaaaa   6000
taaactccac tagaaggata ttgtggggca acaacacaat gggcgttaca ggaatattgc   6060
agttacctcg tgatcgattc aagaggacat cattctttct ttgggtaatt atccttttcc   6120
aaagaacatt ttccatccca cttggagtca tccacaatag cacattacag gttagtgatg   6180
tcgacaaact agtttgtcgt gacaaactgt catccacaaa tcaattgaga tcagttggac   6240
tgaatctcga agggaatgga gtggcaactg acgtgccatc tgcaactaaa gatggggct   6300 tcaggtccgg tgtcccacca aaggtggtca attatgaagc tggtgaatgg gctgaaaact   6360
gctacaatct tgaaatcaaa aaacctgacg ggagtgagtg tctaccagca gcgccagacg   6420
ggattcgggg cttcccccgg tgccggtatg tgcacaaagt atcaggaacg ggaccgtgtg   6480
ccggagactt tgccttccat aaagagggtg ctttcttcct gtatgatcga cttgcttcca   6540
cagttatcta ccgaggaacg actttcgctg aaggtgtcgt tgcatttctg atactgcccc   6600
aagctaagaa ggacttcttc agctcacacc ccttgagaga gccggtcaat gcaacggagg   6660
acccgtctag tggctactat tctaccacaa ttagatatca ggctaccggt tttggaacca   6720
atgagacaga gtacttgttc gaggttgaca atttgaccta cgtccaactt gaatcaagat   6780
tcacaccaca gtttctgctc cagctgaatg agacaatata tacaagtggg aaaaggagca   6840
ataccacggg aaaactaatt tggaaggtca accccgaaat tgatacaaca atcggggagt   6900
gggccttctg ggaaactaaa aaaacctcac tagaaaaatt cgcagtgaag agttgtcttt   6960
cacagttgta tcaaacggag ccaaaaacat cagtggtcag agtccggcgc gaacttcttc   7020
cgacccaggg accaacacaa caactgaaga ccacaaaatc atggcttcag aaaattcctc   7080
tgcaatggtt caagtgcaca gtcaaggaag ggaagctgca gtgtcgcatc taacaaccct   7140
tgccacaatc tccacgagtc cccaatccct cacaaccaaa ccaggtccgg acaacagcac   7200
ccataataca cccgtgtata aacttgacat ctctgaggca actcaagttg aacaacatca   7260
ccgcagaaca gacaacgaca gcacagcctc cgacactccc tctgccacga ccgcagccgg   7320
acccccaaaa gcagagaaca ccaacacgag caagagcact gacttcctgg accccgccac   7380
cacaacaagt ccccaaaacc acagcgagac cgctggcaac aacaacactc atcaccaaga   7440
taccggagaa gagagtgcca gcagcgggaa gctaggctta attaccaata ctattgctgg   7500
agtcgcagga ctgatcacag gcgggagaag aactcgaaga gaagcaattg tcaatgctca   7560
acccaaatgc aaccctaatt tacattactg gactactcag gatgaaggtg ctgcaatcgg   7620
actggcctgg ataccatatt tcgggccagc agccgaggga atttacatag aggggctaat   7680
gcacaatcaa gatggtttaa tctgtgggtt gagacagctg gccaacgaga cgactcaagc   7740
```

```
tcttcaactg ttcctgagag ccacaactga gctacgcacc ttttcaatcc tcaaccgtaa    7800
ggcaattgat ttcttgctgc agcgatgggg cggcacatgc cacattctgg gaccggactg    7860
ctgtatcgaa ccacatgatt ggaccaagaa cataacagac aaaattgatc agattattca    7920
tgattttgtt gataaaaccc ttccggacca gggggacaat gacaattggt ggacaggatg    7980
gagacaatgg ataccggcag gtattggagt tacaggcgtt ataattgcag ttatcgcttt    8040
attctgtata tgcaaatttg tcttttagtt tttcttcaga ttgcttcatg gaaaagctca    8100
gcctcaaatc aatgaaacca ggatttaatt atatggatta cttgaatcta agattacttg    8160
acaaatgata atataataca ctggagcttt aaacatagcc aatgtgattc taactccttt    8220
aaactcacag ttaatcataa acaaggtttg acatcaatct agttatctct ttgagaatga    8280
taaacttgat gaagattaag aaaaaggtaa tctttcgatt atctttaatc ttcatccttg    8340
attctacaat catgacagtt gtctttagtg acaagggaaa gaagcctttt tattaagttg    8400
taataatcag atctgcgaac cggtagagtt tagttgcaac ctaacacaca taaagcattg    8460
gtcaaaaagt caatagaaat ttaaacgtag agtggagaca acttttaaat ggaagcttca    8520
tatgagagag gacgcccacg agctgccaga cagcattcaa gggatggaca cgaccaccat    8580
gttcgagcac gatcatcatc cagagagaat tatcgaggtg agtaccgtca atcaaggagc    8640
gcctcacaag tgcgcgttcc tactgtattt cataagaaga gagttgaacc attaacagtt    8700
cctccagcac ctaaagacat atgtccgacc ttgaaaaaag gattttgtgt tgacagtagt    8760
ttttgcaaaa aagatcacca gttggagagt ttaactgata gggaattact cctactaatc    8820
gcccgtaaga cttgtggatc agtagaacaa caattaaata taactgcacc caaggactcg    8880
cgcttagcaa atccaacggc tgatgatttc cagcaagagg aaggtccaaa aattaccttg    8940
ttgacactga tcaagacggc agaacactgg gcgagacaag acatcagaac catagaggat    9000
tcaaaattaa gagcattgtt gactctatgt gctgtgatga cgaggaaatt ctcaaaatcc    9060
cagctgagtc ttttatgtga gacacaccta aggcgcgagg ggcttgggca agatcaggca    9120
gaacccgttc tcgaagtata tcaacgatta cacagtgata aaggaggcag ttttgaagct    9180
gcactatggc aacaatggga ccgacaatcc ctaattatgt ttatcactgc attcttgaat    9240
attgctctcc agttaccgtg tgaaagttct gctgtcgttg tttcagggtt aagaacattg    9300
gttcctcaat cagataatga ggaagcttca accaacccgg ggacatgctc atggtctgat    9360
gagggtaccc cttaataagg ctgactaaaa cactatataa ccttctactt gatcacaata    9420
ctccgtatac ctatcatcat atatttaatc aagacgatat cctttaaaac ttattcagta    9480
ctataatcac tctcgtttca aattaataag atgtgcatga ttgccctaat atatgaagag    9540
gtatgataca accctaacag tgatcaaaga aaatcataat ctcgtatcgc tcgtaatata    9600
acctgccaag catacctctt gcacaaagtg attcttgtac acaaataatg ttttactcta    9660
caggaggtag caacgatcca tcccatcaaa aaataagtat ttcatgactt actaatgatc    9720
tcttaaaata ttaagaaaaa ctgacggaac ataaattctt tatgcttcaa gctgtggagg    9780
aggtgtttgg tattggctat tgttatatta caatcaataa caagcttgta aaaatattgt    9840
tcttgtttca agaggtagat tgtgaccgga aatgctaaac taatgatgaa gattaatgcg    9900
gaggtctgat aagaataaac cttattattc agattaggcc ccaagaggca ttcttcatct    9960
ccttttagca aagtactatt tcagggtagt ccaattagtg gcacgtcttt tagctgtata   10020
tcagtcgccc ctgagatacg ccacaaaagt gtctctaagc taaattggtc tgtacacatc   10080
ccatacattg tattaggggc aataatatct aattgaactt agccgtttaa aatttagtgc   10140
```

```
ataaatctgg gctaacacca ccaggtcaac tccattggct gaaaagaagc ttacctacaa   10200
cgaacatcac tttgagcgcc ctcacaatta aaaatagga acgtcgttcc aacaatcgag   10260
cgcaaggttt caaggttgaa ctgagagtgt ctagacaaca aaatattgat actccagaca   10320
ccaagcaaga cctgagaaaa aaccatggct aaagctacgg gacgatacaa tctaatatcg   10380
cccaaaaagg acctggagaa aggggttgtc ttaagcgacc tctgtaactt cttagttagc   10440
caaactattc aggggtggaa ggtttattgg gctggtattg agtttgatgt gactcacaaa   10500
ggaatggccc tattgcatag actgaaaact aatgactttg ccctgcatg gtcaatgaca    10560 aggaatctct ttcctcattt atttcaaaat ccgaattcca caattgaatc accgctgtgg   10620
gcattgagag tcatccttgc agcagggata caggaccagc tgattgacca gtctttgatt   10680
gaacccttag caggagccct tggtctgatc tctgattggc tgctaacaac caacactaac   10740
catttcaaca tgcgaacaca acgtgtcaag gaacaattga gcctaaaaat gctgtcgttg   10800
attcgatcca atattctcaa gtttattaac aaattggatg ctctacatgt cgtgaactac   10860
aacggattgt tgagcagtat tgaaattgga actcaaaatc atacaatcat cataactcga   10920
actaacatgg gttttctggt ggagctccaa gaacccgaca atcggcaat gaaccgcatg    10980 aagcctgggc cggcgaaatt ttccctcctt catgagtcca cactgaaagc atttacacaa   11040
ggatcctcga cacgaatgca aagtttgatt cttgaattta atagctctct tgctatctaa   11100
ctaaggtaga atacttcata ttgagctaac tcatatatgc tgactcaata gttatcttga   11160
catctctgct ttcataatca gatatataag cataataaat aaatactcat atttcttgat   11220
aatttgttta accacagata aatcctcact gtaagccagc ttccaagttg acacccttac   11280
aaaaaccagg actcagaatc cctcaaacaa gagattccaa gacaacatca tagaattgct   11340
ttattatatg aataagcatt ttatcaccag aaatcctata tactaaatgg ttaattgtaa   11400
ctgaacccgc aggtcacatg tgttaggttt cacagattct atatattact aactctatac   11460
tcgtaattaa cattagataa gtagattaag aaaaaagcct gaggaagatt aagaaaaact   11520
gcttattggg tctttccgtg ttttagatga agcagttgaa attcttcctc ttgatattaa   11580
atggctacac aacatacccaa ataccccagac gctaggttat catcaccaat tgtattggac  11640
caatgtgacc tagtcactag agcttgcggg ttatattcat catactccct taatccgcaa   11700
ctacgcaact gtaaactccc gaaacatatc taccgtttga aatacgatgt aactgttacc   11760
aagttcttga gtgatgtacc agtggcgaca ttgcccatag atttcatagt cccagttctt   11820
ctcaaggcac tgtcaggcaa tggattctgt cctgttgagc cgcggtgcca acagttctta   11880
gatgaaatca ttaagtacac aatgcaagat gctctcttct tgaaatatta tctcaaaaat   11940
gtgggtgctc aagaagactg tgttgatgaa cactttcaag agaaaatctt atcttcaatt   12000
cagggcaatg aatttttaca tcaaatgttt ttctggtatg atctggctat tttaactcga   12060
aggggtagat taaatcgagg aaactctaga tcaacatggt tgttcatga tgatttaata    12120 gacatcttag gctatgggga ctatgttttt tggaagatcc caatttcaat gttaccactg   12180
aacacacaag gaatccccca tgctgctatg gactggtatc aggcatcagt attcaaagaa   12240
gcggttcaag ggcatacaca cattgttttct gtttctactg ccgacgtctt gataatgtgc  12300
aaagatttaa ttcatgtcg attcaacaca actctaatct caaaaatagc agagattgag    12360
gatccagttt gttctgatta tcccaatttt aagattgtgt ctatgcttta ccagagcgga   12420
gattacttac tctccatatt agggtctgat gggtataaaa ttattaagtt cctcgaacca   12480
```

```
ttgtgcttgg ccaaaattca attatgctca aagtacactg agaggaaggg ccgattctta    12540
acacaaatgc atttagctgt aaatcacacc ctagaagaaa ttacagaaat gcgtgcacta    12600
aagccttcac aggctcaaaa gatccgtgaa ttccatagaa cattgataag gctggagatg    12660
acgccacaac aactttgtga gctatttttcc attcaaaaac actgggggca tcctgtgcta    12720
catagtgaaa cagcaatcca aaagttaaa aaacatgcta cggtgctaaa agcattacgc    12780
cctatagtga ttttcgagac atactgtgtt tttaaatata gtattgccaa acattatttt    12840
gatagtcaag gatcttggta cagtgttact tcagatagga atctaacacc gggtcttaat    12900
tcttatatca aaagaaatca attccctccg ttgccaatga ttaaagaact actatgggaa    12960
ttttaccacc ttgaccaccc tccactttct tcaaccaaaa ttattagtga cttaagtatt    13020
tttataaaag acagagctac cgcagtagaa aggacatgct gggatgcagt attcgagcct    13080
aatgttctag gatataatcc acctcacaaa tttagtacta aacgtgtacc ggaacaattt    13140
ttagagcaag aaaactttc tattgagaat gttctttcct acgcacaaaa actcgagtat    13200
ctactaccac aatatcggaa cttttctttc tcattgaaag agaaagagtt gaatgtaggt    13260
agaaccttcg gaaaattgcc ttatccgact cgcaatgttc aaacactttg tgaagctctg    13320
ttagctgatg gtcttgctaa agcatttcct agcaatatga tggtagttac ggaacgtgag    13380
caaaaagaaa gcttattgca tcaagcatca tggcaccaca caagtgatga ttttggtgaa    13440
catgccacag ttagagggag tagctttgta actgatttag agaaatacaa tcttgcattt    13500
agatatgagt ttacagcacc ttttatagaa tattgcaacc gttgctatgg tgttaagaat    13560 gttttttaatt ggatgcatta caatcccca cagtgttata tgcatgtcag tgattattat    13620
aatccaccac ataacctcac actggagaat cgagacaacc ccccgaagg gcctagttca    13680 tacaggggtc atatgggagg gattgaagga ctgcaacaaa aactctggac aagtatttca    13740
tgtgctcaaa tttctttagt tgaaattaag actggttta agttacgctc agctgtgatg    13800
ggtgacaatg agtgcattac tgttttatca gtcttcccct tagagactga cgcagacgag    13860
caggaacaga gcgccgaaga caatgcagcg agggtggccg ccagcctagc aaaagttaca    13920
agtgcctgtg gaatcttttt aaaacctgat gaaacatttg tacattcagg ttttatctat    13980
tttggaaaaa aacaatattt gaatggggtc caattgcctc agtcccttaa aacggctaca    14040
agaatggcac cattgtctga tgcaattttt gatgatcttc aagggacccct ggctagtata    14100 ggcactgctt ttgagcgatc catctctgag acacgacata tcttttcccttg caggataacc    14160 gcagcttttcc atacgttttt ttcggtgaga atcttgcaat atcatcatct cgggttcaat    14220
aaaggttttg accttggaca gttaacactc ggcaaacctc tggatttcgg aacaatatca    14280
ttggcactag cggtaccgca ggtgcttgga gggttatcct tcttgaatcc tgagaaatgt    14340
ttctaccgga atctaggaga tccagttacc tcaggcttat tccagttaaa aacttatctc    14400
cgaatgattg agatggatga tttattctta cctttaattg cgaagaaccc tgggaactgc    14460
actgccattg actttgtgct aaatcctagc ggattaaatg tccctgggtc gcaagactta    14520
acttcatttc tgcgccagat tgtacgcagg accatcaccc taagtgcgaa aaacaaactt    14580
attaatacct tatttcatgc gtcagctgac ttcgaagacg aaatggtttg taaatggcta    14640
ttatcatcaa ctcctgttat gagtcgtttt gcggccgata tcttttcacg cacgccgagc    14700
gggaagcgat tgcaaattct aggatacctg gaaggaacac gcacattatt agcctctaag    14760
atcatcaaca ataatacaga gacaccggtt ttggacagac tgaggaaaat aacattgcaa    14820
aggtggagcc tatggtttag ttatcttgat cattgtgata atatcctggc ggaggcttta    14880
```

```
acccaaataa cttgcacagt tgatttagca cagattctga gggaatattc atgggctcat    14940
attttagagg gaagacctct tattggagcc acactcccat gtatgattga gcaattcaaa    15000
gtgttttggc tgaaacccta cgaacaatgt ccgcagtgtt caaatgcaaa gcaaccaggt    15060
gggaaaccat tcgtgtcagt ggcagtcaag aaacatattg ttagtgcatg gccgaacgca    15120
tcccgaataa gctggactat cggggatgga atcccataca ttggatcaag gacagaagat    15180
aagataggac aacctgctat taaaccaaaa tgtccttccg cagccttaag agaggccatt    15240
gaattggcgt cccgtttaac atgggtaact caaggcagtt cgaacagtga cttgctaata    15300
aaaccatttt tggaagcacg agtaaattta agtgttcaag aaatacttca aatgacccct    15360
tcacattact caggaaatat tgttcacagg tacaacgatc aatacagtcc tcattctttc    15420
atggccaatc gtatgagtaa ttcagcaacg cgattgattg tttctacaaa cactttaggt    15480
gagttttcag gaggtggcca gtctgcacgc gacagcaata ttattttcca gaatgttata    15540
aattatgcag ttgcactgtt cgatattaaa tttagaaaca ctgaggctac agatatccaa    15600
tataatcgtg ctcaccttca tctaactaag tgttgcaccc gggaagtacc agctcagtat    15660
ttaacataca catctacatt ggatttagat ttaacaagat accgagaaaa cgaattgatt    15720
tatgacagta atcctctaaa aggaggactc aattgcaata tctcattcga taatccattt    15780
ttccaaggta aacggctgaa cattatagaa gatgatctta ttcgactgcc tcacttatct    15840
ggatgggagc tagccaagac catcatgcaa tcaattattt cagatagcaa caattcatct    15900
acagacccaa ttagcagtgg agaaacaaga tcattcacta cccatttctt aacttatccc    15960
aagataggac ttctgtacag ttttggggcc tttgtaagtt attatcttgg caatacaatt    16020
cttcggacta agaaattaac acttgacaat tttttatatt acttaactac tcaaattcat    16080
aatctaccac atcgctcatt gcgaatactt aagccaacat tcaaacatgc aagcgttatg    16140
tcacggttaa tgagtattga tcctcatttt tctatttaca taggcggtgc tgcaggtgac    16200
agaggactct cagatgcggc caggttattt ttgagaacgt ccatttcatc ttttcttaca    16260
tttgtaaaag aatggataat taatcgcgga acaattgtcc ctttatggat agtatatccg    16320
ctagagggtc aaaacccaac acctgtgaat aattttctct atcagatcgt agaactgctg    16380
gtgcatgatt catcaagaca acaggctttt aaaactacca taagtgatca tgtacatcct    16440
cacgacaatc ttgtttacac atgtaagagt acagccagca atttcttcca tgcatcattg    16500
gcgtactgga ggagcagaca cagaaacagc aaccgaaaat acttggcaag agactcttca    16560
actggatcaa gcacaaacaa cagtgatggt catattgaga gaagtcaaga acaaaccacc    16620
agagatccac atgatggcac tgaacggaat ctagtcctac aaatgagcca tgaaataaaa    16680
agaacgacaa ttccacaaga aaacacgcac cagggtccgt cgttccagtc ctttctaagt    16740
gactctgctt gtggtacagc aaatccaaaa ctaaatttcg atcgatcgag acacaatgtg    16800
aaatttcagg atcataactc ggcatccaag agggaaggtc atcaaataat ctcacaccgt    16860
ctagtcctac cttttcttta cattatctca gggacacgcc aattaacgtc atccaatgag    16920
tcacaaaccc aagacgagat atcaaagtac ttacggcaat tgagatccgt cattgatacc    16980
acagtttatt gtagatttac cggtatagtc tcgtccatgc attacaaact tgatgaggtc    17040
ctttgggaaa tagagagttt caagtcggct gtgacgctag cagagggaga aggtgctggt    17100
gccttactat tgattcagaa ataccaagtt aagaccttat ttttcaacac gctagctact    17160
gagtccagta tagagtcaga aatagtatca ggaatgacta ctcctaggat gcttctacct    17220
```

```
gttatgtcaa aattccataa tgaccaaatt gagattattc ttaacaactc agcaagccaa  17280
ataacagaca taacaaatcc tacttggttt aaagaccaaa gagcaaggct acctaagcaa  17340
gtcgaggtta taaccatgga tgcagagaca acagagaata taaacagatc gaaattgtac  17400
gaagctgtat ataaattgat cttacaccat attgatccta gcgtattgaa agcagtggtc  17460
cttaaagtct ttctaagtga tactgagggt atgttatggc taaatgataa tttagccccg  17520
ttttttgcca ctggttattt aattaagcca ataacgtcaa gtgctagatc tagtgagtgg  17580
tatctttgtc tgacgaactt cttatcaact acacgtaaga tgccacacca aaaccatctc  17640
agttgtaaac aggtaatact tacggcattg caactgcaaa ttcaacgaag cccatactgg  17700
ctaagtcatt taactcagta tgctgactgt gagttacatt taagttatat ccgccttggt  17760
tttccatcat tagagaaagt actataccac aggtataacc tcgtcgattc aaaaagaggt  17820
ccactagtct ctatcactca gcacttagca catcttagag cagagattcg agaattaact  17880
aatgattata tcaacagcg acaaagtcgg actcaaacat atcactttat tcgtactgca  17940
aaaggacgaa tcacaaaact agtcaatgat tatttaaaat tctttcttat tgtgcaagca  18000
ttaaaacata tgggacatg caagctgag tttaagaaat taccagagtt gattagtgtg  18060
tgcaataggt tctaccatat tagagattgc aattgtgaag aacgtttctt agttcaaacc  18120
ttatatttac atagaatgca ggattctgaa gttaagctta tcgaaaggct gacagggctt  18180
ctgagtttat ttccggatgg tctctacagg tttgattgaa ttaccgtgca tagtatcctg  18240
atacttgcaa aggttggtta ttaacataca gattataaaa aactcataaa ttgctctcat  18300
acatcatatt gatctaatct caataaacaa ctatttaaat aacgaaagga gtccctatat  18360
tatatactat atttagcctc tctccctgcg tgataatcaa aaaattcaca atgcagcatg  18420
tgtgacatat tactgccgca atgaatttaa cgcaacataa taactctgc actctttata  18480 attaagcttt aacgaaaggt ctgggctcat attgttattg atataataat gttgtatcaa  18540
tatcctgtca gatggaatag tgttttggtt gataacacaa cttcttaaaa caaaattgat  18600
ctttaagatt aagttttttta taattatcat tactttaatt tgtcgtttta aaacggtga  18660 tagccttaat ctttgtgtaa aataagagat taggtgtaat aaccttaaca tttttgtcta  18720
gtaagctact atttcataca gaatgataaa attaaagaa aaggcaggac tgtaaaatca  18780
gaaatacctt ctttcaaata tagcagacta gataataatc ttcgtgttaa tgataattaa  18840
gacattgacc acgctcatca gaaggctcgc cagaataaac gttgcaaaaa ggattcctgg  18900
aaaaatggtc gcacacaaaa atttaaaaat aaatctattt cttctttttt gtgtgtcca   18959
```

<210> SEQ ID NO 38
<211> LENGTH: 739
<212> TYPE: PRT
<213> ORGANISM: Zaire Ebola virus strain Mayinga

<400> SEQUENCE: 38

Met Asp Ser Arg Pro Gln Lys Ile Trp Met Ala Pro Ser Leu Thr Glu
 1               5                   10                  15

Ser Asp Met Asp Tyr His Lys Ile Leu Thr Ala Gly Leu Ser Val Gln
                20                  25                  30

Gln Gly Ile Val Arg Gln Arg Val Ile Pro Val Tyr Gln Val Asn Asn
            35                  40                  45

Leu Glu Glu Ile Cys Gln Leu Ile Ile Gln Ala Phe Glu Ala Gly Val
        50                  55                  60

Asp Phe Gln Glu Ser Ala Asp Ser Phe Leu Leu Met Leu Cys Leu His

```
                65                  70                  75                  80
His Ala Tyr Gln Gly Asp Tyr Lys Leu Phe Leu Glu Ser Gly Ala Val
                    85                  90                  95
Lys Tyr Leu Glu Gly His Gly Phe Arg Phe Glu Val Lys Lys Arg Asp
                100                 105                 110
Gly Val Lys Arg Leu Glu Glu Leu Pro Ala Val Ser Ser Gly Lys
                115                 120                 125
Asn Ile Lys Arg Thr Leu Ala Ala Met Pro Glu Glu Thr Thr Glu
130                 135                 140
Ala Asn Ala Gly Gln Phe Leu Ser Phe Ala Ser Leu Phe Leu Pro Lys
145                 150                 155                 160
Leu Val Val Gly Glu Lys Ala Cys Leu Glu Lys Val Gln Arg Gln Ile
                165                 170                 175
Gln Val His Ala Glu Gln Gly Leu Ile Gln Tyr Pro Thr Ala Trp Gln
                180                 185                 190
Ser Val Gly His Met Met Val Ile Phe Arg Leu Met Arg Thr Asn Phe
                195                 200                 205
Leu Ile Lys Phe Leu Leu Ile His Gln Gly Met His Met Val Ala Gly
210                 215                 220
His Asp Ala Asn Asp Ala Val Ile Ser Asn Ser Val Ala Gln Ala Arg
225                 230                 235                 240
Phe Ser Gly Leu Leu Ile Val Lys Thr Val Leu Asp His Ile Leu Gln
                245                 250                 255
Lys Thr Glu Arg Gly Val Arg Leu His Pro Leu Ala Arg Thr Ala Lys
                260                 265                 270
Val Lys Asn Glu Val Asn Ser Phe Lys Ala Ala Leu Ser Ser Leu Ala
                275                 280                 285
Lys His Gly Glu Tyr Ala Pro Phe Ala Arg Leu Leu Asn Leu Ser Gly
                290                 295                 300
Val Asn Asn Leu Glu His Gly Leu Phe Pro Gln Leu Ser Ala Ile Ala
305                 310                 315                 320
Leu Gly Val Ala Thr Ala His Gly Ser Thr Leu Ala Gly Val Asn Val
                325                 330                 335
Gly Glu Gln Tyr Gln Gln Leu Arg Glu Ala Ala Thr Glu Ala Glu Lys
                340                 345                 350
Gln Leu Gln Gln Tyr Ala Glu Ser Arg Glu Leu Asp His Leu Gly Leu
                355                 360                 365
Asp Asp Gln Glu Lys Lys Ile Leu Met Asn Phe His Gln Lys Lys Asn
                370                 375                 380
Glu Ile Ser Phe Gln Gln Thr Asn Ala Met Val Thr Leu Arg Lys Glu
385                 390                 395                 400
Arg Leu Ala Lys Leu Thr Glu Ala Ile Thr Ala Ala Ser Leu Pro Lys
                405                 410                 415
Thr Ser Gly His Tyr Asp Asp Asp Asp Ile Pro Phe Pro Gly Pro
                420                 425                 430
Ile Asn Asp Asp Asp Asn Pro Gly His Gln Asp Asp Pro Thr Asp
                435                 440                 445
Ser Gln Asp Thr Thr Ile Pro Asp Val Val Asp Pro Asp Asp Gly
                450                 455                 460
Ser Tyr Gly Glu Tyr Gln Ser Tyr Ser Glu Asn Gly Met Asn Ala Pro
465                 470                 475                 480
Asp Asp Leu Val Leu Phe Asp Leu Asp Glu Asp Glu Asp Thr Lys
                485                 490                 495
```

Pro Val Pro Asn Arg Ser Thr Lys Gly Gly Gln Gln Lys Asn Ser Gln
            500                 505                 510

Lys Gly Gln His Ile Glu Gly Arg Gln Thr Gln Phe Arg Pro Ile Gln
        515                 520                 525

Asn Val Pro Gly Pro His Arg Thr Ile His His Ala Ser Ala Pro Leu
    530                 535                 540

Thr Asp Asn Asp Arg Arg Asn Glu Pro Ser Gly Ser Thr Ser Pro Arg
545                 550                 555                 560

Met Leu Thr Pro Ile Asn Glu Glu Ala Asp Pro Leu Asp Asp Ala Asp
                565                 570                 575

Asp Glu Thr Ser Ser Leu Pro Pro Leu Glu Ser Asp Glu Glu Gln
            580                 585                 590

Asp Arg Asp Gly Thr Ser Asn Arg Thr Pro Thr Val Ala Pro Pro Ala
            595                 600                 605

Pro Val Tyr Arg Asp His Ser Glu Lys Lys Glu Leu Pro Gln Asp Glu
        610                 615                 620

Gln Gln Asp Gln Asp His Thr Gln Glu Ala Arg Asn Gln Asp Ser Asp
625                 630                 635                 640

Asn Thr Gln Ser Glu His Ser Leu Glu Glu Met Tyr Arg His Ile Leu
                645                 650                 655

Arg Ser Gln Gly Pro Phe Asp Ala Val Leu Tyr Tyr His Met Met Lys
            660                 665                 670

Asp Glu Pro Val Val Phe Ser Thr Ser Asp Gly Lys Glu Tyr Thr Tyr
        675                 680                 685

Pro Asp Ser Leu Glu Glu Tyr Pro Pro Trp Leu Thr Glu Lys Glu
    690                 695                 700

Ala Met Asn Glu Glu Asn Arg Phe Val Thr Leu Asp Gly Gln Gln Phe
705                 710                 715                 720

Tyr Trp Pro Val Met Asn His Lys Asn Lys Phe Met Ala Ile Leu Gln
                725                 730                 735

His His Gln

<210> SEQ ID NO 39
<211> LENGTH: 340
<212> TYPE: PRT
<213> ORGANISM: Zaire Ebola virus strain Mayinga

<400> SEQUENCE: 39

Met Thr Thr Arg Thr Lys Gly Arg Gly His Thr Ala Ala Thr Thr Gln
1               5                   10                  15

Asn Asp Arg Met Pro Gly Pro Glu Leu Ser Gly Trp Ile Ser Glu Gln
                20                  25                  30

Leu Met Thr Gly Arg Ile Pro Val Ser Asp Ile Phe Cys Asp Ile Glu
            35                  40                  45

Asn Asn Pro Gly Leu Cys Tyr Ala Ser Gln Met Gln Gln Thr Lys Pro
        50                  55                  60

Asn Pro Lys Thr Arg Asn Ser Gln Thr Gln Thr Asp Pro Ile Cys Asn
65                  70                  75                  80

His Ser Phe Glu Glu Val Val Gln Thr Leu Ala Ser Leu Ala Thr Val
                85                  90                  95

Val Gln Gln Gln Thr Ile Ala Ser Glu Ser Leu Glu Gln Arg Ile Thr
            100                 105                 110

Ser Leu Glu Asn Gly Leu Lys Pro Val Tyr Asp Met Ala Lys Thr Ile
        115                 120                 125

```
Ser Ser Leu Asn Arg Val Cys Ala Glu Met Val Ala Lys Tyr Asp Leu
        130                 135                 140

Leu Val Met Thr Thr Gly Arg Ala Thr Ala Ala Ala Thr Glu
145                 150                 155                 160

Ala Tyr Trp Ala Glu His Gly Gln Pro Pro Gly Pro Ser Leu Tyr
                165                 170                 175

Glu Glu Ser Ala Ile Arg Gly Lys Ile Glu Ser Arg Asp Glu Thr Val
            180                 185                 190

Pro Gln Ser Val Arg Glu Ala Phe Asn Asn Leu Asn Ser Thr Thr Ser
            195                 200                 205

Leu Thr Glu Glu Asn Phe Gly Lys Pro Asp Ile Ser Ala Lys Asp Leu
210                 215                 220

Arg Asn Ile Met Tyr Asp His Leu Pro Gly Phe Gly Thr Ala Phe His
225                 230                 235                 240

Gln Leu Val Gln Val Ile Cys Lys Leu Gly Lys Asp Ser Asn Ser Leu
                245                 250                 255

Asp Ile Ile His Ala Glu Phe Gln Ala Ser Leu Ala Glu Gly Asp Ser
                260                 265                 270

Pro Gln Cys Ala Leu Ile Gln Ile Thr Lys Arg Val Pro Ile Phe Gln
            275                 280                 285

Asp Ala Ala Pro Pro Val Ile His Ile Arg Ser Arg Gly Asp Ile Pro
290                 295                 300

Arg Ala Cys Gln Lys Ser Leu Arg Pro Val Pro Pro Ser Pro Lys Ile
305                 310                 315                 320

Asp Arg Gly Trp Val Cys Val Phe Gln Leu Gln Asp Gly Lys Thr Leu
                325                 330                 335

Gly Leu Lys Ile
            340
```

<210> SEQ ID NO 40
<211> LENGTH: 326
<212> TYPE: PRT
<213> ORGANISM: Zaire Ebola virus strain Mayinga

<400> SEQUENCE: 40

```
Met Arg Arg Val Ile Leu Pro Thr Ala Pro Pro Glu Tyr Met Glu Ala
1               5                   10                  15

Ile Tyr Pro Val Arg Ser Asn Ser Thr Ile Ala Arg Gly Gly Asn Ser
                20                  25                  30

Asn Thr Gly Phe Leu Thr Pro Glu Ser Val Asn Gly Asp Thr Pro Ser
            35                  40                  45

Asn Pro Leu Arg Pro Ile Ala Asp Asp Thr Ile Asp His Ala Ser His
        50                  55                  60

Thr Pro Gly Ser Val Ser Ser Ala Phe Ile Leu Glu Ala Met Val Asn
65                  70                  75                  80

Val Ile Ser Gly Pro Lys Val Leu Met Lys Gln Ile Pro Ile Trp Leu
                85                  90                  95

Pro Leu Gly Val Ala Asp Gln Lys Thr Tyr Ser Phe Asp Ser Thr Thr
            100                 105                 110

Ala Ala Ile Met Leu Ala Ser Tyr Thr Ile Thr His Phe Gly Lys Ala
        115                 120                 125

Thr Asn Pro Leu Val Arg Val Asn Arg Leu Gly Pro Gly Ile Pro Asp
130                 135                 140

His Pro Leu Arg Leu Leu Arg Ile Gly Asn Gln Ala Phe Leu Gln Glu
```

```
                145                 150                 155                 160
            Phe Val Leu Pro Pro Val Gln Leu Pro Gln Tyr Phe Thr Phe Asp Leu
                            165                 170                 175

Thr Ala Leu Lys Leu Ile Thr Gln Pro Leu Pro Ala Ala Thr Trp Thr
                            180                 185                 190

Asp Asp Thr Pro Thr Gly Ser Asn Gly Ala Leu Arg Pro Gly Ile Ser
                            195                 200                 205

Phe His Pro Lys Leu Arg Pro Ile Leu Leu Pro Asn Lys Ser Gly Lys
                            210                 215                 220

Lys Gly Asn Ser Ala Asp Leu Thr Ser Pro Glu Lys Ile Gln Ala Ile
            225                 230                 235                 240

Met Thr Ser Leu Gln Asp Phe Lys Ile Val Pro Ile Asp Pro Thr Lys
                            245                 250                 255

Asn Ile Met Gly Ile Glu Val Pro Glu Thr Leu Val His Lys Leu Thr
                            260                 265                 270

Gly Lys Lys Val Thr Ser Lys Asn Gly Gln Pro Ile Ile Pro Val Leu
                            275                 280                 285

Leu Pro Lys Tyr Ile Gly Leu Asp Pro Val Ala Pro Gly Asp Leu Thr
                            290                 295                 300

Met Val Ile Thr Gln Asp Cys Asp Thr Cys His Ser Pro Ala Ser Leu
            305                 310                 315                 320

Pro Ala Val Ile Glu Lys
                            325

<210> SEQ ID NO 41
<211> LENGTH: 676
<212> TYPE: PRT
<213> ORGANISM: Zaire Ebola virus strain Mayinga

<400> SEQUENCE: 41

Met Gly Val Thr Gly Ile Leu Gln Leu Pro Arg Asp Arg Phe Lys Arg
            1               5                   10                  15

Thr Ser Phe Phe Leu Trp Val Ile Ile Leu Phe Gln Arg Thr Phe Ser
                            20                  25                  30

Ile Pro Leu Gly Val Ile His Asn Ser Thr Leu Gln Val Ser Asp Val
                            35                  40                  45

Asp Lys Leu Val Cys Arg Asp Lys Leu Ser Ser Thr Asn Gln Leu Arg
                            50                  55                  60

Ser Val Gly Leu Asn Leu Glu Gly Asn Gly Val Ala Thr Asp Val Pro
            65                  70                  75                  80

Ser Ala Thr Lys Arg Trp Gly Phe Arg Ser Gly Val Pro Pro Lys Val
                            85                  90                  95

Val Asn Tyr Glu Ala Gly Glu Trp Ala Glu Asn Cys Tyr Asn Leu Glu
                            100                 105                 110

Ile Lys Lys Pro Asp Gly Ser Glu Cys Leu Pro Ala Ala Pro Asp Gly
                            115                 120                 125

Ile Arg Gly Phe Pro Arg Cys Arg Tyr Val His Lys Val Ser Gly Thr
                            130                 135                 140

Gly Pro Cys Ala Gly Asp Phe Ala Phe His Lys Glu Gly Ala Phe Phe
            145                 150                 155                 160

Leu Tyr Asp Arg Leu Ala Ser Thr Val Ile Tyr Arg Gly Thr Thr Phe
                            165                 170                 175

Ala Glu Gly Val Val Ala Phe Leu Ile Leu Pro Gln Ala Lys Lys Asp
                            180                 185                 190
```

```
Phe Phe Ser Ser His Pro Leu Arg Glu Pro Val Asn Ala Thr Glu Asp
            195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
            340                 345                 350

Val His Ser Gln Gly Arg Glu Ala Ala Val Ser His Leu Thr Thr Leu
        355                 360                 365

Ala Thr Ile Ser Thr Ser Pro Gln Ser Leu Thr Thr Lys Pro Gly Pro
    370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                405                 410                 415

Ala Ser Asp Thr Pro Ser Ala Thr Thr Ala Ala Gly Pro Pro Lys Ala
            420                 425                 430

Glu Asn Thr Asn Thr Ser Lys Ser Thr Asp Phe Leu Asp Pro Ala Thr
        435                 440                 445

Thr Thr Ser Pro Gln Asn His Ser Glu Thr Ala Gly Asn Asn Asn Thr
    450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Ile
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
```

```
                   610                 615                 620
Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
            645                 650                 655

Gly Val Thr Gly Val Ile Ile Ala Val Ile Ala Leu Phe Cys Ile Cys
                660                 665                 670

Lys Phe Val Phe
        675

<210> SEQ ID NO 42
<211> LENGTH: 364
<212> TYPE: PRT
<213> ORGANISM: Zaire Ebola virus strain Mayinga

<400> SEQUENCE: 42

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
            35                  40                  45

Asp Lys Leu Val Cys Arg Asp Lys Leu Ser Ser Thr Asn Gln Leu Arg
50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Thr Ser Leu Glu Lys Phe Ala Val Lys
    290                 295                 300
```

```
Ser Cys Leu Ser Gln Leu Tyr Gln Thr Glu Pro Lys Thr Ser Val Val
305                 310                 315                 320

Arg Val Arg Arg Glu Leu Leu Pro Thr Gln Gly Pro Thr Gln Gln Leu
                325                 330                 335

Lys Thr Thr Lys Ser Trp Leu Gly Lys Ile Pro Leu Gln Trp Phe Lys
                340                 345                 350

Cys Thr Val Lys Glu Gly Lys Leu Gln Cys Arg Ile
                355                 360

<210> SEQ ID NO 43
<211> LENGTH: 288
<212> TYPE: PRT
<213> ORGANISM: Zaire Ebola virus strain Mayinga

<400> SEQUENCE: 43

Met Glu Ala Ser Tyr Glu Arg Gly Arg Pro Arg Ala Ala Arg Gln His
1               5                   10                  15

Ser Arg Asp Gly His Asp His His Val Arg Ala Arg Ser Ser Ser Arg
                20                  25                  30

Glu Asn Tyr Arg Gly Glu Tyr Arg Gln Ser Arg Ser Ala Ser Gln Val
            35                  40                  45

Arg Val Pro Thr Val Phe His Lys Lys Arg Val Glu Pro Leu Thr Val
50                  55                  60

Pro Pro Ala Pro Lys Asp Ile Cys Pro Thr Leu Lys Lys Gly Phe Leu
65                  70                  75                  80

Cys Asp Ser Ser Phe Cys Lys Lys Asp His Gln Leu Glu Ser Leu Thr
                85                  90                  95

Asp Arg Glu Leu Leu Leu Leu Ile Ala Arg Lys Thr Cys Gly Ser Val
            100                 105                 110

Glu Gln Gln Leu Asn Ile Thr Ala Pro Lys Asp Ser Arg Leu Ala Asn
        115                 120                 125

Pro Thr Ala Asp Asp Phe Gln Gln Glu Glu Gly Pro Lys Ile Thr Leu
    130                 135                 140

Leu Thr Leu Ile Lys Thr Ala Glu His Trp Ala Arg Gln Asp Ile Arg
145                 150                 155                 160

Thr Ile Glu Asp Ser Lys Leu Arg Ala Leu Leu Thr Leu Cys Ala Val
                165                 170                 175

Met Thr Arg Lys Phe Ser Lys Ser Gln Leu Ser Leu Leu Cys Glu Thr
            180                 185                 190

His Leu Arg Arg Glu Gly Leu Gly Gln Asp Gln Ala Glu Pro Val Leu
        195                 200                 205

Glu Val Tyr Gln Arg Leu His Ser Asp Lys Gly Gly Ser Phe Glu Ala
    210                 215                 220

Ala Leu Trp Gln Gln Trp Asp Arg Gln Ser Leu Ile Met Phe Ile Thr
225                 230                 235                 240

Ala Phe Leu Asn Ile Ala Leu Gln Leu Pro Cys Glu Ser Ser Ala Val
                245                 250                 255

Val Val Ser Gly Leu Arg Thr Leu Val Pro Gln Ser Asp Asn Glu Glu
            260                 265                 270

Ala Ser Thr Asn Pro Gly Thr Cys Ser Trp Ser Asp Glu Gly Thr Pro
        275                 280                 285

<210> SEQ ID NO 44
<211> LENGTH: 251
<212> TYPE: PRT
<213> ORGANISM: Zaire Ebola virus strain Mayinga
```

<400> SEQUENCE: 44

```
Met Ala Lys Ala Thr Gly Arg Tyr Asn Leu Ile Ser Pro Lys Lys Asp
 1               5                  10                  15

Leu Glu Lys Gly Val Val Leu Ser Asp Leu Cys Asn Phe Leu Val Ser
                20                  25                  30

Gln Thr Ile Gln Gly Trp Lys Val Tyr Trp Ala Gly Ile Glu Phe Asp
            35                  40                  45

Val Thr His Lys Gly Met Ala Leu Leu His Arg Leu Lys Thr Asn Asp
        50                  55                  60

Phe Ala Pro Ala Trp Ser Ile Thr Arg Asn Leu Phe Pro His Leu Phe
65                  70                  75                  80

Gln Asn Pro Asn Ser Thr Ile Glu Ser Pro Leu Trp Ala Leu Arg Val
                85                  90                  95

Ile Leu Ala Ala Gly Ile Gln Asp Gln Leu Ile Asp Gln Ser Leu Ile
                100                 105                 110

Glu Pro Leu Ala Gly Ala Leu Gly Leu Ile Ser Asp Trp Leu Leu Thr
            115                 120                 125

Thr Asn Thr Asn His Phe Asn Met Arg Thr Gln Arg Val Lys Glu Gln
        130                 135                 140

Leu Ser Pro Lys Met Leu Ser Leu Ile Arg Ser Asn Ile Leu Lys Phe
145                 150                 155                 160

Ile Asn Lys Leu Asp Ala Leu His Val Val Asn Tyr Asn Gly Leu Leu
                165                 170                 175

Ser Ser Ile Glu Ile Gly Thr Gln Asn His Ile Ile Ile Thr Arg
            180                 185                 190

Thr Asn Met Gly Phe Leu Val Glu Leu Gln Glu Pro Asp Lys Ser Ala
        195                 200                 205

Met Asn Arg Met Lys Pro Gly Pro Ala Lys Phe Ser Leu Leu His Glu
    210                 215                 220

Ser Thr Leu Lys Ala Phe Thr Gln Gly Ser Ser Thr Arg Met Gln Ser
225                 230                 235                 240

Leu Ile Leu Glu Phe Asn Ser Ser Leu Ala Ile
                245                 250
```

<210> SEQ ID NO 45
<211> LENGTH: 2212
<212> TYPE: PRT
<213> ORGANISM: Zaire Ebola virus strain Mayinga

<400> SEQUENCE: 45

```
Met Ala Thr Gln His Thr Gln Tyr Pro Asp Ala Arg Leu Ser Ser Pro
 1               5                  10                  15

Ile Val Leu Asp Gln Cys Asp Leu Val Thr Arg Ala Cys Gly Leu Tyr
                20                  25                  30

Ser Ser Tyr Ser Leu Asn Pro Gln Leu Arg Asn Cys Lys Leu Pro Lys
            35                  40                  45

His Ile Tyr Arg Leu Lys Tyr Asp Val Thr Val Thr Lys Phe Leu Ser
        50                  55                  60

Asp Val Pro Val Ala Thr Leu Pro Ile Asp Phe Ile Val Pro Val Leu
65                  70                  75                  80

Leu Lys Ala Leu Ser Gly Asn Gly Phe Cys Pro Val Glu Pro Arg Cys
                85                  90                  95

Gln Gln Phe Leu Asp Glu Ile Ile Lys Tyr Thr Met Gln Asp Ala Leu
                100                 105                 110
```

-continued

```
Phe Leu Lys Tyr Tyr Leu Lys Asn Val Gly Ala Gln Glu Asp Cys Val
            115                 120                 125

Asp Glu His Phe Gln Glu Lys Ile Leu Ser Ser Ile Gln Gly Asn Glu
        130                 135                 140

Phe Leu His Gln Met Phe Phe Trp Tyr Asp Leu Ala Ile Leu Thr Arg
145                 150                 155                 160

Arg Gly Arg Leu Asn Arg Gly Asn Ser Arg Ser Thr Trp Phe Val His
                165                 170                 175

Asp Asp Leu Ile Asp Ile Leu Gly Tyr Gly Asp Tyr Val Phe Trp Lys
            180                 185                 190

Ile Pro Ile Ser Met Leu Pro Leu Asn Thr Gln Gly Ile Pro His Ala
        195                 200                 205

Ala Met Asp Trp Tyr Gln Ala Ser Val Phe Lys Glu Ala Val Gln Gly
210                 215                 220

His Thr His Ile Val Ser Val Ser Thr Ala Asp Val Leu Ile Met Cys
225                 230                 235                 240

Lys Asp Leu Ile Thr Cys Arg Phe Asn Thr Thr Leu Ile Ser Lys Ile
                245                 250                 255

Ala Glu Ile Glu Asp Pro Val Cys Ser Asp Tyr Pro Asn Phe Lys Ile
            260                 265                 270

Val Ser Met Leu Tyr Gln Ser Gly Asp Tyr Leu Leu Ser Ile Leu Gly
        275                 280                 285

Ser Asp Gly Tyr Lys Ile Ile Lys Phe Leu Glu Pro Leu Cys Leu Ala
290                 295                 300

Lys Ile Gln Leu Cys Ser Lys Tyr Thr Glu Arg Lys Gly Arg Phe Leu
305                 310                 315                 320

Thr Gln Met His Leu Ala Val Asn His Thr Leu Glu Glu Ile Thr Glu
                325                 330                 335

Met Arg Ala Leu Lys Pro Ser Gln Ala Gln Lys Ile Arg Glu Phe His
            340                 345                 350

Arg Thr Leu Ile Arg Leu Glu Met Thr Pro Gln Gln Leu Cys Glu Leu
        355                 360                 365

Phe Ser Ile Gln Lys His Trp Gly His Pro Val Leu His Ser Glu Thr
370                 375                 380

Ala Ile Gln Lys Val Lys Lys His Ala Thr Val Leu Lys Ala Leu Arg
385                 390                 395                 400

Pro Ile Val Ile Phe Glu Thr Tyr Cys Val Phe Lys Tyr Ser Ile Ala
                405                 410                 415

Lys His Tyr Phe Asp Ser Gln Gly Ser Trp Tyr Ser Val Thr Ser Asp
            420                 425                 430

Arg Asn Leu Thr Pro Gly Leu Asn Ser Tyr Ile Lys Arg Asn Gln Phe
        435                 440                 445

Pro Pro Leu Pro Met Ile Lys Glu Leu Leu Trp Glu Phe Tyr His Leu
450                 455                 460

Asp His Pro Pro Leu Phe Ser Thr Lys Ile Ile Ser Asp Leu Ser Ile
465                 470                 475                 480

Phe Ile Lys Asp Arg Ala Thr Ala Val Glu Arg Thr Cys Trp Asp Ala
                485                 490                 495

Val Phe Glu Pro Asn Val Leu Gly Tyr Asn Pro Pro His Lys Phe Ser
            500                 505                 510

Thr Lys Arg Val Pro Glu Gln Phe Leu Glu Gln Glu Asn Phe Ser Ile
        515                 520                 525
```

```
Glu Asn Val Leu Ser Tyr Ala Gln Lys Leu Glu Tyr Leu Leu Pro Gln
            530                 535                 540

Tyr Arg Asn Phe Ser Phe Ser Leu Lys Glu Lys Glu Leu Asn Val Gly
545                 550                 555                 560

Arg Thr Phe Gly Lys Leu Pro Tyr Pro Thr Arg Asn Val Gln Thr Leu
                565                 570                 575

Cys Glu Ala Leu Leu Ala Asp Gly Leu Ala Lys Ala Phe Pro Ser Asn
            580                 585                 590

Met Met Val Val Thr Glu Arg Glu Gln Lys Glu Ser Leu Leu His Gln
            595                 600                 605

Ala Ser Trp His His Thr Ser Asp Asp Phe Gly Glu His Ala Thr Val
610                 615                 620

Arg Gly Ser Ser Phe Val Thr Asp Leu Glu Lys Tyr Asn Leu Ala Phe
625                 630                 635                 640

Arg Tyr Glu Phe Thr Ala Pro Phe Ile Glu Tyr Cys Asn Arg Cys Tyr
                645                 650                 655

Gly Val Lys Asn Val Phe Asn Trp Met His Tyr Thr Ile Pro Gln Cys
            660                 665                 670

Tyr Met His Val Ser Asp Tyr Tyr Asn Pro His Asn Leu Thr Leu
            675                 680                 685

Glu Asn Arg Asp Asn Pro Pro Glu Gly Pro Ser Ser Tyr Arg Gly His
690                 695                 700

Met Gly Gly Ile Glu Gly Leu Gln Gln Lys Leu Trp Thr Ser Ile Ser
705                 710                 715                 720

Cys Ala Gln Ile Ser Leu Val Glu Ile Lys Thr Gly Phe Lys Leu Arg
                725                 730                 735

Ser Ala Val Met Gly Asp Asn Gln Cys Ile Thr Val Leu Ser Val Phe
            740                 745                 750

Pro Leu Glu Thr Asp Ala Asp Glu Gln Glu Gln Ser Ala Glu Asp Asn
            755                 760                 765

Ala Ala Arg Val Ala Ala Ser Leu Ala Lys Val Thr Ser Ala Cys Gly
770                 775                 780

Ile Phe Leu Lys Pro Asp Glu Thr Phe Val His Ser Gly Phe Ile Tyr
785                 790                 795                 800

Phe Gly Lys Lys Gln Tyr Leu Asn Gly Val Gln Leu Pro Gln Ser Leu
                805                 810                 815

Lys Thr Ala Ala Arg Met Ala Pro Leu Ser Asp Ala Ile Phe Asp Asp
            820                 825                 830

Leu Gln Gly Thr Leu Ala Ser Ile Gly Thr Ala Phe Glu Arg Ser Ile
            835                 840                 845

Ser Glu Thr Arg His Ile Phe Pro Cys Arg Ile Thr Ala Ala Phe His
850                 855                 860

Thr Phe Phe Ser Val Arg Ile Leu Gln Tyr His His Leu Gly Phe Asn
865                 870                 875                 880

Lys Gly Phe Asp Leu Gly Gln Leu Thr Leu Gly Lys Pro Leu Asp Phe
                885                 890                 895

Gly Thr Ile Ser Leu Ala Leu Ala Val Pro Gln Val Leu Gly Gly Leu
            900                 905                 910

Ser Phe Leu Asn Pro Glu Lys Cys Phe Tyr Arg Asn Leu Gly Asp Pro
            915                 920                 925

Val Thr Ser Gly Leu Phe Gln Leu Lys Thr Tyr Leu Arg Met Ile Glu
930                 935                 940

Met Asp Asp Leu Phe Leu Pro Leu Ile Ala Lys Asn Pro Gly Asn Cys
```

```
                945                 950                 955                 960
            Thr Ala Ile Asp Phe Val Leu Asn Pro Ser Gly Leu Asn Val Pro Gly
                            965                 970                 975
            Ser Gln Asp Leu Thr Ser Phe Leu Arg Gln Ile Val Arg Arg Thr Ile
                            980                 985                 990
            Thr Leu Ser Ala Lys Asn Lys Leu Ile Asn Thr Leu Phe His Ala Ser
                            995                 1000                1005
            Ala Asp Phe Glu Asp Glu Met Val Cys Lys Trp Leu Leu Ser Ser Thr
                            1010                1015                1020
            Pro Val Met Ser Arg Phe Ala Ala Asp Ile Phe Ser Arg Thr Pro Ser
            1025                1030                1035                1040
            Gly Lys Arg Leu Gln Ile Leu Gly Tyr Leu Glu Gly Thr Arg Thr Leu
                            1045                1050                1055
            Leu Ala Ser Lys Ile Ile Asn Asn Asn Thr Glu Thr Pro Val Leu Asp
                            1060                1065                1070
            Arg Leu Arg Lys Ile Thr Leu Gln Arg Trp Ser Leu Trp Phe Ser Tyr
                            1075                1080                1085
            Leu Asp His Cys Asp Asn Ile Leu Ala Glu Ala Leu Thr Gln Ile Thr
                            1090                1095                1100
            Cys Thr Val Asp Leu Ala Gln Ile Leu Arg Glu Tyr Ser Trp Ala His
            1105                1110                1115                1120
            Ile Leu Glu Gly Arg Pro Leu Ile Gly Ala Thr Leu Pro Cys Met Ile
                            1125                1130                1135
            Glu Gln Phe Lys Val Phe Trp Leu Lys Pro Tyr Glu Gln Cys Pro Gln
                            1140                1145                1150
            Cys Ser Asn Ala Lys Gln Pro Gly Gly Lys Pro Phe Val Ser Val Ala
                            1155                1160                1165
            Val Lys Lys His Ile Val Ser Ala Trp Pro Asn Ala Ser Arg Ile Ser
                            1170                1175                1180
            Trp Thr Ile Gly Asp Gly Ile Pro Tyr Ile Gly Ser Arg Thr Glu Asp
            1185                1190                1195                1200
            Lys Ile Gly Gln Pro Ala Ile Lys Pro Lys Cys Pro Ser Ala Ala Leu
                            1205                1210                1215
            Arg Glu Ala Ile Glu Leu Ala Ser Arg Leu Thr Trp Val Thr Gln Gly
                            1220                1225                1230
            Ser Ser Asn Ser Asp Leu Leu Ile Lys Pro Phe Leu Glu Ala Arg Val
                            1235                1240                1245
            Asn Leu Ser Val Gln Glu Ile Leu Gln Met Thr Pro Ser His Tyr Ser
                            1250                1255                1260
            Gly Asn Ile Val His Arg Tyr Asn Asp Gln Tyr Ser Pro His Ser Phe
            1265                1270                1275                1280
            Met Ala Asn Arg Met Ser Asn Ser Ala Thr Arg Leu Ile Val Ser Thr
                            1285                1290                1295
            Asn Thr Leu Gly Glu Phe Ser Gly Gly Gly Gln Ser Ala Arg Asp Ser
                            1300                1305                1310
            Asn Ile Ile Phe Gln Asn Val Ile Asn Tyr Ala Val Ala Leu Phe Asp
                            1315                1320                1325
            Ile Lys Phe Arg Asn Thr Glu Ala Thr Asp Ile Gln Tyr Asn Arg Ala
                            1330                1335                1340
            His Leu His Leu Thr Lys Cys Cys Thr Arg Glu Val Pro Ala Gln Tyr
            1345                1350                1355                1360
            Leu Thr Tyr Thr Ser Thr Leu Asp Leu Asp Leu Thr Arg Tyr Arg Glu
                            1365                1370                1375
```

```
Asn Glu Leu Ile Tyr Asp Ser Asn Pro Leu Lys Gly Gly Leu Asn Cys
        1380                1385                1390

Asn Ile Ser Phe Asp Asn Pro Phe Phe Gln Gly Lys Arg Leu Asn Ile
        1395                1400                1405

Ile Glu Asp Asp Leu Ile Arg Leu Pro His Leu Ser Gly Trp Glu Leu
        1410                1415                1420

Ala Lys Thr Ile Met Gln Ser Ile Ile Ser Asp Ser Asn Asn Ser Ser
1425                1430                1435                1440

Thr Asp Pro Ile Ser Ser Gly Glu Thr Arg Ser Phe Thr Thr His Phe
                1445                1450                1455

Leu Thr Tyr Pro Lys Ile Gly Leu Leu Tyr Ser Phe Gly Ala Phe Val
        1460                1465                1470

Ser Tyr Tyr Leu Gly Asn Thr Ile Leu Arg Thr Lys Lys Leu Thr Leu
        1475                1480                1485

Asp Asn Phe Leu Tyr Tyr Leu Thr Thr Gln Ile His Asn Leu Pro His
        1490                1495                1500

Arg Ser Leu Arg Ile Leu Lys Pro Thr Phe Lys His Ala Ser Val Met
1505                1510                1515                1520

Ser Arg Leu Met Ser Ile Asp Pro His Phe Ser Ile Tyr Ile Gly Gly
                1525                1530                1535

Ala Ala Gly Asp Arg Gly Leu Ser Asp Ala Ala Arg Leu Phe Leu Arg
                1540                1545                1550

Thr Ser Ile Ser Ser Phe Leu Thr Phe Val Lys Glu Trp Ile Ile Asn
                1555                1560                1565

Arg Gly Thr Ile Val Pro Leu Trp Ile Val Tyr Pro Leu Glu Gly Gln
        1570                1575                1580

Asn Pro Thr Pro Val Asn Asn Phe Leu Tyr Gln Ile Val Glu Leu Leu
1585                1590                1595                1600

Val His Asp Ser Ser Arg Gln Gln Ala Phe Lys Thr Thr Ile Ser Asp
                1605                1610                1615

His Val His Pro His Asp Asn Leu Val Tyr Thr Cys Lys Ser Thr Ala
                1620                1625                1630

Ser Asn Phe Phe His Ala Ser Leu Ala Tyr Trp Arg Ser Arg His Arg
        1635                1640                1645

Asn Ser Asn Arg Lys Tyr Leu Ala Arg Asp Ser Ser Thr Gly Ser Ser
        1650                1655                1660

Thr Asn Asn Ser Asp Gly His Ile Glu Arg Ser Gln Glu Gln Thr Thr
1665                1670                1675                1680

Arg Asp Pro His Asp Gly Thr Glu Arg Asn Leu Val Leu Gln Met Ser
                1685                1690                1695

His Glu Ile Lys Arg Thr Thr Ile Pro Gln Glu Asn Thr His Gln Gly
        1700                1705                1710

Pro Ser Phe Gln Ser Phe Leu Ser Asp Ser Ala Cys Gly Thr Ala Asn
        1715                1720                1725

Pro Lys Leu Asn Phe Asp Arg Ser Arg His Asn Val Lys Phe Gln Asp
        1730                1735                1740

His Asn Ser Ala Ser Lys Arg Glu Gly His Gln Ile Ile Ser His Arg
1745                1750                1755                1760

Leu Val Leu Pro Phe Phe Thr Leu Ser Gln Gly Thr Arg Gln Leu Thr
                1765                1770                1775

Ser Ser Asn Glu Ser Gln Thr Gln Asp Glu Ile Ser Lys Tyr Leu Arg
                1780                1785                1790
```

-continued

Gln Leu Arg Ser Val Ile Asp Thr Thr Val Tyr Cys Arg Phe Thr Gly
        1795                1800                1805

Ile Val Ser Ser Met His Tyr Lys Leu Asp Glu Val Leu Trp Glu Ile
    1810                1815                1820

Glu Ser Phe Lys Ser Ala Val Thr Leu Ala Glu Gly Glu Gly Ala Gly
1825                1830                1835                1840

Ala Leu Leu Leu Ile Gln Lys Tyr Gln Val Lys Thr Leu Phe Phe Asn
            1845                1850                1855

Thr Leu Ala Thr Glu Ser Ser Ile Glu Ser Glu Ile Val Ser Gly Met
        1860                1865                1870

Thr Thr Pro Arg Met Leu Leu Pro Val Met Ser Lys Phe His Asn Asp
        1875                1880                1885

Gln Ile Glu Ile Ile Leu Asn Asn Ser Ala Ser Gln Ile Thr Asp Ile
        1890                1895                1900

Thr Asn Pro Thr Trp Phe Lys Asp Gln Arg Ala Arg Leu Pro Lys Gln
1905                1910                1915                1920

Val Glu Val Ile Thr Met Asp Ala Glu Thr Thr Glu Asn Ile Asn Arg
            1925                1930                1935

Ser Lys Leu Tyr Glu Ala Val Tyr Lys Leu Ile Leu His His Ile Asp
        1940                1945                1950

Pro Ser Val Leu Lys Ala Val Val Leu Lys Val Phe Leu Ser Asp Thr
        1955                1960                1965

Glu Gly Met Leu Trp Leu Asn Asp Asn Leu Ala Pro Phe Phe Ala Thr
        1970                1975                1980

Gly Tyr Leu Ile Lys Pro Ile Thr Ser Ser Ala Arg Ser Ser Glu Trp
1985                1990                1995                2000

Tyr Leu Cys Leu Thr Asn Phe Leu Ser Thr Thr Arg Lys Met Pro His
            2005                2010                2015

Gln Asn His Leu Ser Cys Lys Gln Val Ile Leu Thr Ala Leu Gln Leu
        2020                2025                2030

Gln Ile Gln Arg Ser Pro Tyr Trp Leu Ser His Leu Thr Gln Tyr Ala
        2035                2040                2045

Asp Cys Glu Leu His Leu Ser Tyr Ile Arg Leu Gly Phe Pro Ser Leu
    2050                2055                2060

Glu Lys Val Leu Tyr His Arg Tyr Asn Leu Val Asp Ser Lys Arg Gly
2065                2070                2075                2080

Pro Leu Val Ser Ile Thr Gln His Leu Ala His Leu Arg Ala Glu Ile
            2085                2090                2095

Arg Glu Leu Thr Asn Asp Tyr Asn Gln Gln Arg Gln Ser Arg Thr Gln
        2100                2105                2110

Thr Tyr His Phe Ile Arg Thr Ala Lys Gly Arg Ile Thr Lys Leu Val
        2115                2120                2125

Asn Asp Tyr Leu Lys Phe Phe Leu Ile Val Gln Ala Leu Lys His Asn
    2130                2135                2140

Gly Thr Trp Gln Ala Glu Phe Lys Lys Leu Pro Glu Leu Ile Ser Val
2145                2150                2155                2160

Cys Asn Arg Phe Tyr His Ile Arg Asp Cys Asn Cys Glu Arg Phe
            2165                2170                2175

Leu Val Gln Thr Leu Tyr Leu His Arg Met Gln Asp Ser Glu Val Lys
        2180                2185                2190

Leu Ile Glu Arg Leu Thr Gly Leu Leu Ser Leu Phe Pro Asp Gly Leu
        2195                2200                2205

Tyr Arg Phe Asp

2210

<210> SEQ ID NO 46
<211> LENGTH: 18959
<212> TYPE: DNA
<213> ORGANISM: Zaire Ebola virus strain Mayinga

<400> SEQUENCE: 46

```
cggacacaca aaaagaaaga agaattttta ggatcttttg tgtgcgaata actatgagga      60
agattaataa ttttcctctc attgaaattt atatcggaat ttaaattgaa attgttactg     120
taatcacacc tggtttgttt cagagccaca tcacaaagat agagaacaac ctaggtctcc     180
gaagggagca agggcatcag tgtgctcagt tgaaaatccc ttgtcaacac ctaggtctta     240
tcacatcaca agttccacct cagactctgc agggtgatcc aacaacctta atagaaacat     300
tattgttaaa ggacagcatt agttcacagt caaacaagca agattgagaa ttaaccttgg     360
ttttgaactt gaacacttag gggattgaag attcaacaac cctaaagctt ggggtaaaac     420
attggaaata gttaaaagac aaaattgctcg gaatcacaaa attccgagta tggattctcg     480
tcctcagaaa atctggatgg cgccgagtct cactgaatct gacatggatt accacaagat     540
cttgacagca ggtctgtccg ttcaacaggg gattgttcgg caaagagtca tcccagtgta     600
tcaagtaaac aatcttgaag aaatttgcca acttatcata caggcctttg aagcaggtgt     660
tgattttcaa gagagtgcgg acagtttcct tctcatgctt gtgtcttcatc atgcgtacca     720
gggagattac aaacttttct tggaaagtgg cgcagtcaag tatttggaag gcacgggtt      780
ccgttttgaa gtcaagaagc gtgatggagt gaagcgcctt gaggaattgc tgccagcagt     840
atctagtgga aaaaacatta agagaacact tgctgccatg ccggaagagg agacaactga     900
agctaatgcc ggtcagtttc tctcctttgc aagtctattc cttccgaaat tggtagtagg     960
agaaaaggct tgccttgaga aggttcaaag gcaaattcaa gtacatgcag agcaaggact    1020
gatacaatat ccaacagctt ggcaatcagt aggacacatg atggtgattt ccgtttgat     1080
gcgaacaaat tttctgatca aattctcct aatacaccaa gggatgcaca tggttgccgg    1140
gcatgatgcc aacgatgctg tgatttcaaa ttcagtggct caagtcgtt tttcaggctt     1200
attgattgtc aaaacagtac ttgatcatat cctacaaaag acagaacgag gagttcgtct     1260
ccatcctctt gcaaggaccg ccaaggtaaa aatgaggtg aactccttta aggctgcact     1320
cagctccctg gccaagcatg gagagtatgc tcctttcgcc cgacttttga acctttctgg    1380
agtaaataat cttgagcatg gtcttttccc tcaactatcg gcaattgcac tcggagtcgc    1440
cacagcacac gggagtaccc tcgcaggagt aaatgttgga gaacagtatc aacaactcag    1500
agaggctgcc actgaggctg agaagcaact ccaacaatat gcagagtctc gcgaacttga    1560
ccatcttgga cttgatgatc aggaaaagaa aattcttatg aacttccatc agaaaaagaa    1620
cgaaatcagc ttccagcaaa caaacgctat ggtaactcta agaaaagagc gcctggccaa    1680
gctgacagaa gctatcactg ctgcgtcact gcccaaaaca agtggacatt acgatgatga    1740
tgacgacatt cccttttccag gacccatcaa tgatgacgac aatcctggcc atcaagatga    1800
tgatccgact gactcacagg atacgaccat tcccgatgtg gtggttgatc ctgatgatgg    1860
aagctacggc gaataccaga gttactcgga aaacggcatg aatgcaccag atgacttggt    1920
cctattcgat ctagacgagg acgacgagga cactaagcca gtgcctaata gatcgaccaa    1980
gggtggacaa cagaagaaca gtcaaaaggg ccagcatata gagggcagac agacacaatt    2040
caggccaatt caaaatgtcc caggcccctca cagaacaatc caccacgcca gtgcgccact    2100
```

```
cacggacaat gacagaagaa atgaaccctc cggctcaacc agccctcgca tgctgacacc  2160
aattaacgaa gaggcagacc cactggacga tgccgacgac gagacgtcta gccttccgcc  2220
cttggagtca gatgatgaag agcaggacag ggacggaact tccaaccgca cacccactgt  2280
cgccccaccg gctcccgtat acagagatca ctctgaaaag aaagaactcc cgcaagacga  2340
gcaacaagat caggaccaca ctcaagaggc caggaaccag gacagtgaca cacccagtc   2400
agaacactcc cttgaggaga tgtatcgcca cattctaaga tcacagggc catttgatgc   2460
tgttttgtat tatcatatga tgaaggatga gcctgtagtt ttcagtacca gtgatggcaa  2520
agagtacacg tatccagact cccttgaaga ggaatatcca ccatggctca ctgaaaaaga  2580
ggctatgaat gaagagaata gatttgttac attggatggt caacaatttt attggccggt  2640
gatgaatcac aagaataaat tcatggcaat cctgcaacat catcagtgaa tgagcatgga  2700
acaatgggat gattcaaccg acaaatagct aacattaagt agtcaaggaa cgaaaacagg  2760
aagaattttt gatgtctaag gtgtgaatta ttatcacaat aaaagtgatt cttattttg   2820
aatttaaagc tagcttatta ttactagccg tttttcaaag ttcaatttga gtcttaatgc  2880
aaataggcgt taagccacag ttatagccat aattgtaact caatattcta actagcgatt  2940
tatctaaatt aaattacatt atgctttat aacttaccta ctagcctgcc caacatttac   3000
acgatcgttt tataattaag aaaaaactaa tgatgaagat taaaaccttc atcatcctta  3060
cgtcaattga attctctagc actcgaagct tattgtcttc aatgtaaaag aaaagctggt  3120
ctaacaagat gacaactaga acaaagggca ggggccatac tgcggccacg actcaaaacg  3180
acagaatgcc aggccctgag ctttcgggct ggatctctga gcagctaatg accggaagaa  3240
ttcctgtaag cgacatcttc tgtgatattg agaacaatcc aggattatgc tacgcatccc  3300
aaatgcaaca aacgaagcca aacccgaaga cgcgcaacag tcaaacccaa acggacccaa  3360
tttgcaatca tagttttgag gaggtagtac aaacattggc ttcattggct actgttgtgc  3420
aacaacaaac catcgcatca gaatcattag acaacgcat tacgagtctt gagaatggtc   3480
taaagccagt ttatgatatg gcaaaaacaa tctcctcatt gaacagggtt gtgctgaga   3540
tggttgcaaa atatgatctt ctggtgatga caaccggtcg ggcaacagca accgctgcgg  3600
caactgaggc ttattgggcc gaacatggtc aaccaccacc tggaccatca ctttatgaag  3660
aaagtgcgat tcggggtaag attgaatcta gagatgagc cgtccctcaa agtgttaggg   3720
aggcattcaa caatctaaac agtaccactt cactaactga ggaaaatttt gggaaacctg  3780
acatttcggc aaaggatttg agaaacatta tgtatgatca cttgcctggt tttgaactg   3840
ctttccacca attagtacaa gtgatttgta aattgggaaa agatagcaac tcattggaca  3900
tcattcatgc tgagttccag gccagcctgg ctgaaggaga ctctcctcaa tgtgccctaa  3960
ttcaaattac aaaaagagtt ccaatcttcc aagatgctgc tccacctgtc atccacatcc  4020
gctctcgagg tgacattccc cgagcttgcc agaaaagctt gcgtccagtc ccaccatcgc  4080
ccaagattga tcgaggttgg gtatgtgttt ttcagcttca agatggtaaa acacttggac  4140
tcaaaatttg agccaatctc ccttccctcc gaaagaggcg aataaatagca gaggcttcaa  4200
ctgctgaact ataggtacg ttacattaat gatacttg tgagtatcag ccctggataa    4260
tataagtcaa ttaaacgacc aagataaaat tgttcatatc tcgctagcag cttaaaatat  4320
aaatgtaata ggagctatat ctctgacagt attataatca attgttatta agtaacccaa  4380
accaaaagtg atgaagatta agaaaaacct acctcggctg agagagtgtt ttttcattaa  4440
```

```
ccttcatctt gtaaacgttg agcaaaattg ttaaaaatat gaggcgggtt atattgccta    4500
ctgctcctcc tgaatatatg gaggccatat accctgtcag gtcaaattca acaattgcta    4560
gaggtggcaa cagcaataca ggcttcctga caccggagtc agtcaatggg gacactccat    4620
cgaatccact caggccaatt gccgatgaca ccatcgacca tgccagccac acaccaggca    4680
gtgtgtcatc agcattcatc cttgaagcta tggtgaatgt catatcgggc cccaaagtgc    4740
taatgaagca aattccaatt tggcttcctc taggtgtcgc tgatcaaaag acctacagct    4800
ttgactcaac tacggccgcc atcatgcttg cttcatacac tatcacccat tcggcaagg     4860
caaccaatcc acttgtcaga gtcaatcggc tgggtcctgg aatcccggat catcccctca    4920
ggctcctgcg aattggaaac caggcttttcc tccaggagtt cgttcttccg ccagtccaac    4980
taccccagta tttcaccttt gatttgacag cactcaaact gatcacccaa ccactgcctg    5040
ctgcaacatg gaccgatgac actccaacag gatcaaatgg agcgttgcgt ccaggaattt    5100
catttcatcc aaaacttcgc cccattcttt tacccaacaa agtgggaag aagggg aaca    5160
gtgccgatct aacatctccg gagaaaatcc aagcaataat gacttcactc caggacttta    5220
agatcgttcc aattgatcca accaaaaata tcatgggaat cgaagtgcca gaaactctgg    5280
tccacaagct gaccggtaag aaggtgactt ctaaaaatgg acaaccaatc atccctgttc    5340
ttttgccaaa gtacattggg ttggacccgg tggctccagg agacctcacc atggtaatca    5400
cacaggattg tgacacgtgt cattctcctg caagtcttcc agctgtgatt gagaagtaat    5460
tgcaataatt gactcagatc cagttttata gaatcttctc agggatagtg ataacatcta    5520
tttagtaatc cgtccattag aggagacact tttaattgat caatatacta aaggtgcttt    5580
acaccattgt cttttttctc tcctaaatgt agaacttaac aaaagactca taatatactt    5640
gttttttaaag gattgattga tgaaagatca taactaataa cattacaaat aatcctacta    5700
taatcaatac ggtgattcaa atgttaatct ttctcattgc acatactttt tgcccttatc    5760
ctcaaattgc ctgcatgctt acatctgagg atagccagtg tgacttggat tggaaatgtg    5820
gagaaaaaat cgggacccat ttctaggttg ttcacaatcc aagtacagac attgcccttc    5880
taattaagaa aaaatcggcg atgaagatta agccgacagt gagcgtaatc ttcatctctc    5940
ttagattatt tgttttccag agtaggggtc gtcaggtcct tttcaatcgt gtaaccaaaa    6000
taaactccac tagaaggata ttgtggggca acaacacaat gggcgttaca ggaatattgc    6060
agttacctcg tgatcgattc aagaggacat cattctttct ttgggtaatt atccttttcc    6120
aaagaacatt ttccatccca cttggagtca tccacaatag cacattacag gttagtgatg    6180
tcgacaaact agtttgtcgt gacaaactgt catccacaaa tcaattgaga tcagttggac    6240
tgaatctcga agggaatgga gtggcaactg acgtgccatc tgcaactaaa agatggggct    6300
tcaggtccgg tgtcccacca aaggtggtca attatgaagc tggtgaatgg gctgaaaact    6360
gctacaatct tgaaatcaaa aaacctgacg ggagtgagtg tctaccagca gcgccagacg    6420
ggattcgggg cttcccccgg tgccggtatg tgcacaaagt atcaggaacg ggaccgtgtg    6480
ccggagactt tgccttccat aaagagggtg ctttcttcct gtatgatcga cttgcttcca    6540
cagttatcta ccgaggaacg actttcgctg aaggtgtcgt tgcatttctg atactgcccc    6600
aagctaagaa ggacttcttc agctcacacc ccttgagaga gccggtcaat gcaacggagg    6660
acccgtctag tggctactat tctaccacaa ttagatatca ggctaccggt tttggaacca    6720
atgagacaga gtacttgttc gaggttgaca atttgaccta cgtccaactt gaatcaagat    6780
tcacaccaca gtttctgctc cagctgaatg agacaatata tacaagtggg aaaaggagca    6840
```

```
ataccacggg aaaactaatt tggaaggtca accccgaaat tgatacaaca atcggggagt     6900
gggccttctg ggaaactaaa aaaacctcac tagaaaaatt cgcagtgaag agttgtcttt     6960
cacagttgta tcaaacggag ccaaaaacat cagtggtcag agtccggcgc gaacttcttc     7020
cgacccaggg accaacacaa caactgaaga ccacaaaatc atggcttcag aaaattcctc     7080
tgcaatggtt caagtgcaca gtcaaggaag ggaagctgca gtgtcgcatc taacaaccct     7140
tgccacaatc tccacgagtc cccaatccct cacaaccaaa ccaggtccgg acaacagcac     7200
ccataataca cccgtgtata aacttgacat ctctgaggca actcaagttg aacaacatca     7260
ccgcagaaca gacaacgaca gcacagcctc cgacactccc tctgccacga ccgcagccgg     7320 accccaaaa gcagagaaca ccaacacgag caagagcact gacttcctgg accccgccac     7380
cacaacaagt cccaaaacc acagcgagac cgctggcaac aacaacactc atcaccaaga     7440
taccggagaa gagagtgcca gcagcgggaa gctaggctta attaccaata ctattgctgg     7500
agtcgcagga ctgatcacag gcgggagaag aactcgaaga gaagcaattg tcaatgctca     7560
acccaaatgc aaccctaatt tacattactg gactactcag gatgaaggtg ctgcaatcgg     7620
actggcctgg ataccatatt tcgggccagc agccgaggga atttacatag aggggctaat     7680
gcacaatcaa gatggtttaa tctgtgggtt gagacagctg ccaacgaga cgactcaagc     7740 tcttcaactg ttcctgagag ccacaactga gctacgcacc ttttcaatcc tcaaccgtaa     7800
ggcaattgat ttcttgctgc agcgatgggg cggcacatgc cacattctgg gaccggactg     7860
ctgtatcgaa ccacatgatt ggaccaagaa cataacagac aaaattgatc agattattca     7920
tgattttgtt gataaaaccc ttccggacca gggggacaat gacaattggt ggacaggatg     7980
gagacaatgg ataccggcag gtattggagt tacaggcgtt ataattgcag ttatcgcttt     8040
attctgtata tgcaaatttg tcttttagtt tttcttcaga ttgcttcatg gaaaagctca     8100
gcctcaaatc aatgaaacca ggatttaatt atatggatta cttgaatcta agattacttg     8160
acaaatgata atataataca ctggagcttt aaacatagcc aatgtgattc taactccttt     8220
aaactcacag ttaatcataa acaaggtttg acatcaatct agttatctct ttgagaatga     8280
taaacttgat gaagattaag aaaaaggtaa tctttcgatt atctttaatc ttcatccttg     8340
attctacaat catgacagtt gtctttagtg acaagggaaa gaagccttt tattaagttg     8400 taataatcag atctgcgaac cggtagagtt tagttgcaac ctaacacaca taagcattg     8460 gtcaaaagt caatagaaat ttaaacagtg agtggagaca acttttaaat ggaagcttca     8520
tatgagagag acgcccacg agctgccaga cagcattcaa gggatggaca cgaccaccat     8580
gttcgagcac gatcatcatc cagagagaat tatcgaggtg agtaccgtca atcaaggagc     8640
gcctcacaag tgcgcgttcc tactgtattt cataagaaga gagttgaacc attaacagtt     8700
cctccagcac ctaaagacat atgtccgacc ttgaaaaaag gatttttgtg tgacagtagt     8760
ttttgcaaaa aagatcacca gttggagagt ttaactgata gggaattact cctactaatc     8820
gcccgtaaga cttgtggatc agtagaacaa caattaaata taactgcacc caaggactcg     8880
cgcttagcaa atccaacggc tgatgatttc cagcaagagg aaggtccaaa aattaccttg     8940
ttgacactga tcaagacggc agaacactgg gcgagacaag acatcagaac catagaggat     9000
tcaaaattaa gagcattgtt gactctatgt gctgtgatga cgaggaaatt ctcaaaatcc     9060
cagctgagtc ttttatgtga gacacaccta aggcgcgagg ggcttgggca agatcaggca     9120
gaacccgttc tcgaagtata tcaacgatta cacagtgata aaggaggcag ttttgaagct     9180
```

-continued

```
gcactatggc aacaatggga ccgacaatcc ctaattatgt ttatcactgc attcttgaat    9240
attgctctcc agttaccgtg tgaaagttct gctgtcgttg tttcagggtt aagaacattg    9300
gttcctcaat cagataatga ggaagcttca accaacccgg ggacatgctc atggtctgat    9360
gagggtaccc cttaataagg ctgactaaaa cactatataa ccttctactt gatcacaata    9420
ctccgtatac ctatcatcat atatttaatc aagacgatat cctttaaaac ttattcagta    9480
ctataatcac tctcgtttca aattaataag atgtgcatga ttgccctaat atatgaagag    9540
gtatgataca accctaacag tgatcaaaga aaatcataat ctcgtatcgc tcgaaatata    9600
acctgccaag catacctctt gcacaaagtg attcttgtac acaaataatg ttttactcta    9660
caggaggtag caacgatcca tcccatcaaa aaataagtat ttcatgactt actaatgatc    9720
tcttaaaata ttaagaaaaa ctgacggaac ataaattctt tatgcttcaa gctgtggagg    9780
aggtgtttgg tattggctat tgttatatta caatcaataa caagcttgta aaaatattgt    9840
tcttgtttca agaggtagat tgtgaccgga aatgctaaac taatgatgaa gattaatgcg    9900
gaggtctgat aagaataaac cttattattc agattaggcc ccaagaggca ttcttcatct    9960
ccttttagca aagtactatt tcagggtagt ccaattagtg gcacgtcttt tagctgtata   10020
tcagtcgccc ctgagatacg ccacaaaagt gtctctaagc taaattggtc tgtacacatc   10080
ccatacattg tattagggc aataatatct aattgaactt agccgtttaa aatttagtgc   10140
ataaatctgg gctaacacca ccaggtcaac tccattggct gaaaagaagc ttacctacaa   10200
cgaacatcac tttgagcgcc ctcacaatta aaaaatagga acgtcgttcc aacaatcgag   10260
cgcaaggttt caaggttgaa ctgagagtgt ctagacaaca aaatattgat actccagaca   10320
ccaagcaaga cctgagaaaa aaccatggct aaagctacgg gacgatacaa tctaatatcg   10380
cccaaaaagg acctggagaa aggggttgtc ttaagcgacc tctgtaactt cttagttagc   10440
caaactattc aggggtggaa ggtttattgg gctggtattg agtttgatgt gactcacaaa   10500
ggaatggccc tattgcatag actgaaaact aatgactttg cccctgcatg gtcaataaca   10560
aggaatctct ttcctcattt atttcaaaat ccgaattcca caattgaatc accgctgtgg   10620
gcattgagag tcatccttgc agcagggata caggaccagc tgattgacca gtctttgatt   10680
gaacccttag caggagccct tggtctgatc tctgattggc tgctaacaac caacactaac   10740
catttcaaca tgcgaacaca acgtgtcaag gaacaattga gcccaaaaat gctgtcgttg   10800
attcgatcca atattctcaa gtttattaac aaattggatg ctctacatgt cgtgaactac   10860
aacggattgt tgagcagtat tgaaattgga actcaaaatc atataatcat cataactcga   10920
actaacatgg gttttctggt ggagctccaa gaacccgaca aatcggcaat gaaccgcatg   10980
aagcctgggc cggcgaaatt ttccctcctt catgagtcca cactgaaagc atttacacaa   11040
ggatcctcga cacgaatgca aagtttgatt cttgaattta atagctctct tgctatctaa   11100
ctaaggtaga atacttcata ttgagctaac tcatatatgc tgactcaata gttatcttga   11160
catctctgct ttcataatca gatatataag cataataaat aaatactcat atttcttgat   11220
aatttgttta accacagata aatcctcact gtaagccagc ttccaagttg acacccttac   11280
aaaaaccagg actcagaatc cctcaaacaa gagattccaa gacaacatca tagaattgct   11340
ttattatatg aataagcatt ttatcaccag aaatcctata tactaaatgg ttaattgtaa   11400
ctgaacccgc aggtcacatg tgttaggttt cacagattct atatattact aactctatac   11460
tcgtaattaa cattagataa gtagattaag aaaaagcct gaggaagatt aagaaaaact   11520
gcttattggg tctttccgtg ttttagatga agcagttgaa attcttcctc ttgatattaa   11580
```

```
atggctacac aacatacccc ataccccagac gctaggttat catcaccaat tgtattggac   11640
caatgtgacc tagtcactag agcttgcggg ttatattcat catactccct taatccgcaa   11700
ctacgcaact gtaaactccc gaaacatatc taccgtttga aatacgatgt aactgttacc   11760
aagttcttga gtgatgtacc agtggcgaca ttgcccatag atttcatagt cccagttctt   11820
ctcaaggcac tgtcaggcaa tggattctgt cctgttgagc cgcggtgcca acagttctta   11880
gatgaaatca ttaagtacac aatgcaagat gctctcttct tgaaatatta tctcaaaaat   11940
gtgggtgctc aagaagactg tgttgatgaa cactttcaag agaaaatctt atcttcaatt   12000
cagggcaatg aattttttaca tcaaatgttt ttctggtatg atctggctat tttaactcga   12060
aggggtagat taaatcgagg aaactctaga tcaacatggt ttgttcatga tgatttaata   12120
gacatcttag gctatgggga ctatgttttt tggaagatcc caatttcaat gttaccactg   12180
aacacacaag gaatcccca tgctgctatg gactggtatc aggcatcagt attcaaagaa   12240
gcggttcaag gcatacaca cattgtttct gtttctactg ccgacgtctt gataatgtgc   12300
aaagatttaa ttacatgtcg attcaacaca actctaatct caaaaatagc agagattgag   12360
gatccagttt gttctgatta tcccaatttt aagattgtgt ctatgcttta ccagagcgga   12420
gattacttac tctccatatt agggtctgat gggtataaaa ttattaagtt cctcgaacca   12480
ttgtgcttgg ccaaaattca attatgctca aagtacactg agaggaaggg ccgattctta   12540
acacaaatgc atttagctgt aaatcacacc ctagaagaaa ttacagaaat gcgtgcacta   12600
aagccttcac aggctcaaaa gatccgtgaa ttccatagaa cattgataag gctggagatg   12660
acgccacaac aactttgtga gctattttcc attcaaaaac actgggggca tcctgtgcta   12720
catagtgaaa cagcaatcca aaaagttaaa aaacatgcta cggtgctaaa agcattacgc   12780
cctatagtga ttttcgagac atactgtgtt tttaaatata gtattgccaa acattatttt   12840
gatagtcaag gatcttggta cagtgttact tcagatagga atctaacacc gggtcttaat   12900
tcttatatca aaagaaatca attccctccg ttgccaatga ttaaagaact actatgggaa   12960
ttttaccacc ttgaccaccc tccacttttc tcaaccaaaa ttattagtga cttaagtatt   13020
tttataaaag acagagctac cgcagtagaa aggacatgct gggatgcagt attcgagcct   13080
aatgttctag gatataatcc acctcacaaa tttagtacta aacgtgtacc ggaacaattt   13140
ttagagcaag aaaactttc tattgagaat gttctttcct acgcacaaaa actcgagtat   13200
ctactaccac aatatcggaa cttttctttc tcattgaaag agaaagagtt gaatgtaggt   13260
agaaccttcg gaaaattgcc ttatccgact cgcaatgttc aaacactttg tgaagctctg   13320
ttagctgatg gtcttgctaa agcatttcct agcaatatga tggtagttac ggaacgtgag   13380
caaaaagaaa gcttattgca tcaagcatca tggcaccaca caagtgatga ttttggtgaa   13440
catgccacag ttagagggag tagctttgta actgatttag agaaatacaa tcttgcattt   13500
agatatgagt ttacagcacc ttttatagaa tattgcaacc gttgctatgg tgttaagaat   13560
gtttttaatt ggatgcatta tacaatccca cagtgttata tgcatgtcag tgattattat   13620
aatccaccac ataacctcac actggagaat cgagacaacc cccccgaagg gcctagttca   13680
tacaggggtc atatgggagg gattgaagga ctgcaacaaa aactctggac aagtatttca   13740
tgtgctcaaa tttctttagt tgaaattaag actggtttta agttacgctc agctgtgatg   13800
ggtgacaatc agtgcattac tgtttttatca gtcttcccct tagagactga cgcagacgag   13860
caggaacaga gcgccgaaga caatgcagcg agggtggccg ccagcctagc aaaagttaca   13920
```

```
agtgcctgtg gaatcttttt aaaacctgat gaaacatttg tacattcagg ttttatctat   13980
tttggaaaaa aacaatattt gaatggggtc caattgcctc agtcccttaa aacggctgca   14040
agaatggcac cattgtctga tgcaattttt gatgatcttc aagggaccct ggctagtata   14100
ggcactgctt ttgagcgatc catctctgag acacgacata tctttccttg caggataacc   14160
gcagctttcc atacgttttt ttcggtgaga atcttgcaat atcatcatct cgggttcaat   14220
aaaggttttg accttggaca gttaacactc ggcaaacctc tggatttcgg aacaatatca   14280
ttggcactag cggtaccgca ggtgcttgga gggttatcct tcttgaatcc tgagaaatgt   14340
ttctaccgga atctaggaga tccagttacc tcaggcttat tccagttaaa aacttatctc   14400
cgaatgattg agatggatga tttattctta cctttaattg cgaagaaccc tgggaactgc   14460
actgccattg actttgtgct aaatcctagc ggattaaatg tccctgggtc gcaagactta   14520
acttcatttc tgcgccagat tgtacgcagg accatcaccc taagtgcgaa aaacaaactt   14580
attaatacct tatttcatgc gtcagctgac ttcgaagacg aaatggtttg taaatggcta   14640
ttatcatcaa ctcctgttat gagtcgtttt gcggccgata tcttttcacg cacgccgagc   14700
gggaagcgat tgcaaattct aggatacctg gaaggaacac gcacattatt agcctctaag   14760
atcatcaaca ataatacaga gacaccggtt ttggacagac tgaggaaaat aacattgcaa   14820
aggtggagcc tatggtttag ttatcttgat cattgtgata atatcctggc ggaggcttta   14880
acccaaataa cttgcacagt tgatttagca cagattctga gggaatattc atgggctcat   14940
attttagagg gaagacctct tattggagcc acactcccat gtatgattga gcaattcaaa   15000
gtgttttggc tgaaaccta cgaacaatgt ccgcagtgtt caaatgcaaa gcaaccaggt   15060
gggaaaccat tcgtgtcagt ggcagtcaag aaacatattg ttagtgcatg gccgaacgca   15120
tcccgaataa gctggactat cggggatgga atcccataca ttggatcaag gacagaagat   15180
aagataggac aacctgctat taaaccaaaa tgtccttccg cagccttaag agaggccatt   15240
gaattggcgt cccgtttaac atgggtaact caaggcagtt cgaacagtga cttgctaata   15300
aaaccatttt tggaagcacg agtaaattta agtgttcaag aaatacttca aatgacccct   15360
tcacattact caggaaatat tgttcacagg tacaacgatc aatacagtcc tcattctttc   15420
atggccaatc gtatgagtaa ttcagcaacg cgattgattg tttctacaaa cactttaggt   15480
gagttttcag gaggtggcca gtctgcacgc gacagcaata ttattttcca gaatgttata   15540
aattatgcag ttgcactgtt cgatattaaa tttagaaaca ctgaggctac agatatccaa   15600
tataatcgtg ctcaccttca tctaactaag tgttgcaccc gggaagtacc agctcagtat   15660
ttaacataca catctacatt ggatttagat ttaacaagat accgagaaaa cgaattgatt   15720
tatgacagta atcctctaaa aggaggactc aattgcaata tctcattcga taatccatttt  15780 ttccaaggta aacggctgaa cattatagaa gatgatctta ttcgactgcc tcacttatct   15840
ggatgggagc tagccaagac catcatgcaa tcaattattt cagatagcaa caattcatct   15900
acagacccaa ttagcagtgg agaaacaaga tcattcacta cccatttctt aacttatccc   15960
aagataggac ttctgtacag ttttgggggcc tttgtaagtt attatcttgg caatacaatt   16020
cttcggacta gaaaattaac acttgacaat tttttatatt acttaactac tcaaattcat   16080
aatctaccac atcgctcatt gcgaatactt aagccaacat tcaaacatgc aagcgttatg   16140
tcacggttaa tgagtattga tcctcatttt tctatttaca taggcggtgc tgcaggtgac   16200
agaggactct cagatgcggc caggttattt ttgagaacgt ccatttcatc ttttcttaca   16260
tttgtaaaag aatggataat taatcgcgga acaattgtcc ctttatggat agtatatccg   16320
```

```
ctagagggtc aaaacccaac acctgtgaat aattttctct atcagatcgt agaactgctg   16380
gtgcatgatt catcaagaca acaggctttt aaaactacca taagtgatca tgtacatcct   16440
cacgacaatc ttgtttacac atgtaagagt acagccagca atttcttcca tgcatcattg   16500
gcgtactgga ggagcagaca cagaaacagc aaccgaaaat acttggcaag agactcttca   16560
actggatcaa gcacaaacaa cagtgatggt catattgaga gaagtcaaga acaaaccacc   16620
agagatccac atgatggcac tgaacggaat ctagtcctac aaatgagcca tgaaataaaa   16680
agaacgacaa ttccacaaga aaacacgcac cagggtccgt cgttccagtc ctttctaagt   16740
gactctgctt gtggtacagc aaatccaaaa ctaaatttcg atcgatcgag acacaatgtg   16800
aaatttcagg atcataactc ggcatccaag agggaaggtc atcaaataat ctcacaccgt   16860
ctagtcctac ctttctttac attatctcaa gggacacgcc aattaacgtc atccaatgag   16920
tcacaaaccc aagacgagat atcaaagtac ttacggcaat tgagatccgt cattgatacc   16980
acagtttatt gtagatttac cggtatagtc tcgtccatgc attacaaact tgatgaggtc   17040
ctttgggaaa tagagagttt caagtcggct gtgacgctag cagagggaga aggtgctggt   17100
gccttactat tgattcagaa ataccaagtt aagaccttat ttttcaacac gctagctact   17160
gagtccagta tagagtcaga aatagtatca ggaatgacta ctcctaggat gcttctacct   17220
gttatgtcaa aattccataa tgaccaaatt gagattattc ttaacaactc agcaagccaa   17280
ataacagaca taacaaatcc tacttggttt aaagaccaaa gagcaaggct acctaagcaa   17340
gtcgaggtta taaccatgga tgcagagaca acagagaata taaacagatc gaaattgtac   17400
gaagctgtat ataaattgat cttacaccat attgatccta gcgtattgaa agcagtggtc   17460
cttaaagtct ttctaagtga tactgagggt atgttatggc taaatgataa tttagccccg   17520
tttttttgcca ctggttattt aattaagcca ataacgtcaa gtgctagatc tagtgagtgg   17580
tatctttgtc tgacgaactt cttatcaact acacgtaaga tgccacacca aaaccatctc   17640
agttgtaaac aggtaatact tacggcattg caactgcaaa ttcaacgaag cccatactgg   17700
ctaagtcatt taactcagta tgctgactgt gagttacatt taagttatat ccgccttggt   17760
tttccatcat tagagaaagt actataccac aggtataacc tcgtcgattc aaaaagaggt   17820
ccactagtct ctatcactca gcacttagca catcttagag cagagattcg agaattaact   17880
aatgattata atcaacagcg acaaagtcgg actcaaacat atcactttat tcgtactgca   17940
aaaggacgaa tcacaaaact agtcaatgat tatttaaaat tctttcttat tgtgcaagca   18000
ttaaaacata atgggacatg gcaagctgag tttaagaaat taccagagtt gattagtgtg   18060
tgcaataggt tctaccatat tagagattgc aattgtgaag aacgtttctt agttcaaacc   18120
ttatatttac atagaatgca ggattctgaa gttaagctta tcgaaaggct gacagggctt   18180
ctgagtttat ttccggatgg tctctacagg tttgattgaa ttaccgtgca tagtatcctg   18240
atacttgcaa aggttggtta ttaacataca gattataaaa aactcataaa ttgctctcat   18300
acatcatatt gatctaatct caataaacaa ctatttaaat aacgaaagga gtccctatat   18360
tatatactat atttagcctc tctccctgcg tgataatcaa aaaattcaca atgcagcatg   18420
tgtgacatat tactgccgca atgaatttaa cgcaacataa taaactctgc actctttata   18480
attaagcttt aacgaaaggt ctgggctcat attgttattg atataataat gttgtatcaa   18540
tatcctgtca gatggaatag tgttttggtt gataacacaa cttcttaaaa caaaattgat   18600
ctttaagatt aagttttttta taattatcat tactttaatt tgtcgtttta aaacggtga    18660
```

```
tagccttaat ctttgtgtaa aataagagat taggtgtaat aaccttaaca tttttgtcta   18720
gtaagctact atttcataca gaatgataaa attaaaagaa aaggcaggac tgtaaaatca   18780
gaaatacctt ctttacaata tagcagacta gataataatc ttcgtgttaa tgataattaa   18840
gacattgacc acgctcatca gaaggctcgc cagaataaac gttgcaaaaa ggattcctgg   18900
aaaaatggtc gcacacaaaa atttaaaaat aaatctattt cttctttttt gtgtgtcca    18959
```

```
<210> SEQ ID NO 47
<211> LENGTH: 5
<212> TYPE: PRT
<213> ORGANISM: Artificial Sequence
<220> FEATURE:
<223> OTHER INFORMATION: A peptide

<400> SEQUENCE: 47

Pro Pro Glu Tyr Met
 1               5

<210> SEQ ID NO 48
<211> LENGTH: 5
<212> TYPE: PRT
<213> ORGANISM: Artificial Sequence
<220> FEATURE:
<223> OTHER INFORMATION: A peptide

<400> SEQUENCE: 48

Pro Pro Glu Tyr Ala
 1               5

<210> SEQ ID NO 49
<211> LENGTH: 5
<212> TYPE: PRT
<213> ORGANISM: Artificial Sequence
<220> FEATURE:
<223> OTHER INFORMATION: A peptide

<400> SEQUENCE: 49

Ala Ala Glu Tyr Met
 1               5

<210> SEQ ID NO 50
<211> LENGTH: 4
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 3
<223> OTHER INFORMATION: Xaa = any amino acid

<400> SEQUENCE: 50

Pro Pro Xaa Tyr
 1

<210> SEQ ID NO 51
<211> LENGTH: 4
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 3
<223> OTHER INFORMATION: Xaa = Glu

<400> SEQUENCE: 51
```

Ala Ala Xaa Tyr
1

<210> SEQ ID NO 52
<211> LENGTH: 4
<212> TYPE: PRT
<213> ORGANISM: Zaire Ebola virus

<400> SEQUENCE: 52

Pro Pro Glu Tyr
1

<210> SEQ ID NO 53
<211> LENGTH: 4
<212> TYPE: PRT
<213> ORGANISM: Artificial Sequence
<220> FEATURE:
<223> OTHER INFORMATION: A synthetic peptide

<400> SEQUENCE: 53

Ala Ala Glu Tyr
1

<210> SEQ ID NO 54
<211> LENGTH: 4
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 2
<223> OTHER INFORMATION: Xaa = any amino acid
<220> FEATURE:
<221> NAME/KEY: SITE
<222> LOCATION: 3
<223> OTHER INFORMATION: Xaa = Lys or Arg

<400> SEQUENCE: 54

Arg Xaa Xaa Arg
1

<210> SEQ ID NO 55
<211> LENGTH: 5
<212> TYPE: PRT
<213> ORGANISM: Zaire Ebola virus

<400> SEQUENCE: 55

Arg Arg Thr Arg Arg
1               5

<210> SEQ ID NO 56
<211> LENGTH: 4
<212> TYPE: PRT
<213> ORGANISM: Zaire Ebola virus

<400> SEQUENCE: 56

Arg Val Arg Arg
1

<210> SEQ ID NO 57
<211> LENGTH: 4
<212> TYPE: PRT
<213> ORGANISM: Zaire Ebola virus

<400> SEQUENCE: 57

```
Arg Thr Arg Arg
 1

<210> SEQ ID NO 58
<211> LENGTH: 5
<212> TYPE: PRT
<213> ORGANISM: Artificial Sequence
<220> FEATURE:
<223> OTHER INFORMATION: A synthetic peptide

<400> SEQUENCE: 58

Ala Gly Thr Ala Ala
 1               5
```

FILOVIRUS VECTORS AND NONINFECTIOUS FILOVIRUS-BASED PARTICLES

CROSS-REFERENCE TO RELATED APPLICATIONS

This application is a continuation of U.S. patent application Ser. No. 11/654,863, filed Jan. 18, 2007, which application is a divisional of U.S. patent application Ser. No. 10/353,856, filed Jan. 29, 2003, now U.S. Pat. No. 7,211,378, which claims the benefit of the filing date of U.S. application Ser. No. 60/353,972, filed on Jan. 31, 2002, under 35 U.S.C. 119(e), which applications are incorporated by reference herein.

STATEMENT OF GOVERNMENT RIGHTS

This invention was made with government support awarded by the National Institutes of Health, Grant Nos. AI42774 and AI44386. The Government has certain rights in this invention.

BACKGROUND OF THE INVENTION

Ebola virus, a member of the family Filoviridae and the order Mononegavirales, is an enveloped, nonsegmented negative-strand RNA virus and is one of the most lethal human and nonhuman primate pathogens recognized to date (Feldmann et al., 1998; Vanderzanden et al., 1998). Four subtypes of Ebola virus have been identified, including Zaire, Sudan, Ivory Coast, and Reston (Sanchez et al., 1993). Human infection with subtype Zaire causes a fulminating, febrile, hemorrhagic disease that results in extensive mortality (Feldmann et al., 1993). Thus, Ebola virus infection presents a much-needed model to study virus-induced mechanisms leading to coagulation disorders and vascular instability. However, identification of major determinants of Ebola virus pathogenicity has been hampered by the lack of effective strategies for experimental mutagenesis.

Ebola virus particles have a filamentous appearance, but its shape may be branched, circular, U- or 6-shaped, or long and straight (Feldmann et al., 1996). Virions show a uniform diameter of approximately 80 nm, but vary greatly in length. Ebola virus particles consist of seven structural proteins. The glycoprotein (GP) of Ebola virus forms spikes of approximately 7 nm, which are spaced at 5- to 10-nm intervals on the virion surface (Feldmann et al., 1996 and Peters et al., 1995). Cleavage of the GP is thought to be an important determinant of viral pathogenicity (Volchkov et al., 1998; Sanchez et al., 1996; Takada et al., 1997; Volchkov et al., 1998a; Volchkov et al., 1998b; Wool-Lewis et al., 1998; Yang et al., 2000). The Ebola virus GP contains a highly conserved consensus motif for the subtilisin-like endoprotease furin, and previous studies demonstrated GP cleavage by this protease (Nina et al., 1991). Nonetheless, studies of murine leukemia virus (Wood-Lewis et al., 1999) or vesicular stomatitis virus (VSV) (Ito et al., 2001) pseudotyped with mutant Ebola virus GPs lacking the furin recognition motif at the cleavage site, showed that GP cleavage by furin was not essential for infectivity of the pseudotyped viruses. In many viruses, GP cleavage by furin and related endoproteases is essential for their infectivity. Thus, the significance of GP cleavage for the Ebola virus life cycle remains in question.

GP is the only transmembrane protein of Ebola virus, and is responsible for receptor binding and membrane fusion (Takada et al., 1997). Cells infected with recombinant vaccinia virus expressing the GP produced virosomes that varied in shape and diameter but uniformly possessed spike structures on their surface (Volchkov et al., 1998c), although the effects of over 80 vaccinia viral proteins (Moss, 1995) on the formation of particles are unknown. Similar virosomes are also released from Ebola virus-infected cells (Volchkov et al., 1998c). These findings suggest that the GP contributes not only to an early stage of the viral infection cycle but also to viral budding.

In addition, although recent studies have begun to address the immune response to viral infection (Baize et al., 1999; Basler et al., 2000; Vanderzanden et al., 1998; and Wilson et al., 2000), as well as the functions of the viral proteins involved in the replicative process (VP30, VP35, NP, L) (Basler et al., 2000 and Muhlberger et al., 1999) and GP, little is known about the functions of the viral proteins associated with the membrane, including viral protein 40 (VP40), which appears equivalent to matrix protein of other viruses.

The matrix proteins of many nonsegmented, negative-sense RNA viruses play a critical role in viral particle formation (virus assembly) and budding (Garoff et al., 1998). Expression of the matrix protein of VSV in insect and mammalian cells results in evagination of matrix protein-containing vesicles from the plasma membrane surface (Justice et al., 1995; and Li et al., 1993). Matrix proteins interact with membranes in a hydrophobic and/or electrostatic manner and electron micrographs of nonsegmented, negative-sense RNA viruses have demonstrated that the matrix protein forms a layer associated with the inner leaflet of the lipid bilayer (Garoff et al., 1998).

VP40 is the most abundant protein in virions (it represents 38% of the protein in the viral particle) and is located beneath the viral membrane, where is presumably maintains the structural integrity of the particle (Feldmann et al., 1996). VP40 is encoded by the third gene in the linear 3'-5' RNA genome of Ebola virus and is 326 amino acids in length, which includes a number of hydrophobic regions (Elliott et al., 1985 and Sanchez et al., 1996). VP40 contains a PPXY motif (SEQ ID NO:50; X denotes any amino acid) at amino acids 10-13 (Harty et al., 1996) that is also present at amino acids 16-19 in Marburg virus, strain Popp (Sanchez et al., 1993). This motif has been shown to play an important role in the budding of rabies virus and VSV: when either of the prolines or the tyrosine of this motif is altered in the matrix proteins of these viruses, viral budding is markedly reduced by comparison to findings with wild-type virus (Harty et al., 1996). Mutation of the PPXY (SEQ ID NO:50) motif in the matrix protein of VSV appears to reduce virus yield by pre-empting budding of assembled virions at the plasma membrane (Jayakar et al., 2000). This motif interacts with the WW domain found in many cellular regulatory and signal transduction proteins (Bork et al., 1994 and Chen et al., 1995) and interactions between one or more cellular proteins and the matrix proteins of these viruses are thought to be crucial for efficient virus release from cells (Harty et al., 1999).

The matrix proteins of many enveloped viruses are thought to interact with the cytoplasmic tails of viral glycoproteins. Such interaction is believed to be important for virus assembly. In influenza viruses, the removal of the cytoplasmic tail of the hemagglutinin or neuraminidase glycoprotein alters virion morphology (Jin et al., 1997; Mitnaul et al., 1996). Although not essential for normal particle formation in rabies virus and VSV, glycoproteins enhance the efficiency of particle formation (Mebatsion et al., 1996; Mebatsion et al., 1999; Schnell et al., 1998).

Thus, what is needed is a method to readily manipulate the filovirus genome.

SUMMARY OF THE INVENTION

The invention provides methods to prepare filovirus, e.g., Marburg virus and Ebola virus, from cloned DNA and compositions useful therefor. As described herein, a reverse genetics system was employed to generate filovirus, e.g., Ebola virus, from cloned cDNA. The genomic sequence was prepared by reverse transcription and amplification of viral RNA. The expression of the resulting genomic cDNA, e.g., in host cells, in sense and antisense orientation yields cRNA or vRNA, which in the presence of certain viral proteins, e.g., L, NP, VP30 and VP35, yielded infectious virus. This system was also used to generate a mutant virus with an altered furin cleavage motif in GP. When expressed in cells, the GP of the wild-type, but not of the mutant, virus was cleaved into GP1 and GP2. Although posttranslational furin-mediated cleavage of GP was thought to be an essential step in Ebola virus infection, generation of a viable mutant Ebola virus lacking a furin recognition motif in the GP cleavage site demonstrated that GP cleavage is not essential for replication of Ebola virus in cell culture.

Thus, the invention provides a composition comprising a plurality of filovirus vectors. The composition comprises a vector comprising a promoter operably linked to a nucleic acid molecule comprising a filovirus genomic cDNA linked to a transcription termination sequence, a vector comprising a promoter operably linked to a nucleic acid molecule, for instance, a DNA segment, encoding a filovirus RNA transcriptase-polymerase, a vector comprising a promoter operably linked to a nucleic acid molecule encoding a filovirus NP, a vector comprising a promoter operably linked to a nucleic acid molecule encoding filovirus VP30, and a vector comprising a promoter operably linked to a nucleic acid molecule encoding filovirus VP35. Preferred promoters for the vector comprising the filovirus cDNA include, but are not limited to, a RNA polymerase I promoter, RNA polymerase II promoter, RNA polymerase III promoter, T7 RNA polymerase promoter, or T3 RNA polymerase promoter, and preferred transcription termination sequences include, but are not limited to, a RNA polymerase I transcription termination sequence, RNA polymerase II transcription termination sequence, RNA polymerase III transcription termination sequence, or a ribozyme. The sequence of the filovirus genomic cDNA may be that of wild-type or may have one or more nucleotide deletions, insertions or substitutions relative to the genomic sequence of a corresponding wild-type filovirus. Virus, either wild-type or mutant, such as a randomly mutagenized sequence or one subjected to directed evolution, prepared from such a cDNA, is useful to screen for antiviral compounds or other desirable properties such as immunogenicity, to prepare a vaccine which results in a protective immune response when administered to animals, e.g., mammals and preferably primates, or to deliver a nucleic acid sequence of interest to cells, e.g., a marker gene, a gene encoding an immunogenic protein from a pathogen including viruses other than a filovirus, bacteria, fungi or yeast, or a therapeutic protein, e.g., ADA, CFTR, factor VIII or factor IX. Further, as the length of a filovirus virion is variable, the nucleic acid sequence of interest may be introduced into cloned filovirus cDNA, as an individual open reading frame, e.g., one encoding a functional protein, or so as to encode a fusion protein with a filovirus protein, or as a replacement (substitution) for one or more coding regions in the filovirus genome. Depending on whether or not virus replication is desirable, a filovirus cDNA which lacks one or more filovirus coding regions but comprises a DNA of interest may be introduced into a cell along with the full-length (genomic) cDNA, optionally with vectors encoding filovirus proteins. In particular, each of the coding regions for genes not associated with filovirus replication, e.g., GP, VP40 and VP24, may be replaced with a DNA of interest. The resulting virus-like particles may be employed to screen for compounds with desirable pharmacological profiles, e.g., antiviral compounds. Alternatively, a filovirus cDNA which lacks one or more viral coding regions, but includes filovirus sequences for encapsidation and/or replication and includes a DNA of interest, may be introduced into a cell along with vectors encoding filovirus proteins, to form virus-like particles.

The invention thus also provides a method to prepare filovirus. The method comprises contacting a cell with a vector comprising a promoter operably linked to a filovirus genomic cDNA or a portion thereof, e.g., a portion which, when expressed as vRNA is packaged into virions and can be replicated in the presence of filovirus proteins, linked to a transcription termination sequence, a vector comprising a promoter operably linked to a nucleic acid molecule, e.g., a DNA segment, encoding a filovirus RNA transcriptase-polymerase, a vector comprising a promoter operably linked to a nucleic acid molecule encoding filovirus NP, a vector comprising a promoter operably linked to a nucleic acid molecule encoding filovirus VP30, and a vector comprising a promoter operably linked to a nucleic acid molecule encoding filovirus VP35, so as to yield infectious filovirus. A portion of a filovirus cDNA includes portions which, when transcribed, yield a RNA which is capable of being packaged into filovirus virions or which is capable of being replicated in the presence of filovirus proteins. In one embodiment, the genomic cDNA may have been recombinantly manipulated, for example, by introducing one or more nucleotide deletions, insertions or substitutions. The promoters may be recognized by RNA polymerases expressed in the cells to be transfected, transformed or transduced with the vectors of the invention, or may be recognized by a RNA polymerase that is introduced to the cell concurrently or sequentially with the filoviral vectors, e.g., by introduction of the polymerase itself or a vector encoding the polymerase. In one embodiment, the filovirus genomic cDNA may be manipulated to encode a fusion protein, encode a therapeutic protein or a protein useful in a vaccine, e.g., an immunogenic tumor-specific protein or an immunogenic peptide or protein of a pathogen, such as a bacteria, virus, yeast, or fungus. Also provided are cells contacted sequentially or concurrently with a composition, vector or virus of the invention, virus obtained by the methods of the invention, and cells infected with the virus.

As also described herein, VP40, when expressed apart from other viral proteins in mammalian cells, induced particle formation, which differed in length but with uniform diameters of approximately 65 nm. Efficient particle formation may rely on a conserved N-terminal PPXY (SEQ ID NO:50) motif, as mutation or loss of this motif resulted in markedly reduced particle formation. These findings demonstrate that VP40 alone possesses the information necessary to induce particle formation, and this process most likely requires cellular WW-domain-containing proteins that interact with the PPXY (SEQ ID NO:50) motif of VP40. Flotation gradient analysis indicated that VP40 binds to membranes in a hydrophobic manner, as NaCl at 1 M did not release the protein from the lipid bilayer. Triton X-114 phase-partitioning analysis suggested that VP40 possesses only minor features of an integral membrane protein. Truncation of the C-terminal 50 amino acids of VP40 resulted in decreased association with cellular membranes, and demonstrated that this deletion disrupts hydrophobic interactions of VP40 with the lipid bilayer, as well as abolishing particle formation. Truncation of the C-terminal 150 amino acids or N-terminal 100 amino acids of VP40 enhanced the protein's hydrophobic association with cellular membranes. These mutants may be useful as dominant negatives, to determine targets for antivirals.

When the Ebola virus GP was expressed in cells, pleomorphic particles were found budding from the plasma membrane. By contrast, when GP was co-expressed with VP40, GP was found on the filamentous particles induced by VP40. These results demonstrated the central role of VP40 in the formation of the filamentous structure of Ebola virions and suggests an interaction between VP40 and GP in morphogenesis.

Thus, the invention provides a method to prepare lipid encapsulated particles comprising recombinant filovirus matrix protein. The method comprises providing a culture of eukaryotic cells contacted with a vector comprising a promoter operably linked to a nucleic acid, e.g., DNA, encoding a filovirus matrix protein or a portion thereof which is capable of being incorporated into a filovirus particle. Supernatant from the culture which comprises lipid encapsulated particles comprising filovirus matrix protein is then collected. Preferred eukaryotic cells are mammalian cells, including primate cells such as monkey or human cells, although any eukaryotic cell, in which the expression of VP40 results in VP40-containing particles in supernatants, may be employed. The particles prepared by the method are useful as nucleic acid (DNA or RNA) or protein delivery vehicles, e.g., as replication incompetent virus-like particles useful as a vaccine or a tolerogen, e.g., to suppress or inhibit an immune response to an endogenous antigen, e.g., myelin basic protein, collagen, thyroglobulin, acetylcholine receptor, DNA, or islet cell antigens, or an exogenous antigen, e.g., protein antigens of *Alternaria altemata* (Alt a I), *Artemisia vulgaris* (Art v II), *Aspergillus fumigatus* (Asp f II), *Dermatophagoides pteron*. (Der p I, Der pIII, Der p IV, Der p VI and Der p VIII), and domestic animals such as *Felis domesticus* (Fel d I), cows, pigs, poultry, mice, hamsters, rabbits, rats, guinea pigs, dogs and horses. Common fungal antigens include those of Basidiomycetes such as *Ustilago, Ganoderma, Alternaria, Cladosporium, Aspergillus, Sporobolomyces, Penicillium, Epicoccum, Fusarium, Phoma, Borrytis, Helminthosporium, Stemphylium* and *Cephalosporium*; Phycomycetes such as *Mucor* and *Rhizopus*; and Ascomycetes such *Eurotium* and *Chaetomium*.

Accordingly, the eukaryotic cell may also express a nucleic acid, e.g., DNA, fragment of interest, including, but not limited to, one which encodes a therapeutic protein or peptide, an immunogenic peptide or protein of a pathogen, a tumor antigen or an immunogenic peptide thereof, a transmembrane protein such as one which specifically binds to a receptor on a particular cell type or tissue, a viral glycoprotein which specifically binds to a receptor on a particular cell type or tissue, or a fusion thereof with a filovirus GP. In one embodiment, cells express filovirus matrix protein and a fusion (chimera) of a filovirus glycoprotein, e.g., the transmembrane domain and intracellular domain of the filovirus glycoprotein and the extracellular portion of a non-filovirus protein, e.g., the extracellular domain of a cellular or viral transmembrane protein, such as influenza virus HA, or a soluble peptide or protein (one which does not comprise a transmembrane domain) which binds to a particular receptor. The resulting lipid encapsulated particles specifically bind to cells having a receptor for the extracellular non-filovirus protein or the soluble peptide or protein. In this manner, the lipid encapsulated particles may be targeted to a specific cell type or tissue in an animal and can deliver the encapsulated content(s) of the particle to the specific cell type or tissue. Also provided are isolated and/or purified lipid encapsulated particles obtained by the method. Such particles may be employed to screen for antiviral compounds, e.g., antivirals for other nonsegmented viruses.

BRIEF DESCRIPTION OF THE FIGURES

FIG. 1. Generation of Ebola virus entirely from cloned cDNA. (A) Schematic diagram of cDNA plasmids for Ebola virus cRNA or (B) vRNA synthesis and their efficiencies for virus generation. T7 and Rib indicate T7 RNA polymerase promoter and ribozyme sequences, respectively. G designates a guanine nucleotide inserted between the promoter and Ebola virus cDNA. Synthesis of positive-sense Ebola virus cRNA is represented by AEbola,@ while the inverse lettering denotes synthesis of negative-sense vRNA.

FIG. 3. Replication kinetics of wild-type Ebola virus and its GP cleavage mutant.

FIG. 4. Comparison of GP cleavage between wild-type and mutant Ebola virus. Labeled proteins were separated on 8% (A) and 15% (B) sodium dodecyl sulfate-polyacrylamide gels under reducing conditions. M, molecular mass marker; lane 1, mock-infected Vero E6 cells; lane 2, wild-type Ebola virus generated from plasmids; lane 3, GP cleavage mutant virus.

FIG. 7. Particle formation by VP40 and its mutants. Lanes represent fractions from a sucrose gradient (numbered from the top) loaded with VP40 (A) or a mutant VP40(B-D) from cells transfected with VP40-encoding constructs. Proteins were separated by SDS-PAGE (12%) and detected by Western blotting. AAXY corresponds to SEQ ID NO:51.

FIGS. 11A-G. Triton X-114 phase partitioning analysis of VP40 and its deletion mutants. The homogenate was partitioned into aqueous (A) and detergent (D) phases. Proteins were separated by SDS-PAGE (12%) and detected by Western blotting.

Figure 12A:
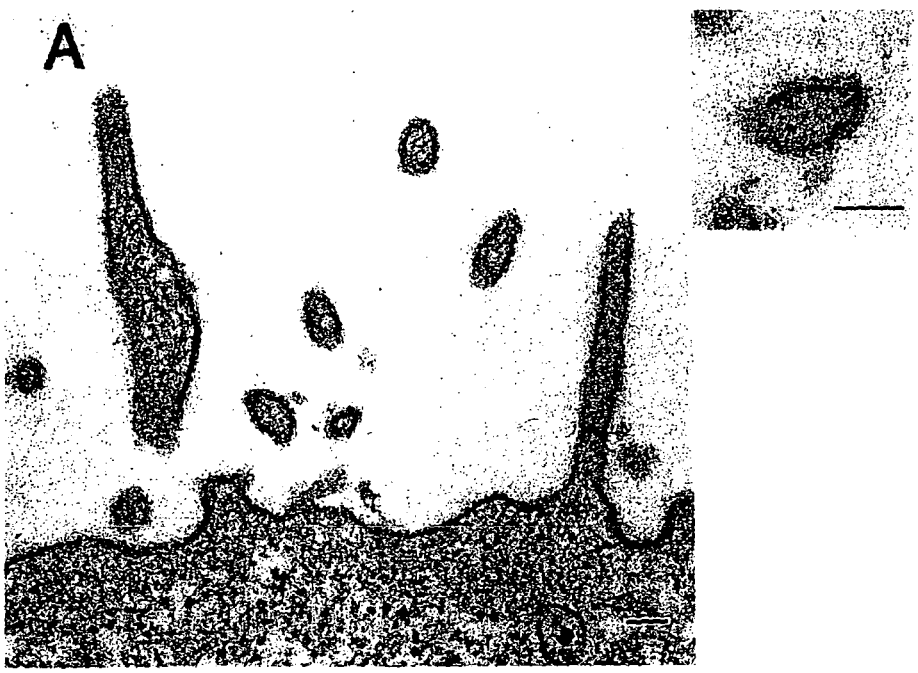

FIG. 12. Budding of GP-associated particles from the plasma membrane. Twenty four hours post-transfection of 293T cells with a GP-expressing plasmid (A). 293T cells transfected with an empty expression vector lack such particle formation (B). Bar, 100 nm.

FIG. 13. Pleomorphic particles resulting from GP expression. The supernatants of cells expressing GP were centrifuged through 20% sucrose, and the pelleted material was then negatively stained with 2% PTA. Pleomorphic particles with surface spikes were observed (A and B). Pelleted material was also immunolabeled with a mixture of anti-GP monoclonal antibodies conjugated to 15-nm gold particles C) and D). Bar, 100 nm.

FIG. 14. Morphologic changes in 293T cells expressing VP40. At 24 h post-transfection of 293T cells with a VP40-expressing plasmid, filamentous particles budding from the plasma membrane (A), membrane ruffles and the adhering site of two bilayers (C, arrows), as well as aggregated ribosomes (E, arrows) were apparent. Intracellular electron-dense filamentous structures (F, arrowheads) were also observed. The filamentous particles and membrane ruffles were immunolabeled with an anti-VP40 antibody conjugated with 5-nm gold particles (B and D). M, mitochondrion; mt, microtubule. Bar, 100 nm (A, B, C, D, F) or 200 nm (E).

FIG. 15. Filamentous particles induced by VP40 expression. The supernatants of cells expressing VP40 were centrifuged through 20% sucrose, and the pelleted material was then negatively stained with 2% PTA. Particles with uniform diameters of approximately 65 nm and varied lengths were observed (A-C). Bar, 100 nm.

FIG. 16. Filamentous, spiked particles budding from the plasma membrane 24 hours after-transfection of 293T cells with plasmids coexpressing VP40 and GP (A and B). Bar, 100 nm.

FIG. 17. Ebola virus-like particles produced by coexpression of VP40 and GP. The supernatants of cells coexpressing these two proteins were centrifuged through 20% sucrose, and the pelleted material was then negatively stained with 2% PTA. Filamentous particles with surface spikes and varied lengths were observed (A-C). Pelleted material was also immunolabeled with a mixture of anti-GP monoclonal antibodies conjugated to 15-nm gold particles (D, arrowheads), or treated with 0.03% Triton X-100 at room temperature for 15 minutes, and then immunolabeled with a mixture of anti-GP antibodies conjugated to 15-nm gold particles (E, arrowheads) and an anti-VP40 antibody conjugated to 5-nm gold particles (E, arrows). Bar, 1 μm (A) or 100 nm (B-E).

FIGS. 18A-18KKK. Representative filovirus sequences (Accession numbers AB050936, NC002549, NC001608, AF086833 and AF272001). The nucleotide sequence spanning FIGS. 18E-18M corresponds to SEQ ID NO:9; RVRR in FIG. 18AAA corresponds to SEQ ID NO:56; RTRR in FIG. 18AAA corresponds to SEQ ID NO:57.

DETAILED DESCRIPTION OF THE INVENTION

The invention provides isolated and/or purified vectors or plasmids, which encode filovirus proteins, and/or express filovirus genomic RNA. When introduced into a cell, these vectors yield infectious filovirus. Thus, the invention includes isolated and/or purified filovirus prepared by the methods disclosed herein. As also described, the invention provides isolated and/or purified noninfectious lipid encapsulated particles, i.e., the contacting of cells with nonifectious particles does not yield progeny virus. As used herein, the terms Aisolated and/or purified@ refer to in vitro preparation, isolation and/or purification of a vector, plasmid, virus or lipid encapsulated particle of the invention, so that it is not associated with in vivo substances, or is substantially purified from in vitro substances. As used herein, the term "recombinant nucleic acid" or "recombinant DNA sequence, fragment or segment" refers to a nucleic acid, e.g., to DNA, that has been derived or isolated from a source, that may be subsequently chemically altered in vitro, and includes, but is not limited to, a sequence that is naturally occurring, is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

The vectors or plasmids of the invention comprise filovirus cDNA, for example, one or more open reading frames encoding filovirus proteins or portions of the genomic sequence which are capable of being replicated and packaged into virions in the presence of filovirus proteins. Therefore, gene(s) or portions thereof other than those of a filovirus may be employed in the vectors or plasmids, or methods, of the invention. A vector or plasmid of the invention may comprise a gene or open reading frame of interest, e.g., a foreign gene encoding an immunogenic peptide or protein useful as a vaccine or a therapeutic protein. If more than one vector is employed, the vectors may be physically linked or each vector may be present on an individual plasmid or other, e.g., linear, nucleic acid delivery vehicle. The vectors or plasmids may be introduced to any host cell, preferably a eukaryotic cell. Preferred host cells to prepare virus or lipid encapsulated particles of the invention include insect, avian or mammalian host cells such as canine, feline, equine, bovine, ovine, or primate cells including simian or human cells.

The filovirus genomic cDNA of the invention allows easy manipulation of filovirus, e.g., by the introduction of mutations into the viral genome. The methods of producing virus described herein, which do not require helper virus infection, are useful in viral mutagenesis studies, and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, ornithine transcarbamylase deficiency and central nervous system tumors). In particular, the use of lipid encapsulated particles of the invention which induce strong humoral and cellular immunity may be preferred as vaccine vectors as they are noninfectious and unlikely to give rise to infectious recombinant virus.

Thus, a virus for use in medical therapy (e.g., for a vaccine or gene therapy) is provided. For example, the invention provides a method to immunize an animal against a pathogen, e.g., a bacteria, virus, or parasite, or a malignant tumor. The method comprises administering to the animal an amount of at least one isolated virus of the invention which encodes and expresses, or comprises, an immunogenic peptide or protein of a pathogen or tumor, optionally in combination with an adjuvant, effective to immunize the animal. Alternatively, a lipid encapsulated particle of the invention may be used for immunization, either by delivering a DNA vaccine, or via expression of the immunogenic protein on the surface of the particle, for instance, the particle comprises a fusion protein comprising the extracellular domain of an immunogenic protein and the transmembrane and cytoplasmic portion of filovirus GP.

Also provided is a method to augment or increase the expression of an endogenous protein in an animal, e.g., a mammal such as a rodent, nonhuman primate or human, having an indication or disease characterized by a decreased amount or a lack of the endogenous protein. The method comprises administering to the animal an amount of an isolated virus of the invention effective to augment or increase the amount of the endogenous protein in the animal. Alternatively, a lipid encapsulated particle of the invention can be employed to deliver DNA encoding the protein or the protein itself. When the particle is used to deliver protein, optionally the particle comprises a chimeric transmembrane protein comprising an extracellular protein for targeting the particle to a specific tissue or cell type and the transmembrane and cytoplasmic portion of a filovirus GP.

The invention will be further described by the following non-limiting examples.

EXAMPLE 1

Generation of Transfectant Ebola Virus

Materials and Methods

Efficiency of Virus Generation.

To determine the efficiency of virus generation, Vero E6 cells were cotransfected with protein expression plasmids and the plasmid for Ebola virus vRNA or cRNA synthesis. Four days after transfection, the efficiency of virus generation was measured by determining the dose required to infect 50% of tissue culture cells ($TCID_{50}$) per ml of supernatant. The data shown in FIG. 1A are representative results from three independent experiments. Experiments for the generation of Ebola virus as well as the characterization of recombinant Ebola virus were carried out in the BSL4 facility at the Canadian Science Centre for Human and Animal Health, Winnipeg, Canada. Cells were transfected with plasmids for the expression of the Ebola virus NP, L, VP30, and VP35 proteins, and with the plasmid for Ebola virus cRNA or vRNA synthesis, controlled by T7 RNA polymerase promoter and ribozyme sequences. T7 RNA polymerase was provided by cotransfection of cells with pC-T7Pol.

Immunofluorescence Assay.

Vero E6 cells were infected at a multiplicity of infection of $10^{-2}$ with either wild-type Ebola virus generated from plasmids or Ebola virus with an altered furin recognition sequence in its GP. Six days later, cells were observed under a light microscope. Three days after infection, cells were permeabilized and stained with antiserum. Three days after infection, cells were fixed with 2% paraformaldehyde in phosphate-buffered saline, followed by inactivation by gamma irradiation (2 Mrads). Cells were permeabilized with 0.1% Triton X-100 in phosphate-buffered saline for 15 minutes, washed three times with phosphate-buffered saline, and incubated for 1 hour at room temperature with an anti-Ebola virus Zaire rabbit antiserum (1:100 dilution in phosphate-buffered saline). After three washes with phosphate-buffered saline, Cy3-labeled anti-rabbit (1:500) conjugate (Rockland, Gilbertsville, Pa.) was added for 1 hour at room temperature. The cells were then washed with phosphate-buffered saline, mounted, and analyzed using an Axioplan 2 microscope (Zeiss).

Replication Kinetics.

Vero E6 cells were infected with the wild-type or cleavage site mutant at a multiplicity of infection of $10^{-2}$. Supernatants were harvested at 2, 24, 48, and 72 hours postinfection. The $TCID_{50}$ was determined by infecting Vero E6 cells with 10-fold dilutions of the supernatants obtained at the above-mentioned time points.

Labeling of Protein and Immunoprecipitation Analysis.

Vero E6 cells were infected at a multiplicity of infection of $10^{-2}$ and incubated until a cytopathic effect was observed. After the medium was removed, the cells were washed once with methionine- and cysteine-free DMEM and labeled for 24 hours in 2 ml of methionine- and cysteine-free Dulbecco=s modified Eagle=s medium containing 2% dialyzed fetal calf serum and 10 µCi of protein labeling mix (NEN, Mississauga, Canada)/ml. The supernatants were then clarified by centrifugation (1,000×g for 5 minutes at 4EC). An equal volume of 2×RIPA buffer (2% Triton X-100, 2% sodium deoxycholate, 0.2% sodium dodecyl sulfate, 0.3 M NaCl, 40 mM Tris-HCl [pH 7.7], 20 mM EDTA [pH 8.0], 0.4 U of aprotinin/ml, 2 mM phenylmethylsulfonyl fluoride, 20 mM iodoacetamide) was added to the supernatants, and the solutions were subsequently inactivated by gamma irradiation (2 Mrad). Aliquots of the inactivated labeled material were mixed with an anti-Ebola virus Zaire horse serum and incubated at 4EC overnight. The immune complexes were mixed with 30 µl of protein G sepharose for 3 hours at 4EC with rotation. After 3 washes with RIPA buffer, the immunoprecipitated proteins were recovered by boiling them in 1×RIPA buffer.

Results

To generate a cDNA clone encoding the entire genome of Ebola virus (Zaire species, strain Maying a), viral RNA was reverse transcribed with ThermoScript Reverse Transcriptase (Gibco/BRL, Rockville, Md.) and amplified by PCR with Pfu Turbo (Stratagene, La Jolla, Calif.). The resulting cDNA fragments were cloned in a Bluescript vector or its derivatives. A consensus sequence was determined and compared to a reference sequence (GenBank accession number AF086833). An A insertion was found between nucleotides 9,744 and 9,745, which was also detected in a partial Ebola virus genomic sequence (GenBank accession number L11365). In addition, an A insertion was found between nucleotides 18,495 and 18,496, and an A-to-T replacement was detected at position 18,226. The latter two changes have also been reported for a functional Ebola virus minigenome (Muhlberger et al., 1999). A full-length Ebola virus cDNA construct was assembled in a modified pTM1 vector (Moss et al., 1990), using conventional cloning techniques. Sequence analysis of the resulting full-length clone proved that no mutations had occurred during cloning procedures in E. coli.

Negative-sense RNA viruses have been generated from constructs encoding either the negative-sense viral RNA (vRNA) or the positive-sense complementary RNA (cRNA) (Marriott et al., 1999; Nagai et al., 1999; Neumann et al., 1999; Roberts et al., 1999; Schnell et al., 1994), albeit with higher efficiencies from the latter (Durbin et al., 1997; and Kato et al., 1996). cDNA constructs encoding the entire viral genome were generated, flanked by the T7 RNA polymerase promoter and a ribozyme, in both positive-sense and negative-sense orientations (FIG. 1A). To achieve efficient transcription, the wild-type T7 RNA polymerase promoter, which yields transcripts with an additional G at the 5' end, was used to generate pTM-T7G-Ebo-Rib and pTM-Rib-Ebo-GT7 (FIG. 1A).

The generation of negative-sense RNA viruses requires viral proteins and genomic RNA for replication and transcription. For Ebola virus, the proteins necessary for replication and transcription include the RNA-dependent RNA polymerase L, and the nucleoprotein (NP), and two additional auxiliary proteins (VP30 and VP35) (Muhlberger et al., 1999). To generate constructs for the expression of Ebola viral proteins, the respective cDNA fragments were amplified by PCR, the products sequenced and then cloned into the eukaryotic expression vector pCAGGS/MCS (controlled by the chicken β-actin promoter) (Kobasa et al., 1997; Niwa et al., 1991), resulting in four plasmids (pCEZ-NP, pCEZ-VP30, pCEZ-VP35, and pCEZ-L).

To generate Ebola virus, $5 \times 10^5$ Vero E6 (African green monkey kidney) cells were transfected with 1 µg of the respective plasmid for Ebola virus vRNA or cRNA synthesis and with the following amounts of protein expression plasmids: 1 µg of pCEZ-NP, 0.3 µg of pCEZ-VP30, 0.5 µg of pCEZ-VP35, and 2 µg of pCEZ-L (FIG. 1B). To drive the transcription of viral RNA from the T7 RNA polymerase promoter, cells were cotransfected with 1 µg of an expression plasmid for T7 RNA polymerase (pC-T7pol). Four days later, supernatants were collected and used to infect fresh Vero E6 cells. When examined at 6 to 8 days postinfection, the cells showed cytopathic effects, indicating the generation of infectious Ebola virus entirely from cloned cDNA. Ebola virus was produced from constructs encoding either negative-sense vRNA or positive-sense cRNA (FIG. 1A). To determine the efficiency of virus generation, supernatants of transfected cells were collected 4 days after transfection, and the titer of virus in the supernatant was determined in Vero E6 cells. The efficiencies of virus generation from negative-sense vRNA or positive-sense cRNA were comparable, resulting in the generation of $10^2$ 50% tissue culture infective doses ($TCID_{50}$) per ml of supernatant.

Figure 2A:
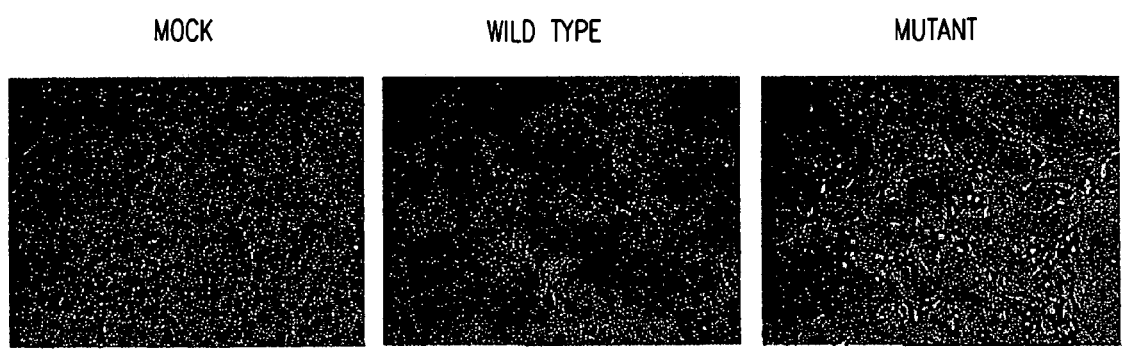
FIG. 2. Replication of Ebola virus in cell culture. A) Six days after infection (light microscope). B) Three days after infection (antibody-based staining for virus). Mutant refers to an Ebola virus with an altered furin recognition sequence in GP.
Figure 2B:
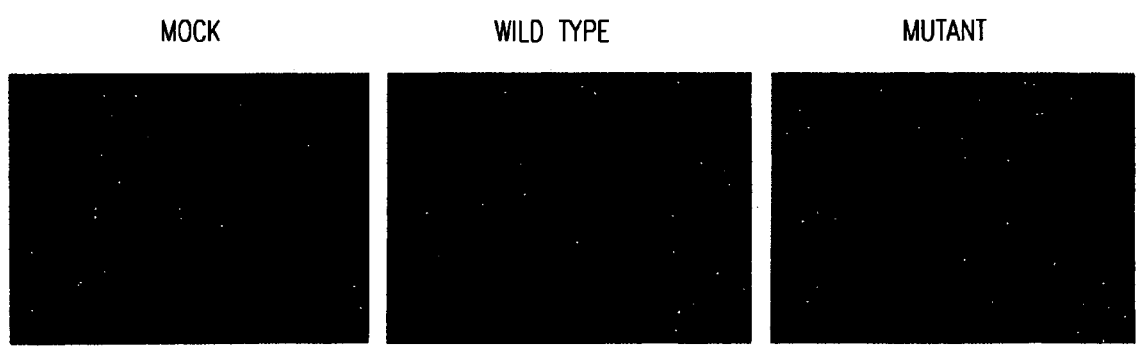

A subsequent passage of the virus in Vero E6 cells was performed to confirm the authenticity of the replicating agent. The first signs of a cytopathic effect were observed at 48 hours postinfection and became more prominent during the following days (FIG. 2A). Indirect immunofluorescence assays with a rabbit antiserum to Ebola virus GP/secreted GP (sGP) demonstrated the presence of Ebola virus GPs (FIG. 2B). None of the negative controls (untreated cells or cells transfected with the full-length cDNA construct or the protein expression plasmids alone) showed cytopathic effects or reacted with the anti-GP/sGP antiserum.

The availability of a method for generating Ebola virus mutants greatly increases opportunities to dissect mechanisms of viral pathogenesis. For many viruses, postranslational cleavage of membrane glycoproteins by host proteolytic enzymes, including subtilisin-like proteases such as furin, is a prerequisite for fusion between the viral envelope and cellular membranes and therefore an important step in pathogenesis (Klenk et al., 1994). The Ebola virus GP is cleaved by furin or furin-like proteases at a highly conserved sequence motif (R-X-K/R-R; X, any amino acid; SEQ ID NO:54) (Volchkov et al., 1998). Since the amino acid sequence of the GP of the Reston species, the least pathogenic of all Ebola virus subtypes in humans, deviates from the optimal furin recognition sequence, GP cleavage has been thought to be an important determinant of Ebola virus pathogenicity (Feldmann et al., 1999).

Figure 3:
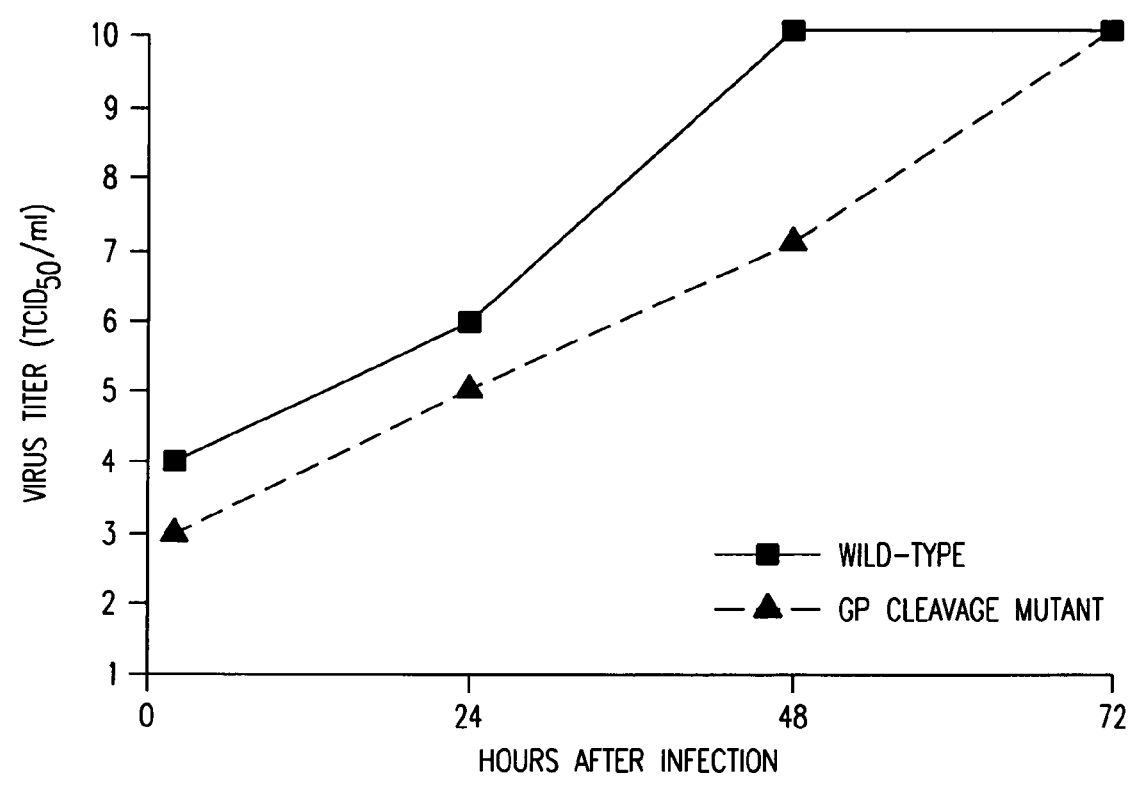

The effect of an altered furin recognition motif on Ebola virus replication was studied by modifying pTM-T7G-Ebo-Rib. The multibase furin recognition site (RRTRR, SEQ ID NO:55, at amino acid positions 497 to 501 of the GP) in pTM-T7G-Ebo-Rib was replaced with 497-AGTAA-501 (SEQ ID NO:58). The modified plasmid, designated pTM-T7G-Ebo-Rib-Cl(−), was transfected into Vero E6 cells, together with protein expression plasmids for the NP, VP30, VP35, and L proteins and for T7 RNA polymerase. Fresh Vero E6 cells were subsequently incubated with supernatants derived from the transfected cells. Six days later, cytopathic effects were observed in these cells. Indirect immunofluorescence assays with antiserum to Zaire Ebola virus GP/sGP verified virus replication (FIG. 2). Growth curves in Vero E6 cells demonstrated that although the mutant virus grew slightly more slowly than the wild-type virus (FIG. 3), it reached $10^{10}$ $TCID_{50}$/ml at 3 days postinfection.

To confirm the presence of mutations in the GP cleavage motif, wild-type and mutant viruses were passaged three times in Vero E6 cells, RNA extracted from virions, and reverse transcriptase PCR performed with primers spanning the altered furin recognition motif. Direct sequencing of the PCR products confirmed the retention of mutations in the GP cleavage site (data not shown).

FIG. 4 shows the results of experiments testing the cleavability of the Ebola virus mutant GP lacking a furin recognition motif. Virions derived from labeled Vero E6 cells infected with wild-type or mutant virus were lysed, and viral proteins were detected by immunoprecipitation using a horse antiserum to Zaire Ebola virus. For wild-type virus, both cleavage products $GP_1$ (140 kDa) and $GP_2$ (26 kDa) were detected (FIGS. 4A and B, lanes 2). By contrast, alteration of the furin recognition sequence abolished the generation of $GP_1$ and $GP_2$, and only the precursor, $GP_0$, was detected (FIGS. 4A and B, lanes 3), confirming that furin or related proteases are the major host cell proteases for GP cleavage. These results indicate that the furin recognition motif at the Ebola GP cleavage site is dispensable for replication of the virus in cell culture.

Discussion

Marburg and Ebola viruses have been difficult to study because they must be handled in high-containment facilities, and effective methods of experimental mutagenesis were lacking. These limitations have restricted the development of antiviral drugs and vaccines, although reports of potentially useful experimental vaccines (Hevey et al., 1998; Sullivan et al., 2000; Vanderzanden et al., 1998; Xu et al., 1998) and antibody-mediated treatments (Maruyama et al., 1999; and Wilson et al., 2000) are beginning to emerge. The use of a reverse genetics system, which enables one to generate Ebola virus mutants entirely from cloned cDNA as described herein, opens a new era of filovirus research.

For many viruses in the Orthomyxoviridae and Paramyxoviridae families, GP cleavage by furin and other host cell proteases is absolutely required for their infectivity and thus determines the extent of viral pathogenicity (Klenk et al., 1994). In contrast, findings with viruses pseudotyped with Ebola GPs as well as the present results demonstrate that GP cleavage is dispensable for replication of Ebola virus, at least in cell culture. The furin cleavage motif is highly conserved among all Ebola GP sequences determined thus far, and its conservation suggests a role in the viral life cycle. Hence, GP cleavage by furin is not critical for Ebola virus replication in the cells tested, but it may be required for Ebola virus replication in vivo and/or in its natural reservoir. Further studies with animal models will be needed to establish the role of GP cleavage in Ebola virus replication and pathogenicity.

T7 RNA polymerase-based reverse genetics systems rely on the expression of this enzyme within the transfected cells. To this end, two approaches have been explored (reviewed in Marriott et al., 1999; Nagai et al., 1999; and Roberts et al., 1999). T7 RNA polymerase has been provided from recombinant vaccinia virus or from stable cell lines constitutively expressing this enzyme. The former approach leaves investigators with the task of separating the artificially generated recombinant virus from vaccinia virus. On the other hand, cell lines expressing T7 RNA polymerase may produce insufficient amounts to efficiently transcribe the viral genome. In contrast to Volchkov et al. (2001), who used a BHK-21 cell line stably expressing T7 RNA polymerase, an entirely plasmid-based system is described herein which was achieved using T7 RNA polymerase expression under control of the strong chicken β-actin promoter. This approach resulted in $10^2$ PFU of virus per ml of culture supernatant. Expression of T7 RNA polymerase from plasmids may therefore be an alternative for the generation of other nonsegmented, negative-sense RNA viruses, thereby circumventing restraints encountered with the established systems.

The reverse genetics systems for the generation of Ebola virus can be used to identify key regulatory elements and structure-function relationships in the viral life cycle, and allows the study of mechanisms of filovirus pathogenicity in animal models. The system also promotes the development of new vaccines and the development of replication-deficient viruses.

EXAMPLE 2

Generation of Noninfectious Ebola Particles

Materials and Methods
Cells.
293 and 293T human embryonic kidney cells were maintained in DMEM supplemented with 10% fetal calf serum, 2% L-glutamine, and penicillin-streptomycin solution (DMEM-FCS) (Sigma). The cells were grown at 37EC in 5% $CO_2$.

Construction of Plasmids.
To generate cDNA constructs encoding the VP40 protein, primers were used that bind to the start and stop codons (positions 4479 and 5459 of the positive-sense antigenomic RNA) to reverse transcribe and PCR-amplify purified viral RNA (Titan RT-PCR Kit, Roche). The PCR product was cloned in the pT7Blue vector (Novagen) resulting in pT7EboZVP40. The cloned Ebola VP40 gene was sequenced to ensure that unwanted nucleotide replacements were not present.

Figure 5A:
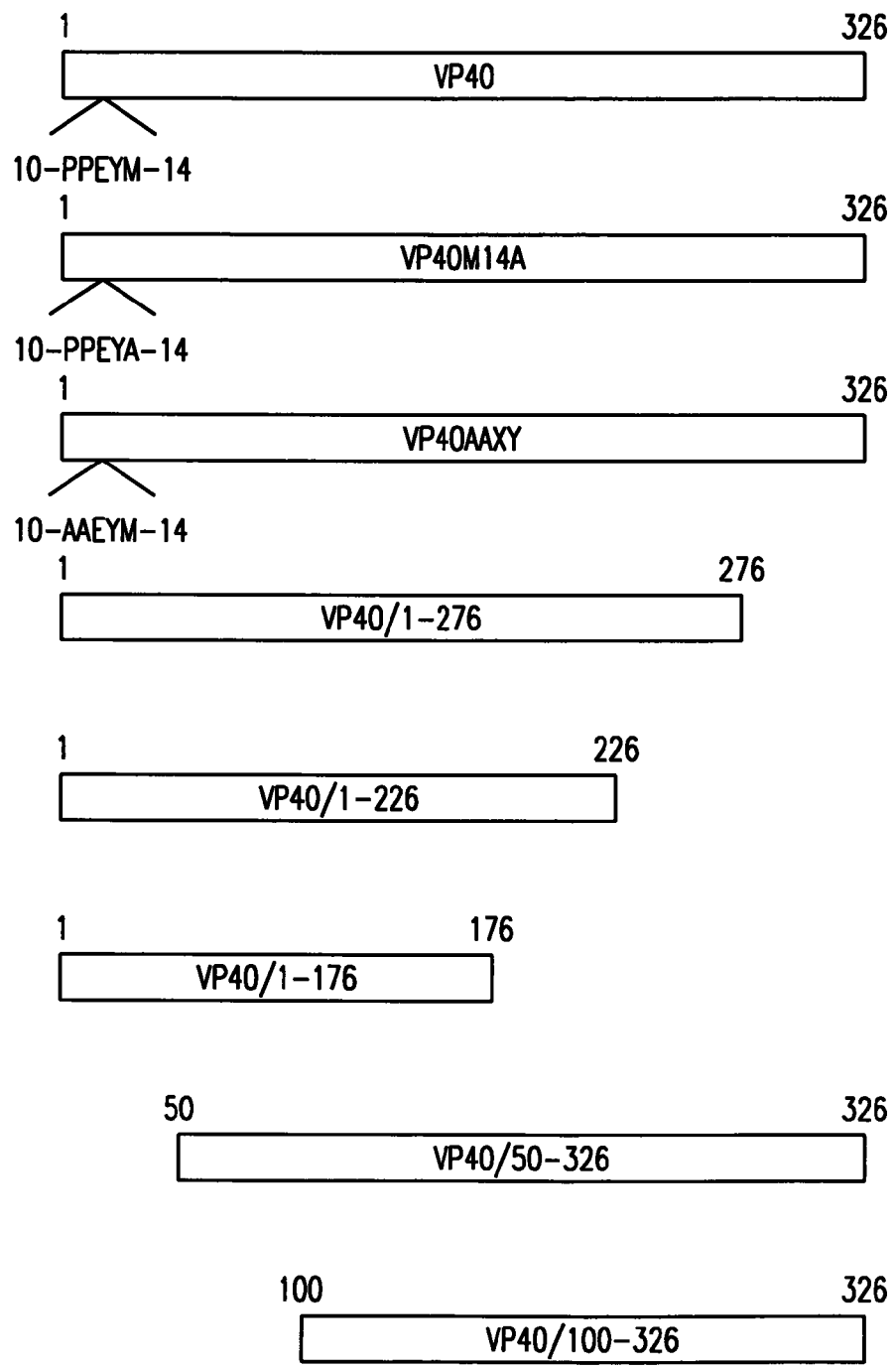
FIG. 5. (A) Schematic representation of wild-type VP40 and VP40 mutants (SEQ ID NOs:47-49; 51). Substituted residues are indicated in bold-face type. (B) Kyte-Doolittle hydrophobicity plot of Ebola virus VP40 over a window of 17 amino acids (Justice et al., 1995).

To generate plasmid pETEBoZVP40His for the expression of 6-histidine-tagged VP40 in *Escherichia coli*, pT7EboZVP40 was used as a template for PCR amplification with the appropriate primers. The PCR product was blunt-end ligated into the SmaI-digested site of vector pM (CLONETECH). This construct was digested with NdeI and EcoRI and the fragment containing VP40 was ligated into the expression vector pET-5a (Promega). To generate plasmids pCEboZVP40, pCEboZVP40AAXY (AAXY corresponds to SEQ ID NO:51), pCEboZVP40M 14A, pCEboZVP40/1-276, pCEboZVP40/1-226, pCEboZVP40/1-176, pCEboZVP40/50-326, and pCEboZVP40/100-326 (proteins expressed from these plasmids are designated VP40, VP40AAXY, and the like; AAXY corresponds to SEQ ID NO:51) for expression of VP40 and its mutants in eukaryotic cells, the Ebola Zaire VP40 gene was amplified from pT7EboZVP40 using specific forward primers, each containing an EcoRI site 5' to the start of the coding region, and specific reverse primers, each containing a BglII site 3' to the stop codon for each construct, and blunt-end ligated into the EcoRV-digested site of vector pT7Blue. Each construct was digested with EcoRI and BglII, and the fragment containing the VP40 gene or modified VP40 gene was cloned into the EcoRI and BglII-digested eukaryotic expression vector pCAGGS/MCS (expression controlled by the chicken β-actin promoter) (Kobasa et al., 1997; and Niwa et al., 1991). Eukaryotic expression constructs employed in this study are schematically presented in FIG. 5A.

Antibody.
A polyclonal antibody against Ebola Zaire VP40 was produced as follows: BL21 *E. coli* cells were transformed with plasmid pETEboZVP40H is. Expression of the 6-His-tagged VP40 protein was induced with 1 mM IPTG for 3 hours. The *E. coli* cells were lysed and cellular debris was remove by centrifugation. The supernatant was purified over an Ni-NTA agarose column (Qiagen). Expression of VP40 was verified by SDS-PAGE followed by Western blotting using a monoclonal antibody against the histidine tag (Kodak). Rabbits were immunized with approximately 0.5 mg of VP40, and antibody against keratin present in the antiserum was removed with a keratin column (Girault et al., 1989).

Cell Transfection for Expression of VP40 and its Mutants.
293 or 293T cells (60-mm plates) were transfected with expression vectors with the use of the Trans IT LT-1 liposomal reagent (Panvera) according to the manufacturer's instructions. Briefly, DNA and transfection reagent were mixed (6 µl of Trans IT LT-1 with 3 µg of DNA) in 0.2 ml OPTI-MEM (Gibco-BRL), incubated for 30 minutes at room temperature, and added to the cells. Transfected cells were incubated at 37EC until harvest of the supernatant and/or cell monolayer.

Particle Formation Assay.
Particles were assayed by the method of Li et al (1993) with some modifications. Forty-eight hours after transfection of 293T cells with pCEboZVP40, pCEboZVP40AAXY (AAXY corresponds to SEQ ID NO:51), pCEboZVP40M14A, or pCEboZVP40/1-276, the culture medium was removed and placed on ice. The cell monolayer was washed with phosphate-buffered saline (PBS), scraped into lysis buffer (0.25 M Tris-HCl, pH 8.0, 0.5% Triton X-100) and kept at 4° C. The culture medium (2 ml) was centrifuged at 2,000 rpm in a microcentrifuge for 5 minutes to remove cellular debris, layered over 20% sucrose in STE buffer (0.01 M Tris-Cl, pH 7.5, 0.01 M NaCl, 0.001 M EDTA, pH 8.0) (2 ml), and centrifuged at 150,000×g for 2 hours at 4° C. After centrifugation, the supernatant was removed and added to the cell lysate. This mixture was saved for analysis of total protein expression. The pellet was resuspended in 1 ml STE buffer overnight at 4° C. The resuspended pellet was layered over a 10-50% discontinuous sucrose gradient in STE buffer, centrifuged at 150,000×g for 4 hours at 4° C., and fractions (1 ml) were collected from the top of the gradient. Each fraction was mixed with 0.25 ml of 50% trichloroacetic acid (TCA) (10% TCA), the fractions were incubated for 30 minutes on ice, and the precipitated proteins were pelleted by microcentrifugation for 15 minutes. The pellets were washed once with cold acetone, air-dried, and resuspended in 0.05 ml SDS-PAGE sample buffer. Proteins in the mixture of cell lysate and supernatant from centrifugation through 20% sucrose were precipitated with 10% TCA, washed with acetone, and resuspended in 0.5 ml SDS-PAGE sample buffer. Proteins were separated by 12% SDS-PAGE and detected by Western blotting. Fractions are numbered from the top to the bottom of the gradient.

Protease Protection Assay.
293T cells were transfected with pCEboZVP40 and, at 48 hours post-transfection, the culture medium was removed. The medium was microcentrifuged at 2,000 rpm for 5 minutes to remove cellular debris, layered over a 20% sucrose cushion, and centrifuged at 165,000×g for 1 hour at 4EC. The supernatant was removed and the pellet was resuspended overnight at 4EC in 0.4 ml STE buffer. This resuspension was divided into six aliquots and treated following a protocol previously described (Mik et al., 1989): Aliquot 1 received no further treatment; aliquot 2 was treated with soybean trypsin inhibitor (Biofluids) to a final concentration of 3 mg/ml; aliquot 3 with triton X-100 to a final concentration of 1%; aliquot 4 with trypsin (Worthington) to a final concentration of 0.1 mg/ml; aliquot 5 with both Triton X-100 to 1% and trypsin to 0.1 mg/ml final concentration; and aliquot 6 with both trypsin inhibitor (3 mg/ml final) and trypsin (0.1 mg/ml final). The samples were incubated at room temperature for 30 minutes, after which an excess of trypsin inhibitor (5 mg/ml) was added to each aliquot. SDS-PAGE sample buffer (6×) was added to each aliquot. Proteins from each aliquot were separated by 12% SDS-PAGE and detected by Western blotting.

Membrane-Association Assay.

The method of Bergmann and Fusco (1988) was used, with some modifications, to determine membrane-association of VP40 and its mutants. Briefly, 48 hours after transfection of 293 cells with pCEboZVP40 or a mutant-VP40 expression plasmid, the culture medium was removed, and the cell monolayer, after a wash with (PBS), was scraped into ice-cold sucrose homogenization buffer (10% wt/wt sucrose, 10 mM Tris-HCl (pH 7.4), 1 mM EDTA, and 10 mM iodoacetamide). Cells were disrupted with 30 strokes of a Dounce homogenizer on ice and microcentrifuged for 3 minutes at 2,000 rpm to remove nuclei. The resulting supernatant was made to 1 M NaCl or left untreated, incubated at room temperature for 20 minutes, made to 80% sucrose (wt/vol), placed at the bottom of a Beckman SW41 centrifuge tube, and overlaid with 5 ml of 65% (wt/vol) sucrose and 2.5 ml of 10% sucrose. The gradient was centrifuged to equilibrium at 150,000×g for 18 hours at 4EC. Fractions (1 ml) were collected from the top of the gradient, diluted 1:1 with TBS-Triton buffer (0.025 M Tris-HCl, pH 7.5, 0.15 M NaCl, 0.5% Triton X-100) or, for experiments involving expression of VP40/100-326, precipitated with TCA (as described for the particle formation assay) owing to the weak signal of this deletion construct in Western analysis, and mixed with SDS-PAGE sample buffer. Proteins from each aliquot were separated by 12% SDS-PAGE and detected by Western blotting.

Triton X-114 Phase Partitioning Analysis.

The method used was essentially that of Bordier (1981). Forty-eight hours post-transfection of 293 cells pCEboZY40, pCEboZVP40/1-276, pCEboZVP40/1-226, pCEboZVP40/1-176, pCEboZP40/50-326, pCEboZVP40/100-326, or, as a control, a vector expressing A/WSN/33 ($H_1N_1$) influenza virus hemagglutinin (HA), cells were scraped into cold TN buffer (10 mM Tris-HCl, pH 7.4, 150 mM NaCl), disrupted with 30 strokes in a Dounce homogenizer, and subjected to centrifugation at 2,000 rpm for 3 minutes to remove nuclei. Triton X-114 (Sigma) was added to each supernatant to 1%, and the resulting solution was incubated for 15 minutes at 4EC with agitation. Unsolubilized material was pelleted by centrifugation in a picofuge for 5 minutes at 4EC, and the supernatant was heated to 37EC for 5 minutes. The supernatant was layered onto a 37EC sucrose (6%) cushion in TN buffer containing 0.06% Triton X-114 and centrifuged at 2,000 rpm for 3 minutes at room temperature. The detergent (lower) and aqueous (upper) phases were recovered separately, the aqueous phase was extracted a second time, like phases were pooled, and the detergent phase was diluted in TN buffer. Proteins in each phase were precipitated with 50% acetone and resuspended in SDS-PAGE sample buffer. Proteins were separated by 12% SDS-PAGE and analyzed by Western blotting.

Western Blotting.

Samples in sample buffer (10 µl) were incubated at 100EC for 5 minutes and separated on 12% polyacrylamide gels. Resolved proteins were transferred to Westran polyvinylidine difluoride membranes (Schleicher & Schuell) and blocked overnight at 4EC with 5% skim milk in PBST (0.05% Tween 20 (Sigma) in PBS). Blots were incubated in primary antibody for 1 hour at room temperature, washed three times with PBST, incubated in biotinylated anti-rabbit secondary antibody (Vector Laboratories) for 30 minutes, washed three times with PBST, incubated in streptavidin-horseradish peroxidase reagent (Vector Laboratories) for 30 minutes and washed three times with PBST. Blots were then incubated in Lumi-Light Western blotting substrate (Boehringer-Mannheim) for 5 minutes and exposed to x-ray film (Kodak).

Results

Expression of VP40 in Mammalian Cells.

Figure 6:
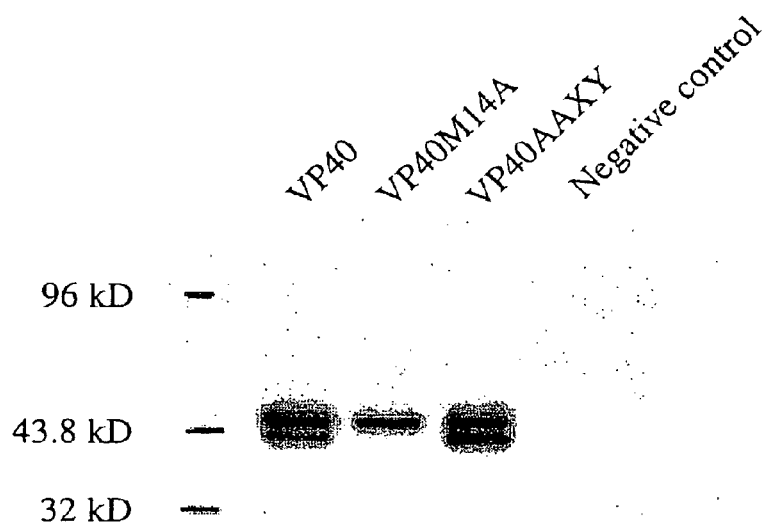
FIG. 6. Expression of VP40, VP40/M14A and VP40AAXY (AAXY corresponds to SEQ ID NO:51) in 293T cells. The sample for the negative control was prepared from cells transfected with the empty vector (pCAGGS/MCS). Lysates were harvested 24 hours post-transfection, and proteins were separated by SDS-PAGE (12%) and detected by Western blotting.
Figure 8:
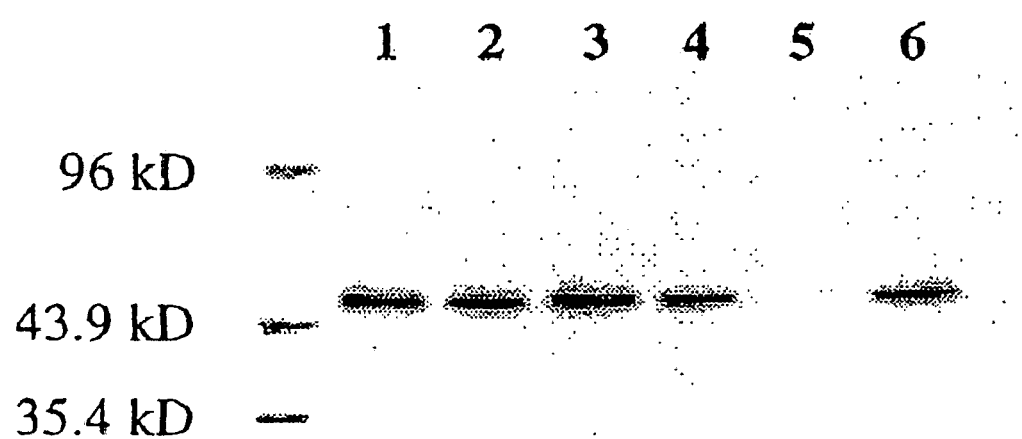
FIG. 8. Protease protection analysis of VP40-induced particles. Lane 1: no treatment; lane 2: soybean trypsin inhibitor; lane 3: Triton X-100; lane 4: trypsin; lane 5: Triton X-100 and trypsin; and lane 6: trypsin inhibitor and trypsin. Proteins were separated by SDS-PAGE (12%) and detected by Western blotting.
Figure 9A:
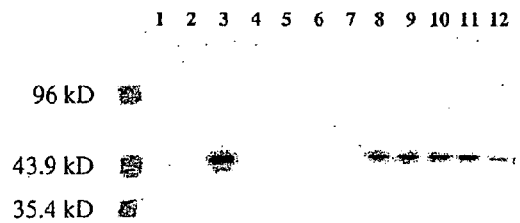
FIG. 9. Membrane-association analysis of VP40 and its deletion mutants. Shown are gradients from cells expressing VP40 (A-B), VP40/1-276 (C-D), VP40/1-226 (E-F), VP40/1-176 (G-H), VP40/50-326 (I-J), and VP40/100-326 (K-L). Fractions are numbered from the top to the bottom of the gradient. Proteins were separated by SDS-PAGE (12%) and detected by Western blotting.
Figure 9B:
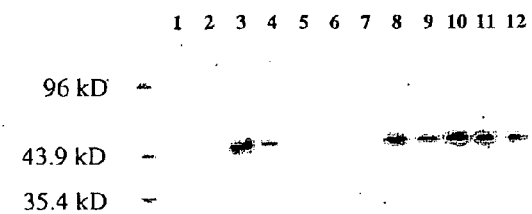
Figure 9C:
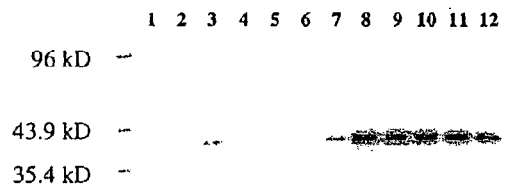
Figure 9D:
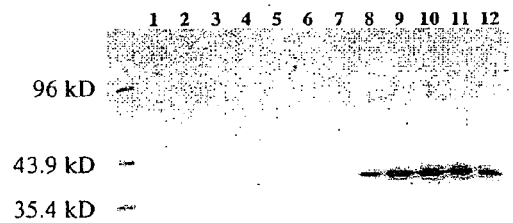
Figure 9E:
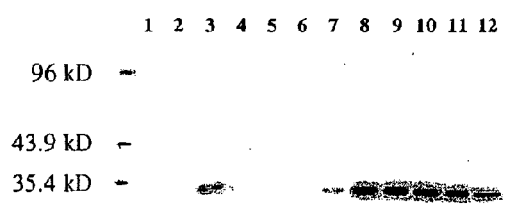
Figure 9F:
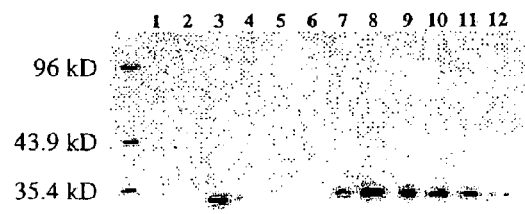
Figure 9G:
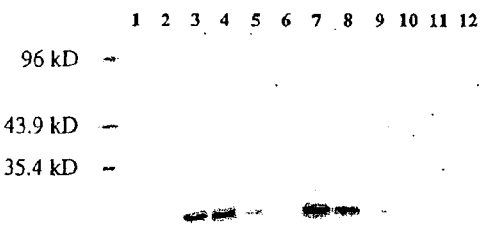
Figure 9H:
Figure 9I:
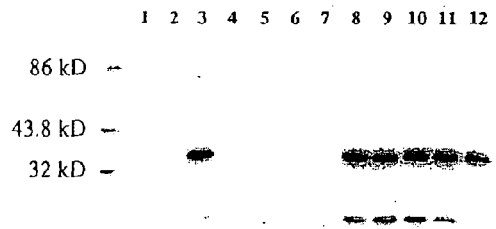
Figure 9J:
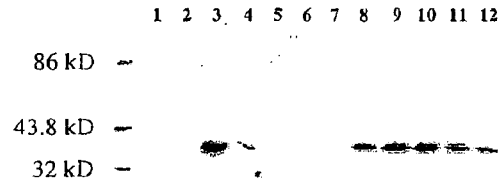
Figure 9K:
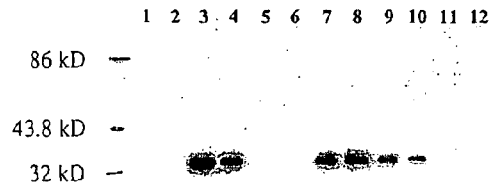
Figure 9L:
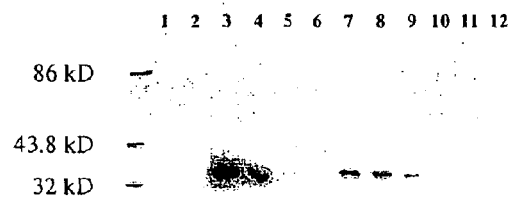

To ensure that VP40 is expressed at efficient levels in human embryonic kidney 293T cells, the cell lysate was analyzed 24 hours after transfection with pCEboZVP40 by Western blotting. Two bands reacting with anti-VP40 polyclonal antibody were found, a small distance apart, in the range of 40 kDa (FIG. 6). The lysate from cells transfected with the expression vector alone did not react with the antibody.

VP40 contains an internal start codon at nucleotides 40-42 (codon 14) that is in frame with the first AUG. To determine whether protein synthesis from this internal start codon was responsible for the faster-migrating band on the gel, a construct was generated, pCEboZVP40M14A, which expresses a mutant VP40 with this second AUG changed to GCG, which encodes alanine, and expressed it as described above. Analysis of the cell lysate revealed a single, larger-sized band (FIG. 6), suggesting that the second AUG is used as a start codon to an appreciable extent in this system.

To determine whether loss of the PPXY (SEQ ID NO:50) motif at amino acids 10-13 of VP40 affects expression of the protein, 293T cells were transfected with pCEboZVP40AAXY (AAXY corresponds to SEQ ID NO:51), which expresses a mutant VP40 in which the PPEY (SEQ ID NO:52) sequence at amino acids 10-13 was changed to AAEY (SEQ ID NO:53). Two bands corresponding to those seen with the expression of wild-type VP40 were detected (FIG. 6). However, in contrast to the results obtained with wild-type VP40 expression, where the slower-migrating band was the predominate product, pCEboZVP40AAXY (AAXY corresponds to SEQ ID NO:51) expressed the two products at similar levels, indicating that loss of the PPXY (SEQ ID NO:50) motif affects either the translation of VP40 or its stability.

Production of Membrane-Bound Particles.

To determine whether VP40-associated vesicles are produced when the protein is expressed in the absence of other viral proteins, 293T cells were transfected with pCEboZVP40 and, after 48 hours, collected the supernatant. After removal of cellular debris, the supernatant was subjected to ultracentrifugation over a 20% sucrose cushion. The pellet was resuspended and centrifuged through a 10-50% discontinuous sucrose gradient, and fractions were analyzed by Western blotting (FIG. 7). Fractions 6-8 contained VP40, with the majority of the protein found in fraction 7. The VP40 in fractions 6-8 was most likely associated with membrane lipids in a particle-like structure, as the sucrose densities in these fractions ranged from 1.11 to 1.13 g/ml, which corresponds to findings for matrix protein-generated particles of other viruses (Giddings et al., 1998; Sandefur et al., 1998). Bands detected below full-length protein in the total protein fraction are likely degradation products. These data indicate that VP40 expressed in the absence of other viral proteins can produce membrane-bound particles.

Protease Protection Assay.

To confirm the ability of VP40 to produce membrane-bound particles when expressed alone, a trypsin protection assay was employed. Culture supernatant from cells transfected with pCEboZVP40 was centrifuged at 165,000×g through 20% sucrose, and the pellet was resuspended in STE buffer and divided into six equal aliquots. Aliquots 1-3 served as controls (untreated, trypsin inhibitor treated, and triton X-100 treated), aliquot 4 was treated with trypsin, aliquot 5 with trypsin and triton X-100, and aliquot 6 with trypsin inhibitor and trypsin. Trypsin degraded VP40 only in the presence of triton X-100 (FIG. 7), indicating that the viral protein does induce the production of fully membrane-bound particles; that is, trypsin digestion of VP40 required disruption of the lipid-bilayer surrounding the protein.

VP40 Mutants and Membrane-Bound Particle Formation.

Does the PPXY (SEQ ID NO:50) motif at amino acids 10-13 of VP40 contribute to particle production? To address this question, VP40AAXY (AAXY corresponds to SEQ ID NO:51) was expressed in 293T cells and assayed for particles as described for wild-type VP40. VP40AAXY (AAXY corresponds to SEQ ID NO:51) was not detected in fractions corresponding to the sucrose densities to which wild-type VP40 particles migrated (FIG. 7). Since VP40AAXY (AAXY corresponds to SEQ ID NO:51) was synthesized at levels similar to wild-type VP40, this finding indicates that mutation of the PPXY (SEQ ID NO:50) motif markedly disrupts VP40-generated vesicle formation.

FIG. 7 also shows the effect of loss of the second AUG codon on particle formation. A substantial amount of VP40M14A was present in fractions 5-8 in the gradient, and the percentage of total VP40M14A expressed in 293T cells that contributed to membrane-bound particle formation was much greater than the percentage of total wild-type VP40 involved in particle formation. This result is consistent with the finding that the PPXY (SEQ ID NO:50) motif present immediately upstream of the second AUG is critical for VP40-associated particle formation (FIG. 7).

To determine whether the C-terminus of VP40 is essential for particle formation, a deletion mutant, VP40/1-276, was assayed which lacks the final 50 amino acids of VP40, for particle generation. Since this deletion mutant was not present at the same sucrose densities that characterized the migration of wild-type VP40, it was concluded that the first 276 amino acids of VP40 are not sufficient for particle formation (FIG. 7).

VP40 Association with Cell Membranes and Structural Requirements for Activity.

Flotation analysis was used to determine if VP40 binds cellular membranes efficiently in mammalian cells. In this method, postnuclear membrane fractions in 80% sucrose are loaded at the bottom of a centrifuge tube and overlaid with 65% and 10% sucrose. During centrifugation, cellular membranes and their associated proteins float to the 10-65% sucrose interface, while soluble proteins remain in the dense sucrose fractions at the bottom of the tube.

A large percentage of wild-type VP40 was found at the 10-65% sucrose interface (fraction 3), while the remaining protein was found in the loading zone (fractions 8-12) (FIG. 9), indicating that VP40 does indeed bind cellular membranes. To clarify the interactions involved in this association, VP40-associated membranes were treated with 1 M NaCl to determine whether electrostatic interactions were required for this association and subjected them to flotation analysis. Salt treatment had a negligible affect on the ability of VP40 to associate with membranes (FIG. 9), suggesting that the protein contains at least one hydrophobic domain able to associate with membranes.

To elucidate the domain(s) of VP40 important for membrane association, deletion mutants were generated. Constructs expressing amino acids 50-326 (pCEboZVP40/50-326), amino acids 100-326 (pCEboZVP40/100-326), amino acids 1-176 (pCEboZVP40/1-176), amino acids 1-226 (pCEboZVP40/1-226), and amino acids 1-276 (pCEboZVP40/1-276) of VP40 were expressed in 293 cells and their membrane association in the presence or absence of 1 M NaCl was examined. The mutants with the largest truncations, VP40/1-176 and VP40/100-326, showed the highest level of association with the lipid bilayer (FIG. 9). Salt treatment did not affect these interactions. Mutants VP40/1-226 and VP40/50-326 associated with membranes to the extent found with wild-type VP40, and these interactions were also relatively unperturbed by treatment with salt. By contrast, only a small portion of VP40/1-276 associated with the lipid bilayer, and this interaction was eliminated upon treatment with salt. These results indicate that loss of the C-terminal 50 amino acids of VP40 markedly alters the membrane-binding capabilities of VP40, primarily by disrupting hydrophobic interactions. This effect was ameliorated when 50 additional C-terminal amino acids were deleted, and membrane-association was promoted when the protein was further truncated to 176 amino acids. Deletion of the N-terminal 49 amino acids of VP40 did not alter the membrane-binding characteristics of the protein, although truncation of 50 additional N-terminal amino acids did enhance protein-membrane association, as seen with VP40/1-176 (FIG. 9).

Figures 10A, 10B:
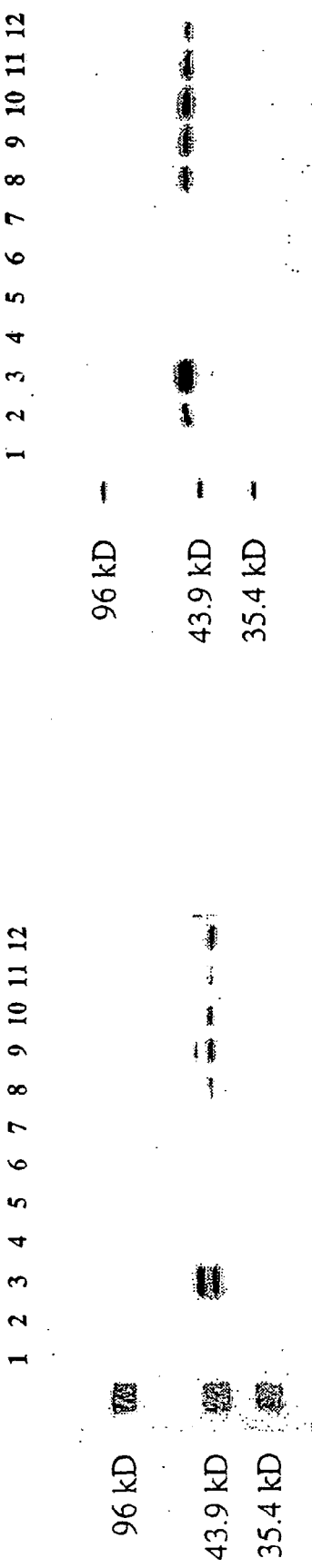
FIG. 10. Membrane-association analysis of VP40 mutants VP40AAXY (A; AAXY corresponds to SEQ ID NO:51) and VP40M14A (B). Lanes represent fractions collected from the top of a gradient formed with a homogenate in 80% sucrose overlaid with 65% and 10% sucrose layers. Lanes represent fractions collected from the top of a gradient formed with a homogenate in 80% sucrose overlaid with 65% and 10% sucrose layers. Proteins were separated by SDS-PAGE (12%) and detected by Western blotting.

Since particle formation was markedly reduced with VP40AAXY (AAXY corresponds to SEQ ID NO:51), cells expressing this mutant were subjected to flotation analysis in order to determine whether a decreased ability to bind membranes was involved in this deficiency. As shown in FIG. 10, the loss of the PPXY (SEQ ID NO:50) motif in VP40 did not affect the ability of the protein to bind membranes, indicating that lack of particle production with this mutant was not due to the loss of membrane association.

Flotation analysis was also used to determine whether the more efficient particle formation induced by VP40M14A, by comparison to wild-type VP40, could be attributed, at least in part, to increased membrane binding by this mutant. The percentage of VP40M14A associated with membranes was only slightly greater than that determined for wild-type VP40 (FIG. 10), indicating that this mutant relies on another mechanism to increase particle formation.

Triton X-114 Phase Partitioning Analysis.

To probe the nature of the VP40-membrane interaction further, Triton X-114 phase partitioning analysis was used as integral membrane proteins and lipid anchored proteins partition in the detergent phase of a protein extraction and peripheral membrane proteins partition in the aqueous phase. FIG. 11 shows the results of this analysis for wild-type VP40, the five deletion mutants of VP40, and influenza virus HA. HA, an integral membrane protein, was found entirely in the detergent phase of the extraction, as expected. Only a small portion of total VP40 was found in the detergent phase, while VP40/1-276 was found almost entirely in the aqueous phase. VP40/1-226 and VP40/50-326 partitioned in the detergent phase in proportions similar to that found for wild-type VP40. By contrast, when VP40/1-176 and VP40/100-326 were expressed, large proportions of each partitioned in the detergent phase. These results indicate that wild-type VP40 possesses only minor traits of an integral membrane protein, and that deletion of its C-terminal 50 amino acids (VP40/1-276) abrogates these features. Further truncation of the C-terminus (VP40/1-226 and VP40/1-176) enhances the integral membrane character of protein. Deletion of the N-terminal 49 amino acids of VP40 (VP40/50-326) does not alter the general structural features of the protein, while deletion of amino acids 1-99 (VP40/100-326) appears to increase the extent of anchoring to lipids.

Discussion

Thus, VP40 of Ebola virus, when expressed in the absence of other viral proteins, can induce the formation of membrane-encompassed particles, much in the manner of the matrix proteins of VSV, rabies, and simian immunodeficiency virus (Giddings et al., 1998; Harty et al., 1999; Justice et al., 1995; Li et al., 1993). Cellular proteins containing the WW domain are, in all likelihood, crucial for this process, as VP40 containing an altered version of a PPXY (SEQ ID NO:50) motif at amino acids 10-13 induces little or no particle formation. Harty et al. (1999) demonstrated that the matrix proteins of VSV and rabies viruses, which possess this motif at their N-termini, bind the cellular Yes-kinase-associated and Nedd4 proteins via a PPXY (SEQ ID NO:50) motif-WW domain, interaction, and that the loss of this motif results in impaired virus release from infected cells. Jayakar et al. (2000) recently demonstrated that mutation of the PPXY (SEQ ID NO:50) motif in the matrix protein of VSV impedes budding of fully assembled virions at the plasma membrane. The data described herein provides evidence for an important role of the PPXY (SEQ ID NO:50) motif in particle formation induced by VP40, and suggest that cellular proteins are crucial players in this process.

The efficiency of particle production markedly increased when the second ATG codon of VP40 (codon 14) was changed to GCG (alanine), but the reason for this enhancement remains unclear. This ATG codon immediately follows the PPXY (SEQ ID NO:50) motif. Perhaps the faster-migrating version of VP40, which lacks the PPXY (SEQ ID NO:50) motif, interferes with the assembly or budding of full-length VP40 molecules at the cell surface, or with the interaction between VP40 and a cellular protein. Whether translation from this second ATG occurs in actual viral infection or is an artifact of the system employed in this study is unknown.

Figure 5B:
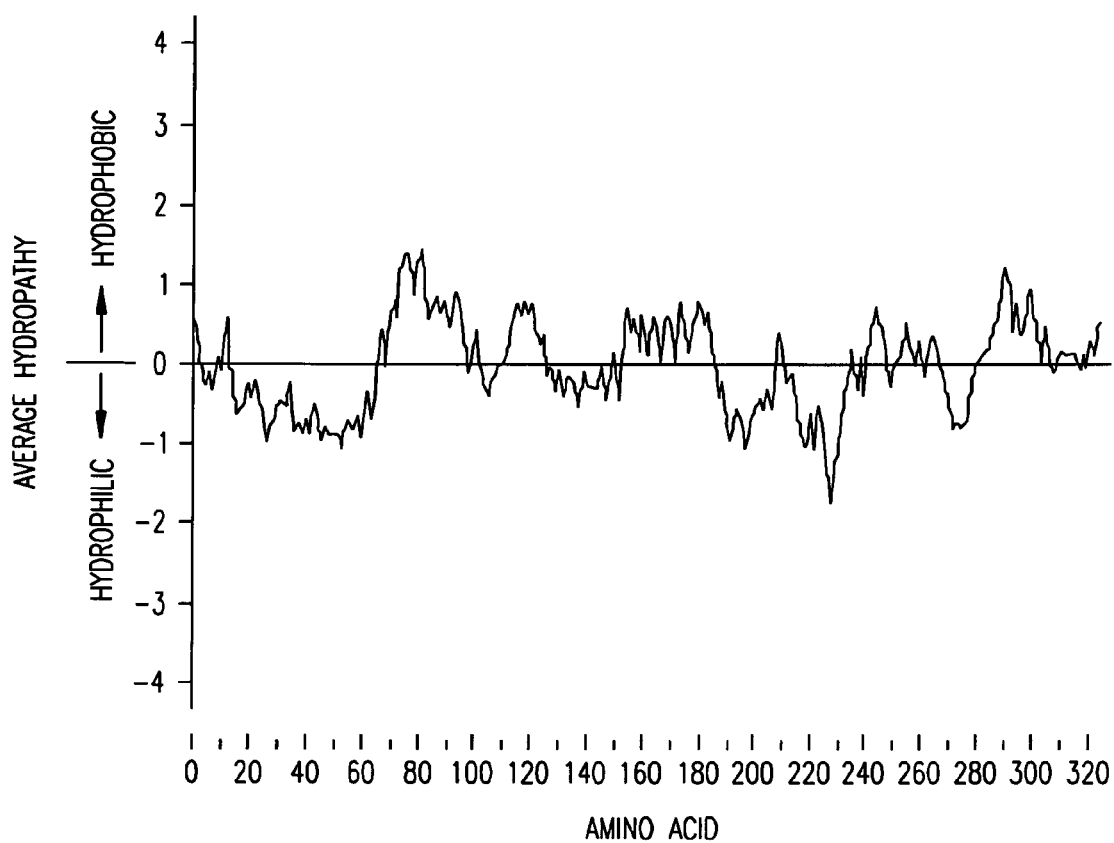

Ruigrok et al. (2000) reported that VP40 expressed in E. coli can bind liposomes in vitro and that this interaction is largely electrostatic. In mammalian cells, a substantial amount of VP40 bound to the cellular membrane, and that this interaction was disrupted negligibly by the presence of 1 M NaCl, indicating that at least one hydrophobic domain is involved in this interaction. A small but appreciable portion of VP40 partitioned with detergent in the manner of an integral membrane or lipid-anchored protein in Triton X-114 phase-partitioning analysis. This result, together with the inability of 1 M NaCl to dissociate VP40 from the lipid bilayer, indicates that the protein has certain properties of an integral membrane protein, as do a number of matrix proteins of negative-stranded RNA viruses (Chong et al., 1993; Zhang et al., 1996), even though Ebola VP40 does not appear to contain a region of significant length and hydrophobicity to span the cell membrane (FIG. 5B). Short hydrophobic stretches of VP40 may be able to penetrate the lipid bilayer to some extent, lending modest integral-membrane character to the protein.

Ruigrok et al. (2000) also reported that a deletion mutant of VP40 containing amino acids 31-212 failed to bind liposomes efficiently, indicating that the C-terminus of VP40 is absolutely required for membrane binding. To elucidate the domains involved in the association of VP40 with cellular membranes, carboxy and amino-terminal deletion mutants were constructed. VP40 lacking its C-terminal 50 amino acids demonstrated appreciably reduced membrane association. The Kyte-Doolittle hydrophobicity plot (1982) of VP40 (FIG. 5B) indicates that amino acids 277-326 of the protein are primarily hydrophobic, so that deletion of amino acids 277-326 eliminates a substantial hydrophobic region that is likely important for efficient membrane-binding by the full-length protein. This hypothesis is supported by the fact that 1 M NaCl completely disrupted this association, suggesting that affinity of this deletion construct with the lipid bilayer depends primarily on electrostatic interactions.

When amino acids 227-326 of VP40 were deleted, the resulting truncated protein associated with the lipid bilayer as efficiently as wild-type VP40; moreover, C-terminal deletion of amino acids 177-326 resulted in a protein with much higher affinity for the lipid bilayer than was found for wild-type VP40. Salt treatment did not perturb membrane association of these truncated versions of VP40, indicating the presence of hydrophobic interactions mediated by the N-terminal 176 amino acids of the protein.

The hydrophobicity plot indicates that amino acids 227-276, and particularly amino acids 177-226, are primarily hydrophilic. Deletion of the hydrophilic residues present in this region of VP40 may allow the truncated protein to fold into a structure capable of strong hydrophobic association with the cell membrane, perhaps by effectively exposing the highly hydrophobic central domain of the protein. These results are consistent with data obtained by Triton X-114 extraction analysis (FIG. 11). Since VP40 lacking its C-terminal 50 amino acids was unable to produce particles (FIG. 7), and these C-terminal residues appear to be required for efficient membrane association of VP40, binding of this highly hydrophobic region to the lipid bilayer may be an essential step in the particle formation process.

The crystal structure of amino acids 31-326 of Ebola virus was recently elucidated by Dessen et al. (2000). It shows VP40 to be distinct from other viral matrix proteins, in that it consists of two similar domains connected by a flexible linker at amino acids 195-200. Ruigrok et al. (2000) showed that amino acids 31-212 of VP40 form hexamers spontaneously in solution. Dessen and associates postulate that, during the life cycle of Ebola virus, VP40 molecules associate with the lipid bilayer through interactions contributed primarily by their C-termini. After membrane binding, the molecules undergo a conformational change that frees their N-termini for hexamerization. These hexamers then form building blocks for a lattice that underlies the plasma membrane, and subsequently may interact with the cytoplasmic tails of viral glycoproteins and/or the ribonucleoprotein complex. This model is based on data demonstrating the hexamerization of VP40 molecules that lack their N-terminal 30 amino acids as well as their C-terminal 114 amino acids. The PPXY (SEQ ID NO:50) motif that appears crucial for membrane-bound particle formation is located at amino acids 10-13 of VP40, and this motif most likely interacts with a cellular protein that exhibits a WW domain during virus particle assembly or budding. It has not yet been demonstrated that VP40 with a truncated C-terminus can form hexamers when the entire N-terminus is present. If hexamerization does occur during virion morphogenesis, the 18 hexamers that form presumably must leave the PPXY (SEQ ID NO:50) motif accessible to cellular proteins that participate in particle formation and/or budding.

EXAMPLE 3

Particles Comprising Filovirus Matrix Protein and Glycoprotein

Materials and Methods

Cells.

293T human embryonic kidney cells were maintained in Dulbecco's modified Eagle medium supplemented with 10% fetal calf serum, L-glutamine and penicillin-streptomycin-gentamicin solution. The cells were grown in an incubator at 37EC in 5% $CO_2$.

Plasmids.

Full-length cDNAs encoding the Ebola virus (species Zaire) VP40 or GP were cloned separately into a mammalian expression vector, pCAGGS/MCS (Kobasa et al., 1997; Niwa et al., 1991), which contains the chicken β-actin promoter. The resultant constructs were designated pCEboZVP40 and pCEboZGP, respectively.

Cell Transfection for Expression of VP40 and GP.

293T cells ($1 \times 10^6$) were transfected with plasmids using the Trans IT LT-1 reagent (Panvera, Madison, Wis.) according to the manufacturer's instructions. Briefly, 1 μg of DNA in 0.1 ml Opti-MEM (Gibco-BRL) and 3 μl of the transfection reagent were mixed, incubated for 10 minutes at room temperature, and added to the cells. Transfected cells were incubated at 37EC for 24 or 48 hours.

Electron Microscopy.

Ultrathin section electron microscopy was performed as follows. Twenty-four hours post-transfection of 293T cells with plasmids, the cells were washed with phosphate-buffered saline (PBS) and fixed for 20 minutes with 2.5% glutaraldehyde (GLA) in 0.1 M cacodylate buffer (pH 7.4). They were scraped off the dish, pelleted by low-speed centrifugation and then fixed for 30 minutes with the same fixative. Small pieces of fixed pellet were washed with the same buffer, postfixed with 2% osmium tetroxide in the same buffer for 1 hour at 4EC, dehydrated with a series of ethanol gradients followed by propylene oxide, embedded in Epon 812 Resin mixture (TAAB) and polymerized at 70EC for 2 days. For immune electron microscopy, cells were fixed with 4% paraformaldehyde and 0.1% GLA, dehydrated and embedded in LR White Resin (London Resin Company Ltd.). Thin sections were stained with uranil acetate and lead citrate, and examined with a JEM-1200EX electron microscope at 80 Kv.

For negative staining, culture media of 293T cells were collected at 24 hours post-transfection onto a Formvar-coated copper grid, stained with 2% phosphotungstic acid solution (PTA) and examined with a JEM-1200 electron microscope at 80 Kv.

For immune electron microscopy, the samples were absorbed to Formvar-coated nickel grids and washed with PBS containing 0.5% bovine serum albumin (PBS-BSA). The grids were then treated with mouse anti-GP monoclonal antibody (a mixture of ZGP12, ZGP42, and ZGP133 (31); 1:150 in PBS-BSA) or rabbit anti-VP40 polyclonal antibody (1:300 in PBS-BSA), and rinsed six times with PBS, followed by incubation with a goat antimouse immunoglobulin conjugated to 15-nm gold particles (1:50 dilution; BBlnternational) or a goat antirabbit immunoglobulin conjugated to 5-nm gold particles (1:100 dilution; BBInternational). After washing, the samples were fixed for 10 min in 2% glutaraldehyde and negatively stained with 2% PTA.

Results

Pleomorphic Particle Formation by GP.

Figure 12B:
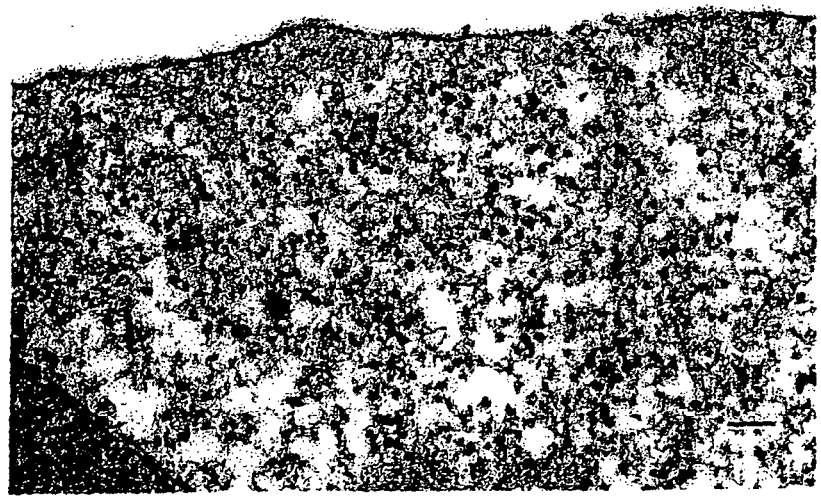
Figure 13A:
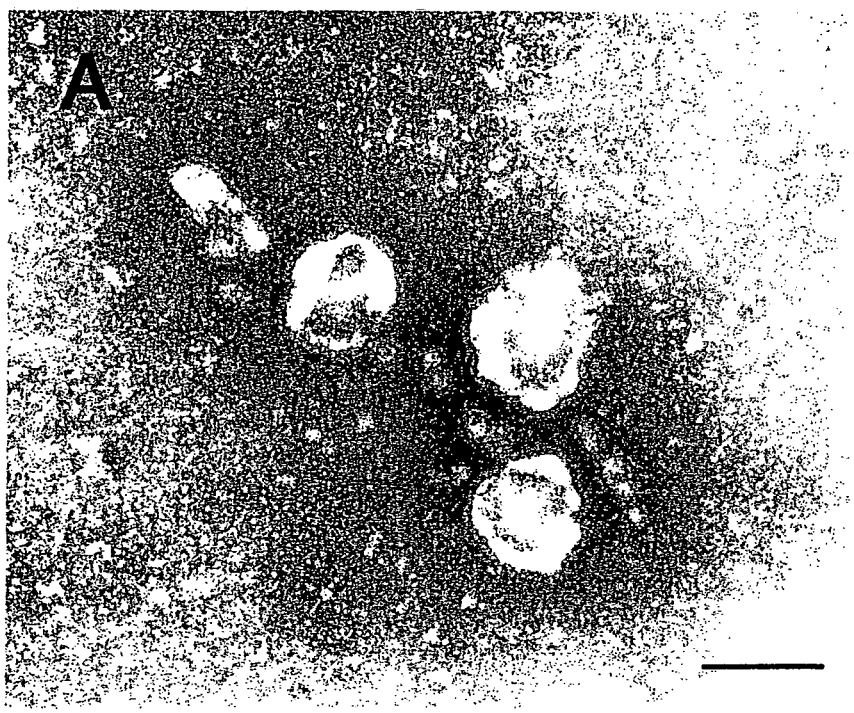
Figure 13B:
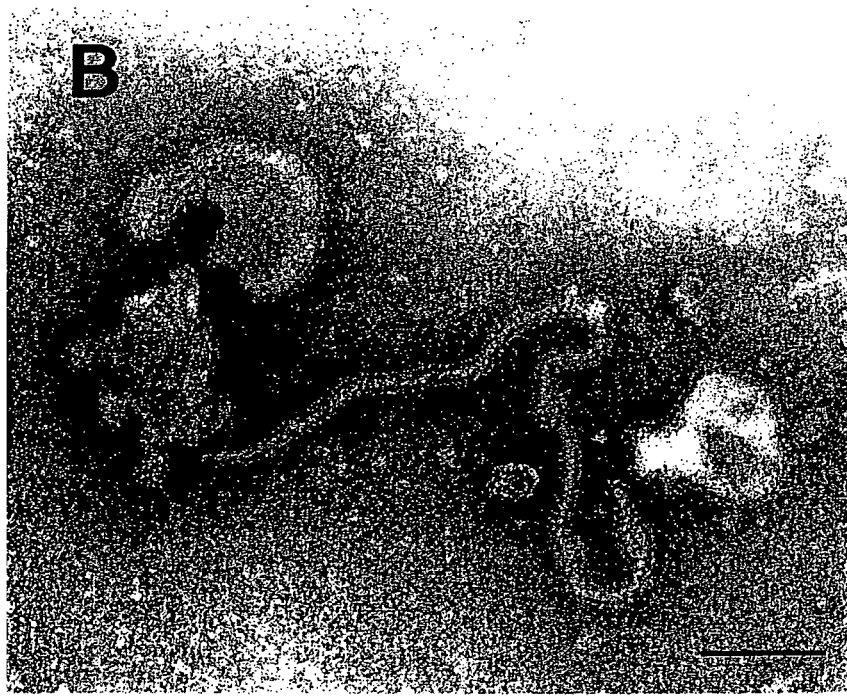
Figure 13C:
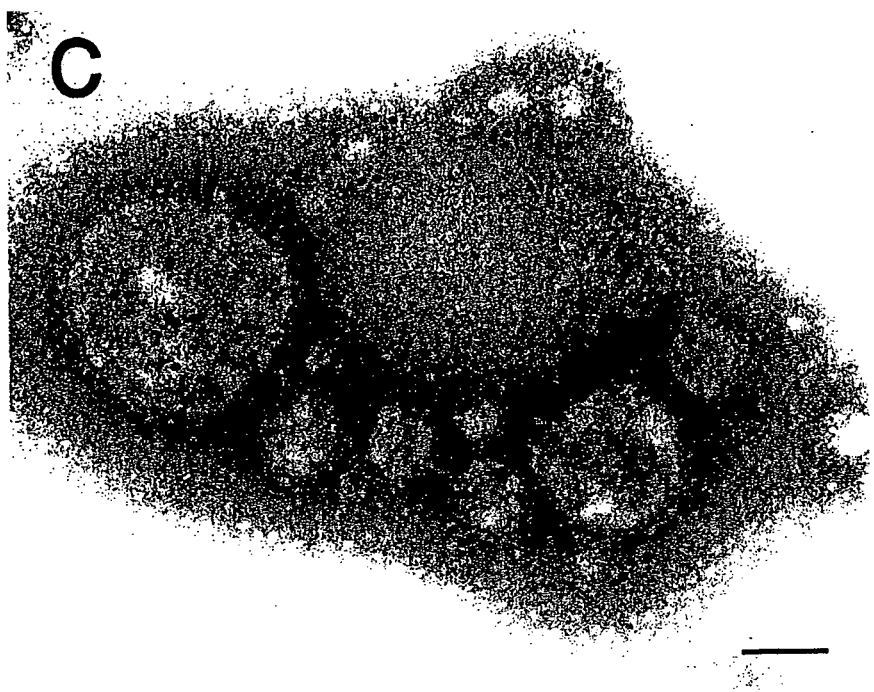
Figure 13D:
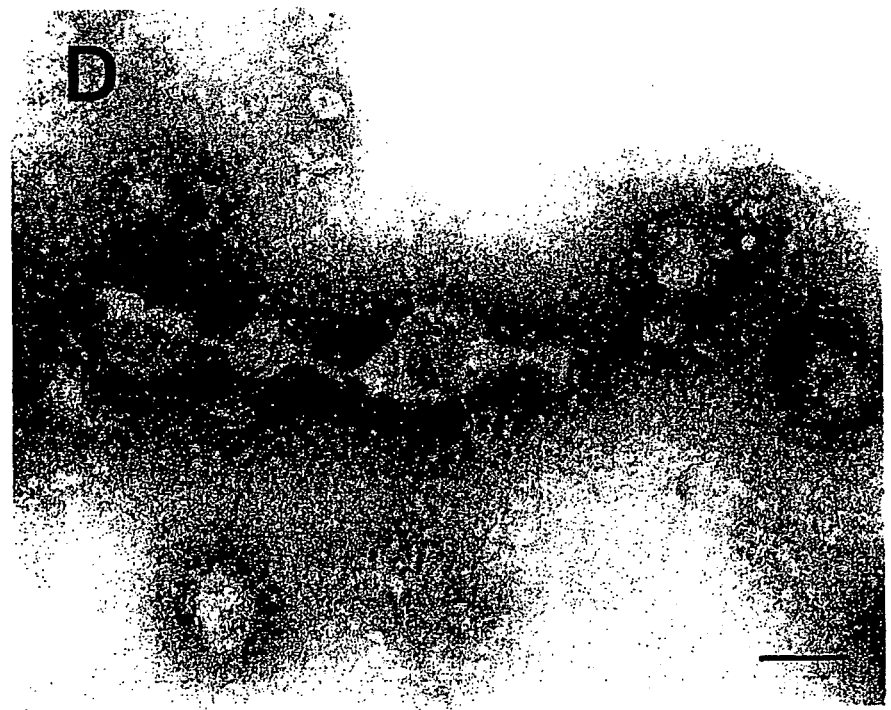

To determine the morphology of vesicles induced by Ebola virus GP expression, GP-expressing cells and their supernatants were analyzed by electron microscopy. The ultrathin sections of these cells showed particle-like structures with surface spikes budding from the plasma membrane (FIG. 12A); no such structures were observed using cells transfected with the expression vector alone (FIG. 12B). As previously observed in the recombinant vaccinia virus system (Volchkov et al., 1998), pleomorphic structures similar to virosomes with a range of diameters were apparent in the supernatants of GP-expressing cells (FIGS. 13 A and B). The spikes on the surface of the vesicles reacted with anti-GP monoclonal antibodies (FIGS. 13 C and D), confirming the GP derivation of the structures.

VP40 Induces Filamentous Particle Formation.

Figure 14A:
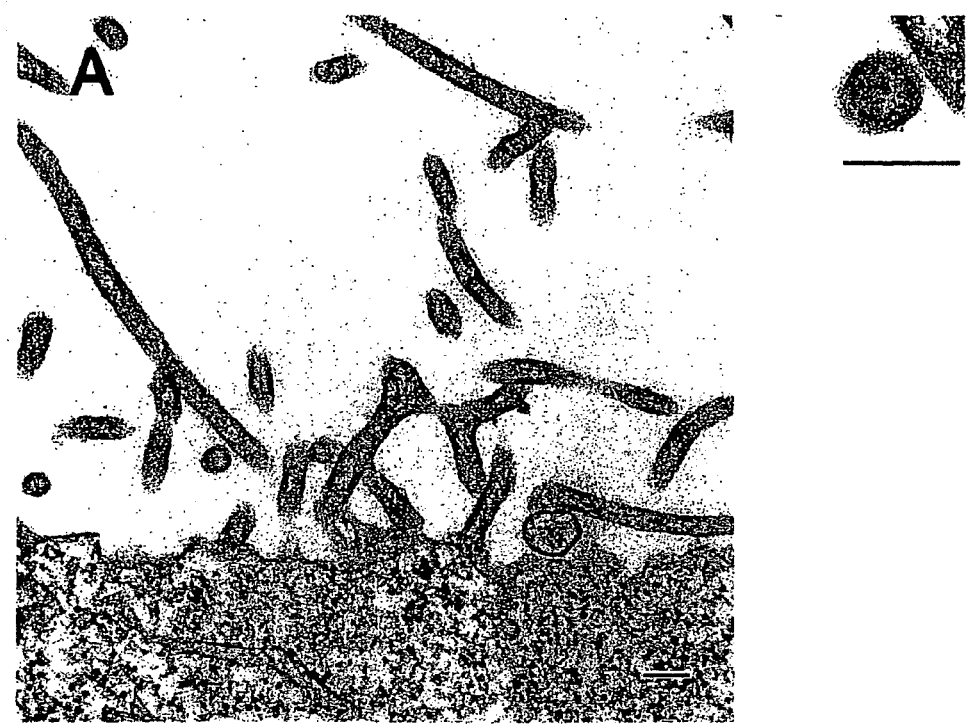
Figure 14B:
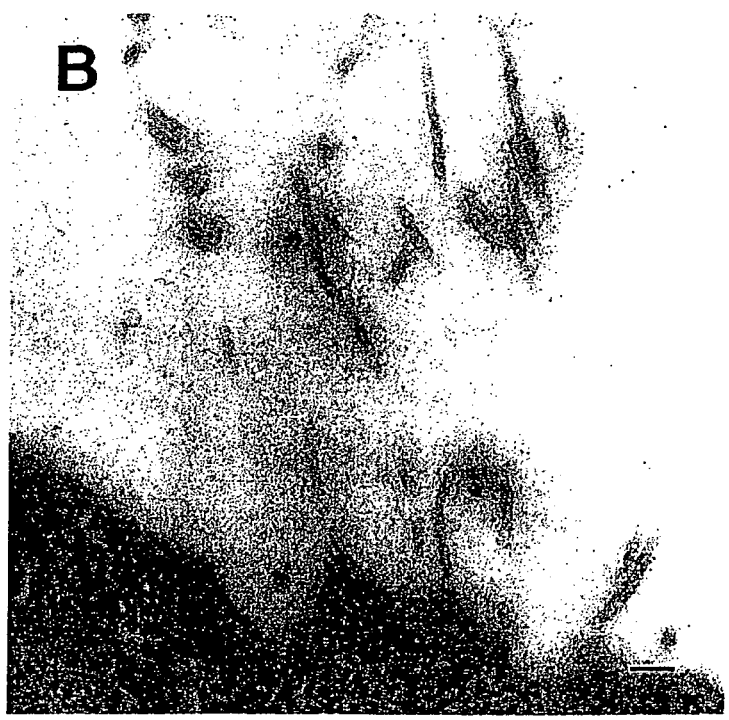
Figure 14C:
Figure 14D:
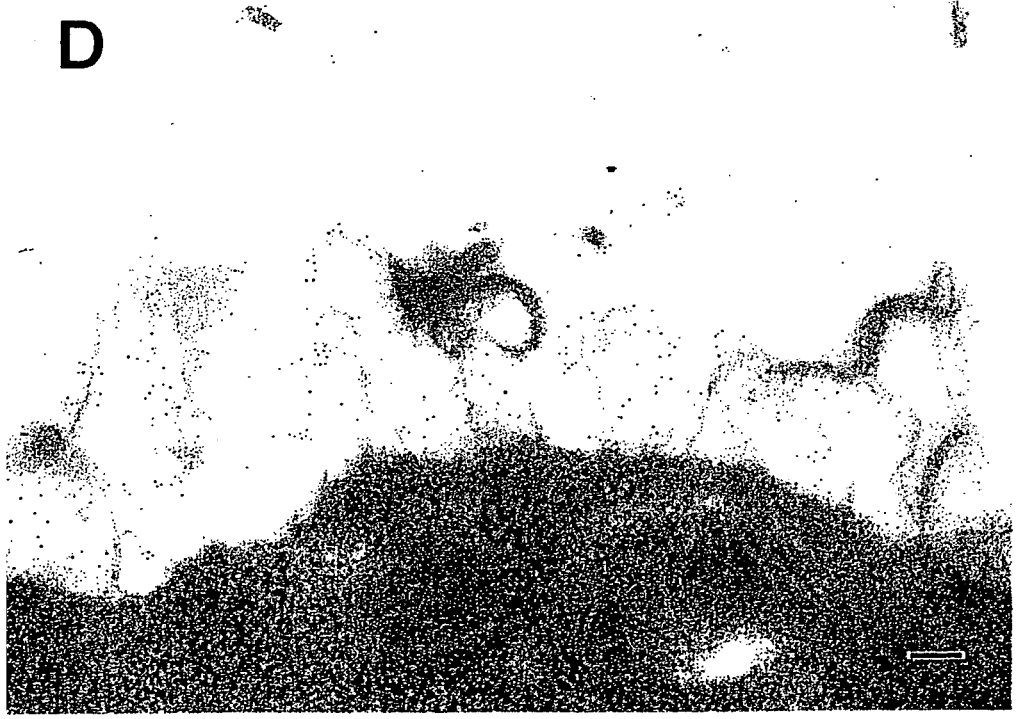
Figure 14E:
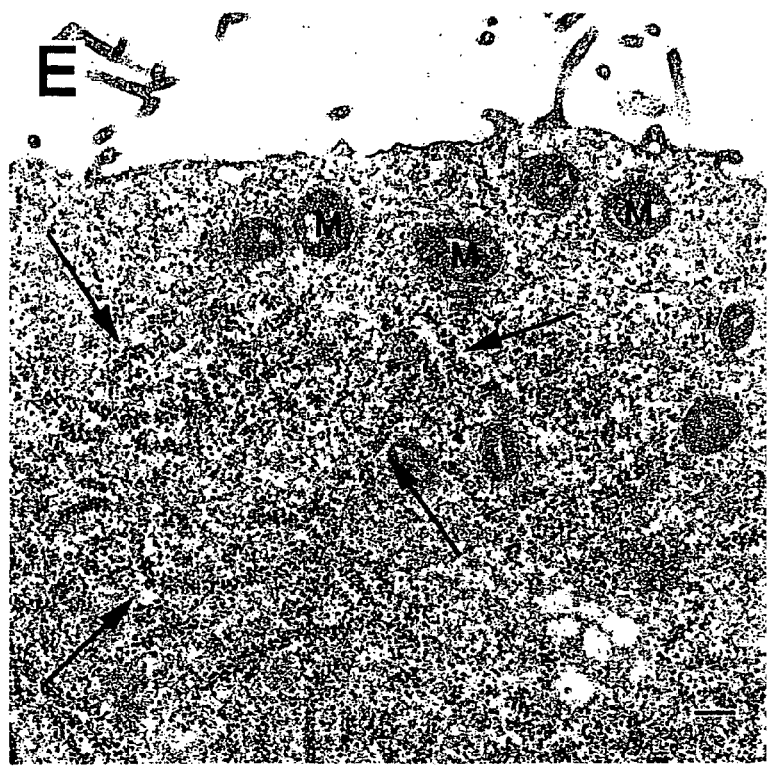
Figure 14F:
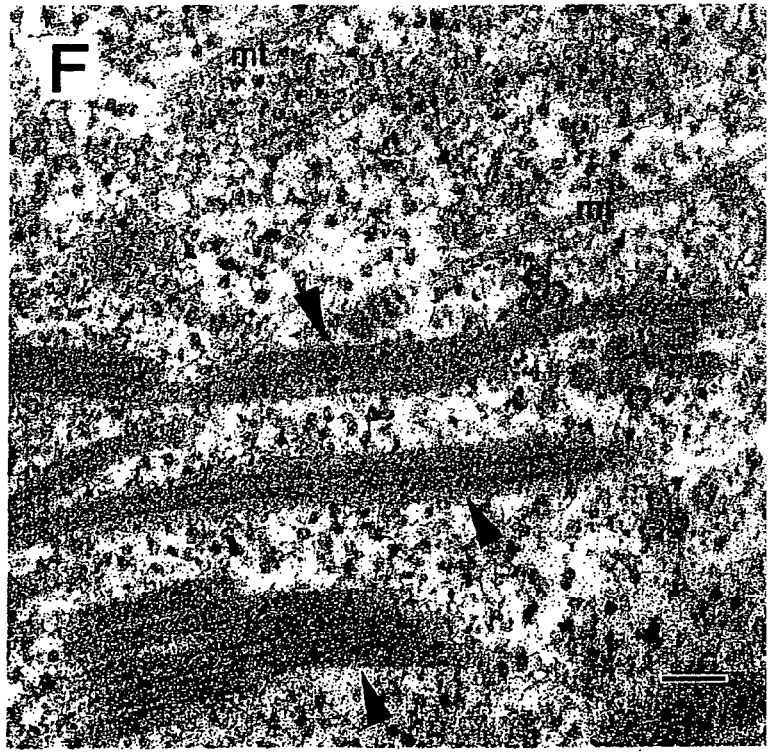
Figure 15A:
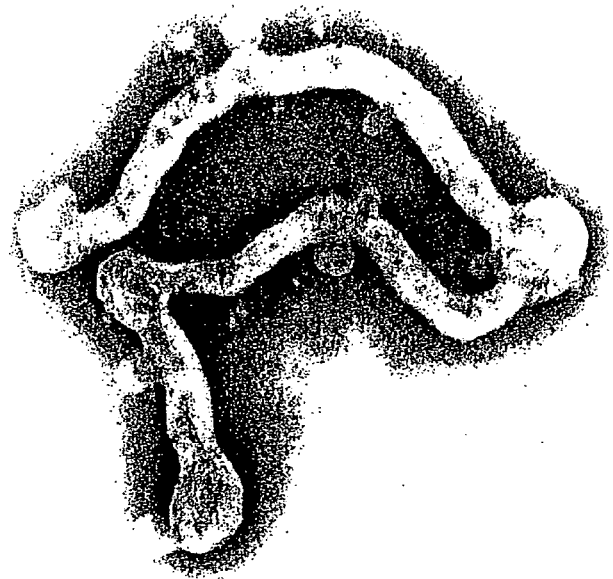
Figure 15B:
Figure 15C:
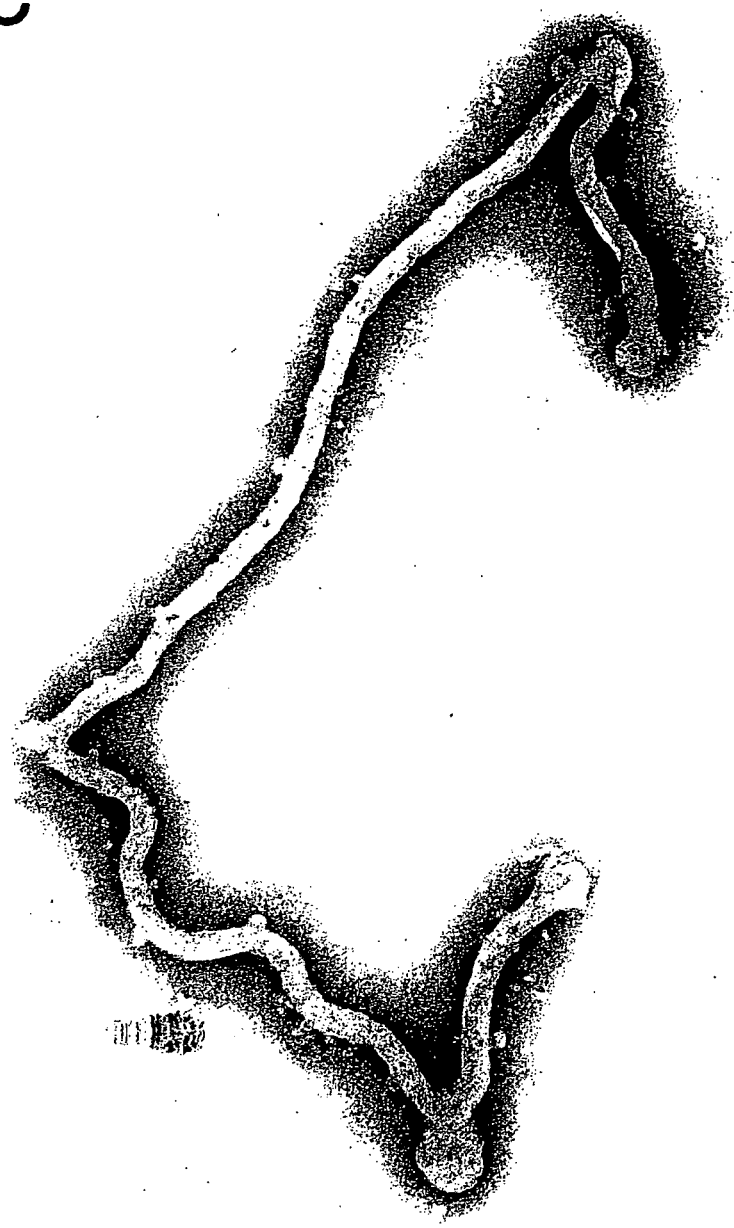

To determine how VP40 protein expressed in 293T cells is released into culture medium (Harty et al., 2000; Timmins et al., 2001; Example 2), the VP40-expressing cells were analyzed by transmission electron microscopy. The ultrathin sections of the cells expressing VP40 showed budding of filamentous structures (approximately 65 nm in diameter) on the cell surface (FIG. 14A). In some cells, the plasma membranes appeared ruffled and to consist of two bilayers (FIG. 14C). Aggregated ribosomes (FIG. 14E, arrows) were occasionally found in the cytoplasm of cells expressing VP40, as were electron-dense filamentous structures (approximately 45 nm in diameter; FIG. 14F, arrowheads), which were never seen in cells transfected with the expression vector alone. The budding particles and membrane ruffles reacted with rabbit anti-VP40 polyclonal antibody (FIGS. 14B and D), confirming that VP40 had contributed to the generation of these structures. In studies to further determine the size and morphology of the VP40 particles released from cells, the supernatants of cells expressing this protein were centrifuged through 20% sucrose, and the pelleted material was negatively stained with 2% PTA and analyzed by electron microscopy. Filamentous particles, which had uniform diameters of approximately 65 nm but varied lengths, were observed (FIGS. 15A-C). These results indicate that VP40 alone can induce the formation of filamentous particles, which bud from the cell surface.

VP40-GP Interaction in Particle Morphogenesis.

Figure 16A:
Figure 16B:
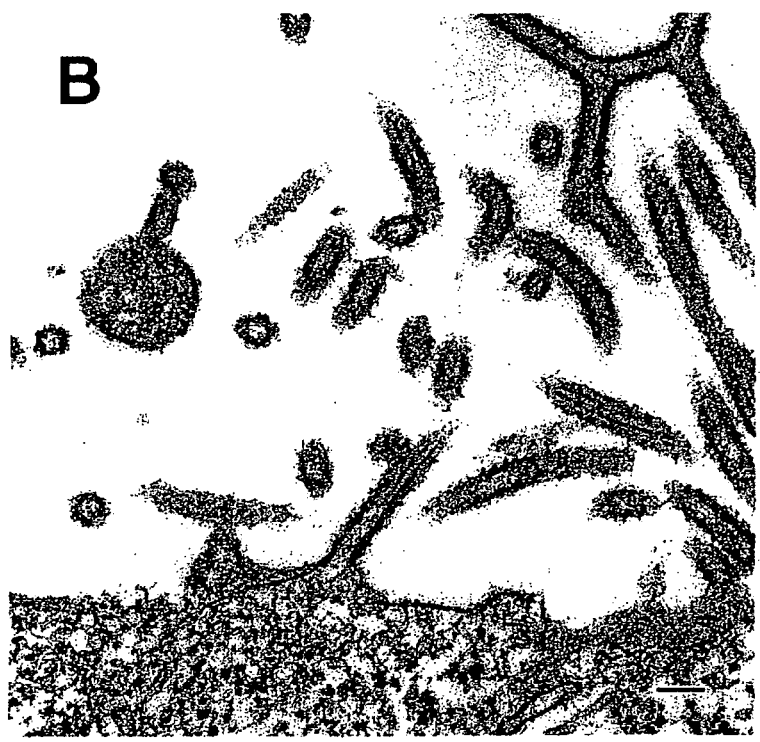
Figure 17A:
Figure 17B:
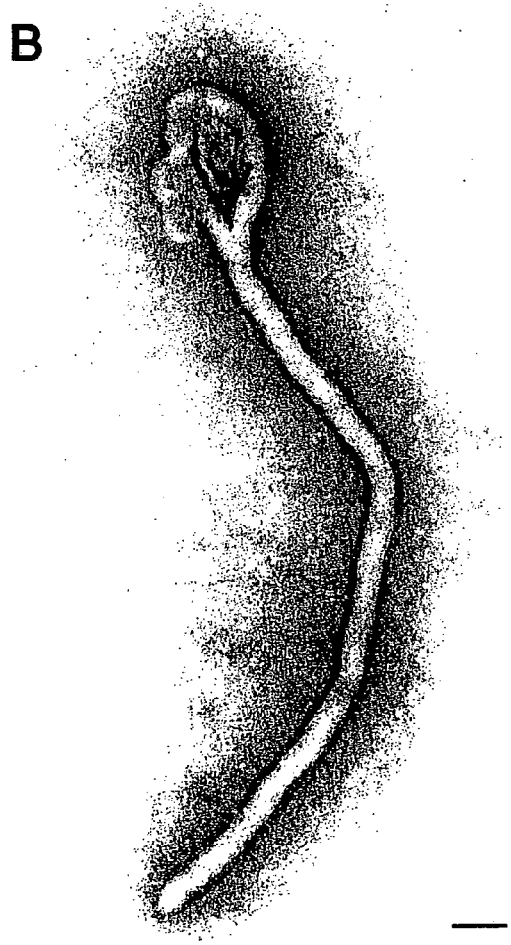
Figure 17C:
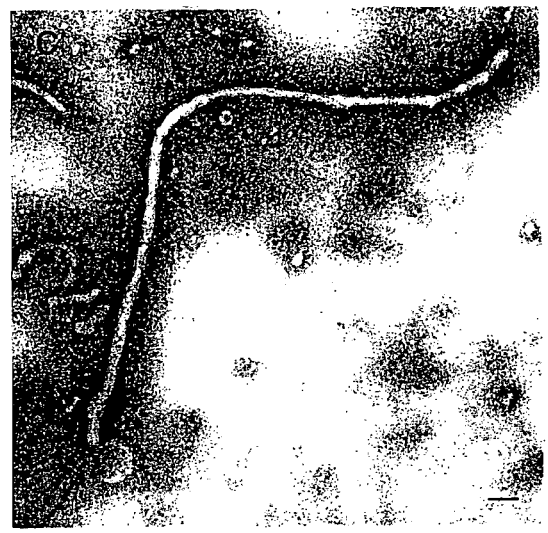
Figure 17D:
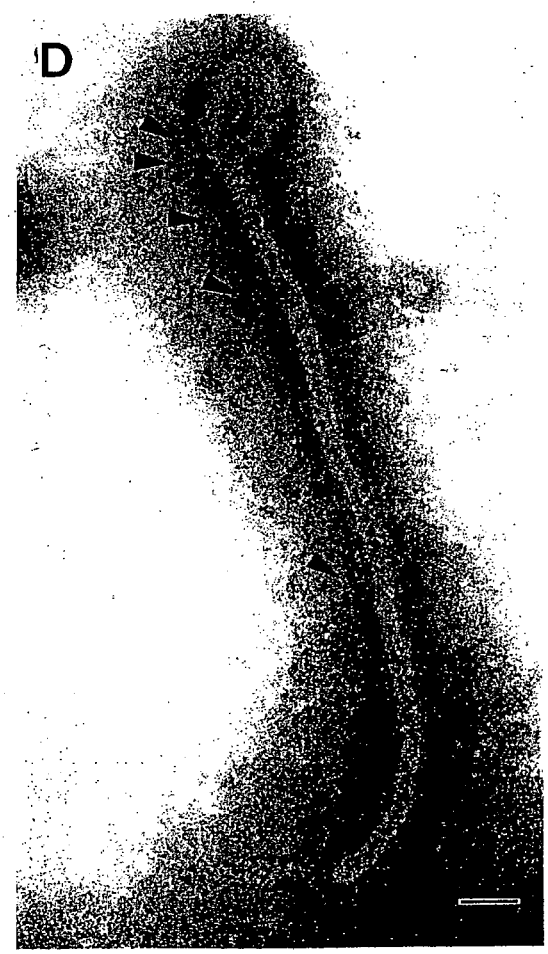
Figure 17E:

To determine how GP expression affects VP40-driven particle formation, 293T cells were transfected with both VP40- and GP-expressing plasmids. In ultrathin sections of the transfected cells, filamentous particle-like structures of 80-nm external diameter were observed that were budding from the plasma membrane (FIGS. 16A and B). The structures possessed spikes of approximately 10 nm on their surface, in contrast to the structures observed in cells expressing VP40 alone (FIG. 14A). Also, unlike the findings with expression of GP alone, few pleomorphic particles were observed. The particle structures were studied in more detail after negative staining of the particles in culture supernatants of cells expressing both VP40 and GP. Filamentous Ebola virus-like particles with surface spikes of approximately 85-nm in external diameter and lengths that ranged to 10 μm were observed (FIGS. 17A-C). The spikes projected from the particle surface at 5- to 10-nm intervals and were morphologically indistinguishable from those on the Ebola virion surface (Feldmann et al., 1996; Peters et al., 1995). Labeling of the spikes with a mixture of anti-GP monoclonal antibodies conjugated with gold particles confirmed their identity as GP (FIG. 17D). Furthermore, when treated with 0.03% Triton X-100 and with both the anti-VP40 antibody conjugated to 5-nm gold particles and a mixture of anti-GP monoclonal antibodies conjugated to 15-nm gold particles, the filamentous particles became labeled with both antibodies, demonstrating that the Ebola vires-like particles contained GP as well as VP40 proteins (FIG. 17E). These results demonstrate GP incorporation into VP40-generated filamentous structures, without affecting filamentous particle formation.

Discussion

A hallmark of Ebola virus is its filamentous virions as featured in its family name Filoviridae. The shape of enveloped viruses are determined by viral proteins in retroviruses (Campbell et al., 1997; Gay et al., 1998; Joshi et al., 2000) or by both viral RNA length and proteins in VSV (Pattnaik et al., 1991). Because specific interactions among viral components are required for the formation of defined virion shapes, understanding of such interactions can lead to the identification of targets for the development of antiviral compounds.

As shown herein by electron microscopy, the expression of VP40 in the absence of any other Ebola vires proteins leads to the formation of filamentous particles, which resemble spikeless virions released into the supernatant of cultured Ebola virus-infected cells (Geisbert et al., 1995). Thus, these results suggest that the Ebola virus VP40 possesses structural information necessary and sufficient to induce the formation of filamentous particles, which then bud from the plasma membrane. Interestingly, some filamentous structures were observed in the cytoplasm of cells expressing VP40 as have been found in the cytoplasm of the cells infected with Ebola virus. Similar structures have also been observed in cells expressing the M1 protein of influenza virus or the GAG protein of retrovirus (Delchambre et al., 1989; Gheyson et al., 1989; Gomez-Puertas et al., 2000). However, the tubular structures observed upon expression of influenza virus M1 alone were not seen during normal viral infection or when M1 was coexpressed with other influenza viral proteins. Thus, VP40 may form intracellular filamentous structures by self-aggregation.

Membrane ruffles containing VP40 protein were observed in some VP40-expressing cells (FIGS. 14C and D). The M protein of VSV induces similar double-layered membranes at the cell surface when expressed from recombinant Sendai virus (Sakaguchi et al, 1999). IpaC protein secreted by *Shigella flexneri* has also been linked to large-scale membrane extension in macrophages, including lamellipodia and membrane ruffles (Kuwae et al, 2001; Tran Van Nhieu et al., 1999), while *Salmonella typhimurium* triggers the formation of host cell membrane ruffles in nonphagocytic cells (Ginocchio et al., 1994; Zhou et al., 1999). These membrane ruffles are thought to result from interactions between the bacterial proteins, including IpaC, and the actin cytoskeletons of host cells (Tran Van Nhieu et al., 1999; Zhou et al., 1999). In Ebola virus-infected cells, host cell plasma membranes proliferate extensively at the peak stage of viral budding (Geisbert et al, 1995), as observed in cells expressing VP40 alone. Thus, VP40 may interact with actin filaments during the assembly or budding of Ebola virus at the cell surface.

The impact of glycoprotein interaction with the matrix protein on virion morphology differs among viruses. For example, deletion of the cytoplasmic tails of the influenza virus hemagglutinin and neuraminidase alters virus morphology (Jin et al., 1997; Mitnaul et al., 1996), while the characteristic morphology of rabies virus and VSV do not depend on glycoprotein-matrix protein interaction (Mebatsion et al, 1996; Mebatsion et al., 1994; Schnell et al., 1998; Takada et al., 1997). The Ebola virus GP, like VSV-G, was incorporated into filamentous particles without affecting the morphology of the particles. However, such interaction may contribute to the efficiency of budding, as demonstrated by research on VSV (Jayakar et al., 2000; Mebatsion et al., 1999).

In conclusion, VP40 induces VP40 containing-filamentous particle formation and GP spikes are incorporated into VP40 induced-filamentous particles upon coexpression of GP and VP40, resulting in Ebola virus-like particles. This virus-like particle formation system will be useful to further elucidate the mechanism of Ebola virus particle formation, including the functional link among Ebola viral and cellular components.

REFERENCES

Baize et al., *Nat. Med.*, 5, 423 (1999).
Basler et al., *Proc. Natl. Acad. Sci. U.S.A.*, 97, 12289 (2000).
Bergmann et al., *J. Cell Biol.*, 107, 1707 (1988).
Bordier, *J. Biol. Chem.*, 256, 1604 (1981).
Bork et al., *Trends Biochem. Sci.*, 19, 531 (1994).
Campbell et al., *J. Virol.*, 71, 4425 (1997).
Chen et al., *Proc. Natl. Acad. Sci. U.S.A.*, 92, 7819 (1995).
Chong et al., *J. Virol.*, 67, 407 (1993).
Coronel et al., *J. Virol.*, 73, 7035 (1999).
Delchambre et al., *EMBO. J.*, 8, 2653 (1989).
Dessen et al., *EMBO J.*, 19, 4228 (2000).
Durbin et al., *Virology*, 235, 323 (1997).
Elliott et al., *Virology*, 147, 169 (1985).
Feldmann et al., *Arch. Virol. Suppl.*, 15, 159 (1999).
Feldmann et al., *Arch. Virol. Suppl.*, 7, 81 (1993).
Feldmann et al., 1996. Marburg and Ebola viruses. P. 1-52. In Maramorosch, K., Murphy, F. A. and Shatkin, A. J. (ed.), Advances in virus research 47, Academic Press.
Feldmann et al., Filoviruses, p. 651-664, 9$^{th}$ ed. Edward Arnold, London, United Kingdom (1998).
Garoff et al., *Microbiol. Mol. Biol. Rev.*, 62, 1171 (1998).
Gay et al., *Virology*, 247, 160 (1998).
Geisbert et al., *Virus Res.*, 39, 129 (1995).
Gheysen et al., *Cell*, 59, 103 (1989).
Giddings et al., *Virology*, 248, 108 (1998).
Ginocchio et al., *Cell*, 76, 717 (1994).
Girault et al., *Anal. Biochem.*, 182, 193 (1989).
Gomez-Puertas et al., *J. Virol.*, 74, 11538 (2000).
Haffer et al., *J. Virol.*, 64, 2653 (1990).
Harty et al., *J. Virol.*, 73, 2921 (1999).
Harty et al., *Proc. Natl. Acad. Sci. U.S.A.*, 97, 13871 (2000).
Hevey et al., *Virology*, 251, 28 (1998).
Ito et al., *J. Virol.*, 75, 1576 (2001).
Jasenosky et al., *J. Virol.*, 75, 5205 (2001).
Jayakar et al., *J. Virol.*, 74, 9818 (2000).
Jin et al., *EMBO. J.*, 16, 1236 (1997).
Joshi et al., *J. Virol.*, 74, 10260 (2000).
Justice et al., *J. Virol.*, 69, 3156 (1995).
Kato et al., *Genes Cells*, 1, 569 (1996).
Klenk et al., *Trends Microbiol.*, 2, 39 (1994).
Kobasa et al., *J. Virol.*, 71, 6706 (1997).
Kuwae et al., *J. Biol. Chem.*, 276, 32230 (2001).
Kyte et al., *J. Mol. Biol.*, 157, 105 (1982).
Li et al., *J. Virol.*, 67, 4415 (1993).
Marriott et al., *Adv. Virus Res.*, 53, 321 (1999).
Maruyama et al., *J. Virol.*, 73, 6024 (1999).
Mebatsion et al., *Cell*, 84, 941 (1996).
Mebatsion et al., *J. Virol.*, 73, 242 (1999).
Mitnaul et al., *J. Virol.*, 70, 873 (1996).
Moss et al., *Nature*, 348, 91 (1990).
Moss, Poxyiridae: The viruses and their replication. P. 2637-2672. In B. N. Fields, D. M. Knipe, and P. M. Howley (ed.), Fields virology, Lippincott-Raven Publishers, Philadelphia, Pa. 1996.

Muhlberger et al., *J. Virol.*, 73, 2333 (1999).
Nagai et al., *Microbiol. Immunol.*, 43, 613 (1999).
Neumann et al., *J. Virol.*, 74, 547 (2000).
Neumann et al., *Proc. Natl. Acad. Sci. USA*, 96, 9345 (1999).
Niwa et al., *Gene*, 108, 193 (1991).
Pattnaik et al., *Proc. Natl. Acad. Sci. USA*, 88, 1379 (1991).
Peters et al., 1995. Filoviridae: Marburg and Ebola viruses. P. 1161-1176. In B. N. Fields, D. M. Knipe, and P. M. Howley (ed.), Fields virology, Lippincott-Raven Publishers, Philadelphia, Pa.
Roberts et al., *Adv. Virus Res.*, 53, 301 (1999).
Ruigrok et al., *J. Mol. Biol.*, 300, 103 (2000).
Sakaguchi et al., *Virology*, 263, 230 (1999).
Sanchez et al., *Proc. Natl. Acad. Sci. U.S.A.*, 93, 3602 (1996).
Sanchez et al., *Virus Res.*, 29, 215 (1993).
Sandefur et al., *J. Virol.*, 72, 2723 (1998).
Schnell et al., *EMBO J.*, 13, 4195 (1994).
Schnell et al., *EMBO. J.*, 17, 1289 (1998).
Sudol et al., *FEBS Lett.*, 369, 67 (1995).
Sullivan et al., *Nature*, 408, 605 (2000).
Takada et al., *J. Virol.*, 75, 2324 (2001).
Takada et al., *Proc. Natl. Acad. Sci. U.S.A.*, 94, 14764 (1997).
Takimoto et al., *J. Virol.*, 75, 11384 (2001).
Timmins et al., *Virology*, 283, 1 (2001).
Tran Van Nhieu et al., *EMBO. J.*, 18, 3249 (1999).
Vanderzanden et al., *Virology*, 246, 134 (1998).
Volchkov et al., *J. Gen. Virol.*, 80, 355 (1999).
Volchkov et al., *Proc. Natl. Acad. Sci. USA*, 95, 5762 (1998).
Volchkov et al., *Science*, 291, 1965 (2001).
Volchkov et al., *Virology*, 245, 110 (1998).
Wills et al., *J. Virol.*, 63, 4331 (1989).
Wilson et al., *Science*, 287, 1664 (2000).
Wilson et al., *Science*, 287, 1664 (2000).
Wool-Lewis et al., *J. Virol.*, 73, 1419 (1999).
Wool-Lewis, et al., *J. Virol.* 72, 3155 (1998).
Xu et al., *Nat. Med.*, 5, 373 (1998).
Yang et al., *Nat. Med.*, 6, 886 (2000).
Yang et al., *Science*, 279, 1034 (1998).
Zhang et al., *Virology*, 225, 255 (1996).
Zhou et al., *Proc. Natl. Acad. Sci. USA*, 96, 10176 (1999).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method to prepare a vaccine comprising filamentous filovirus-like particles, comprising: isolating filamentous filovirus-like particles from a mammalian cell contacted with a vector comprising a promoter operably linked to a DNA segment encoding a filovirus matrix protein and a vector comprising a promoter operably linked to a DNA segment encoding a filovirus glycoprotein; and preparing a vaccine comprising an amount of the isolated filamentous filovirus-like particles effective to induce an immune response.

2. The method of claim 1 wherein the cell is further contacted with a vector comprising a promoter operably linked to a DNA segment encoding a protein of interest.

3. The method of claim 1 wherein the filovirus matrix protein is an Ebola virus matrix protein.

4. A method to prepare a vaccine comprising filamentous filovirus-like particles, comprising: isolating filamentous filovirus-like particles from a mammalian cell contacted with a vector comprising a promoter operably linked to a DNA segment encoding a filovirus matrix protein and a vector comprising a promoter operably linked to a DNA segment encoding a filovirus glycoprotein; and preparing a vaccine comprising an amount of the isolated filamentous filovirus-like particles effective to induce an immune response, wherein the glycoprotein is a heterologous filovirus glycoprotein.

5. The method of claim 1 wherein the filovirus matrix protein comprises the amino acid motif PPAY at positions corresponding to positions 10 to 13 of SEQ ID NO:3.

6. A vaccine comprising the isolated filovirus-like particles prepared by the method of claim 1.

7. A vaccine comprising isolated filovirus-like particles comprising filovirus matrix protein and filovirus glycoprotein.

* * * * *